US012714732B2

(12) United States Patent
Kohn et al.

(10) Patent No.: US 12,714,732 B2
(45) Date of Patent: Aug. 25, 2026

(54) LENTIVIRAL VECTORS IN HEMATOPOIETIC STEM CELLS TO TREAT WISKOTT-ALDRICH SYNDROME (WAS)

(71) Applicant: The Regents of the University of California, Oakland, CA (US)

(72) Inventors: Donald B. Kohn, Tarzana, CA (US); Ryan L. Wong, Los Angeles, CA (US); Roger Paul Hollis, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 952 days.

(21) Appl. No.: 17/775,846

(22) PCT Filed: Nov. 10, 2020

(86) PCT No.: PCT/US2020/059886
§ 371 (c)(1),
(2) Date: May 10, 2022

(87) PCT Pub. No.: WO2021/096887
PCT Pub. Date: May 20, 2021

(65) Prior Publication Data

US 2022/0387528 A1 Dec. 8, 2022

Related U.S. Application Data

(60) Provisional application No. 62/933,875, filed on Nov. 11, 2019.

(51) Int. Cl.
*A61K 35/76* (2015.01)
*C12N 15/867* (2006.01)

(52) U.S. Cl.
CPC ............ *A61K 35/76* (2013.01); *C12N 15/867* (2013.01); *C12N 2740/16043* (2013.01); *C12N 2800/22* (2013.01)

(58) Field of Classification Search
CPC .................. A61K 35/76; C12N 15/867; C12N 2740/16043; C12N 2800/22
See application file for complete search history.

(56) References Cited

U.S. PATENT DOCUMENTS

| | | | |
|---|---|---|---|
| 4,522,811 | A | 6/1985 | Eppstein et al. |
| 5,686,279 | A | 11/1997 | Finer et al. |
| 5,994,136 | A | 11/1999 | Naldini et al. |
| 6,136,597 | A | 10/2000 | Hope et al. |
| 2002/0173454 | A1 | 11/2002 | Rosen et al. |
| 2003/0039636 | A1 | 2/2003 | Leboulch et al. |
| 2006/0024786 | A1 | 2/2006 | Tomasevic et al. |

FOREIGN PATENT DOCUMENTS

| | | |
|---|---|---|
| WO | WO2017191274 | 11/2017 |
| WO | WO-2018195360 A1 | 10/2018 |

OTHER PUBLICATIONS

Richart, L., Bidard, FC. & Margueron, R. Enhancer rewiring in tumors: an opportunity for therapeutic intervention. Oncogene 40, 3475-3491 (2021). https://doi.org/10.1038/s41388-021-01793-7 (Year: 2021).*

Morgan RA, Unti MJ, Aleshe B, et al. Improved Titer and Gene Transfer by Lentiviral Vectors Using Novel, Small B-Globin Locus Control Region Elements. Mol Ther. 2020;28(1):328-340. doi: 10.1016/j.ymthe.2019.09.020 (Year: 2019).*

Dupré, L. et al., "Lentiviral Vector-mediated Gene Transfer in T Cells From Wiskott-Aldrich Syndrome Patients Leads to Functional Correction", Molecular Therapy, Nov. 2004, vol. 10, No. 5, pp. 903-915.

International Preliminary Report on Patentability dated May 27, 2022, in PCT Application No. PCT/US2020/059886.

International Search Report and Written Opinion dated Apr. 5, 2021 in PCT Application No. PCT/US2020/059886.

Martin, F. et al., "Lentiviral Vectors Transcriptionally Targeted to Hematopoietic Cells by WASP Gene Proximal Promoter Sequences", Gene Therapy, Apr. 2005, vol. 12, No. 8, pp. 715-723.

Wen, G. et al., "*Homo sapiens* chromosome X multiple clones map p11.23, complete sequence" 1-3. GenBank Accession AF207550, NCBI Database, Sep. 23, 2004, 3 pages.

Auti et al., "Lentivirus-based Gene Therapy of Hematopoietic Stem Cells in Wiskott-Aldrich Syndrome", Science, Aug. 2013; 341(6148):1233151.

Charrier et al. "Lentiviral vectors targeting WASp expression to hematopoietic cells, efficiently transduce and correct cells from WAS patients", Gene Therapy (2007) 14(5):415-428.

Zhan et al., "The identification of hematopoietic-specific regulatory elements for WASp gene expression", Molecular Therapy—Methods and Clinical Development, Jan. 2016; 3(16077):1-10.

Dupre et al., "Efficacy of Gene Therapy for Wiskott-Aldrich Syndrome Using a WAS Promoter/cDNA-Containing Lentiviral Vector and Nonlethal Irradiation", Human Gene Therapy, Mar. 2006; 17:303-313.

Frecha et al., "Improved lentiviral vectors for Wiskott-Aldrich syndrome gene therapy mimic endogenous expression profiles throughout haematopoiesis", Gene Therapy, Mar. 2008; 15(12):930-941.

Database EMBL (Online), Nov. 9, 1999, Wen G: "*Homo sapiens* chromosome X multiple clones map p11.23, complete sequence", XP093102422.

(Continued)

*Primary Examiner* — Maria G Leavitt
*Assistant Examiner* — Kodye Lee Abbott
(74) *Attorney, Agent, or Firm* — Mark S. Cohen; PEARL COHEN LLP

(57) ABSTRACT

In certain embodiments a lentiviral vector for the treatment of Wiskott-Aldrich Syndrome (WAS) is provided. In certain embodiments the vector comprises an expression cassette comprising a nucleic acid construct comprising an effective fragment of the endogenous promoter of the WAS gene where said promoter has maximum length of 600 bp and contains the sequence of HS1pro, and a nucleic acid that encodes the Wiskott-Aldrich Syndrome protein (WASp) operably linked to the effective fragment of the endogenous promoter of the WAS gene.

11 Claims, 27 Drawing Sheets

Specification includes a Sequence Listing.

(56) References Cited

OTHER PUBLICATIONS

Database EMBL (Online), Nov. 9, 1999, Wen G: "*Homo sapiens* chromosome X multiple clones map p11.23, complete sequence", XP093102427.
Braun et al., "Gene Therapy for Wiskott-Aldrich Syndrome-Long-Term Efficacy and Genotoxicity", Science Translational Medicine (2014), 6(227): 227ra33.
Grote et al., "JCat: a novel tool to adapt codon usage of a target gene to its potential expression host", Nucleic Acids Res., 2005, 33(suppl 2): W526-W531.
Zufferey et al., "Self-Inactivating Lentivirus Vector for Safe and Efficient In Vivo Gene Delivery", Journal of Virology, Dec. 1998; 72(12): 9873-9880.
Dull et al., "A Third-Generation Lentivirus Vector with a Conditional Packaging System", Journal of Virology, Nov. 1998; 72(11): 8463-8471.
Burgess-Beusse et al., "The insulation of genes from external enhancers and silencing chromatin", Proc. Natl. Acad. Sci. USA, Dec. 2002; 99(suppl.4): 16433-16437.
Zhan et al., "Insulator: from chromatin domain boundary to gene regulation", Human Genetics, Oct. 2001; 109(5) :471-478.
Prioleau et al., "An insulator element and condensed chromatin region separate the chickenβ-globin locus from an independently regulated erythroid-specific folate receptor gene", The EMBO Journal, 1999; 18(14):4035-4048.
Chung et al., "A 5' Element of the Chicken p-Globin Domain Serves as an Insulator in Human Erythroid Cells and Protects against Position Effect in *Drosophila*", Cell, Aug. 1993; 74(3):505-514.
Pikaart et al., "Loss of transcriptional activity of a transgene is accompanied by DNA methylation and histone deacetylation and is prevented by insulators", Genes & Development, 1998; 12: 2852-2862.
Wang et al., "Ligand-inducible and liver-specific target gene expression in transgenic mice", Nature Biotechnology, 1997; 15(3):239-243.
Taboit-Dameron et al., "Association of the 5' HS4 sequence of the chicken β-globin locus control region with human EF1α gene promoter induces ubiquitous and high expression of human CD55 and CD59 cDNAs in transgenic rabbits", Transgenic Research, Jun. 1999; 8(3):223-235.
Chung et al., "Characterization of the chicken β-globin insulator", Proc. Natl. Acad. Sci. USA, Jan. 1997; 94: 575-580.
Bell et al., "The Protein CTCF Is Required for the Enhancer Blocking Activity of Vertebrate Insulators", Cell, Aug. 1999; 98:387-396.
Ramezani et al., "Combinatorial Incorporation of Enhancer-Blocking Components of the Chicken β-Globin 5'HS4 and Human T-Cell Receptor α/δ BEAD-1 Insulators in Self-Inactivating Retroviral Vectors Reduces Their Genotoxic Potential", Stem Cells, 2008; 26:3257-3266.
Chen et al., "Gene therapy for brain tumors: Regression of experimental gliomas by adenovirus-mediated gene transfer in vivo", Proc. Nati. Acad. Sci. USA, Apr. 1994; 91:3054-3057.
Thurman et al., "The accessible chromatin landscape of the human genome", Nature, Sep. 2012; 489:75-82.
Koldej et al., "Comparison of Insulators and Promoters for Expression of the Wiskott-Aldrich Syndrome Protein Using Lentiviral Vectors", Human Gene Therapy Clinical Development, Jun. 2013; 24:1-9.
Leuci et al., "Efficient Transcriptional Targeting of Human Hematopoietic Stem Cells and Blood Cell Lineages by Lentiviral Vectors Containing the Regulatory Element of the Wiskott-Aldrich Syndrome Gene", Stem Cells, 2009; 27:2815-2823.

* cited by examiner

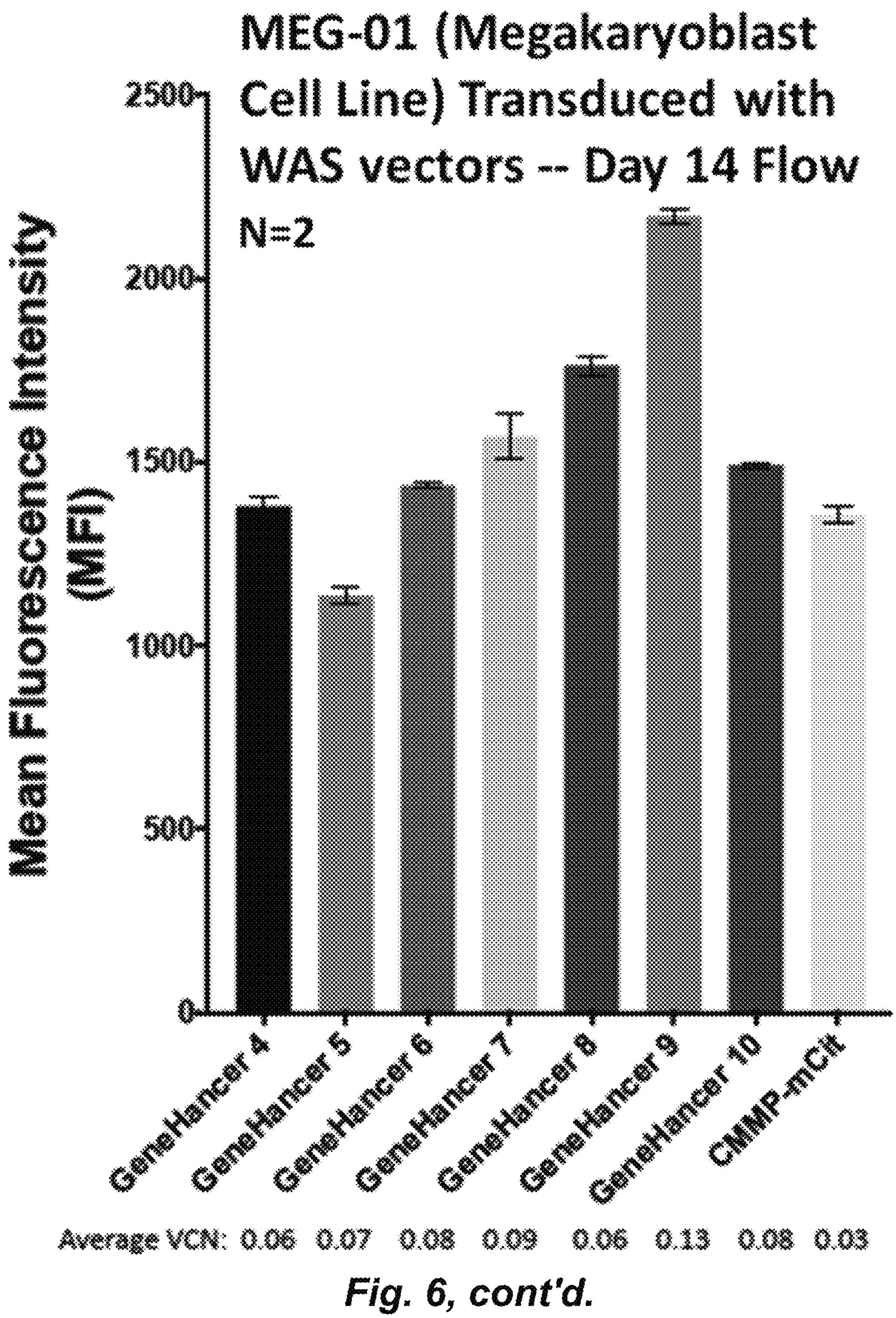
*Fig. 6, cont'd.*

E9(slim)-HS3(slim)-E2(all slim)-HS1pro-mCit-WPRE:

- (added the E9(slim) and HS3(slim) elements)

E9(slim)-HS3(slim)-E2(1,4,5 slim)-HS1pro-mCit-WPRE:

- (Deleted Core Sub-Element 2 of Element 2 and Core Sub-Element 3 of Element 2)

6) E9(slim)-HS3(slim)-E2(1,4,5 slim)-HS1pro-mCit-WPRE

E9(slim)-HS3(slim)-E2(1st half of 1 and 5 slim)-HS1pro-mCit-WPRE

- Deleted 2nd half of Core Sub-Element 1 of Element 2 and Core-Sub Element 4 of Element 2

SEQUENCE LISTING

<160> NUMBER OF SEQ ID NOS: 29

<210> SEQ ID NO 1
<211> LENGTH: 417
<212> TYPE: DNA
<213> ORGANISM: Artificial
<220> FEATURE:
<223> OTHER INFORMATION: WAS promoter

<400> SEQUENCE: 1
tcagcctcag gctacctagg tgctttagaa aggaggccac ccaggcccat gactactcct 60
tgccacaggg agccctgcac acagatgtgc taagctctcg ctgccagcca gagggaggag 120
ggtctgagcc agtcagaagg agatgggccc cagagagtaa gaaaggggga ggaggaccca 180
agctgatcca aaaggtgggt ctaagcagtc aagtggagga gggttccaat ctgatggcgg 240
agggcccaag ctcagcctaa cgaggaggcc aggcccacca aggggcccct ggaggacttg 300
tttcccttgt cccttgtggt tttttgcatt tcctgttccc ttgctgctca ttgcggaagt 360
tcctcttctt accctgcacc cagagcctcg ccagagaaga caagggcaga aagcacc 417

<210> SEQ ID NO 2
<211> LENGTH: 1794
<212> TYPE: DNA
<213> ORGANISM: Artificial
<220> FEATURE:
<223> OTHER INFORMATION: Enhancer element -continued

<400> SEQUENCE: 2

```
gacctgaagg gtaagggggt gtggaggttg tgaaggcggg aagggggta gcccttcac     60
caatgtaaac aaggatgtgg gttctgcggc cacactctcc cccgccctcc ccagcggcat   120
ttccagcaag tcacatgtcc tgcgcacagg ctgggggccc cctgctgctg cctttcttag   180
aagccaggac cacagagccc gcacagtgag ctacttgggg agctatttct gtagactgag   240
cttggggtac tgggaggcag tgctgttggc gatctggggg aaaacccccct gagggtccca   300
tttctctgcc actgacccct ttgcctggca gaaaggctct gctgcctcct agctgtgtag   360
caatggataa ggcctttaac ctctctaagc tgaaatgtcc tcatgcataa ggtggagaca   420
gtaactcctc ttccatctgc tgggtgttgt caaaactaca caggaggttt gccaagcacc   480
taaggcacag taggtggtca agaaacagga acacaatttg tcatgacgac aatgattcct   540
tcatatgcta gttacccacg agtcagccag aatgttgcca taaccactta tgaagccctt   600
cctcatttct gttgcaattc ctcagccaga ggaaagcccc accacctctg tcctccagaa   660
agccctcctc ttcccagaag gctggcacac agggctgggg gccaggcttg acttccctgt   720
ggaggggtct gaggttgggg ggatgacctg cagaggtagg ggaattcaga gaacttgttt   780
tgatagaaac tgaaactcct cctcttgctg acgctgcact tgtgggcaat ctgcacctgt   840
tctcccctcc cagaggccag ctggaagggg gtcccccacc attctacctc tgttcccatc   900
tcaaacaggg ctcagaaatc ctcagagagc ctggattatc ttcctatagg gtcctaccat   960
ttgctttaga gacatctgag aactgcctac tccccaggta gctgcctgcc tcccagaaga  1020
gccacagcaa gttccgctaa gggcaaaaaa ggaagctagg tgtctacagg gaacctaaaa  1080
acaaaccaca ctaacgtgtg tacacacagc tgcagaggga gacagggacc tggtctgctc  1140
acagcccttg ccactccccc atggcccatg tagaaacaac catgtggcct tcactctgcc  1200
cacagaagct agcaccagga ccctggtcag ggttagaggt ttctgctgag tcaaagccac  1260
atggagggag ggagcaaggg agagatgcag agtcatgttt ccaggaggag gttatctgag  1320
cataacaggg acagggtggg ccacaggata cctctgaggc tcaggttccc acctccactc  1380
caccctccaa ctctctgctc cacgttcctt ccactattca acacatggca ggaagtcagc  1440
ctgtagggct tcacactaca gtctaagctg actgccatct gtccccatcc aggcgaggct  1500
ggaaacgggg gcagcaaaaa gcccagggac aaagtcccct tcccaggcac atgtattatg  1560
cactctgcac caaggaaacc tccagataag gtctagagac caagggccat gtacttcggg  1620
ggagaggcca gaggacttct gaggttttac agagaaaagc caaaggcagc ccagtcaggg  1680
gaaatgtgta gccatagtgc cgataaggaa aggccttcaa cctgccctgg tcagctcttc  1740
ctgtaagtag aggcccctta ccgaaggccc cagtgggagg aagggtcggg agta         1794
```

<210> SEQ ID NO 3
<211> LENGTH: 270
<212> TYPE: DNA
<213> ORGANISM: Artificial
<220> FEATURE:
<223> OTHER INFORMATION: Enhancer element

<400> SEQUENCE: 3

```
gacctgaagg gtaagggggt gtggaggttg tgaaggcggg aagggggta gcccttcac     60
caatgtaaac aaggatgtgg gttctgcggc cacactctcc cccgccctcc ccagcggcat   120
ttccagcaag tcacatgtcc tgcgcacagg ctgggggccc cctgctgctg cctttcttag   180
aagccaggac cacagagccc gcacagtgag ctacttgggg agctatttct gtagactgag   240
```

cttggggtac tgggaggcag tgctgttggc 270

<210> SEQ ID NO 4
<211> LENGTH: 371
<212> TYPE: DNA
<213> ORGANISM: Artificial
<220> FEATURE:
<223> OTHER INFORMATION: Enhancer element

<400> SEQUENCE: 4
gatctggggg aaaaccccct gagggtccca tttctctgcc actgacccct ttgcctggca 60
gaaaggctct gctgcctcct agctgtgtag caatggataa ggcctttaac ctctctaagc 120
tgaaatgtcc tcatgcataa ggtggagaca gtaactcctc ttccatctgc tgggtgttgt 180
caaaactaca caggaggttt gccaagcacc taaggcacag taggtggtca agaaacagga 240
acacaatttg tcatgacgac aatgattcct tcatatgcta gttacccacg agtcagccag 300
aatgttgcca taaccactta tgaagccctt cctcatttct gttgcaattc ctcagccaga 360
ggaaagcccc a 371

<210> SEQ ID NO 5
<211> LENGTH: 283
<212> TYPE: DNA
<213> ORGANISM: Artificial
<220> FEATURE:
<223> OTHER INFORMATION: Enhancer element

<400> SEQUENCE: 5
ccacctctgt cctccagaaa gccctcctct tcccagaagg ctggcacaca gggctggggg 60
ccaggcttga cttccctgtg gaggggtctg aggttggggg gatgacctgc agaggtaggg 120
gaattcagag aacttgtttt gatagaaact gaaactcctc ctcttgctga cgctgcactt 180
gtgggcaatc tgcacctgtt ctcccctccc agaggccagc tggaaggggg tcccccacca 240
ttctacctct gttcccatct caaacagggc tcagaaatcc tca 283

<210> SEQ ID NO 6
<211> LENGTH: 215
<212> TYPE: DNA
<213> ORGANISM: Artificial
<220> FEATURE:
<223> OTHER INFORMATION: Enhancer element

<400> SEQUENCE: 6
gagagcctgg attatcttcc tatagggtcc taccatttgc tttagagaca tctgagaact 60
gcctactccc caggtagctg cctgcctccc agaagagcca cagcaagttc cgctaagggc 120
aaaaaaggaa gctaggtgtc tacagggaac ctaaaaacaa accacactaa cgtgtgtaca 180
cacagctgca gagggagaca gggacctggt ctgct 215

<210> SEQ ID NO 7
<211> LENGTH: 245
<212> TYPE: DNA
<213> ORGANISM: Artificial
<220> FEATURE:
<223> OTHER INFORMATION: Enhancer element

<400> SEQUENCE: 7
cacagccctt gccactcccc catggcccat gtagaaacaa ccatgtggcc ttcactctgc 60
ccacagaagc tagcaccagg accctggtca gggttagagg tttctgctga gtcaaagcca 120

-continued

```
catggaggga gggagcaagg gagagatgca gagtcatgtt tccaggagga ggttatctga    180

gcataacagg gacagggtgg gccacaggat acctctgagg ctcaggttcc cacctccact    240

ccacc                                                                245


<210> SEQ ID NO 8
<211> LENGTH: 410
<212> TYPE: DNA
<213> ORGANISM: Artificial
<220> FEATURE:
<223> OTHER INFORMATION: Enhancer element

<400> SEQUENCE: 8

ctccaactct ctgctccacg ttccttccac tattcaacac atggcaggaa gtcagcctgt     60

agggcttcac actacagtct aagctgactg ccatctgtcc ccatccaggc gaggctggaa    120

acgggggcag caaaaagccc agggacaaag tccccttccc aggcacatgt attatgcact    180

ctgcaccaag gaaacctcca gataaggtct agagaccaag ggccatgtac ttcgggggag    240

aggccagagg acttctgagg ttttacagag aaaagccaaa ggcagcccag tcaggggaaa    300

tgtgtagcca tagtgccgat aaggaaaggc cttcaacctg ccctggtcag ctcttcctgt    360

aagtagaggc cccttaccga aggccccagt gggaggaagg gtcgggagta              410


<210> SEQ ID NO 9
<211> LENGTH: 531
<212> TYPE: DNA
<213> ORGANISM: Artificial
<220> FEATURE:
<223> OTHER INFORMATION: Enhancer element

<400> SEQUENCE: 9

ctaaaagcca ccaaaaccaa gacagcaatg aaagtaacct ctggtcttcc taactgctca     60

ttatacacta attatgatgc actagcatgc taagagacac ttccaccagc gccatgacag    120

tgccatggca acatcaagaa gtcaccccac atggtctaaa aaggggaaga accttcagtt    180

cccggaattg cccacccctt tcctggaaaa ctcatgaata atccacccct tgtttagcat    240

ataattaaga aataactgta agtatcctta gtccagcagc ccaagctgct gctctgccta    300

tggagtagcc attctttatt cctttacttt cttaataaac ttgctttcac attaaaaaca    360

acaacaacaa caccaacaac cagcaaatat atcagaggct tagcatcccc tattcaaggg    420

gacagttctg gaggccgaga aagaagtaga aaggtggaga ataaaagaca caaaggagca    480

gaagaatttt atcttggcct ccatgtggca cctcacagct tgggaacaac a             531


<210> SEQ ID NO 10
<211> LENGTH: 245
<212> TYPE: DNA
<213> ORGANISM: Artificial
<220> FEATURE:
<223> OTHER INFORMATION: Enhancer element

<400> SEQUENCE: 10

ctaaaagcca ccaaaaccaa gacagcaatg aaagtaacct ctggtcttcc taactgctca     60

ttatacacta attatgatgc actagcatgc taagagacac ttccaccagc gccatgacag    120

tgccatggca acatcaagaa gtcaccccac atggtctaaa aaggggaaga accttcagtt    180

cccggaattg cccacccctt tcctggaaaa ctcatgaata atccacccct tgtttagcat    240

ataat                                                                245
```

<210> SEQ ID NO 11
<211> LENGTH: 555
<212> TYPE: DNA
<213> ORGANISM: Artificial
<220> FEATURE:
<223> OTHER INFORMATION: Enhancer element

<400> SEQUENCE: 11
gggatctgtg tgcagattta cctctaccta cacctggctg gggatcataa agaaaatcaa 60
gggatgcgct acctccatga atccaggttt cagcagagct aagggagtga aatttggggc 120
cattttactt gtctcaaacc ttgttatctg agagaaagct agagcttcct tctttcagcc 180
cccagagaca atgtggccag gctccggagg gctgggaaga tgagcaatgc ttgtgagtca 240
ccatgatagg aagcagaagg gtcaggaagt ccctgggagc aaggcttagg gttagggtta 300
gggagaaaac acttgggcct ggaggctcgg ggcaggcttc ctagagggga ggggtaggaa 360
gaggcagtga cagggcccac agcaatggag aggagttgga ctgcagggat ggggtagggg 420
gacagacgac aagggacact cagaagacta atgtctggga gtgggaaaac agtgtttgct 480
cagccaggaa gctgcatcca gctcttttat catttgtaga agaccaagta cccaggcctg 540
ggaggagccc agaga 555

<210> SEQ ID NO 12
<211> LENGTH: 222
<212> TYPE: DNA
<213> ORGANISM: Artificial
<220> FEATURE:
<223> OTHER INFORMATION: Enhancer element

<400> SEQUENCE: 12
caaaccttgt tatctgagag aaagctagag cttccttctt tcagcccca gagacaatgt 60 ggccaggctc cggagggctg ggaagatgag caatgcttgt gagtcaccat gataggaagc 120
agaagggtca ggaagtccct gggagcaagg cttagggtta gggttaggga gaaaacactt 180
gggcctggag gctcggggca ggcttcctag aggggagggg ta 222

<210> SEQ ID NO 13
<211> LENGTH: 1509
<212> TYPE: DNA
<213> ORGANISM: Artificial
<220> FEATURE:
<223> OTHER INFORMATION: WAS cDNA

<400> SEQUENCE: 13
atgagtgggg gcccaatggg aggaaggccc gggggccgag gagcaccagc ggttcagcag 60
aacataccct ccaccctcct ccaggaccac gagaaccagc gactctttga gatgcttgga 120
cgaaaatgct tgacgctggc cactgcagtt gttcagctgt acctggcgct gccccctgga 180
gctgagcact ggaccaagga gcattgtggg gctgtgtgct tcgtgaagga taacccccag 240
aagtcctact tcatccgcct ttacggcctt caggctggtc ggctgctctg ggaacaggag 300
ctgtactcac agcttgtcta ctccaccccc accccccttct tccacacctt cgctggagat 360
gactgccaag cggggctgaa ctttgcagac gaggacgagg cccaggcctt ccgggccctc 420
gtgcaggaga agatacaaaa aaggaatcag aggcaaagtg gagacagacg ccagctaccc 480
ccaccaccaa caccagccaa tgaagagaga agaggagggc tcccacccct gcccctgcat 540
ccaggtggag accaaggagg ccctccagtg ggtccgctct ccctggggct ggcgacagtg 600
gacatccaga accctgacat cacgagttca cgataccgtg ggctcccagc acctggacct 660
agcccagctg ataagaaacg ctcagggaag aagaagatca gcaaagctga tattggtgca 720
cccagtggat tcaagcatgt cagccacgtg gggtgggacc cccagaatgg atttgacgtg 780
aacaacctcg acccagatct gcggagtctg ttctccaggg caggaatcag cgaggcccag 840
ctcaccgacg ccgagacctc taaacttatc tacgacttca ttgaggacca gggtgggctg 900
gaggctgtgc ggcaggagat gaggcgccag gagccacttc cgccgccccc accgccatct 960
cgaggaggga accagctccc ccggcccccct attgtggggg gtaacaaggg tcgttctggt 1020
ccactgcccc ctgtaccttt ggggattgcc ccacccccac caacaccccg gggaccccca 1080
cccccaggcc gagggggccc tccaccacca ccccctccag ctactggacg ttctggacca 1140 ctgcccccctc cacccccctgg agctggtggg ccacccatgc caccaccacc gccaccaccg 1200
ccaccgccgc ccagctccgg gaatggacca gcccctcccc cactccctcc tgctctggtg 1260
cctgccgggg gcctggcccc tggtgggggt cggggagcgc ttttggatca aatccggcag 1320
ggaattcagc tgaacaagac ccctggggcc ccagagagct cagcgctgca gccaccacct 1380
cagagctcag agggactggt gggggccctg atgcacgtga tgcagaagag aagcagagcc 1440
atccactcct ccgacgaagg ggaggaccag gctggcgatg aagatgaaga tgatgaatgg 1500
gatgactga 1509

<210> SEQ ID NO 14
<211> LENGTH: 1509
<212> TYPE: DNA
<213> ORGANISM: Artificial
<220> FEATURE:
<223> OTHER INFORMATION: Codon optimized WAS DNA

<400> SEQUENCE: 14
atgagcggcg gccccatggg cggccgcccc ggcggccgcg gcgcccccgc cgtgcagcag 60
aacatcccca gcaccctgct gcaggaccac gagaaccagc gcctgttcga gatgctgggc 120
cgcaagtgcc tgaccctggc caccgccgtg gtgcagctgt acctggccct gccccccggc 180
gccgagcact ggaccaagga gcactgcggc gccgtgtgct tcgtgaagga caacccccag 240
aagagctact tcatccgcct gtacggcctg caggccggcc gcctgctgtg ggagcaggag 300
ctgtacagcc agctggtgta cagcaccccc accccccttct tccacacctt cgccggcgac 360
gactgccagg ccggcctgaa cttcgccgac gaggacgagg cccaggcctt ccgcgccctg 420
gtgcaggaga agatccagaa gcgcaaccag cgccagagcg gcgaccgccg ccagctgccc 480
ccccccccca cccccgccaa cgaggagcgc cgcggcggcc tgccccccct gcccctgcac 540
cccggcggcg accagggcgg cccccccgtg ggcccccctga gcctgggcct ggccaccgtg 600
gacatccaga accccgacat caccagcagc cgctaccgcg gcctgcccgc ccccggcccc 660
agccccgccg acaagaagcg cagcggcaag aagaagatca gcaaggccga catcggcgcc 720
cccagcggct tcaagcacgt gagccacgtg ggctgggacc cccagaacgg cttcgacgtg 780
aacaacctgg accccgacct gcgcagcctg ttcagccgcg ccggcatcag cgaggcccag 840
ctgaccgacg ccgagaccag caagctgatc tacgacttca tcgaggacca gggcggcctg 900
gaggccgtgc gccaggagat gcgccgccag gagcccctgc cccccccccc cccccccagc 960
cgcggcggca accagctgcc ccgccccccc atcgtgggcg gcaacaaggg ccgcagcggc 1020
cccctgcccc ccgtgcccct gggcatcgcc cccccccccc ccaccccccg cggccccccc 1080
ccccccggcc gcggcggccc cccccccccc cccccccccg ccaccggccg cagcggcccc 1140
ctgccccccc cccccccggg cgccggcggc ccccccatgc cccccccccc cccccccccc 1200
cccccccccc ccagcagcgg caacggcccc gccccccccc ccctgccccc cgccctggtg 1260
cccgccggcg gcctggcccc cggcggcggc cgcggcgccc tgctggacca gatccgccag 1320
ggcatccagc tgaacaagac ccccggcgcc cccgagagca gcgccctgca gccccccccc 1380
cagagcagcg agggcctggt gggcgccctg atgcacgtga tgcagaagcg cagccgcgcc 1440
atccacagca gcgacgaggg cgaggaccag gccggcgacg aggacgagga cgacgagtgg 1500
gacgactaa 1509

<210> SEQ ID NO 15
<211> LENGTH: 9587
<212> TYPE: DNA
<213> ORGANISM: Artificial
<220> FEATURE:
<223> OTHER INFORMATION: WAS lentiviral vector

<400> SEQUENCE: 15
agttccgcgt tacataactt acggtaaatg gcccgcctgg ctgaccgccc aacgaccccc 60
gcccattgac gtcaataatg acgtatgttc ccatagtaac gccaataggg actttccatt 120
gacgtcaatg ggtggagtat ttacggtaaa ctgcccactt ggcagtacat caagtgtatc 180
atatgccaag tacgccccct attgacgtca atgacggtaa atggcccgcc tggcattatg 240
cccagtacat gaccttatgg gactttccta cttggcagta catctacgta ttagtcatcg 300
ctattaccat ggtgatgcgg ttttggcagt acatcaatgg gcgtggatag cggtttgact 360
cacggggatt tccaagtctc caccccattg acgtcaatgg gagtttgttt tggcaccaaa 420
atcaacggga ctttccaaaa tgtcgtaaca actccgcccc attgacgcaa atgggcggta 480
ggcgtgtacg gtgggaggtc tatataagca gagctcgttt agtgaaccgg ggtctctctg 540
gttagaccag atctgagcct gggagctctc tggctaacta gggaacccac tgcttaagcc 600
tcaataaagc ttgccttgag tgcttcaagt agtgtgtgcc cgtctgttgt gtgactctgg 660
taactagaga tccctcagac ccttttagtc agtgtggaaa atctctagca gtggcgcccg 720
aacagggact tgaaagcgaa agggaaacca gaggagctct ctcgacgcag gactcggctt 780
gctgaagcgc gcacggcaag aggcgagggg cggcgactgg tgagtacgcc aaaaattttg 840
actagcggag gctagaagga gagagatggg tgcgagagcg tcagtattaa gcgggggaga 900
attagatcgc gatgggaaaa aattcggtta aggccagggg gaaagaaaaa atataaatta 960
aaacatatag tatgggcaag cagggagcta gaacgattcg cagttaatcc tggcctgtta 1020
gaaacatcag aaggctgtag acaaatactg ggacagctac aaccatccct tcagacagga 1080
tcagaagaac ttagatcatt atataataca gtagcaaccc tctattgtgt gcatcaaagg 1140
atagagataa aagacaccaa ggaagcttta gacaagatag aggaagagca aaacaaaagt 1200
aagaccaccg cacagcaagc ggccgctgat cttcagacct ggaggaggag atatgaggga 1260
caattggaga agtgaattat ataaatataa agtagtaaaa attgaaccat taggagtagc 1320
acccaccaag gcaaagagaa gagtggtgca gagagaaaaa agagcagtgg gaataggagc 1380
tttgttcctt gggttcttgg gagcagcagg aagcactatg ggcgcagcgt caatgacgct 1440
gacggtacag gccagacaat tattgtctgg tatagtgcag cagcagaaca atttgctgag 1500
ggctattgag gcgcaacagc atctgttgca actcacagtc tggggcatca agcagctcca 1560
ggcaagaatc ctggctgtgg aaagatacct aaaggatcaa cagctcctgg ggatttgggg 1620
ttgctctgga aaactcattt gcaccactgc tgtgccttgg aatgctagtt ggagtaataa 1680

-continued atctctggaa cagatttgga atcacacgac ctggatggag tgggacagag aaattaacaa 1740
ttacacaagc ttaatacact ccttaattga agaatcgcaa aaccagcaag aaaagaatga 1800
acaagaatta ttggaattag ataaatgggc aagtttgtgg aattggttta acataacaaa 1860
ttggctgtgg tatataaaat tattcataat gatagtagga ggcttggtag gtttaagaat 1920
agtttttgct gtactttcta tagtgaatag agttaggcag ggatattcac cattatcgtt 1980
tcagacccac ctcccaaccc cgaggggacc cgacaggccc gaaggaatag aagaagaagg 2040
tggagagaga gacagagaca gatccattcg attagtgaac ggatctcgac ggtatcggtt 2100
aacttttaaa agaaaagggg ggattggggg gtacagtgca ggggaaagaa tagtagacat 2160
aatagcaaca gacatacaaa ctaaagaatt acaaaaacaa attacaaaaa ttcaaaattt 2220
tatcgatcac gagactagcc tcgaggacct gaagggtaag gggtgtgga ggttgtgaag 2280 gcgggaaggg gggtagcccc ttcaccaatg taaacaagga tgtgggttct gcggccacac 2340
tctcccccgc cctccccagc ggcatttcca gcaagtcaca tgtcctgcgc acaggctggg 2400 ggcccctgc tgctgccttt cttagaagcc aggaccacag agcccgcaca gtgagctact 2460
tggggagcta tttctgtaga ctgagcttgg ggtactggga ggcagtgctg ttggcgatct 2520
gggggaaaac cccctgaggg tcccatttct ctgccactga cccctttgcc tggcagaaag 2580
gctctgctgc ctcctagctg tgtagcaatg gataaggcct ttaacctctc taagctgaaa 2640
tgtcctcatg cataaggtgg agacagtaac tcctcttcca tctgctgggt gttgtcaaaa 2700
ctacacagga ggtttgccaa gcacctaagg cacagtaggt ggtcaagaaa caggaacaca 2760
atttgtcatg acgacaatga ttccttcata tgctagttac ccacgagtca gccagaatgt 2820
tgccataacc acttatgaag cccttcctca tttctgttgc aattcctcag ccagaggaaa 2880
gccccaccac ctctgtcctc cagaaagccc tcctcttccc agaaggctgg cacacagggc 2940
tgggggccag gcttgacttc cctgtggagg ggtctgaggt tggggggatg acctgcagag 3000
gtaggggaat tcagagaact tgttttgata gaaactgaaa ctcctcctct tgctgacgct 3060
gcacttgtgg gcaatctgca cctgttctcc cctcccagag gccagctgga agggggtccc 3120
ccaccattct acctctgttc ccatctcaaa cagggctcag aaatcctcag agagcctgga 3180
ttatcttcct atagggtcct accatttgct ttagagacat ctgagaactg cctactcccc 3240
aggtagctgc ctgcctccca gaagagccac agcaagttcc gctaagggca aaaaaggaag 3300
ctaggtgtct acagggaacc taaaaacaaa ccacactaac gtgtgtacac acagctgcag 3360
agggagacag ggacctggtc tgctcacagc ccttgccact cccccatggc ccatgtagaa 3420
acaaccatgt ggccttcact ctgcccacag aagctagcac caggaccctg gtcagggtta 3480
gaggtttctg ctgagtcaaa gccacatgga gggagggagc aagggagaga tgcagagtca 3540
tgtttccagg aggaggttat ctgagcataa cagggacagg gtgggccaca ggatacctct 3600
gaggctcagg ttcccacctc cactccaccc tccaactctc tgctccacgt tccttccact 3660
attcaacaca tggcaggaag tcagcctgta gggcttcaca ctacagtcta agctgactgc 3720
catctgtccc catccaggcg aggctggaaa cgggggcagc aaaaagccca gggacaaagt 3780
ccccttccca ggcacatgta ttatgcactc tgcaccaagg aaacctccag ataaggtcta 3840
gagaccaagg gccatgtact tcgggggaga ggccagagga cttctgaggt tttacagaga 3900
aaagccaaag gcagcccagt caggggaaat gtgtagccat agtgccgata aggaaaggcc 3960
ttcaacctgc cctggtcagc tcttcctgta agtagaggcc ccttaccgaa ggccccagtg 4020
ggaggaaggg tcgggagtac tcgagtcagc ctcaggctac ctaggtgctt tagaaaggag 4080

```
gccacccagg cccatgacta ctccttgcca cagggagccc tgcacacaga tgtgctaagc   4140
tctcgctgcc agccagaggg aggagggtct gagccagtca gaaggagatg ggccccagag   4200
agtaagaaag gggaggaggg acccaagctg atccaaaagg tgggtctaag cagtcaagtg   4260
gaggagggtt ccaatctgat ggcggagggc ccaagctcag cctaacgagg aggccaggcc   4320
caccaagggg cccctggagg acttgtttcc cttgtccctt gtggtttttt gcatttcctg   4380
ttcccttgct gctcattgcg gaagttcctc ttcttaccct gcacccagag cctcgccaga   4440
gaagacaagg gcagaaagca ccatggtgag caagggcgag gagctgttca ccggggtggt   4500
gcccatcctg gtcgagctgg acggcgacgt aaacggccac aagttcagcg tgtccggcga   4560
gggcgagggc gatgccacct acggcaagct gaccctgaag ttcatctgca ccaccggcaa   4620
gctgcccgtg ccctggccca ccctcgtgac caccttcggc tacggcctga tgtgcttcgc   4680
ccgctacccc gaccacatga agcagcacga cttcttcaag tccgccatgc ccgaaggcta   4740
cgtccaggag cgcaccatct tcttcaagga cgacggcaac tacaagaccc gcgccgaggt   4800
gaagttcgag ggcgacaccc tggtgaaccg catcgagctg aagggcatcg acttcaagga   4860
ggacggcaac atcctggggc acaagctgga gtacaactac aacagccaca acgtctatat   4920
catggccgac aagcagaaga acggcatcaa ggtgaacttc aagatccgcc acaacatcga   4980
ggacggcagc gtgcagctcg ccgaccacta ccagcagaac acccccatcg gcgacggccc   5040
cgtgctgctg cccgacaacc actacctgag ctaccagtcc gccctgagca aagaccccaa   5100
cgagaagcgc gatcacatgg tcctgctgga gttcgtgacc gccgccggga tcactctcgg   5160
catggacgag ctgtacaagt gactgcagga attcgagcat cttaccgcca tttattccca   5220
tatttgttct gtttttcttg atttgggtat acatttaaat gttaataaaa caaaatggtg   5280
gggcaatcat ttacattttt agggatatgt aattactagt tcaggtgtat tgccacaaga   5340
caaacatgtt aagaaacttt cccgttattt acgctctgtt cctgttaatc aacctctgga   5400
ttacaaaatt tgtgaaagat tgactgatat tcttaactat gttgctcctt ttacgctgtg   5460
tggatatgct gctttaatgc ctctgtatca tgctattgct tcccgtacgg ctttcgtttt   5520
ctcctccttg tataaatcct ggttgctgtc tctttatgag gagttgtggc ccgttgtccg   5580
tcaacgtggc gtggtgtgct ctgtgtttgc tgacgcaacc cccactggct ggggcattgc   5640
caccacctgt caactccttt ctgggacttt cgctttcccc ctcccgatcg ccacggcaga   5700
actcatcgcc gcctgccttg cccgctgctg gacaggggct aggttgctgg gcactgataa   5760
ttccgtggtg ttgtcgggga agggcctgct gccggctctg cggcctcttc cgcgtcttcg   5820
ccttcgccct cagacgagtc ggatctccct ttgggccgcc tccccgcctg gaattcgagc   5880
tcggtacctt taagaccaat gacttacaag gcagctgtag atcttagcca ctttttaaaa   5940
gaaaaggggg gactggaagg gctaattcac tcccaacgaa gacaagatct gctttttgct   6000
tgtactgggt ctctctggtt agaccagatc tgagcctggg agctctctgg ctaactaggg   6060
aacctactgc ttaagcctca ataaagcttg ccttgagtgc ttcaagtagt gtgtgcccgt   6120
ctgttgtgtg actctggtaa ctagagatcc ctcagaccct tttagtcagt gtggaaaatc   6180
tctagcagta gtagttcatg tcatcttatt attcagtatt tataacttgc aaagaaatga   6240
atatcagaga gtgagaggaa cttgtttatt gcagcttata atggttacaa ataaagcaat   6300
agcatcacaa atttcacaaa taaagcattt ttttcactgc attctagttg tggtttgtcc   6360
aaactcatca atgtatctta tcatgtctgg ctctagctat cccgccccta actccgccca   6420
```

-continued

```
tcccgcccct aactccgccc agttccgccc attctccgcc ccatggctga ctaatttttt   6480
ttatttatgc agaggccgag gccgcctcgg cctctgagct attccagaag tagtgaggag   6540
gctttttgg aggcctaggg acgtacccaa ttcgccctat agtgagtcgt attacgcgcg   6600
ctcactggcc gtcgttttac aacgtcgtga ctgggaaaac cctggcgtta cccaacttaa   6660
tcgccttgca gcacatcccc ctttcgccag ctggcgtaat agcgaagagg cccgcaccga   6720
tcgcccttcc caacagttgc gcagcctgaa tggcgaatgg gacgcgccct gtagcggcgc   6780
attaagcgcg gcgggtgtgg tggttacgcg cagcgtgacc gctacacttg ccagcgccct   6840
agcgcccgct cctttcgctt tcttcccttc ctttctcgcc acgttcgccg gctttccccg   6900
tcaagctcta aatcgggggc tccctttagg gttccgattt agtgctttac ggcacctcga   6960
ccccaaaaaa cttgattagg gtgatggttc acgtagtggg ccatcgccct gatagacggt   7020
ttttcgccct ttgacgttgg agtccacgtt ctttaatagt ggactcttgt tccaaactgg   7080
aacaacactc aaccctatct cggtctattc ttttgattta taagggattt tgccgatttc   7140
ggcctattgg ttaaaaaatg agctgattta acaaaaattt aacgcgaatt ttaacaaaat   7200
attaacgctt acaatttagg tggcactttt cggggaaatg tgcgcggaac ccctatttgt   7260
ttatttttct aaatacattc aaatatgtat ccgctcatga gacaataacc ctgataaatg   7320
cttcaataat agcacctaga tcaagagaca ggatgaggat cgtttcgcat gattgaacaa   7380
gatggattgc acgcaggttc tccggccgct tgggtggaga ggctattcgg ctatgactgg   7440
gcacaacaga caatcggctg ctctgatgcc gccgtgttcc ggctgtcagc gcaggggcgc   7500
ccggttcttt ttgtcaagac cgacctgtcc ggtgccctga atgaactgca agacgaggca   7560
gcgcggctat cgtggctggc cacgacgggc gttccttgcg cagctgtgct cgacgttgtc   7620
actgaagcgg gaagggactg gctgctattg ggcgaagtgc cggggcagga tctcctgtca   7680
tctcaccttg ctcctgccga gaaagtatcc atcatggctg atgcaatgcg gcggctgcat   7740
acgcttgatc cggctacctg cccattcgac caccaagcga aacatcgcat cgagcgagca   7800
cgtactcgga tggaagccgg tcttgtcgat caggatgatc tggacgaaga gcatcagggg   7860
ctcgcgccag ccgaactgtt cgccaggctc aaggcgagca tgcccgacgg cgaggatctc   7920
gtcgtgaccc atggcgatgc ctgcttgccg aatatcatgg tggaaaatgg ccgcttttct   7980
ggattcatcg actgtggccg gctgggtgtg gcggaccgct atcaggacat agcgttggct   8040
acccgtgata ttgctgaaga gcttggcggc gaatgggctg accgcttcct cgtgctttac   8100
ggtatcgccg ctcccgattc gcagcgcatc gccttctatc gccttcttga cgagttcttc   8160
tgaattatta acgcttacaa tttcctgatg cggtattttc tccttacgca tctgtgcggt   8220
atttcacacc gcatcaggtg gcacttttcg gggaaatgtg cgcggaaccc ctatttgttt   8280
atttttctaa atacattcaa atatgtatcc gctcatgacc aaaatccctt aacgtgagtt   8340
ttcgttccac tgagcgtcag accccgtaga aaagatcaaa ggatcttctt gagatccttt   8400
ttttctgcgc gtaatctgct gcttgcaaac aaaaaaacca ccgctaccag cggtggtttg   8460
tttgccggat caagagctac caactctttt tccgaaggta actggcttca gcagagcgca   8520
gataccaaat actgttcttc tagtgtagcc gtagttaggc caccacttca agaactctgt   8580
agcaccgcct acatacctcg ctctgctaat cctgttacca gtggctgctg ccagtggcga   8640
taagtcgtgt cttaccgggt tggactcaag acgatagtta ccggataagg cgcagcggtc   8700
gggctgaacg gggggttcgt gcacacagcc cagcttggag cgaacgacct acaccgaact   8760
gagataccta cagcgtgagc tatgagaaag cgccacgctt cccgaaggga gaaaggcgga   8820
```

caggtatccg gtaagcggca gggtcggaac aggagagcgc acgagggagc ttccaggggg 8880
aaacgcctgg tatctttata gtcctgtcgg gtttcgccac ctctgacttg agcgtcgatt 8940
tttgtgatgc tcgtcagggg ggcggagcct atggaaaaac gccagcaacg cggccttttt 9000
acggttcctg gccttttgct ggccttttgc tcacatgttc tttcctgcgt tatcccctga 9060
ttctgtggat aaccgtatta ccgcctttga gtgagctgat accgctcgcc gcagccgaac 9120
gaccgagcgc agcgagtcag tgagcgagga agcggaagag cgcccaatac gcaaaccgcc 9180
tctccccgcg cgttggccga ttcattaatg cagctggcac gacaggtttc ccgactggaa 9240
agcgggcagt gagcgcaacg caattaatgt gagttagctc actcattagg caccccaggc 9300
tttacacttt atgcttccgg ctcgtatgtt gtgtggaatt gtgagcggat aacaatttca 9360
cacaggaaac agctatgacc atgattacgc caagcgcgca attaaccctc actaaaggga 9420
acaaaagctg gagctgcaag cttggccatt gcatacgttg tatccatatc ataatatgta 9480
catttatatt ggctcatgtc caacattacc gccatgttga cattgattat tgactagtta 9540
ttaatagtaa tcaattacgg ggtcattagt tcatagccca tatatgg 9587

<210> SEQ ID NO 16
<211> LENGTH: 10054
<212> TYPE: DNA
<213> ORGANISM: Artificial
<220> FEATURE:
<223> OTHER INFORMATION: WAS lentiviral vector

<400> SEQUENCE: 16
agttccgcgt tacataactt acggtaaatg gcccgcctgg ctgaccgccc aacgaccccc 60
gcccattgac gtcaataatg acgtatgttc ccatagtaac gccaataggg actttccatt 120
gacgtcaatg ggtggagtat ttacggtaaa ctgcccactt ggcagtacat caagtgtatc 180
atatgccaag tacgccccct attgacgtca atgacggtaa atggcccgcc tggcattatg 240
cccagtacat gaccttatgg gactttccta cttggcagta catctacgta ttagtcatcg 300
ctattaccat ggtgatgcgg ttttggcagt acatcaatgg gcgtggatag cggtttgact 360
cacggggatt tccaagtctc caccccattg acgtcaatgg gagtttgttt tggcaccaaa 420
atcaacggga ctttccaaaa tgtcgtaaca actccgcccc attgacgcaa atgggcggta 480
ggcgtgtacg gtgggaggtc tatataagca gagctcgttt agtgaaccgg ggtctctctg 540
gttagaccag atctgagcct gggagctctc tggctaacta gggaacccac tgcttaagcc 600
tcaataaagc ttgccttgag tgcttcaagt agtgtgtgcc cgtctgttgt gtgactctgg 660
taactagaga tccctcagac ccttttagtc agtgtggaaa atctctagca gtggcgcccg 720
aacagggact tgaaagcgaa agggaaacca gaggagctct ctcgacgcag gactcggctt 780
gctgaagcgc gcacggcaag aggcgagggg cggcgactgg tgagtacgcc aaaaattttg 840
actagcggag gctagaagga gagagatggg tgcgagagcg tcagtattaa gcgggggaga 900
attagatcgc gatgggaaaa aattcggtta aggccagggg gaaagaaaaa atataaatta 960
aaacatatag tatgggcaag cagggagcta gaacgattcg cagttaatcc tggcctgtta 1020
gaaacatcag aaggctgtag acaaatactg ggacagctac aaccatccct tcagacagga 1080
tcagaagaac ttagatcatt atataataca gtagcaaccc tctattgtgt gcatcaaagg 1140
atagagataa aagacaccaa ggaagcttta gacaagatag aggaagagca aaacaaaagt 1200
aagaccaccg cacagcaagc ggccgctgat cttcagacct ggaggaggag atatgaggga 1260

-continued

```
caattggaga agtgaattat ataaatataa agtagtaaaa attgaaccat taggagtagc   1320
acccaccaag gcaaagagaa gagtggtgca gagagaaaaa agagcagtgg gaataggagc   1380
tttgttcctt gggttcttgg gagcagcagg aagcactatg ggcgcagcgt caatgacgct   1440
gacggtacag gccagacaat tattgtctgg tatagtgcag cagcagaaca atttgctgag   1500
ggctattgag gcgcaacagc atctgttgca actcacagtc tggggcatca agcagctcca   1560
ggcaagaatc ctggctgtgg aaagatacct aaaggatcaa cagctcctgg ggatttgggg   1620
ttgctctgga aaactcattt gcaccactgc tgtgccttgg aatgctagtt ggagtaataa   1680
atctctggaa cagatttgga atcacacgac ctggatggag tgggacagag aaattaacaa   1740
ttacacaagc ttaatacact ccttaattga agaatcgcaa aaccagcaag aaaagaatga   1800
acaagaatta ttggaattag ataaatgggc aagtttgtgg aattggttta acataacaaa   1860
ttggctgtgg tatataaaat tattcataat gatagtagga ggcttggtag gtttaagaat   1920
agtttttgct gtactttcta tagtgaatag agttaggcag ggatattcac cattatcgtt   1980
tcagacccac ctcccaaccc cgaggggacc cgacaggccc gaaggaatag aagaagaagg   2040
tggagagaga gacagagaca gatccattcg attagtgaac ggatctcgac ggtatcggtt   2100
aacttttaaa agaaaagggg ggattggggg gtacagtgca ggggaaagaa tagtagacat   2160
aatagcaaca gacatacaaa ctaaagaatt acaaaaacaa attacaaaaa ttcaaaattt   2220
tatcgatcac gagactagcc tcgagcaaac cttgttatct gagagaaagc tagagcttcc   2280
ttctttcagc ccccagagac aatgtggcca ggctccggag ggctgggaag atgagcaatg   2340
cttgtgagtc accatgatag gaagcagaag ggtcaggaag tccctgggag caaggcttag   2400
ggttagggtt agggagaaaa cacttgggcc tggaggctcg ggcaggctt cctagagggg    2460
aggggtacta aaagccacca aaaccaagac agcaatgaaa gtaacctctg gtcttcctaa   2520
ctgctcatta tacactaatt atgatgcact agcatgctaa gagacacttc caccagcgcc   2580
atgacagtgc catggcaaca tcaagaagtc accccacatg gtctaaaaag gggaagaacc   2640
ttcagttccc ggaattgccc acccctttcc tggaaaactc atgaataatc caccccttgt   2700
ttagcatata atgacctgaa gggtaagggg gtgtggaggt tgtgaaggcg ggaagggggg   2760
tagccccttc accaatgtaa acaaggatgt gggttctgcg gccacactct cccccgccct   2820
ccccagcggc atttccagca agtcacatgt cctgcgcaca ggctgggggc cccctgctgc   2880
tgcctttctt agaagccagg accacagagc ccgcacagtg agctacttgg ggagctattt   2940
ctgtagactg agcttggggt actgggaggc agtgctgttg gcgatctggg ggaaaacccc   3000
ctgagggtcc catttctctg ccactgaccc ctttgcctgg cagaaaggct ctgctgcctc   3060
ctagctgtgt agcaatggat aaggccttta acctctctaa gctgaaatgt cctcatgcat   3120
aaggtggaga cagtaactcc tcttccatct gctgggtgtt gtcaaaacta cacaggaggt   3180
ttgccaagca cctaaggcac agtaggtggt caagaaacag gaacacaatt tgtcatgacg   3240
acaatgattc cttcatatgc tagttaccca cgagtcagcc agaatgttgc cataaccact   3300
tatgaagccc ttcctcattt ctgttgcaat tcctcagcca gaggaaagcc ccaccacctc   3360
tgtcctccag aaagccctcc tcttcccaga aggctggcac acagggctgg gggccaggct   3420
tgacttccct gtggaggggt ctgaggttgg ggggatgacc tgcagaggta ggggaattca   3480
gagaacttgt tttgatagaa actgaaactc ctcctcttgc tgacgctgca cttgtgggca   3540
atctgcacct gttctcccct cccagaggcc agctggaagg gggtccccca ccattctacc   3600
tctgttccca tctcaaacag ggctcagaaa tcctcagaga gcctggatta tcttcctata   3660
```

-continued

```
gggtcctacc atttgcttta gagacatctg agaactgcct actccccagg tagctgcctg   3720
cctcccagaa gagccacagc aagttccgct aagggcaaaa aaggaagcta ggtgtctaca   3780
gggaacctaa aaacaaacca cactaacgtg tgtacacaca gctgcagagg gagacaggga   3840
cctggtctgc tcacagccct tgccactccc ccatggccca tgtagaaaca accatgtggc   3900
cttcactctg cccacagaag ctagcaccag gaccctggtc agggttagag gtttctgctg   3960
agtcaaagcc acatggaggg agggagcaag ggagagatgc agagtcatgt ttccaggagg   4020
aggttatctg agcataacag ggacagggtg ggccacagga tacctctgag gctcaggttc   4080
ccacctccac tccaccctcc aactctctgc tccacgttcc ttccactatt caacacatgg   4140
caggaagtca gcctgtaggg cttcacacta cagtctaagc tgactgccat ctgtccccat   4200
ccaggcgagg ctggaaacgg gggcagcaaa aagcccaggg acaaagtccc cttcccaggc   4260
acatgtatta tgcactctgc accaaggaaa cctccagata aggtctagag accaagggcc   4320
atgtacttcg gggggagaggc cagaggactt ctgaggtttt acagagaaaa gccaaaggca   4380
gcccagtcag gggaaatgtg tagccatagt gccgataagg aaaggccttc aacctgccct   4440
ggtcagctct tcctgtaagt agaggcccct taccgaaggc cccagtggga ggaagggtcg   4500
ggagtactcg agtcagcctc aggctaccta ggtgctttag aaaggaggcc acccaggccc   4560
atgactactc cttgccacag ggagccctgc acacagatgt gctaagctct cgctgccagc   4620
cagagggagg agggtctgag ccagtcagaa ggagatgggc cccagagagt aagaaagggg   4680
gaggaggacc caagctgatc caaaaggtgg gtctaagcag tcaagtggag gagggttcca   4740
atctgatggc ggagggccca agctcagcct aacgaggagg ccaggcccac caaggggccc   4800
ctggaggact tgtttccctt gtcccttgtg gttttttgca tttcctgttc ccttgctgct   4860
cattgcggaa gttcctcttc ttaccctgca cccagagcct cgccagagaa gacaagggca   4920
gaaagcacca tggtgagcaa gggcgaggag ctgttcaccg ggtggtgcc catcctggtc   4980
gagctggacg gcgacgtaaa cggccacaag ttcagcgtgt ccggcgaggg cgagggcgat   5040
gccacctacg gcaagctgac cctgaagttc atctgcacca ccggcaagct gcccgtgccc   5100
tggcccaccc tcgtgaccac cttcggctac ggcctgatgt gcttcgcccg ctaccccgac   5160
cacatgaagc agcacgactt cttcaagtcc gccatgcccg aaggctacgt ccaggagcgc   5220
accatcttct tcaaggacga cggcaactac aagacccgcg ccgaggtgaa gttcgagggc   5280
gacaccctgg tgaaccgcat cgagctgaag ggcatcgact tcaaggagga cggcaacatc   5340
ctggggcaca agctggagta caactacaac agccacaacg tctatatcat ggccgacaag   5400
cagaagaacg gcatcaaggt gaacttcaag atccgccaca acatcgagga cggcagcgtg   5460
cagctcgccg accactacca gcagaacacc cccatcggcg acggccccgt gctgctgccc   5520
gacaaccact acctgagcta ccagtccgcc ctgagcaaag accccaacga gaagcgcgat   5580
cacatggtcc tgctggagtt cgtgaccgcc gccgggatca ctctcggcat ggacgagctg   5640
tacaagtgac tgcaggaatt cgagcatctt accgccattt attcccatat ttgttctgtt   5700
tttcttgatt tgggtataca tttaaatgtt aataaaacaa aatggtgggg caatcattta   5760
catttttagg gatatgtaat tactagttca ggtgtattgc cacaagacaa acatgttaag   5820
aaactttccc gttatttacg ctctgttcct gttaatcaac ctctggatta caaaatttgt   5880
gaaagattga ctgatattct taactatgtt gctcctttta cgctgtgtgg atatgctgct   5940
ttaatgcctc tgtatcatgc tattgcttcc cgtacggctt tcgttttctc ctccttgtat   6000
```

-continued aaatcctggt tgctgtctct ttatgaggag ttgtggcccg ttgtccgtca acgtggcgtg 6060
gtgtgctctg tgtttgctga cgcaaccccc actggctggg gcattgccac cacctgtcaa 6120
ctcctttctg ggactttcgc tttccccctc ccgatcgcca cggcagaact catcgccgcc 6180
tgccttgccc gctgctggac aggggctagg ttgctgggca ctgataattc cgtggtgttg 6240
tcggggaagg gcctgctgcc ggctctgcgg cctcttccgc gtcttcgcct tcgccctcag 6300
acgagtcgga tctccctttg ggccgcctcc ccgcctggaa ttcgagctcg gtacctttaa 6360
gaccaatgac ttacaaggca gctgtagatc ttagccactt tttaaaagaa aaggggggac 6420
tggaagggct aattcactcc caacgaagac aagatctgct ttttgcttgt actgggtctc 6480
tctggttaga ccagatctga gcctgggagc tctctggcta actagggaac ctactgctta 6540
agcctcaata aagcttgcct tgagtgcttc aagtagtgtg tgcccgtctg ttgtgtgact 6600
ctggtaacta gagatccctc agaccctttt agtcagtgtg gaaaatctct agcagtagta 6660
gttcatgtca tcttattatt cagtatttat aacttgcaaa gaaatgaata tcagagagtg 6720
agaggaactt gtttattgca gcttataatg gttacaaata aagcaatagc atcacaaatt 6780
tcacaaataa agcatttttt tcactgcatt ctagttgtgg tttgtccaaa ctcatcaatg 6840
tatcttatca tgtctggctc tagctatccc gcccctaact ccgcccatcc cgcccctaac 6900
tccgcccagt tccgcccatt ctccgcccca tggctgacta attttttta tttatgcaga 6960 ggccgaggcc gcctcggcct ctgagctatt ccagaagtag tgaggaggct tttttggagg 7020
cctagggacg tacccaattc gccctatagt gagtcgtatt acgcgcgctc actggccgtc 7080
gttttacaac gtcgtgactg ggaaaaccct ggcgttaccc aacttaatcg ccttgcagca 7140
catccccctt tcgccagctg gcgtaatagc gaagaggccc gcaccgatcg cccttcccaa 7200
cagttgcgca gcctgaatgg cgaatgggac gcgccctgta gcggcgcatt aagcgcggcg 7260
ggtgtggtgg ttacgcgcag cgtgaccgct acacttgcca gcgccctagc gcccgctcct 7320
ttcgctttct tcccttcctt tctcgccacg ttcgccggct ttccccgtca agctctaaat 7380
cgggggctcc ctttagggtt ccgatttagt gctttacggc acctcgaccc caaaaaactt 7440
gattagggtg atggttcacg tagtgggcca tcgccctgat agacggtttt tcgccctttg 7500
acgttggagt ccacgttctt taatagtgga ctcttgttcc aaactggaac aacactcaac 7560
cctatctcgg tctattcttt tgatttataa gggattttgc cgatttcggc ctattggtta 7620
aaaaatgagc tgatttaaca aaaatttaac gcgaatttta acaaaatatt aacgcttaca 7680
atttaggtgg cacttttcgg ggaaatgtgc gcggaacccc tatttgttta tttttctaaa 7740
tacattcaaa tatgtatccg ctcatgagac aataaccctg ataaatgctt caataatagc 7800
acctagatca agagacagga tgaggatcgt ttcgcatgat tgaacaagat ggattgcacg 7860
caggttctcc ggccgcttgg gtggagaggc tattcggcta tgactgggca caacagacaa 7920
tcggctgctc tgatgccgcc gtgttccggc tgtcagcgca ggggcgcccg gttctttttg 7980
tcaagaccga cctgtccggt gccctgaatg aactgcaaga cgaggcagcg cggctatcgt 8040
ggctggccac gacgggcgtt ccttgcgcag ctgtgctcga cgttgtcact gaagcgggaa 8100
gggactggct gctattgggc gaagtgccgg ggcaggatct cctgtcatct caccttgctc 8160
ctgccgagaa agtatccatc atggctgatg caatgcggcg gctgcatacg cttgatccgg 8220
ctacctgccc attcgaccac caagcgaaac atcgcatcga gcgagcacgt actcggatgg 8280
aagccggtct tgtcgatcag gatgatctgg acgaagagca tcaggggctc gcgccagccg 8340
aactgttcgc caggctcaag gcgagcatgc ccgacggcga ggatctcgtc gtgacccatg 8400

```
gcgatgcctg cttgccgaat atcatggtgg aaaatggccg cttttctgga ttcatcgact   8460
gtggccggct gggtgtggcg gaccgctatc aggacatagc gttggctacc cgtgatattg   8520
ctgaagagct tggcggcgaa tgggctgacc gcttcctcgt gctttacggt atcgccgctc   8580
ccgattcgca gcgcatcgcc ttctatcgcc ttcttgacga gttcttctga attattaacg   8640
cttacaattt cctgatgcgg tattttctcc ttacgcatct gtgcggtatt tcacaccgca   8700
tcaggtggca cttttcgggg aaatgtgcgc ggaaccccta tttgtttatt tttctaaata   8760
cattcaaata tgtatccgct catgaccaaa atcccttaac gtgagttttc gttccactga   8820
gcgtcagacc ccgtagaaaa gatcaaagga tcttcttgag atcctttttt tctgcgcgta   8880
atctgctgct tgcaaacaaa aaaaccaccg ctaccagcgg tggtttgttt gccggatcaa   8940
gagctaccaa ctctttttcc gaaggtaact ggcttcagca gagcgcagat accaaatact   9000
gttcttctag tgtagccgta gttaggccac cacttcaaga actctgtagc accgcctaca   9060
tacctcgctc tgctaatcct gttaccagtg gctgctgcca gtggcgataa gtcgtgtctt   9120
accgggttgg actcaagacg atagttaccg gataaggcgc agcggtcggg ctgaacgggg   9180
ggttcgtgca cacagcccag cttggagcga acgacctaca ccgaactgag atacctacag   9240
cgtgagctat gagaaagcgc cacgcttccc gaagggagaa aggcggacag gtatccggta   9300
agcggcaggg tcggaacagg agagcgcacg agggagcttc cagggggaaa cgcctggtat   9360
ctttatagtc ctgtcgggtt tcgccacctc tgacttgagc gtcgattttt gtgatgctcg   9420
tcaggggggc ggagcctatg gaaaaacgcc agcaacgcgg cctttttacg gttcctggcc   9480
ttttgctggc cttttgctca catgttcttt cctgcgttat cccctgattc tgtggataac   9540
cgtattaccg cctttgagtg agctgatacc gctcgccgca gccgaacgac cgagcgcagc   9600
gagtcagtga gcgaggaagc ggaagagcgc ccaatacgca aaccgcctct ccccgcgcgt   9660
tggccgattc attaatgcag ctggcacgac aggtttcccg actggaaagc gggcagtgag   9720
cgcaacgcaa ttaatgtgag ttagctcact cattaggcac cccaggcttt acactttatg   9780
cttccggctc gtatgttgtg tggaattgtg agcggataac aatttcacac aggaaacagc   9840
tatgaccatg attacgccaa gcgcgcaatt aaccctcact aaagggaaca aaagctggag   9900
ctgcaagctt ggccattgca tacgttgtat ccatatcata atatgtacat ttatattggc   9960
tcatgtccaa cattaccgcc atgttgacat tgattattga ctagttatta atagtaatca  10020
attacggggt cattagttca tagcccatat atgg                              10054
```

<210> SEQ ID NO 17
<211> LENGTH: 9556
<212> TYPE: DNA
<213> ORGANISM: Artificial
<220> FEATURE:
<223> OTHER INFORMATION: WAS lentiviral vector

<400> SEQUENCE: 17

```
agttccgcgt tacataactt acggtaaatg gcccgcctgg ctgaccgccc aacgaccccc     60
gcccattgac gtcaataatg acgtatgttc ccatagtaac gccaataggg actttccatt    120
gacgtcaatg ggtggagtat ttacggtaaa ctgcccactt ggcagtacat caagtgtatc    180
atatgccaag tacgccccct attgacgtca atgacggtaa atggcccgcc tggcattatg    240
cccagtacat gaccttatgg gactttccta cttggcagta catctacgta ttagtcatcg    300
ctattaccat ggtgatgcgg ttttggcagt acatcaatgg gcgtggatag cggtttgact    360
```

cacggggatt tccaagtctc caccccattg acgtcaatgg gagtttgttt tggcaccaaa 420
atcaacggga ctttccaaaa tgtcgtaaca actccgcccc attgacgcaa atgggcggta 480
ggcgtgtacg gtgggaggtc tatataagca gagctcgttt agtgaaccgg ggtctctctg 540
gttagaccag atctgagcct gggagctctc tggctaacta gggaacccac tgcttaagcc 600
tcaataaagc ttgccttgag tgcttcaagt agtgtgtgcc cgtctgttgt gtgactctgg 660
taactagaga tccctcagac ccttttagtc agtgtggaaa atctctagca gtggcgcccg 720
aacagggact tgaaagcgaa agggaaacca gaggagctct ctcgacgcag gactcggctt 780
gctgaagcgc gcacggcaag aggcgagggg cggcgactgg tgagtacgcc aaaaattttg 840
actagcggag gctagaagga gagagatggg tgcgagagcg tcagtattaa gcgggggaga 900
attagatcgc gatgggaaaa aattcggtta aggccagggg gaaagaaaaa atataaatta 960
aaacatatag tatgggcaag cagggagcta gaacgattcg cagttaatcc tggcctgtta 1020
gaaacatcag aaggctgtag acaaatactg ggacagctac aaccatccct tcagacagga 1080
tcagaagaac ttagatcatt atataataca gtagcaaccc tctattgtgt gcatcaaagg 1140
atagagataa aagacaccaa ggaagcttta gacaagatag aggaagagca aaacaaaagt 1200
aagaccaccg cacagcaagc ggccgctgat cttcagacct ggaggaggag atatgaggga 1260
caattggaga agtgaattat ataaatataa agtagtaaaa attgaaccat taggagtagc 1320
acccaccaag gcaaagagaa gagtggtgca gagagaaaaa agagcagtgg gaataggagc 1380
tttgttcctt gggttcttgg gagcagcagg aagcactatg ggcgcagcgt caatgacgct 1440
gacggtacag gccagacaat tattgtctgg tatagtgcag cagcagaaca atttgctgag 1500
ggctattgag gcgcaacagc atctgttgca actcacagtc tggggcatca agcagctcca 1560
ggcaagaatc ctggctgtgg aaagatacct aaaggatcaa cagctcctgg ggatttgggg 1620
ttgctctgga aaactcattt gcaccactgc tgtgccttgg aatgctagtt ggagtaataa 1680
atctctggaa cagatttgga atcacacgac ctggatggag tgggacagag aaattaacaa 1740
ttacacaagc ttaatacact ccttaattga agaatcgcaa aaccagcaag aaaagaatga 1800
acaagaatta ttggaattag ataaatgggc aagtttgtgg aattggttta acataacaaa 1860
ttggctgtgg tatataaaat tattcataat gatagtagga ggcttggtag gtttaagaat 1920
agtttttgct gtactttcta tagtgaatag agttaggcag ggatattcac cattatcgtt 1980
tcagacccac ctcccaaccc cgaggggacc cgacaggccc gaaggaatag aagaagaagg 2040
tggagagaga gacagagaca gatccattcg attagtgaac ggatctcgac ggtatcggtt 2100
aacttttaaa agaaaagggg ggattggggg gtacagtgca ggggaaagaa tagtagacat 2160
aatagcaaca gacatacaaa ctaaagaatt acaaaaacaa attacaaaaa ttcaaaattt 2220
tatcgatcac gagactagcc tcgagcaaac cttgttatct gagagaaagc tagagcttcc 2280
ttctttcagc ccccagagac aatgtggcca ggctccggag ggctgggaag atgagcaatg 2340
cttgtgagtc accatgatag gaagcagaag ggtcaggaag tccctgggag caaggcttag 2400
ggttagggtt agggagaaaa cacttgggcc tggaggctcg gggcaggctt cctagagggg 2460
aggggtacta aaagccacca aaaccaagac agcaatgaaa gtaacctctg gtcttcctaa 2520
ctgctcatta tacactaatt atgatgcact agcatgctaa gagacacttc caccagcgcc 2580
atgacagtgc catggcaaca tcaagaagtc accccacatg gtctaaaaag gggaagaacc 2640
ttcagttccc ggaattgccc accccttttcc tggaaaactc atgaataatc cacccccttgt 2700
ttagcatata atgacctgaa gggtaagggg gtgtggaggt tgtgaaggcg ggaagggggg 2760

-continued tagccccttc accaatgtaa acaaggatgt gggttctgcg gccacactct cccccgccct 2820
ccccagcggc atttccagca agtcacatgt cctgcgcaca ggctgggggc cccctgctgc 2880
tgcctttctt agaagccagg accacagagc ccgcacagtg agctacttgg ggagctattt 2940
ctgtagactg agcttggggt actgggaggc agtgctgttg gcgatctggg ggaaaacccc 3000
ctgagggtcc catttctctg ccactgaccc ctttgcctgg cagaaaggct ctgctgcctc 3060
ctagctgtgt agcaatggat aaggccttta acctctctaa gctgaaatgt cctcatgcat 3120
aaggtggaga cagtaactcc tcttccatct gctgggtgtt gtcaaaacta cacaggaggt 3180
ttgccaagca cctaaggcac agtaggtggt caagaaacag gaacacaatt tgtcatgacg 3240
acaatgattc cttcatatgc tagttaccca cgagtcagcc agaatgttgc cataaccact 3300
tatgaagccc ttcctcattt ctgttgcaat tcctcagcca gaggaaagcc ccacacagcc 3360
cttgccactc ccccatggcc catgtagaaa caaccatgtg gccttcactc tgcccacaga 3420
agctagcacc aggaccctgg tcagggttag aggtttctgc tgagtcaaag ccacatggag 3480
ggagggagca agggagagat gcagagtcat gtttccagga ggaggttatc tgagcataac 3540
agggacaggg tgggccacag gatacctctg aggctcaggt tcccacctcc actccaccct 3600
ccaactctct gctccacgtt ccttccacta ttcaacacat ggcaggaagt cagcctgtag 3660
ggcttcacac tacagtctaa gctgactgcc atctgtcccc atccaggcga ggctggaaac 3720
gggggcagca aaaagcccag ggacaaagtc cccttcccag gcacatgtat tatgcactct 3780
gcaccaagga aacctccaga taaggtctag agaccaaggg ccatgtactt cgggggagag 3840
gccagaggac ttctgaggtt ttacagagaa aagccaaagg cagcccagtc aggggaaatg 3900
tgtagccata gtgccgataa ggaaaggcct tcaacctgcc ctggtcagct cttcctgtaa 3960
gtagaggccc cttaccgaag gccccagtgg gaggaagggt cgggagtact cgagtcagcc 4020
tcaggctacc taggtgcttt agaaaggagg ccacccaggc ccatgactac tccttgccac 4080
agggagccct gcacacagat gtgctaagct ctcgctgcca gccagaggga ggagggtctg 4140
agccagtcag aaggagatgg gccccagaga gtaagaaagg gggaggagga cccaagctga 4200
tccaaaaggt gggtctaagc agtcaagtgg aggagggttc caatctgatg gcggagggcc 4260
caagctcagc ctaacgagga ggccaggccc accaaggggc ccctggagga cttgtttccc 4320
ttgtcccttg tggtttttg catttcctgt tcccttgctg ctcattgcgg aagttcctct 4380
tcttaccctg cacccagagc ctcgccagag aagacaaggg cagaaagcac catggtgagc 4440
aagggcgagg agctgttcac cggggtggtg cccatcctgg tcgagctgga cggcgacgta 4500
aacggccaca agttcagcgt gtccggcgag ggcgagggcg atgccaccta cggcaagctg 4560
accctgaagt tcatctgcac caccggcaag ctgcccgtgc cctggcccac cctcgtgacc 4620
accttcggct acggcctgat gtgcttcgcc cgctaccccg accacatgaa gcagcacgac 4680
ttcttcaagt ccgccatgcc cgaaggctac gtccaggagc gcaccatctt cttcaaggac 4740
gacggcaact acaagacccg cgccgaggtg aagttcgagg gcgacaccct ggtgaaccgc 4800
atcgagctga agggcatcga cttcaaggag gacggcaaca tcctggggca caagctggag 4860
tacaactaca acagccacaa cgtctatatc atggccgaca agcagaagaa cggcatcaag 4920
gtgaacttca agatccgcca caacatcgag gacggcagcg tgcagctcgc cgaccactac 4980
cagcagaaca cccccatcgg cgacggcccc gtgctgctgc ccgacaacca ctacctgagc 5040
taccagtccg ccctgagcaa agaccccaac gagaagcgcg atcacatggt cctgctggag 5100
ttcgtgaccg ccgccgggat cactctcggc atggacgagc tgtacaagtg actgcaggaa 5160
ttcgagcatc ttaccgccat ttattcccat atttgttctg tttttcttga tttgggtata 5220
catttaaatg ttaataaaac aaaatggtgg ggcaatcatt tacattttta gggatatgta 5280
attactagtt caggtgtatt gccacaagac aaacatgtta agaaactttc ccgttattta 5340
cgctctgttc ctgttaatca acctctggat tacaaaattt gtgaaagatt gactgatatt 5400
cttaactatg ttgctccttt tacgctgtgt ggatatgctg ctttaatgcc tctgtatcat 5460
gctattgctt cccgtacggc tttcgttttc tcctccttgt ataaatcctg gttgctgtct 5520
ctttatgagg agttgtggcc cgttgtccgt caacgtggcg tggtgtgctc tgtgtttgct 5580
gacgcaaccc ccactggctg gggcattgcc accacctgtc aactcctttc tgggactttc 5640
gctttccccc tcccgatcgc cacggcagaa ctcatcgccg cctgccttgc ccgctgctgg 5700
acaggggcta ggttgctggg cactgataat tccgtggtgt tgtcggggaa gggcctgctg 5760
ccggctctgc ggcctcttcc gcgtcttcgc cttcgccctc agacgagtcg gatctccctt 5820
tgggccgcct ccccgcctgg aattcgagct cggtaccttt aagaccaatg acttacaagg 5880
cagctgtaga tcttagccac tttttaaaag aaaagggggg actggaaggg ctaattcact 5940
cccaacgaag acaagatctg ctttttgctt gtactgggtc tctctggtta gaccagatct 6000
gagcctggga gctctctggc taactaggga acctactgct taagcctcaa taaagcttgc 6060
cttgagtgct tcaagtagtg tgtgcccgtc tgttgtgtga ctctggtaac tagagatccc 6120
tcagaccctt ttagtcagtg tggaaaatct ctagcagtag tagttcatgt catcttatta 6180
ttcagtattt ataacttgca aagaaatgaa tatcagagag tgagaggaac ttgtttattg 6240
cagcttataa tggttacaaa taaagcaata gcatcacaaa tttcacaaat aaagcatttt 6300
tttcactgca ttctagttgt ggtttgtcca aactcatcaa tgtatcttat catgtctggc 6360
tctagctatc ccgcccctaa ctccgcccat cccgccccta actccgccca gttccgccca 6420
ttctccgccc catggctgac taattttttt tatttatgca gaggccgagg ccgcctcggc 6480
ctctgagcta ttccagaagt agtgaggagg cttttttgga ggcctaggga cgtacccaat 6540
tcgccctata gtgagtcgta ttacgcgcgc tcactggccg tcgttttaca acgtcgtgac 6600
tgggaaaacc ctggcgttac ccaacttaat cgccttgcag cacatccccc tttcgccagc 6660
tggcgtaata gcgaagaggc ccgcaccgat cgcccttccc aacagttgcg cagcctgaat 6720
ggcgaatggg acgcgccctg tagcggcgca ttaagcgcgg cgggtgtggt ggttacgcgc 6780
agcgtgaccg ctacacttgc cagcgcccta gcgcccgctc ctttcgcttt cttcccttcc 6840
tttctcgcca cgttcgccgg ctttccccgt caagctctaa atcgggggct ccctttaggg 6900
ttccgattta gtgctttacg gcacctcgac cccaaaaaac ttgattaggg tgatggttca 6960
cgtagtgggc catcgccctg atagacggtt tttcgccctt tgacgttgga gtccacgttc 7020
tttaatagtg gactcttgtt ccaaactgga acaacactca accctatctc ggtctattct 7080
tttgatttat aagggatttt gccgatttcg gcctattggt taaaaaatga gctgatttaa 7140
caaaaattta acgcgaattt taacaaaata ttaacgctta caatttaggt ggcacttttc 7200
ggggaaatgt gcgcggaacc cctatttgtt tatttttcta aatacattca aatatgtatc 7260
cgctcatgag acaataaccc tgataaatgc ttcaataata gcacctagat caagagacag 7320
gatgaggatc gtttcgcatg attgaacaag atggattgca cgcaggttct ccggccgctt 7380
gggtggagag gctattcggc tatgactggg cacaacagac aatcggctgc tctgatgccg 7440
ccgtgttccg gctgtcagcg caggggcgcc cggttctttt tgtcaagacc gacctgtccg 7500
gtgccctgaa tgaactgcaa gacgaggcag cgcggctatc gtggctggcc acgacgggcg 7560
ttccttgcgc agctgtgctc gacgttgtca ctgaagcggg aagggactgg ctgctattgg 7620
gcgaagtgcc ggggcaggat ctcctgtcat ctcaccttgc tcctgccgag aaagtatcca 7680
tcatggctga tgcaatgcgg cggctgcata cgcttgatcc ggctacctgc ccattcgacc 7740
accaagcgaa acatcgcatc gagcgagcac gtactcggat ggaagccggt cttgtcgatc 7800
aggatgatct ggacgaagag catcaggggc tcgcgccagc cgaactgttc gccaggctca 7860
aggcgagcat gcccgacggc gaggatctcg tcgtgaccca tggcgatgcc tgcttgccga 7920
atatcatggt ggaaaatggc cgcttttctg gattcatcga ctgtggccgg ctgggtgtgg 7980
cggaccgcta tcaggacata gcgttggcta cccgtgatat tgctgaagag cttggcggcg 8040
aatgggctga ccgcttcctc gtgctttacg gtatcgccgc tcccgattcg cagcgcatcg 8100
ccttctatcg ccttcttgac gagttcttct gaattattaa cgcttacaat ttcctgatgc 8160
ggtattttct ccttacgcat ctgtgcggta tttcacaccg catcaggtgg cacttttcgg 8220
ggaaatgtgc gcggaacccc tatttgttta tttttctaaa tacattcaaa tatgtatccg 8280
ctcatgacca aaatccctta acgtgagttt tcgttccact gagcgtcaga ccccgtagaa 8340
aagatcaaag gatcttcttg agatcctttt tttctgcgcg taatctgctg cttgcaaaca 8400
aaaaaaccac cgctaccagc ggtggtttgt ttgccggatc aagagctacc aactcttttt 8460
ccgaaggtaa ctggcttcag cagagcgcag ataccaaata ctgttcttct agtgtagccg 8520
tagttaggcc accacttcaa gaactctgta gcaccgccta catacctcgc tctgctaatc 8580
ctgttaccag tggctgctgc cagtggcgat aagtcgtgtc ttaccgggtt ggactcaaga 8640
cgatagttac cggataaggc gcagcggtcg ggctgaacgg ggggttcgtg cacacagccc 8700
agcttggagc gaacgaccta caccgaactg agatacctac agcgtgagct atgagaaagc 8760
gccacgcttc ccgaagggag aaaggcggac aggtatccgg taagcggcag ggtcggaaca 8820
ggagagcgca cgagggagct tccaggggga aacgcctggt atctttatag tcctgtcggg 8880
tttcgccacc tctgacttga gcgtcgattt ttgtgatgct cgtcaggggg gcggagccta 8940
tggaaaaacg ccagcaacgc ggccttttta cggttcctgg ccttttgctg gccttttgct 9000
cacatgttct ttcctgcgtt atcccctgat tctgtggata accgtattac cgcctttgag 9060
tgagctgata ccgctcgccg cagccgaacg accgagcgca gcgagtcagt gagcgaggaa 9120
gcggaagagc gcccaatacg caaaccgcct ctccccgcgc gttggccgat tcattaatgc 9180
agctggcacg acaggtttcc cgactggaaa gcgggcagtg agcgcaacgc aattaatgtg 9240
agttagctca ctcattaggc accccaggct ttacacttta tgcttccggc tcgtatgttg 9300
tgtggaattg tgagcggata acaatttcac acaggaaaca gctatgacca tgattacgcc 9360
aagcgcgcaa ttaaccctca ctaaagggaa caaaagctgg agctgcaagc ttggccattg 9420
catacgttgt atccatatca taatatgtac atttatattg gctcatgtcc aacattaccg 9480
ccatgttgac attgattatt gactagttat taatagtaat caattacggg gtcattagtt 9540
catagcccat atatgg 9556

<210> SEQ ID NO 18
<211> LENGTH: 8940
<212> TYPE: DNA
<213> ORGANISM: Artificial
<220> FEATURE:
<223> OTHER INFORMATION: WAS lentiviral vector

<400> SEQUENCE: 18

```
agttccgcgt tacataactt acggtaaatg gcccgcctgg ctgaccgccc aacgaccccc     60
gcccattgac gtcaataatg acgtatgttc ccatagtaac gccaataggg actttccatt    120
gacgtcaatg ggtggagtat ttacggtaaa ctgcccactt ggcagtacat caagtgtatc    180
atatgccaag tacgccccct attgacgtca atgacggtaa atggcccgcc tggcattatg    240
cccagtacat gaccttatgg gactttccta cttggcagta catctacgta ttagtcatcg    300
ctattaccat ggtgatgcgg ttttggcagt acatcaatgg gcgtggatag cggtttgact    360
cacggggatt tccaagtctc caccccattg acgtcaatgg gagtttgttt tggcaccaaa    420
atcaacggga ctttccaaaa tgtcgtaaca actccgcccc attgacgcaa atgggcggta    480
ggcgtgtacg gtgggaggtc tatataagca gagctcgttt agtgaaccgg ggtctctctg    540
gttagaccag atctgagcct gggagctctc tggctaacta gggaacccac tgcttaagcc    600
tcaataaagc ttgccttgag tgcttcaagt agtgtgtgcc cgtctgttgt gtgactctgg    660
taactagaga tccctcagac ccttttagtc agtgtggaaa atctctagca gtggcgcccg    720
aacagggact tgaaagcgaa agggaaacca gaggagctct ctcgacgcag gactcggctt    780
gctgaagcgc gcacggcaag aggcgagggg cggcgactgg tgagtacgcc aaaaattttg    840
actagcggag gctagaagga gagagatggg tgcgagagcg tcagtattaa gcgggggaga    900
attagatcgc gatgggaaaa aattcggtta aggccagggg gaaagaaaaa atataaatta    960
aaacatatag tatgggcaag cagggagcta gaacgattcg cagttaatcc tggcctgtta   1020
gaaacatcag aaggctgtag acaaatactg ggacagctac aaccatccct tcagacagga   1080
tcagaagaac ttagatcatt atataataca gtagcaaccc tctattgtgt gcatcaaagg   1140
atagagataa aagacaccaa ggaagcttta gacaagatag aggaagagca aaacaaaagt   1200
aagaccaccg cacagcaagc ggccgctgat cttcagacct ggaggaggag atatgaggga   1260
caattggaga agtgaattat ataaatataa agtagtaaaa attgaaccat taggagtagc   1320
acccaccaag gcaaagagaa gagtggtgca gagagaaaaa agagcagtgg gaataggagc   1380
tttgttcctt gggttcttgg gagcagcagg aagcactatg ggcgcagcgt caatgacgct   1440
gacggtacag gccagacaat tattgtctgg tatagtgcag cagcagaaca atttgctgag   1500
ggctattgag gcgcaacagc atctgttgca actcacagtc tggggcatca agcagctcca   1560
ggcaagaatc ctggctgtgg aaagatacct aaaggatcaa cagctcctgg ggatttgggg   1620
ttgctctgga aaactcattt gcaccactgc tgtgccttgg aatgctagtt ggagtaataa   1680
atctctggaa cagatttgga atcacacgac ctggatggag tgggacagag aaattaacaa   1740
ttacacaagc ttaatacact ccttaattga agaatcgcaa aaccagcaag aaaagaatga   1800
acaagaatta ttggaattag ataaatgggc aagtttgtgg aattggttta acataacaaa   1860
ttggctgtgg tatataaaat tattcataat gatagtagga ggcttggtag gtttaagaat   1920
agtttttgct gtactttcta tagtgaatag agttaggcag ggatattcac cattatcgtt   1980
tcagacccac ctcccaaccc cgaggggacc cgacaggccc gaaggaatag aagaagaagg   2040
tggagagaga gacagagaca gatccattcg attagtgaac ggatctcgac ggtatcggtt   2100
aacttttaaa agaaaagggg ggattggggg gtacagtgca ggggaaagaa tagtagacat   2160
aatagcaaca gacatacaaa ctaaagaatt acaaaaacaa attacaaaaa ttcaaaattt   2220
tatcgatcac gagactagcc tcgagcaaac cttgttatct gagagaaagc tagagcttcc   2280
ttctttcagc cccagagac aatgtggcca ggctccggag ggctgggaag atgagcaatg   2340
```

```
cttgtgagtc accatgatag gaagcagaag ggtcaggaag tccctgggag caaggcttag   2400
ggttagggtt agggagaaaa cacttgggcc tggaggctcg gggcaggctt cctagagggg   2460
aggggtacta aaagccacca aaaccaagac agcaatgaaa gtaacctctg gtcttcctaa   2520
ctgctcatta tacactaatt atgatgcact agcatgctaa gagacacttc caccagcgcc   2580
atgacagtgc catggcaaca tcaagaagtc accccacatg gtctaaaaag ggaagaacc    2640
ttcagttccc ggaattgccc acccctttcc tggaaaactc atgaataatc caccccttgt   2700
ttagcatata atgacctgaa gggtaagggg gtgtggaggt tgtgaaggcg ggaagggggg   2760
tagcccctc accaatgtaa acaaggatgt gggttctgcg gccacactct cccccgccct   2820
ccccagcggc atttccagca agtcacatgt cctgcgcaca ggctgggggc cccctgctgc   2880
tgcctttctt agaagccagg accacagagc ccgcacagtg agctacttgg ggagctattt   2940
ctgtagactg agcttggggt actgggaggc agtgctgttg gcctccaact ctctgctcca   3000
cgttccttcc actattcaac acatggcagg aagtcagcct gtagggcttc acactacagt   3060
ctaagctgac tgccatctgt ccccatccag gcgaggctgg aaacgggggc agcaaaaagc   3120
ccagggacaa agtccccttc ccaggcacat gtattatgca ctctgcacca aggaaacctc   3180
cagataaggt ctagagacca agggccatgt acttcggggg agaggccaga ggacttctga   3240
ggttttacag agaaaagcca aaggcagccc agtcagggga aatgtgtagc catagtgccg   3300
ataaggaaag gccttcaacc tgccctggtc agctcttcct gtaagtagag gcccccttacc  3360
gaaggcccca gtgggaggaa gggtcgggag tactcgagtc agcctcaggc tacctaggtg   3420
ctttagaaag gaggccaccc aggcccatga ctactccttg ccacagggag ccctgcacac   3480
agatgtgcta agctctcgct gccagccaga gggaggaggg tctgagccag tcagaaggag   3540
atgggcccca gagagtaaga aagggggagg aggacccaag ctgatccaaa aggtgggtct   3600
aagcagtcaa gtggaggagg gttccaatct gatggcggag ggcccaagct cagcctaacg   3660
aggaggccag gcccaccaag gggcccctgg aggacttgtt tcccttgtcc cttgtggttt   3720
tttgcatttc ctgttccctt gctgctcatt gcggaagttc ctcttcttac cctgcaccca   3780
gagcctcgcc agagaagaca agggcagaaa gcaccatggt gagcaagggc gaggagctgt   3840
tcaccggggt ggtgcccatc ctggtcgagc tggacggcga cgtaaacggc cacaagttca   3900
gcgtgtccgg cgagggcgag ggcgatgcca cctacggcaa gctgaccctg aagttcatct   3960
gcaccaccgg caagctgccc gtgccctggc ccaccctcgt gaccaccttc ggctacggcc   4020
tgatgtgctt cgcccgctac cccgaccaca tgaagcagca cgacttcttc aagtccgcca   4080
tgcccgaagg ctacgtccag gagcgcacca tcttcttcaa ggacgacggc aactacaaga   4140
cccgcgccga ggtgaagttc gagggcgaca ccctggtgaa ccgcatcgag ctgaagggca   4200
tcgacttcaa ggaggacggc aacatcctgg ggcacaagct ggagtacaac tacaacagcc   4260
acaacgtcta tatcatggcc gacaagcaga agaacggcat caaggtgaac ttcaagatcc   4320
gccacaacat cgaggacggc agcgtgcagc tcgccgacca ctaccagcag aacaccccca   4380
tcggcgacgg ccccgtgctg ctgcccgaca accactacct gagctaccag tccgccctga   4440
gcaaagaccc caacgagaag cgcgatcaca tggtcctgct ggagttcgtg accgccgccg   4500
ggatcactct cggcatggac gagctgtaca agtgactgca ggaattcgag catcttaccg   4560
ccatttattc ccatatttgt tctgtttttc ttgatttggg tatacattta aatgttaata   4620
aaacaaaatg gtggggcaat catttacatt tttagggata tgtaattact agttcaggtg   4680
```

-continued

```
tattgccaca agacaaacat gttaagaaac tttcccgtta tttacgctct gttcctgtta   4740
atcaacctct ggattacaaa atttgtgaaa gattgactga tattcttaac tatgttgctc   4800
cttttacgct gtgtggatat gctgctttaa tgcctctgta tcatgctatt gcttcccgta   4860
cggctttcgt tttctcctcc ttgtataaat cctggttgct gtctctttat gaggagttgt   4920
ggcccgttgt ccgtcaacgt ggcgtggtgt gctctgtgtt tgctgacgca acccccactg   4980
gctggggcat tgccaccacc tgtcaactcc tttctgggac tttcgctttc cccctcccga   5040
tcgccacggc agaactcatc gccgcctgcc ttgcccgctg ctggacaggg gctaggttgc   5100
tgggcactga taattccgtg gtgttgtcgg ggaagggcct gctgccggct ctgcggcctc   5160
ttccgcgtct tcgccttcgc cctcagacga gtcggatctc cctttgggcc gcctccccgc   5220
ctggaattcg agctcggtac ctttaagacc aatgacttac aaggcagctg tagatcttag   5280
ccacttttta aaagaaaagg ggggactgga agggctaatt cactcccaac gaagacaaga   5340
tctgcttttt gcttgtactg ggtctctctg gttagaccag atctgagcct gggagctctc   5400
tggctaacta gggaacctac tgcttaagcc tcaataaagc ttgccttgag tgcttcaagt   5460
agtgtgtgcc cgtctgttgt gtgactctgg taactagaga tccctcagac ccttttagtc   5520
agtgtggaaa atctctagca gtagtagttc atgtcatctt attattcagt atttataact   5580
tgcaaagaaa tgaatatcag agagtgagag gaacttgttt attgcagctt ataatggtta   5640
caaataaagc aatagcatca caaatttcac aaataaagca tttttttcac tgcattctag   5700
ttgtggtttg tccaaactca tcaatgtatc ttatcatgtc tggctctagc tatcccgccc   5760
ctaactccgc ccatcccgcc cctaactccg cccagttccg cccattctcc gccccatggc   5820
tgactaattt tttttattta tgcagaggcc gaggccgcct cggcctctga gctattccag   5880
aagtagtgag gaggcttttt tggaggccta gggacgtacc caattcgccc tatagtgagt   5940
cgtattacgc gcgctcactg gccgtcgttt tacaacgtcg tgactgggaa aaccctggcg   6000
ttacccaact taatcgcctt gcagcacatc ccccttcgc cagctggcgt aatagcgaag    6060
aggcccgcac cgatcgccct tcccaacagt tgcgcagcct gaatggcgaa tgggacgcgc   6120
cctgtagcgg cgcattaagc gcggcgggtg tggtggttac gcgcagcgtg accgctacac   6180
ttgccagcgc cctagcgccc gctcctttcg ctttcttccc ttcctttctc gccacgttcg   6240
ccggctttcc ccgtcaagct ctaaatcggg ggctcccttt agggttccga tttagtgctt   6300
tacggcacct cgaccccaaa aaacttgatt agggtgatgg ttcacgtagt gggccatcgc   6360
cctgatagac ggtttttcgc cctttgacgt tggagtccac gttctttaat agtggactct   6420
tgttccaaac tggaacaaca ctcaacccta tctcggtcta ttcttttgat ttataaggga   6480
ttttgccgat ttcggcctat tggttaaaaa atgagctgat ttaacaaaaa tttaacgcga   6540
attttaacaa aatattaacg cttacaattt aggtggcact tttcggggaa atgtgcgcgg   6600
aacccctatt tgtttatttt tctaaataca ttcaaatatg tatccgctca tgagacaata   6660
accctgataa atgcttcaat aatagcacct agatcaagag acaggatgag gatcgtttcg   6720
catgattgaa caagatggat tgcacgcagg ttctccggcc gcttgggtgg agaggctatt   6780
cggctatgac tgggcacaac agacaatcgg ctgctctgat gccgccgtgt tccggctgtc   6840
agcgcagggg cgcccggttc tttttgtcaa gaccgacctg tccggtgccc tgaatgaact   6900
gcaagacgag gcagcgcggc tatcgtggct ggccacgacg ggcgttcctt gcgcagctgt   6960
gctcgacgtt gtcactgaag cgggaaggga ctggctgcta ttgggcgaag tgccggggca   7020
ggatctcctg tcatctcacc ttgctcctgc cgagaaagta tccatcatgg ctgatgcaat   7080
```

-continued

```
gcggcggctg catacgcttg atccggctac ctgcccattc gaccaccaag cgaaacatcg   7140
catcgagcga gcacgtactc ggatggaagc cggtcttgtc gatcaggatg atctggacga   7200
agagcatcag gggctcgcgc cagccgaact gttcgccagg ctcaaggcga gcatgcccga   7260
cggcgaggat ctcgtcgtga cccatggcga tgcctgcttg ccgaatatca tggtggaaaa   7320
tggccgcttt tctggattca tcgactgtgg ccggctgggt gtggcggacc gctatcagga   7380
catagcgttg gctacccgtg atattgctga agagcttggc ggcgaatggg ctgaccgctt   7440
cctcgtgctt tacggtatcg ccgctcccga ttcgcagcgc atcgccttct atcgccttct   7500
tgacgagttc ttctgaatta ttaacgctta caatttcctg atgcggtatt ttctccttac   7560
gcatctgtgc ggtatttcac accgcatcag gtggcacttt tcggggaaat gtgcgcggaa   7620
cccctatttg tttatttttc taaatacatt caaatatgta tccgctcatg accaaaatcc   7680
cttaacgtga gttttcgttc cactgagcgt cagaccccgt agaaaagatc aaaggatctt   7740
cttgagatcc tttttttctg cgcgtaatct gctgcttgca aacaaaaaaa ccaccgctac   7800
cagcggtggt ttgtttgccg gatcaagagc taccaactct ttttccgaag gtaactggct   7860
tcagcagagc gcagatacca aatactgttc ttctagtgta gccgtagtta ggccaccact   7920
tcaagaactc tgtagcaccg cctacatacc tcgctctgct aatcctgtta ccagtggctg   7980
ctgccagtgg cgataagtcg tgtcttaccg ggttggactc aagacgatag ttaccggata   8040
aggcgcagcg gtcgggctga acggggggtt cgtgcacaca gcccagcttg gagcgaacga   8100
cctacaccga actgagatac ctacagcgtg agctatgaga aagcgccacg cttcccgaag   8160
ggagaaaggc ggacaggtat ccggtaagcg gcagggtcgg aacaggagag cgcacgaggg   8220
agcttccagg gggaaacgcc tggtatcttt atagtcctgt cgggtttcgc cacctctgac   8280
ttgagcgtcg atttttgtga tgctcgtcag gggggcggag cctatggaaa aacgccagca   8340
acgcggcctt tttacggttc ctggcctttt gctggccttt tgctcacatg ttctttcctg   8400
cgttatcccc tgattctgtg gataaccgta ttaccgcctt tgagtgagct gataccgctc   8460
gccgcagccg aacgaccgag cgcagcgagt cagtgagcga ggaagcggaa gagcgcccaa   8520
tacgcaaacc gcctctcccc gcgcgttggc cgattcatta atgcagctgg cacgacaggt   8580
ttcccgactg gaaagcgggc agtgagcgca acgcaattaa tgtgagttag ctcactcatt   8640
aggcacccca ggctttacac tttatgcttc cggctcgtat gttgtgtgga attgtgagcg   8700
gataacaatt tcacacagga aacagctatg accatgatta cgccaagcgc gcaattaacc   8760
ctcactaaag ggaacaaaag ctggagctgc aagcttggcc attgcatacg ttgtatccat   8820
atcataatat gtacatttat attggctcat gtccaacatt accgccatgt tgacattgat   8880
tattgactag ttattaatag taatcaatta cggggtcatt agttcatagc ccatatatgg   8940
```

<210> SEQ ID NO 19
<211> LENGTH: 529
<212> TYPE: DNA
<213> ORGANISM: Artificial
<220> FEATURE:
<223> OTHER INFORMATION: CMV promoter

<400> SEQUENCE: 19

```
agttccgcgt tacataactt acggtaaatg gcccgcctgg ctgaccgccc aacgaccccc     60
gcccattgac gtcaataatg acgtatgttc ccatagtaac gccaataggg actttccatt    120
gacgtcaatg ggtggagtat ttacggtaaa ctgcccactt ggcagtacat caagtgtatc    180
```

atatgccaag tacgccccct attgacgtca atgacggtaa atggcccgcc tggcattatg 240
cccagtacat gaccttatgg gactttccta cttggcagta catctacgta ttagtcatcg 300
ctattaccat ggtgatgcgg ttttggcagt acatcaatgg gcgtggatag cggtttgact 360
cacggggatt tccaagtctc caccccattg acgtcaatgg gagtttgttt tggcaccaaa 420
atcaacggga ctttccaaaa tgtcgtaaca actccgcccc attgacgcaa atgggcggta 480
ggcgtgtacg gtgggaggtc tatataagca gagctcgttt agtgaaccg 529

<210> SEQ ID NO 20
<211> LENGTH: 180
<212> TYPE: DNA
<213> ORGANISM: Artificial
<220> FEATURE:
<223> OTHER INFORMATION: Component of lentiviral vector

<400> SEQUENCE: 20
gggtctctct ggttagacca gatctgagcc tgggagctct ctggctaact agggaaccca 60
ctgcttaagc ctcaataaag cttgccttga gtgcttcaag tagtgtgtgc ccgtctgttg 120
tgtgactctg gtaactagag atccctcaga cccttttagt cagtgtggaa aatctctagc 180

<210> SEQ ID NO 21
<211> LENGTH: 138
<212> TYPE: DNA
<213> ORGANISM: Artificial
<220> FEATURE:
<223> OTHER INFORMATION: Packaging signal

<400> SEQUENCE: 21
tcgacgcagg actcggcttg ctgaagcgcg cacggcaaga ggcgaggggc ggcgactggt 60
gagtacgcca aaaattttga ctagcggagg ctagaaggag agagatgggt gcgagagcgt 120
cagtattaag cgggggag 138

<210> SEQ ID NO 22
<211> LENGTH: 205
<212> TYPE: DNA
<213> ORGANISM: Artificial
<220> FEATURE:
<223> OTHER INFORMATION: RRE of lentiviral vector

<400> SEQUENCE: 22
tccttgggtt cttgggagca gcaggaagca ctatgggcgc agcgtcaatg acgctgacgg 60
tacaggccag acaattattg tctggtatag tgcagcagca gaacaatttg ctgagggcta 120
ttgaggcgca acagcatctg ttgcaactca cagtctgggg catcaagcag ctccaggcaa 180
gaatcctggc tgtggaaaga tacct 205

<210> SEQ ID NO 23
<211> LENGTH: 656
<212> TYPE: DNA
<213> ORGANISM: Artificial
<220> FEATURE:
<223> OTHER INFORMATION: WPRE of lentiviral vector

<400> SEQUENCE: 23
cccatatttg ttctgttttt cttgatttgg gtatacattt aaatgttaat aaaacaaaat 60
ggtggggcaa tcatttacat ttttagggat atgtaattac tagttcaggt gtattgccac 120
aagacaaaca tgttaagaaa ctttcccgtt atttacgctc tgttcctgtt aatcaacctc 180
tggattacaa aatttgtgaa agattgactg atattcttaa ctatgttgct ccttttacgc 240

```
tgtgtggata tgctgcttta atgcctctgt atcatgctat tgcttcccgt acggctttcg    300

ttttctcctc cttgtataaa tcctggttgc tgtctcttta tgaggagttg tggcccgttg    360

tccgtcaacg tggcgtggtg tgctctgtgt ttgctgacgc aacccccact ggctggggca    420

ttgccaccac ctgtcaactc ctttctggga ctttcgcttt ccccctcccg atcgccacgg    480

cagaactcat cgccgcctgc cttgcccgct gctggacagg ggctaggttg ctgggcactg    540

ataattccgt ggtgttgtcg gggaagggcc tgctgccggc tctgcggcct cttccgcgtc    600

ttcgccttcg ccctcagacg agtcggatct ccctttgggc cgcctccccg cctgga        656


<210> SEQ ID NO 24
<211> LENGTH: 22
<212> TYPE: DNA
<213> ORGANISM: Artificial
<220> FEATURE:
<223> OTHER INFORMATION: 3' PPT of lentiviral vector

<400> SEQUENCE: 24

tttttaaaag aaaagggggg ac                                              22


<210> SEQ ID NO 25
<211> LENGTH: 233
<212> TYPE: DNA
<213> ORGANISM: Artificial
<220> FEATURE:
<223> OTHER INFORMATION: Component of lentiviral vector

<400> SEQUENCE: 25

tggaagggct aattcactcc caacgaagac aagatctgct tttgcttgt actgggtctc     60

tctggttaga ccagatctga gcctgggagc tctctggcta actagggaac ctactgctta    120

agcctcaata aagcttgcct tgagtgcttc aagtagtgtg tgcccgtctg ttgtgtgact    180

ctggtaacta gagatccctc agaccctttt agtcagtgtg gaaaatctct agc           233


<210> SEQ ID NO 26
<211> LENGTH: 140
<212> TYPE: DNA
<213> ORGANISM: Artificial
<220> FEATURE:
<223> OTHER INFORMATION: SV40 origin of replication

<400> SEQUENCE: 26

atcccgcccc taactccgcc cagttccgcc cattctccgc cccatggctg actaattttt     60

tttatttatg cagaggccga ggccgcctcg gcctctgagc tattccagaa gtagtgagga    120

ggcttttttg gaggcctagg                                                140


<210> SEQ ID NO 27
<211> LENGTH: 792
<212> TYPE: DNA
<213> ORGANISM: Artificial
<220> FEATURE:
<223> OTHER INFORMATION: Drug resistance gene

<400> SEQUENCE: 27

attgaacaag atggattgca cgcaggttct ccggccgctt gggtggagag gctattcggc     60

tatgactggg cacaacagac aatcggctgc tctgatgccg ccgtgttccg gctgtcagcg    120

caggggcgcc cggttctttt tgtcaagacc gacctgtccg gtgccctgaa tgaactgcaa    180

gacgaggcag cgcggctatc gtggctggcc acgacgggcg ttccttgcgc agctgtgctc    240
```

```
gacgttgtca ctgaagcggg aagggactgg ctgctattgg gcgaagtgcc ggggcaggat    300

ctcctgtcat ctcaccttgc tcctgccgag aaagtatcca tcatggctga tgcaatgcgg    360

cggctgcata cgcttgatcc ggctacctgc ccattcgacc accaagcgaa acatcgcatc    420

gagcgagcac gtactcggat ggaagccggt cttgtcgatc aggatgatct ggacgaagag    480

catcaggggc tcgcgccagc cgaactgttc gccaggctca aggcgagcat gcccgacggc    540

gaggatctcg tcgtgaccca tggcgatgcc tgcttgccga atatcatggt ggaaaatggc    600

cgcttttctg gattcatcga ctgtggccgg ctgggtgtgg cggaccgcta tcaggacata    660

gcgttggcta cccgtgatat tgctgaagag cttggcggcg aatgggctga ccgcttcctc    720

gtgctttacg gtatcgccgc tcccgattcg cagcgcatcg ccttctatcg ccttcttgac    780

gagttcttct ga                                                          792
```

```
<210> SEQ ID NO 28
<211> LENGTH: 620
<212> TYPE: DNA
<213> ORGANISM: Artificial
<220> FEATURE:
<223> OTHER INFORMATION: Drug resistance gene

<400> SEQUENCE: 28

agatcaaagg atcttcttga gatccttttt ttctgcgcgt aatctgctgc ttgcaaacaa     60

aaaaaccacc gctaccagcg gtggtttgtt tgccggatca agagctacca actctttttc    120

cgaaggtaac tggcttcagc agagcgcaga taccaaatac tgttcttcta gtgtagccgt    180

agttaggcca ccacttcaag aactctgtag caccgcctac atacctcgct ctgctaatcc    240

tgttaccagt ggctgctgcc agtggcgata agtcgtgtct taccgggttg gactcaagac    300

gatagttacc ggataaggcg cagcggtcgg gctgaacggg gggttcgtgc acacagccca    360

gcttggagcg aacgacctac accgaactga gatacctaca gcgtgagcta tgagaaagcg    420

ccacgcttcc cgaagggaga aaggcggaca ggtatccggt aagcggcagg gtcggaacag    480

gagagcgcac gagggagctt ccagggggaa acgcctggta tctttatagt cctgtcgggt    540

ttcgccacct ctgacttgag cgtcgatttt tgtgatgctc gtcagggggg cggagcctat    600

ggaaaaacgc cagcaacgcg                                                 620
```

```
<210> SEQ ID NO 29
<211> LENGTH: 10345
<212> TYPE: DNA
<213> ORGANISM: Artificial
<220> FEATURE:
<223> OTHER INFORMATION: Lentiviral vector

<400> SEQUENCE: 29

agttccgcgt tacataactt acggtaaatg gcccgcctgg ctgaccgccc aacgaccccc     60

gcccattgac gtcaataatg acgtatgttc ccatagtaac gccaataggg actttccatt    120

gacgtcaatg ggtggagtat ttacggtaaa ctgcccactt ggcagtacat caagtgtatc    180

atatgccaag tacgccccct attgacgtca atgacggtaa atggcccgcc tggcattatg    240

cccagtacat gaccttatgg gactttccta cttggcagta catctacgta ttagtcatcg    300

ctattaccat ggtgatgcgg ttttggcagt acatcaatgg gcgtggatag cggtttgact    360

cacggggatt tccaagtctc caccccattg acgtcaatgg gagtttgttt tggcaccaaa    420

atcaacggga ctttccaaaa tgtcgtaaca actccgcccc attgacgcaa atgggcggta    480

ggcgtgtacg gtgggaggtc tatataagca gagctcgttt agtgaaccgg ggtctctctg    540
```

-continued

```
gttagaccag atctgagcct gggagctctc tggctaacta gggaacccac tgcttaagcc    600
tcaataaagc ttgccttgag tgcttcaagt agtgtgtgcc cgtctgttgt gtgactctgg    660
taactagaga tccctcagac ccttttagtc agtgtggaaa atctctagca gtggcgcccg    720
aacagggact tgaaagcgaa agggaaacca gaggagctct ctcgacgcag gactcggctt    780
gctgaagcgc gcacggcaag aggcgagggg cggcgactgg tgagtacgcc aaaaattttg    840
actagcggag gctagaagga gagagatggg tgcgagagcg tcagtattaa gcgggggaga    900
attagatcgc gatgggaaaa aattcggtta aggccagggg gaaagaaaaa atataaatta    960
aaacatatag tatgggcaag cagggagcta gaacgattcg cagttaatcc tggcctgtta   1020
gaaacatcag aaggctgtag acaaatactg ggacagctac aaccatccct tcagacagga   1080
tcagaagaac ttagatcatt atataataca gtagcaaccc tctattgtgt gcatcaaagg   1140
atagagataa aagacaccaa ggaagcttta gacaagatag aggaagagca aaacaaaagt   1200
aagaccaccg cacagcaagc ggccgctgat cttcagacct ggaggaggag atatgaggga   1260
caattggaga agtgaattat ataaatataa agtagtaaaa attgaaccat taggagtagc   1320
acccaccaag gcaaagagaa gagtggtgca gagagaaaaa agagcagtgg gaataggagc   1380
tttgttcctt gggttcttgg gagcagcagg aagcactatg ggcgcagcgt caatgacgct   1440
gacggtacag gccagacaat tattgtctgg tatagtgcag cagcagaaca atttgctgag   1500
ggctattgag gcgcaacagc atctgttgca actcacagtc tggggcatca agcagctcca   1560
ggcaagaatc ctggctgtgg aaagatacct aaaggatcaa cagctcctgg ggatttgggg   1620
ttgctctgga aaactcattt gcaccactgc tgtgccttgg aatgctagtt ggagtaataa   1680
atctctggaa cagatttgga atcacacgac ctggatggag tgggacagag aaattaacaa   1740
ttacacaagc ttaatacact ccttaattga agaatcgcaa aaccagcaag aaaagaatga   1800
acaagaatta ttggaattag ataaatgggc aagtttgtgg aattggttta acataacaaa   1860
ttggctgtgg tatataaaat tattcataat gatagtagga ggcttggtag gtttaagaat   1920
agtttttgct gtactttcta tagtgaatag agttaggcag ggatattcac cattatcgtt   1980
tcagacccac ctcccaaccc cgaggggacc cgacaggccc gaaggaatag aagaagaagg   2040
tggagagaga gacagagaca gatccattcg attagtgaac ggatctcgac ggtatcggtt   2100
aacttttaaa agaaaagggg ggattggggg gtacagtgca ggggaaagaa tagtagacat   2160
aatagcaaca gacatacaaa ctaaagaatt acaaaaacaa attacaaaaa ttcaaaattt   2220
tatcgatcac gagactagcc tcgagcaaac cttgttatct gagagaaagc tagagcttcc   2280
ttctttcagc ccccagagac aatgtggcca ggctccggag ggctgggaag atgagcaatg   2340
cttgtgagtc accatgatag gaagcagaag ggtcaggaag tccctgggag caaggcttag   2400
ggttagggtt agggagaaaa cacttgggcc tggaggctcg gggcaggctt cctagagggg   2460
aggggtacta aaagccacca aaaccaagac agcaatgaaa gtaacctctg gtcttcctaa   2520
ctgctcatta tacactaatt atgatgcact agcatgctaa gagacacttc caccagcgcc   2580
atgacagtgc catggcaaca tcaagaagtc accccacatg gtctaaaaag gggaagaacc   2640
ttcagttccc ggaattgccc accccttcc tggaaaactc atgaataatc caccccttgt   2700
ttagcatata atgacctgaa gggtaagggg gtgtggaggt tgtgaaggcg ggaagggggg   2760
tagccccttc accaatgtaa acaaggatgt gggttctgcg gccacactct cccccgccct   2820
ccccagcggc atttccagca agtcacatgt cctgcgcaca ggctgggggc cccctgctgc   2880
```

-continued

```
tgcctttctt agaagccagg accacagagc ccgcacagtg agctacttgg ggagctattt   2940
ctgtagactg agcttggggt actgggaggc agtgctgttg gcgatctggg ggaaaacccc   3000
ctgagggtcc catttctctg ccactgaccc ctttgcctgg cagaaaggct ctgctgcctc   3060
ctagctgtgt agcaatggat aaggccttta acctctctaa gctgaaatgt cctcatgcat   3120
aaggtggaga cagtaactcc tcttccatct gctgggtgtt gtcaaaacta cacaggaggt   3180
ttgccaagca cctaaggcac agtaggtggt caagaaacag gaacacaatt tgtcatgacg   3240
acaatgattc cttcatatgc tagttaccca cgagtcagcc agaatgttgc cataaccact   3300
tatgaagccc ttcctcattt ctgttgcaat tcctcagcca gaggaaagcc ccacacagcc   3360
cttgccactc cccatggcc catgtagaaa caaccatgtg gccttcactc tgcccacaga   3420
agctagcacc aggaccctgg tcagggttag aggtttctgc tgagtcaaag ccacatggag   3480
ggagggagca agggagagat gcagagtcat gtttccagga ggaggttatc tgagcataac   3540
agggacaggg tgggccacag gatacctctg aggctcaggt tcccacctcc actccacccct   3600
ccaactctct gctccacgtt ccttccacta ttcaacacat ggcaggaagt cagcctgtag   3660
ggcttcacac tacagtctaa gctgactgcc atctgtcccc atccaggcga ggctggaaac   3720
gggggcagca aaaagcccag ggacaaagtc cccttcccag gcacatgtat tatgcactct   3780
gcaccaagga aacctccaga taaggtctag agaccaaggg ccatgtactt cgggggagag   3840
gccagaggac ttctgaggtt ttacagagaa aagccaaagg cagcccagtc aggggaaatg   3900
tgtagccata gtgccgataa ggaaaggcct tcaacctgcc ctggtcagct cttcctgtaa   3960
gtagaggccc cttaccgaag gccccagtgg gaggaagggt cgggagtact cgagtcagcc   4020
tcaggctacc taggtgcttt agaaaggagg ccacccaggc ccatgactac tccttgccac   4080
agggagccct gcacacagat gtgctaagct ctcgctgcca gccagaggga ggagggtctg   4140
agccagtcag aaggagatgg gccccagaga gtaagaaagg gggaggagga cccaagctga   4200
tccaaaaggt gggtctaagc agtcaagtgg aggagggttc caatctgatg gcggagggcc   4260
caagctcagc ctaacgagga ggccaggccc accaaggggc ccctggagga cttgtttccc   4320
ttgtcccttg tggtttttg catttcctgt tcccttgctg ctcattgcgg aagttcctct   4380
tcttaccctg cacccagagc ctcgccagag aagacaaggg cagaaagcac catgtctggc   4440
ggacctatgg gaggtagacc tggtggaaga ggtgccccg ccgtgcagca gaacatcccc   4500
agcaccctgc tgcaggacca cgagaaccag cgcctgttcg agatgctggg ccgcaagtgc   4560
ctgaccctgg ccaccgccgt ggtgcagctg tacctggccc tgcccccgg cgccgagcac   4620
tggaccaagg agcactgcgg cgccgtgtgc ttcgtgaagg acaaccccca gaagagctac   4680
ttcatccgcc tgtacggcct gcaggccggc cgcctgctgt gggagcagga gctgtacagc   4740
cagctggtgt acagcacccc caccccctc ttccacacct tcgccggcga cgactgccag   4800
gccggcctga acttcgccga cgaggacgag gcccaggcct tccgcgccct ggtgcaggag   4860
aagatccaga agcgcaacca gcgccagagc ggcgacagaa ggcaactgcc tcctccacct   4920
acaccagcca acgaggaaag aagaggcgga ctgcccccc tgcctcttca tcctggcgga   4980
gatcaaggtg gacctcctgt gggaccactg tctcttggcc tggccaccgt ggacatccag   5040
aacccgaca tcaccagcag ccgctaccgc ggcctgcccg cccccggccc cagccccgcc   5100
gacaagaagc gcagcggcaa gaagaagatc agcaaggccg acatcggcgc ccccagcggc   5160
ttcaagcacg tgagccacgt gggctgggac ccccagaacg gcttcgacgt gaacaacctg   5220
gaccccgacc tgcgcagcct gttcagccgc gccggcatca gcgaggccca gctgaccgac   5280
```

-continued

```
gccgagacca gcaagctgat ctacgacttc atcgaggacc agggcggcct ggaggccgtg   5340
cgccaggaga tgcgccgcca ggagcccctg ccaccacctc cacctccatc tagaggcggc   5400
aaccagctgc cccgccctcc tatcgttggc ggcaacaagg gaagatctgg ccctctgcct   5460
cctgtgcctc tgggaatcgc tccaccacca ccaacaccta gaggcccgcc tccaccaggc   5520
agaggtggtc ctccgccgcc acctcctcca gccaccggcc gcagcggccc ccttcctcct   5580
ccaccacctg gtgctggtgg acctccaatg ccaccgccac cgcctccgcc acctccgcct   5640
ccaagttctg gaaatggacc tgctcctcct cctttgcctc ctgctttggt tcctgctggc   5700
ggattggctc caggcggagg aagaggcgca ctgctggacc agatccgcca gggcatccag   5760
ctgaacaaga cccctggcgc tcctgagagt tctgctctgc aaccgccacc acagtctagc   5820
gaaggacttg tgggagccct gatgcacgtg atgcagaagc gcagccgcgc catccacagc   5880
agcgacgagg gcgaggacca ggccggcgac gaggacgagg acgacgagtg ggacgactaa   5940
ctgcaggaat tcgagcatct taccgccatt tattcccata tttgttctgt ttttcttgat   6000
ttgggtatac atttaaatgt taataaaaca aaatggtggg gcaatcattt acatttttag   6060
ggatatgtaa ttactagttc aggtgtattg ccacaagaca aacatgttaa gaaactttcc   6120
cgttatttac gctctgttcc tgttaatcaa cctctggatt acaaaatttg tgaaagattg   6180
actgatattc ttaactatgt tgctcctttt acgctgtgtg gatatgctgc tttaatgcct   6240
ctgtatcatg ctattgcttc ccgtacggct ttcgttttct cctccttgta taaatcctgg   6300
ttgctgtctc tttatgagga gttgtggccc gttgtccgtc aacgtggcgt ggtgtgctct   6360
gtgtttgctg acgcaacccc cactggctgg ggcattgcca ccacctgtca actcctttct   6420
gggactttcg ctttcccccct cccgatcgcc acggcagaac tcatcgccgc ctgccttgcc   6480
cgctgctgga caggggctag gttgctgggc actgataatt ccgtggtgtt gtcggggaag   6540
ggcctgctgc cggctctgcg gcctcttccg cgtcttcgcc ttcgccctca gacgagtcgg   6600
atctcccttt gggccgcctc cccgcctgga attcgagctc ggtaccttta agaccaatga   6660
cttacaaggc agctgtagat cttagccact tttaaaaga aaagggggga ctggaagggc   6720
taattcactc ccaacgaaga caagatctgc tttttgcttg tactgggtct ctctggttag   6780
accagatctg agcctgggag ctctctggct aactagggaa cctactgctt aagcctcaat   6840
aaagcttgcc ttgagtgctt caagtagtgt gtgcccgtct gttgtgtgac tctggtaact   6900
agagatccct cagacccttt tagtcagtgt ggaaaatctc tagcagtagt agttcatgtc   6960
atcttattat tcagtattta taacttgcaa agaaatgaat atcagagagt gagaggaact   7020
tgtttattgc agcttataat ggttacaaat aaagcaatag catcacaaat ttcacaaata   7080
aagcattttt ttcactgcat tctagttgtg gtttgtccaa actcatcaat gtatcttatc   7140
atgtctggct ctagctatcc cgcccctaac tccgcccatc ccgcccctaa ctccgcccag   7200
ttccgcccat tctccgcccc atggctgact aattttttt atttatgcag aggccgaggc   7260
cgcctcggcc tctgagctat tccagaagta gtgaggaggc ttttttggag gcctagggac   7320
gtacccaatt cgccctatag tgagtcgtat tacgcgcgct cactggccgt cgttttacaa   7380
cgtcgtgact gggaaaaccc tggcgttacc caacttaatc gccttgcagc acatccccct   7440
ttcgccagct ggcgtaatag cgaagaggcc cgcaccgatc gcccttccca acagttgcgc   7500
agcctgaatg gcgaatggga cgcgccctgt agcggcgcat taagcgcggc gggtgtggtg   7560
gttacgcgca gcgtgaccgc tacacttgcc agcgccctag cgcccgctcc tttcgctttc   7620
```

-continued

```
ttcccttcct ttctcgccac gttcgccggc tttccccgtc aagctctaaa tcgggggctc   7680
cctttagggt tccgatttag tgctttacgg cacctcgacc ccaaaaaact tgattagggt   7740
gatggttcac gtagtgggcc atcgccctga tagacggttt ttcgcccttt gacgttggag   7800
tccacgttct ttaatagtgg actcttgttc caaactggaa caacactcaa ccctatctcg   7860
gtctattctt ttgatttata agggattttg ccgatttcgg cctattggtt aaaaaatgag   7920
ctgatttaac aaaaatttaa cgcgaatttt aacaaaatat taacgcttac aatttaggtg   7980
gcacttttcg gggaaatgtg cgcggaaccc ctatttgttt atttttctaa atacattcaa   8040
atatgtatcc gctcatgaga caataaccct gataaatgct tcaataatag cacctagatc   8100
aagagacagg atgaggatcg tttcgcatga ttgaacaaga tggattgcac gcaggttctc   8160
cggccgcttg ggtggagagg ctattcggct atgactgggc acaacagaca atcggctgct   8220
ctgatgccgc cgtgttccgg ctgtcagcgc aggggcgccc ggttcttttt gtcaagaccg   8280
acctgtccgg tgccctgaat gaactgcaag acgaggcagc gcggctatcg tggctggcca   8340
cgacgggcgt tccttgcgca gctgtgctcg acgttgtcac tgaagcggga agggactggc   8400
tgctattggg cgaagtgccg gggcaggatc tcctgtcatc tcaccttgct cctgccgaga   8460
aagtatccat catggctgat gcaatgcggc ggctgcatac gcttgatccg gctacctgcc   8520
cattcgacca ccaagcgaaa catcgcatcg agcgagcacg tactcggatg gaagccggtc   8580
ttgtcgatca ggatgatctg gacgaagagc atcaggggct cgcgccagcc gaactgttcg   8640
ccaggctcaa ggcgagcatg cccgacggcg aggatctcgt cgtgacccat ggcgatgcct   8700
gcttgccgaa tatcatggtg gaaaatggcc gcttttctgg attcatcgac tgtggccggc   8760
tgggtgtggc ggaccgctat caggacatag cgttggctac ccgtgatatt gctgaagagc   8820
ttggcggcga atgggctgac cgcttcctcg tgctttacgg tatcgccgct cccgattcgc   8880
agcgcatcgc cttctatcgc cttcttgacg agttcttctg aattattaac gcttacaatt   8940
tcctgatgcg gtattttctc cttacgcatc tgtgcggtat ttcacaccgc atcaggtggc   9000
acttttcggg gaaatgtgcg cggaacccct atttgtttat ttttctaaat acattcaaat   9060
atgtatccgc tcatgaccaa aatcccttaa cgtgagtttt cgttccactg agcgtcagac   9120
cccgtagaaa agatcaaagg atcttcttga gatccttttt ttctgcgcgt aatctgctgc   9180
ttgcaaacaa aaaaaccacc gctaccagcg gtggtttgtt tgccggatca agagctacca   9240
actctttttc cgaaggtaac tggcttcagc agagcgcaga taccaaatac tgttcttcta   9300
gtgtagccgt agttaggcca ccacttcaag aactctgtag caccgcctac atacctcgct   9360
ctgctaatcc tgttaccagt ggctgctgcc agtggcgata agtcgtgtct taccgggttg   9420
gactcaagac gatagttacc ggataaggcg cagcggtcgg gctgaacggg gggttcgtgc   9480
acacagccca gcttggagcg aacgacctac accgaactga gatacctaca gcgtgagcta   9540
tgagaaagcg ccacgcttcc cgaagggaga aaggcggaca ggtatccggt aagcggcagg   9600
gtcggaacag gagagcgcac gagggagctt ccagggggaa acgcctggta tctttatagt   9660
cctgtcgggt ttcgccacct ctgacttgag cgtcgatttt tgtgatgctc gtcagggggg   9720
cggagcctat ggaaaaacgc cagcaacgcg gcctttttac ggttcctggc cttttgctgg   9780
ccttttgctc acatgttctt tcctgcgtta tcccctgatt ctgtggataa ccgtattacc   9840
gcctttgagt gagctgatac cgctcgccgc agccgaacga ccgagcgcag cgagtcagtg   9900
agcgaggaag cggaagagcg cccaatacgc aaaccgcctc tccccgcgcg ttggccgatt   9960
cattaatgca gctggcacga caggtttccc gactggaaag cgggcagtga gcgcaacgca  10020
```

-continued

```
attaatgtga gttagctcac tcattaggca ccccaggctt tacactttat gcttccggct  10080

cgtatgttgt gtggaattgt gagcggataa caatttcaca caggaaacag ctatgaccat  10140

gattacgcca agcgcgcaat taaccctcac taaagggaac aaaagctgga gctgcaagct  10200

tggccattgc atacgttgta tccatatcat aatatgtaca tttatattgg ctcatgtcca  10260

acattaccgc catgttgaca ttgattattg actagttatt aatagtaatc aattacgggg  10320

tcattagttc atagcccata tatgg                                        10345
```

LENTIVIRAL VECTORS IN HEMATOPOIETIC STEM CELLS TO TREAT WISKOTT-ALDRICH SYNDROME (WAS)

CROSS-REFERENCE TO RELATED APPLICATIONS

This application is a U.S. 371 National Phase of PCT/US2020/059886, filed on Nov. 10, 2020, which claims priority to and benefit of U.S. Ser. No. 62/933,875, filed on Nov. 11, 2019, both of which are incorporated herein by reference in their entirety for all purposes.

STATEMENT OF GOVERNMENTAL SUPPORT

Not Applicable

INCORPORATION BY REFERENCE OF SEQUENCE LISTING PROVIDED AS A TEXT FILE

A Sequence Listing is provided herewith as a text file, "UCLA-P220P_ST25.txt" created on Nov. 9, 2020 and having a size of 82.1 kb. The contents of the text file are incorporated by reference herein in their entirety.

BACKGROUND

Wiskott-Aldrich Syndrome (WAS) is an X-linked primary immune deficiency caused by mutations in the Wiskott-Aldrich Syndrome (WAS) gene. Patients with WAS have severe defects in both adaptive and innate immunity and are highly susceptible to life-threatening viral and bacterial infections. Patients also suffer from extremely severe eczema, microthrombocytopenia and have a high risk of developing autoimmunity and cancer, WAS occurs most often in males due to its X-linked recessive pattern of inheritance, affecting between 1 and 10 males per million. The first signs are usually petechiae and bruising, resulting from a low platelet count (i.e, thrombocytopenia). Spontaneous nose bleeds and bloody diarrhea are also common, and eczema typically develops within the first month of life. Recurrent bacterial infections typically develop by three months. The majority of children with WAS develop at least one autoimmune disorder, and cancers (mainly lymphoma and leukemia) develop in up to a third of patients. Immunoglobulin M (IgM) levels are typically reduced, IgA and IgE are typically elevated, and IgG levels can be normal, reduced, or elevated. In addition to thrombocytopenia, WAS patients have abnormally small platelets (i.e. microthrombocytes) and ~30% also have elevated eosinophil counts (i.e., eosinophilia).

Treatment for WAS typically involves prophylactic antibiotic and antiviral therapy to manage infections. Platelet transfusions and splenectomy are used to treat thrombocytopenia (low platelet counts). Additionally, blood transfusions may be required to treat anemia resulting from excessive bleeding and a protective helmet may be used to prevent brain hemorrhages which could result from head injury Immunosuppressive treatment is utilized for autoimmune manifestations.

Because patients with WAS have abnormal T- and B-lymphocyte function, they are typically not administered live virus vaccines since there is a possibility that a vaccine strain of the virus may cause disease. Complications of chicken pox infection occur occasionally and may be prevented by early treatment following exposure with antiviral drugs, high dose immunoglobulin replacement therapy or Varicella zoster Immune Globulin (VZIG). Other "non-live" vaccinations can be given safely to patients with WAS but may not generate protective levels of antibody.

A potential curative therapy is an allogeneic hematopoietic stem cell transplantation from a HLA matched donor. However, this is not a viable option for many patients due to the unavailability of a suitable matched donor.

An alternative curative therapy is an autologous hematopoietic stem cell (HSC) transplantation with ex vivo gene therapy. In this approach, the patient acts as their own donor, eliminating the risk of immunological complications. Successful implementation of this approach relies on the development of a lentiviral vector or CRISPR based therapy to introduce a functional copy of the gene of interest or to correct the pathogenic mutation in the patient's HSCs.

Previous viral-based therapies utilized the CMMP-WAS γ-retroviral vector. This therapy restored function and platelet counts in all patients. However, 7/9 patients developed acute leukemia due to insertional oncogenesis (see, e.g., Braun (2014) *Sci. Transl. Med.* 6(227): 227ra33).

Another therapy uses a safer SIN lentiviral vector driven by a 1.6 kb promoter fragment of the endogenous WAS gene. Using this vector, about 6/7 patients showed clinical improvement post gene therapy. T, B, and NK cells were functional and normal immune cell counts were restored. Additionally, there was a decrease in severity and frequency of infections and severe eczema was resolved. However, platelet counts and mean platelet size remain under normal values. The patients remained microthrombocytopenic and retained a risk of severe bleeding episodes.

SUMMARY

Described herein is the development of novel lentiviral vector(s) (LVs) for the treatment of Wiskott-Aldrich Syndrome (WAS). The vectors described herein show better (higher) expression than the current lentiviral vector in megakaryocytes and are believed to be able to restore platelet counts to normal levels in WAS patients. Additionally, the vectors described herein are believed to maintain levels of expression similar to the previous SIN LV expressing a WAS gene in all other hematopoietic cell lineages and thus is believed to be able to restore T, B and NK cell counts and function).

Accordingly, various embodiments contemplated herein may include, but need not be limited to, one or more of the following:

Embodiment 1: A recombinant lentiviral vector (LV) for the treatment of Wiskott-Aldrich Syndrome (WAS), said vector comprising:

- an expression cassette comprising:
  - a nucleic acid encoding an effective fragment of the endogenous promoter of the WAS gene where said promoter has maximum length of 600 bp and contains the sequence of HS1pro (SEQ ID NO:1); and
  - a nucleic acid that encodes the Wiskott-Aldrich Syndrome protein (WASp) operably linked to said effective fragment of the endogenous promoter of the WAS gene.

Embodiment 2: The vector of embodiment 1, wherein the sequence of said effective fragment of the endogenous promoter of the WAS gene consists of the sequence of HS1pro (SEQ ID NO:1).

Embodiment 3: The vector according to any one of embodiments 1-2, wherein said expression cassette comprises a slim enhancer element 2 (SEQ ID NO:2=SEQ ID NOs:3-8) or an effective fragment thereof.

Embodiment 4: The vector of embodiment 3, wherein said expression cassette comprises an effective fragment of enhancer element 2 wherein said fragment comprises or consists of enhancer element 2 core sub-element 1 (SEQ ID NO:3+SEQ ID NO:4), enhancer element 2 core sub-element 4 (SEQ ID NO:7), and enhancer element 2 core sub-element 5 (SEQ ID NO:8).

Embodiment 5: The vector of embodiment 4, wherein said expression cassette comprises an effective fragment of enhancer element 2 wherein said fragment consists of enhancer element 2 core sub-element 1 (SEQ ID NO:3+SEQ ID NO:4), enhancer element 2 core sub-element 4 (SEQ ID NO:7), and enhancer element 2 core sub-element 5 (SEQ ID NO:8).

Embodiment 6: The vector of embodiment 3, wherein said expression cassette comprises an effective fragment of enhancer element 2 wherein said fragment comprises or consists of the first half of enhancer element 2 core sub-element 1 (SEQ ID NO:3), and enhancer element 2 core sub-element 5 (SEQ ID NO:8).

Embodiment 7: The vector of embodiment 6, wherein said expression cassette comprises an effective fragment of enhancer element 2 wherein said fragment consists of the first half of enhancer element 2 core sub-element 1 (SEQ ID NO:3), and enhancer element 2 core sub-element 5 (SEQ ID NO:8).

Embodiment 8: The vector of embodiment 3, wherein said expression cassette comprises an effective fragment of enhancer element 2 wherein said fragment comprises or consists of the $1^{st}$ half of Core Sub-Element 1 of Enhancer Element 2 (SEQ ID NO:3).

Embodiment 9: The vector according to any one of embodiments 3 and 8, wherein said expression cassette comprises an effective fragment of enhancer element 2 wherein said fragment comprises or consists of the second half of Core Sub-Element 1 of Enhancer Element 2 (SEQ ID NO:4).

Embodiment 10: The vector according to any one of embodiments 3 and 8-9, wherein said expression cassette comprises an effective fragment of enhancer element 2 wherein said fragment comprises or consists of Core Sub-Element 2 of Enhancer Element 2 (SEQ ID NO:5).

Embodiment 11: The vector according to any one of embodiments 3 and 8-10, wherein said expression cassette comprises an effective fragment of enhancer element 2 wherein said fragment comprises or consists of Core Sub-Element 3 of Enhancer Element 2 (SEQ ID NO:6).

Embodiment 12: The vector according to any one of embodiments 3 and 8-11, wherein said expression cassette comprises an effective fragment of enhancer element 2 wherein said fragment comprises or consists of Core-Sub Element 4 of Enhancer Element 2 (SEQ ID NO:7).

Embodiment 13: The vector according to any one of embodiments 3 and 8-12, wherein said expression cassette comprises an effective fragment of enhancer element 2 wherein said fragment comprises or consists of Core-Sub Element 5 of Enhancer Element 2 (SEQ ID NO:8).

Embodiment 14: The vector according to any one of embodiments 1-13, wherein said expression cassette comprises enhancer element HS3 (SEQ ID NO:9) or an effective fragment thereof.

Embodiment 15: The vector of embodiment 14, wherein said expression cassette comprises an effective fragment of enhancer element HS3 wherein said fragment comprises or consists of HS3 core sequence (SEQ ID NO: 10).

Embodiment 16: The vector of embodiment 15, wherein said expression cassette comprises an effective fragment of enhancer element HS3 wherein said fragment consists of HS3 core sequence (SEQ ID NO: 10).

Embodiment 17: The vector according to any one of embodiments 1-16, wherein said expression cassette comprises enhancer element E9 (SEQ ID NO:11) or an effective fragment thereof.

Embodiment 18: The vector of embodiment 17, wherein said expression cassette comprises an effective fragment of enhancer element E9 wherein said fragment comprises or consists of enhancer element E9 core sequence (SEQ ID NO:12).

Embodiment 19: The vector of embodiment 18, wherein said expression cassette comprises an effective fragment of enhancer element E9 wherein said fragment consists of enhancer element E9 core sequence (SEQ ID NO:12).

Embodiment 20: The vector according to any one of embodiments 1-2, wherein said expression cassette comprises: a slim enhancer element 2 (SEQ ID NO:2=SEQ ID NOs:3-8); and a fragment of the endogenous promoter of the WAS gene consisting of the sequence of HS1pro (SEQ ID NO:1).

Embodiment 21: The vector of embodiment 20, wherein said vector comprises the features shown in FIG. 18 where the sequence encoding mCitrine is replaced with a nucleic acid that encodes the Wiskott-Aldrich Syndrome protein (WASp).

Embodiment 22: The vector of embodiment 20, wherein said vector comprises the sequence show in SEQ ID NO:15 where the sequence encoding mCitrine is replaced with a nucleic acid that encodes the Wiskott-Aldrich Syndrome protein (WASp).

Embodiment 23: The vector according to any one of embodiments 1-2, wherein said expression cassette comprises:

- enhancer element E9 sequence comprising or consisting of the E9 core sequence (SEQ ID NO:12);
- enhancer element HS3 sequence comprising or consisting of HS3 core sequence (SEQ ID NO: 10);
- a slim enhancer element 2 (SEQ ID NO:2=SEQ ID NOs:3-8); and
- a fragment of the endogenous promoter of the WAS gene comprising or consisting of the sequence of HS1pro (SEQ ID NO:1).

Embodiment 24: The vector of embodiment 23, wherein said vector comprises the features shown in FIG. 19 where the sequence encoding mCitrine is replaced with a nucleic acid that encodes the Wiskott-Aldrich Syndrome protein (WASp).

Embodiment 25: The vector of embodiment 23, wherein said vector comprises the sequence show in SEQ ID NO:16 where the sequence encoding mCitrine is replaced with a nucleic acid that encodes the Wiskott-Aldrich Syndrome protein (WASp).

Embodiment 26: The vector according to any one of embodiments 1-2, wherein said expression cassette comprises:

- enhancer element E9 sequence comprising or consisting of the E9 core sequence (SEQ ID NO:12);
- enhancer element HS3 sequence comprising or consisting of HS3 core sequence (SEQ ID NO: 10);
- enhancer element 2 core sub-element 1 (SEQ ID NO:3+SEQ ID NO:4), enhancer element 2 core sub-element 4 (SEQ ID NO:7), and enhancer element 2 core sub-element 5 (SEQ ID NO:8); and a fragment of the endogenous promoter of the WAS gene comprising or consisting of the sequence of HS1pro (SEQ ID NO:1).

Embodiment 27: The vector of embodiment 26, wherein said vector comprises the features shown in FIG. 20 where the sequence encoding mCitrine is replaced with a nucleic acid that encodes the Wiskott-Aldrich Syndrome protein (WASp).

Embodiment 28: The vector of embodiment 26, wherein said vector comprises the sequence show in SEQ ID NO:17 where the sequence encoding mCitrine is replaced with a nucleic acid that encodes the Wiskott-Aldrich Syndrome protein (WASp).

Embodiment 29: The vector according to any one of embodiments 1-2, wherein said expression cassette comprises:

enhancer element E9 sequence comprising or consisting of the E9 core sequence (SEQ ID NO:12);

enhancer element HS3 sequence comprising or consisting of HS3 core sequence (SEQ ID NO: 10); a first half of enhancer element 2 core sub-element 1 (SEQ ID NO:3), and enhancer element 2 core sub-element 5 (SEQ ID NO:8); and a fragment of the endogenous promoter of the WAS gene comprising or consisting of the sequence of HS1pro (SEQ ID NO:1).

Embodiment 30: The vector of embodiment 29, wherein said vector comprises the features shown in FIG. 21 where the sequence encoding mCitrine is replaced with a nucleic acid that encodes the Wiskott-Aldrich Syndrome protein (WASp).

Embodiment 31: The vector of embodiment 29, wherein said vector comprises the sequence show in SEQ ID NO:18 where the sequence encoding mCitrine is replaced with a nucleic acid that encodes the Wiskott-Aldrich Syndrome protein (WASp).

Embodiment 32: The vector according to any one of embodiments 1-31, wherein said nucleic acid that encodes a nucleic acid that encodes WASp protein is a WAS cDNA or a codon-optimized WAS gene.

Embodiment 33: The vector of embodiment 32, wherein said nucleic acid that encodes a nucleic acid that encodes WASp protein is a WAS cDNA (SEQ ID NO:13).

Embodiment 34: The vector of embodiment 32, wherein said nucleic acid that encodes a nucleic acid that encodes WASp protein is a codon optimized WAS.

Embodiment 35: The vector of embodiment 34, wherein the sequence of said nucleic acid that encodes WASP is a codon optimized WAS selected from the group consisting of jCAT codon optimized WAS, GeneArt optimized WAS, and IDT optimized WAS.

Embodiment 36: The vector according to any one of embodiments 1-35, wherein said vector comprises a ψ region vector genome packaging signal.

Embodiment 37: The vector according to any one of embodiments 1-36, wherein said vector comprise a 5' LTR comprising a CMV enhancer/promoter.

Embodiment 38: The vector according to any one of embodiments 1-37, wherein said vector comprises a Rev Responsive Element (RRE).

Embodiment 39: The vector according to any one of embodiments 1-38, wherein said vector comprises a central polypurine tract.

Embodiment 40: The vector according to any one of embodiments 1-39, wherein said vector comprises a post-translational regulatory element.

Embodiment 41: The vector of embodiment 40, wherein the posttranscriptional regulatory element is modified Woodchuck Post-transcriptional Regulatory Element (WPRE).

Embodiment 42: The vector according to any one of embodiments 1-41, wherein said vector is incapable of reconstituting a wild-type lentivirus through recombination.

Embodiment 43: The vector according to any one of embodiments 1-42, wherein said vector shows high expression in megakaryocytes.

Embodiment 44: The vector according to any one of embodiments 1-43, wherein said vector restores T, B and NK cell counts and function when administered to a mammal having WAS.

Embodiment 45: A host cell transduced with a vector according to any one of embodiments 1-44.

Embodiment 46: The host cell of embodiment 45, wherein the cell is a stem cell.

Embodiment 47: The host cell of embodiment 46, wherein said cell is a stem cell derived from bone marrow, and/or from umbilical cord blood, and/or from peripheral blood.

Embodiment 48: The host cell of embodiment 45, wherein the cell is a human hematopoietic progenitor cell.

Embodiment 49: The host cell of embodiment 48, wherein the human hematopoietic progenitor cell is a CD34+ cell.

Embodiment 50: A method of treating Wiskott-Aldrich Syndrome (WAS), in a subject, said method comprising:

transducing a stem cell and/or progenitor cell from said subject with a vector according to any one of embodiments 1-44; and transplanting said transduced cell or cells derived therefrom into said subject where said cells or derivatives therefrom express said WASp protein.

Embodiment 51: The method of embodiment 50, wherein the cell is a stem cell.

Embodiment 52: The host cell of embodiment 50, wherein said cell is a stem cell derived from bone marrow.

Embodiment 53: The method of embodiment 50, wherein the cell is a human hematopoietic stem and progenitor cell.

Embodiment 54: The method of embodiment 53, wherein the human hematopoietic progenitor cell is a CD34+ cell.

Embodiment 55: A recombinant nucleic acid comprising one or more of the following:

a nucleic acid sequence comprising or consisting of a minimal endogenous promoter of the WAS gene said minimal endogenous promoter comprising or consisting of HS1pro (SEQ ID NO:1); and/or a nucleic acid sequence comprising or consisting of a slim enhancer element 2 (SEQ ID NO:2=SEQ ID NOs:3-8) or an effective fragment thereof; a nucleic acid sequence comprising or consisting of a 1st half of Core Sub-Element 1 of Enhancer Element 2 (SEQ ID NO: 3); and/or a nucleic acid sequence comprising or consisting of a 2nd half of Core Sub-Element 1 of Enhancer Element 2 (SEQ ID NO:4); and/or a nucleic acid sequence comprising or consisting of a Core Sub-Element 2 of Enhancer Element 2 (SEQ ID NO:5); and/or a nucleic acid sequence comprising or consisting of a Core Sub-Element 3 of Enhancer Element 2 (SEQ ID NO:6); and/or a nucleic acid sequence comprising or consisting of a Core-Sub Element 4 of Enhancer Element 2 (SEQ ID NO:7); and/or a nucleic acid sequence comprising or consisting of a Core-Sub Element 5 of Enhancer Element 2 (SEQ ID NO: 8); and/or a nucleic acid sequence comprising or consisting of enhancer element HS3 (full) (SEQ ID NO:9) or an effective fragment thereof; and/or a nucleic acid sequence comprising or consisting of Enhancer element HS3 core (SEQ ID NO:10); and/or a nucleic acid sequence comprising or consisting of Enhancer element E9 (full) (SEQ ID NO:11) or an effective fragment thereof; and/or a nucleic acid sequence comprising or consisting of Enhancer element E9 core (SEQ ID NO:12).

Embodiment 56: The nucleic acid of embodiment 55, wherein said nucleic acid comprises a nucleic acid sequence comprising or consisting of a minimal endogenous promoter of the WAS gene said minimal endogenous promoter comprising or consisting of HS1pro (SEQ ID NO:1).

Embodiment 57: The nucleic acid of embodiment 55, wherein said nucleic acid comprises a nucleic acid sequence comprising or consisting of a slim enhancer element 2 (SEQ ID NO:2=SEQ ID NOs:3-8) or an effective fragment thereof.

Embodiment 58: The nucleic acid of embodiment 55, wherein said nucleic acid comprises a nucleic acid sequence comprising or consisting of a 1st half of Core Sub-Element 1 of Enhancer Element 2 (SEQ ID NO: 3).

Embodiment 59: The nucleic acid according to any one of embodiments 55, and 58, wherein said nucleic acid comprises a nucleic acid sequence comprising or consisting of a 2nd half of Core Sub-Element 1 of Enhancer Element 2 (SEQ ID NO:4).

Embodiment 60: The nucleic acid according to any one of embodiments 55, and 58-59, wherein said nucleic acid comprises a nucleic acid sequence comprising or consisting of a Core Sub-Element 2 of Enhancer Element 2 (SEQ ID NO:5).

Embodiment 61: The nucleic acid according to any one of embodiments 55, and 58-60, wherein said nucleic acid comprises a nucleic acid sequence comprising or consisting of a Core Sub-Element 3 of Enhancer Element 2 (SEQ ID NO:6).

Embodiment 62: The nucleic acid according to any one of embodiments 55, and 58-61, wherein said nucleic acid comprises a nucleic acid sequence comprising or consisting of a Core-Sub Element 4 of Enhancer Element 2 (SEQ ID NO:7).

Embodiment 63: The nucleic acid according to any one of embodiments 55, and 58-62, wherein said nucleic acid comprises a nucleic acid sequence comprising or consisting of a Core-Sub Element 5 of Enhancer Element 2 (SEQ ID NO: 8).

Embodiment 64: The nucleic acid according to any one of embodiments 55, and 58-63, wherein said nucleic acid comprises a nucleic acid sequence comprising or consisting of enhancer element HS3 (full) (SEQ ID NO:9) or an effective fragment thereof.

Embodiment 65: The nucleic acid according to any one of embodiments 55, and 58-64, wherein said nucleic acid comprises a nucleic acid sequence comprising or consisting of Enhancer element HS3 core (SEQ ID NO:10).

Embodiment 66: The nucleic acid according to any one of embodiments 55, and 58-65, wherein said nucleic acid comprises a nucleic acid sequence comprising or consisting of Enhancer element E9 (full) (SEQ ID NO:11) or an effective fragment thereof.

Embodiment 67: The nucleic acid according to any one of embodiments 55, and 58-66, wherein said nucleic acid comprises a nucleic acid sequence comprising or consisting of Enhancer element E9 core (SEQ ID NO:12).

Embodiment 68: The nucleic acid according to any one of embodiments 55-67, wherein said nucleic acid comprises an expression cassette.

Embodiment 69: The nucleic acid of embodiment 68, wherein said expression cassette is effective to express WASp when transduced into a mammalian cell.

Embodiment 70: The nucleic acid of embodiment 55, wherein said nucleic acid comprises a vector according to any one of embodiments 1-44.

Definitions.

A "promoter" refers to a regulatory sequence in a nucleic acid required to initiate transcription of a gene (e.g., a gene operably coupled to the promoter).

An "enhancer" refers to a regulatory DNA sequence that, when bound by specific proteins called transcription factors, enhance the transcription of an associated gene.

An "effective fragment" when used with respect to a promoter (e.g., an effective fragment of a WAS promoter) refers to a fragment of the full-length promoter that is sufficient to initiate transcription of a gene operably linked to that promoter.

An "effective fragment" when used with respect to an enhancer (e.g., an effective fragment of a WAS enhancer) refers to a fragment of the full-length enhancer that is sufficient to provide regulate expression of an operably linked gene when bound by a transcription factor. In certain embodiments the regulation is comparable with respect to expression level and/or lineage offered by the full-length enhancer.

The term "operably linked" refers to a nucleic acid sequence placed into a functional relationship with another nucleic acid sequence. For example, a promoter is operably linked to a gene when that promoter is placed in a location that permits that promoter to initiate transcription of that gene. An enhancer is operably linked to a gene when that enhancer, when bound by an appropriate transcription factor, is able to regulate (e.g., to upregulate) expression of that gene.

"Recombinant" is used consistently with its usage in the art to refer to a nucleic acid sequence that comprises portions that do not naturally occur together as part of a single sequence or that have been rearranged relative to a naturally occurring sequence. A recombinant nucleic acid is created by a process that involves the hand of man and/or is generated from a nucleic acid that was created by hand of man (e.g., by one or more cycles of replication, amplification, transcription, etc.). A recombinant virus is one that comprises a recombinant nucleic acid. A recombinant cell is one that comprises a recombinant nucleic acid.

As used herein, the term "recombinant lentiviral vector" or "recombinant LV" refers to an artificially created polynucleotide vector assembled from an LV and a plurality of additional segments as a result of human intervention and manipulation.

By "an effective amount" is meant the amount of a required agent or composition comprising the agent to ameliorate or eliminate symptoms of a disease relative to an untreated patient. The effective amount of composition(s) used to practice the methods described herein for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

DETAILED DESCRIPTION

Figure 1:
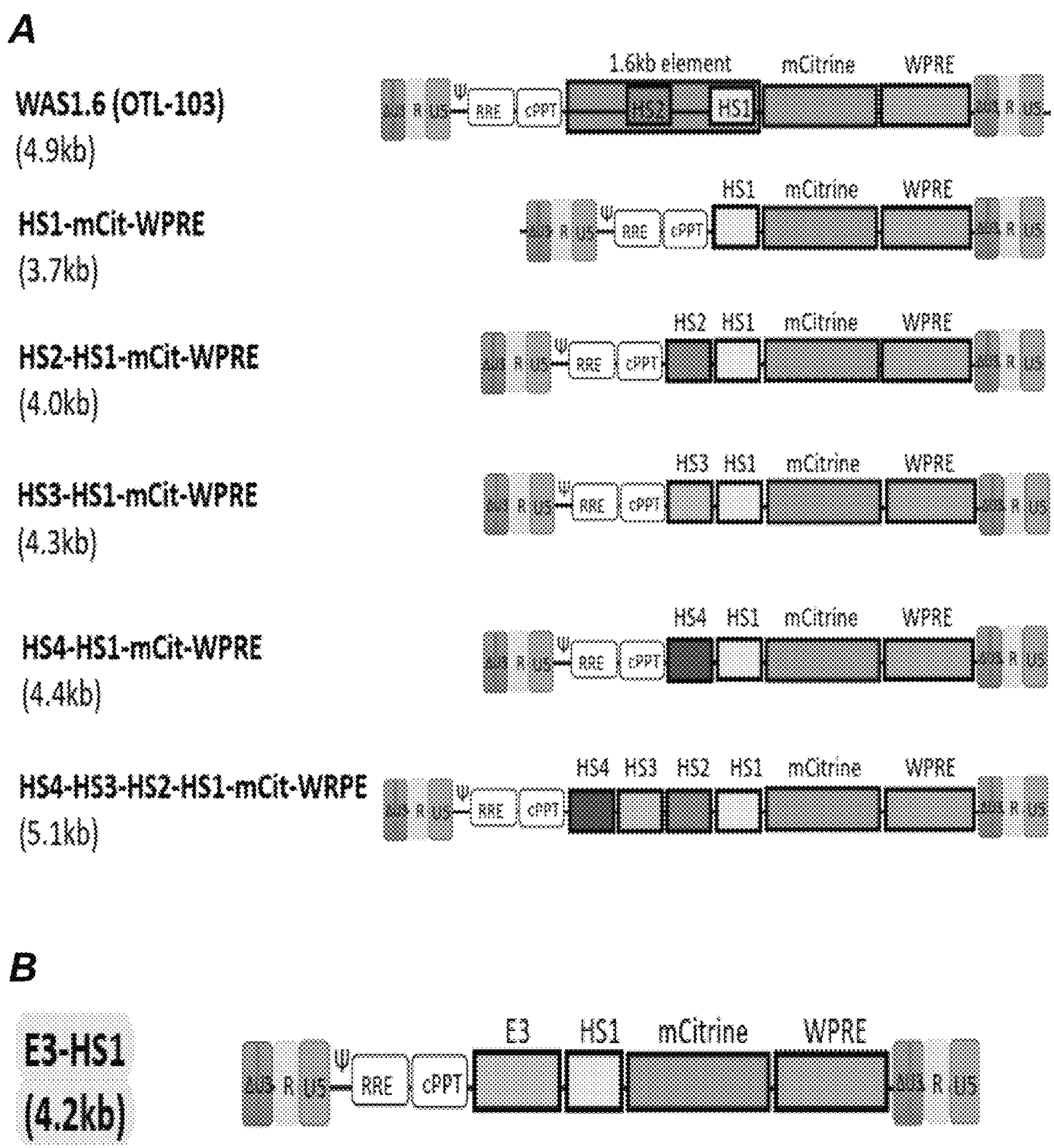
FIG. 1, panel A, shows illustrative LV constructs used to evaluate regulatory activity of various combinations of elements HS1, HS2, HS3, and HS4. Panel B shows a construct used to evaluate the combination of the E3 element and HS1.

In various embodiments, lentiviral vectors are provided for the treatment (or prophylaxis) of Wiskott-Aldrich Syndrome (WAS) are provided. In certain embodiments the vectors are optimized to reduce vector size, increase expression level and titer. Additionally, in various embodiments the vectors to recapitulate the expression pattern of the native WAS gene, e.g., as described herein.

In particular, a bioinformatic analysis (using publicly available databases: Project Encode, Ensemnbl, FANTOM, VISTA Enhancer Browser, GeneHancer) was utilized to elucidate the endogenous regulatory elements of the native WAS gene. Thirteen putative endogenous enhancer elements were identified contained within a 1.1 million base pair window.

A lentiviral library was constructed in order to experimentally validate each of the putative regulatory elements. Each element was validated in MEG-01 cells (Megakaryocyte cell line), Jurkats (T-cell line), RAMOs (B-cell line) as well as in a cord blood CD34+ differentiated megakaryocytes for enhancer activity.

Further experiments were done to identify necessary (core) region(s) of the enhancers and the WAS endogenous promoter and the combinations of minimal promoter and reduced (slim) enhancer elements necessary to achieve suitable expression of the WAS gene were identified. The validated enhancer elements will be used to design our lead candidate lentiviral vector for the treatment of WAS.

Accordingly, in certain embodiments a recombinant lentiviral vector (LV) for the treatment of Wiskott-Aldrich Syndrome (WAS) is provided where the vector comprises an expression cassette comprising a nucleic acid encoding an effective fragment of the endogenous promoter of the WAS gene where the promoter has maximum length of 600 bp and contains the sequence of HS1pro (SEQ ID NO:1); and a nucleic acid that encodes the Wiskott-Aldrich Syndrome protein (WASp) operably linked to the effective fragment of the endogenous promoter of the WAS gene. In certain embodiments the effective fragment of the endogenous promoter of the WAS gene consists of the sequence of HS1pro (SEQ ID NO:1).

In certain embodiments the expression cassette comprises a slim enhancer element 2 (SEQ ID NO:2=SEQ ID NOs:3-8) or an effective fragment thereof. In certain embodiments the expression cassette comprises an effective fragment of enhancer element 2 where the fragment comprises or consists of enhancer element 2 core sub-element 1 (SEQ ID NO:3+SEQ ID NO:4), enhancer element 2 core sub-element 4 (SEQ ID NO:7), and enhancer element 2 core sub-element 5 (SEQ ID NO:8). In certain embodiments the expression cassette comprises an effective fragment of enhancer element 2 where the fragment consists of enhancer element 2 core sub-element 1 (SEQ ID NO:3+SEQ ID NO:4), enhancer element 2 core sub-element 4 (SEQ ID NO:7), and enhancer element 2 core sub-element 5 (SEQ ID NO:8). In certain embodiments the expression cassette comprises an effective fragment of enhancer element 2 where the fragment comprises or consists of the first half of enhancer element 2 core sub-element 1 (SEQ ID NO:3), and enhancer element 2 core sub-element 5 (SEQ ID NO:8). In certain embodiments the expression cassette comprises an effective fragment of enhancer element 2 where the fragment consists of the first half of enhancer element 2 core sub-element 1 (SEQ ID NO:3), and enhancer element 2 core sub-element 5 (SEQ ID NO:8).

In certain embodiments the expression cassette comprises an effective fragment of enhancer element 2 where the fragment comprises or consists of the $1^{st}$ half of Core Sub-Element 1 of Enhancer Element 2 (SEQ ID NO:3), and/or an effective fragment of enhancer element 2 where the fragment comprises or consists of the second half of Core Sub-Element 1 of Enhancer Element 2 (SEQ ID NO:4), and/or an effective fragment of enhancer element 2 where the fragment comprises or consists of Core Sub-Element 2 of Enhancer Element 2 (SEQ ID NO:5); and/or an effective fragment of enhancer element 2 where the fragment comprises or consists of Core Sub-Element 3 of Enhancer Element 2 (SEQ ID NO:6); and/or an effective fragment of enhancer element 2 where the fragment comprises or consists of Core-Sub Element 4 of Enhancer Element 2 (SEQ ID NO:7); and/or an effective fragment of enhancer element 2 where the fragment comprises or consists of Core-Sub Element 5 of Enhancer Element 2 (SEQ ID NO:8).

In certain embodiments the expression cassette comprises enhancer element HS3 (SEQ ID NO:9) or an effective fragment thereof. In certain embodiments the expression cassette comprises an effective fragment of enhancer element HS3 where the fragment comprises or consists of HS3 core sequence (SEQ ID NO: 10). In certain embodiments the expression cassette comprises an effective fragment of enhancer element HS3 where the fragment consists of HS3 core sequence (SEQ ID NO: 10).

In certain embodiments the expression cassette comprises enhancer element E9 (SEQ ID NO:11) or an effective fragment thereof. In certain embodiments the expression cassette comprises an effective fragment of enhancer element E9 where the fragment comprises or consists of enhancer element E9 core sequence (SEQ ID NO:12). In certain embodiments the expression cassette comprises an effective fragment of enhancer element E9 where the fragment consists of enhancer element E9 core sequence (SEQ ID NO:12).

Figure 18:
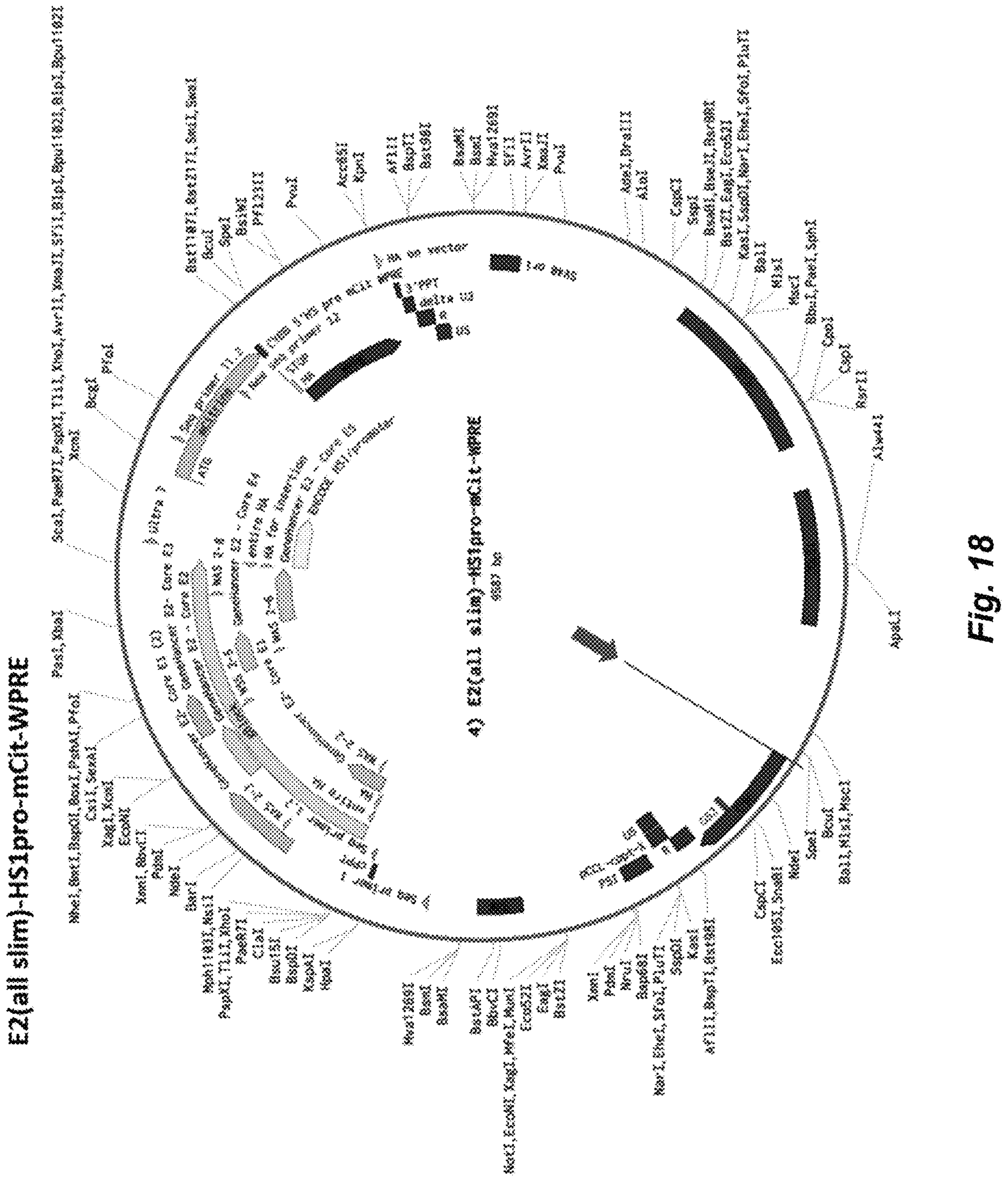
FIG. 18 shows a schematic of the E2(all slim) vector (E2(all slim)-HS1pro-mCit-WPRE).

In certain embodiments the expression cassette comprises a slim enhancer element 2 (SEQ ID NO:2=SEQ ID NOs:3-8), and a fragment of the endogenous promoter of the WAS gene consisting of the sequence of HS1pro (SEQ ID NO:1). In certain embodiments this vector comprises the features shown in FIG. 18 where the sequence encoding mCitrine is replaced with a nucleic acid that encodes the Wiskott-Aldrich Syndrome protein (WASp). In certain embodiments this vector comprises the sequence show in SEQ ID NO:15 where the sequence encoding mCitrine is replaced with a nucleic acid that encodes the Wiskott-Aldrich Syndrome protein (WASp).

In certain embodiments the expression cassette comprises enhancer element E9 sequence comprising or consisting of the E9 core sequence (SEQ ID NO:12), enhancer element HS3 sequence comprising or consisting of HS3 core sequence (SEQ ID NO: 10), a slim enhancer element 2 (SEQ ID NO:2=SEQ ID NOs:3-8); and a fragment of the endogenous promoter of the WAS gene consisting of the sequence of HS1pro (SEQ ID NO:1). In certain embodiments this vector comprises the features shown in FIG. 19 where the sequence encoding mCitrine is replaced with a nucleic acid that encodes the Wiskott-Aldrich Syndrome protein (WASp). In certain embodiments this vector comprises the sequence show in SEQ ID NO:16 where the sequence encoding mCitrine is replaced with a nucleic acid that encodes the Wiskott-Aldrich Syndrome protein (WASp).

In certain embodiments the expression cassette comprises an enhancer element E9 sequence comprising or consisting of the E9 core sequence (SEQ ID NO:12), enhancer element HS3 sequence comprising or consisting of HS3 core sequence (SEQ ID NO: 10), enhancer element 2 core sub-element 1 (SEQ ID NO:3+SEQ ID NO:4), enhancer element 2 core sub-element 4 (SEQ ID NO:7), and enhancer element 2 core sub-element 5 (SEQ ID NO:8); and a fragment of the endogenous promoter of the WAS gene consisting of the sequence of HS1pro (SEQ ID NO:1). In certain embodiments this vector comprises the features shown in FIG. 20 where the sequence encoding mCitrine is replaced with a nucleic acid that encodes the Wiskott-Aldrich Syndrome protein (WASp). In certain embodiments this vector comprises the sequence show in SEQ ID NO:17 where the sequence encoding mCitrine is replaced with a nucleic acid that encodes the Wiskott-Aldrich Syndrome protein (WASp).

In certain embodiments the expression cassette comprises enhancer element E9 sequence comprising or consisting of the E9 core sequence (SEQ ID NO:12), enhancer element HS3 sequence comprising or consisting of HS3 core sequence (SEQ ID NO: 10), a first half of enhancer element 2 core sub-element 1 (SEQ ID NO:3), and enhancer element 2 core sub-element 5 (SEQ ID NO:8); and a fragment of the endogenous promoter of the WAS gene consisting of the sequence of HS1pro (SEQ ID NO:1). In certain embodiments this vector comprises the features shown in FIG. 21 where the sequence encoding mCitrine is replaced with a nucleic acid that encodes the Wiskott-Aldrich Syndrome protein (WASp). In certain embodiments this vector comprises the sequence show in SEQ ID NO:18 where the sequence encoding mCitrine is replaced with a nucleic acid that encodes the Wiskott-Aldrich Syndrome protein (WASp).

It will be recognized that, for clinical use, the mCitrine reporter can be replaced with a nucleic acid encoding a WASp protein. In certain embodiments such a nucleic acid is a WAS cDNA or a codon-optimized WAS gene (e.g., a jCAT optimized WAS). In certain embodiments the sequence of the nucleic acid that encodes WASP is a codon optimized WAS selected from the group consisting of jCAT codon optimized WAS, GeneArt optimized WAS, and IDT optimized WAS.

It will also be recognized that the expression cassettes described herein with respect to lentiviral vectors need not be limited to this use, and can be incorporated in essentially any other construct (e.g., a CRISPR construct) where expression of a WASp is desired. Thus, in certain embodiments, nucleic acid constructs comprising any of the expression cassette components described herein are contemplated.

TABLE 1

Nucleic acid sequences of various components of the lentiviral vectors for treatment of WAS as described herein.

| Element SEQ ID NO | Nucleic Acid Sequence |
|---|---|
| HS1pro (what we define | TCAGCCTCAGGCTACCTAGGTGCTT TAGAAAGGAGGCCACCCAGGCCCAT |

TABLE 1-continued

Nucleic acid sequences of various components of the lentiviral vectors for treatment of WAS as described herein.

| Element SEQ ID NO | Nucleic Acid Sequence |
|---|---|
| as the | GACTACTCCTTGCCACAGGGAGCCC |
| minimal | TGCACACAGATGTGCTAAGCTCTCG |
| endogenous | CTGCCAGCCAGAGGGAGGAGGGTCT |
| promoter | GAGCCAGTCAGAAGGAGATGGGCCC |
| of the | CAGAGAGTAAGAAAGGGGGAGGAGG |
| WAS gene) | ACCCAAGCTGATCCAAAAGGTGGGT |
| (SEQ ID | CTAAGCAGTCAAGTGGAGGAGGGTT |
| NO: 1) | CCAATCTGATGGCGGAGGGCCCAAG |
| | CTCAGCCTAACGAGGAGGCCAGGCC |
| | CACCAAGGGGCCCCTGGAGGACTTG |
| | TTTCCCTTGTCCCTTGTGGTTTTTT |
| | GCATTTCCTGTTCCCTTGCTGCTCA |
| | TTGCGGAAGTTCCTCTTCTTACCCT |
| | GCACCCAGAGCCTCGCCAGAGAAGA |
| | CAAGGGCAGAAAGCACC |
| Enhancer | |
| Element 2 | AGGCAAAGGG |
| (Full) | CAGTTCACACCAAAGTCCACCCCCA |
| | GCTCAGGGCCCGATACAGTAAAGGA |
| | AATCAGGAAAAGTTTACTGAGCAAA |
| | TGGATAGGCTGGGTAAGCCAGGGAG |
| | CTCTTCTCCCTGTGAAATTAAAGTG |
| | GGCCTGAAGATCATGCAAGTCTGAT |
| | TTCCACTGGTTTTGGGAATTTCCCT |
| | TTGTTTCCCCAGAGGACCACTGCTC |
| | TGATGGGATCTCCCTGGGGCATGGG |
| | GCTAGGGTCAGGTCACACAGGAACA |
| | CTCCTGAGTTCTTCCCTGTCAGTCT |
| | ACCTCTCTGAAGAACTGTCAGAAGA |
| | ACACCTTCCCTGCCTTCCCCTTCCT |
| | ACCCTGGAGTGTTCTGTGAGAAAGG |
| | CTACTCTGAGATAGAAAATAGGGCC |
| | CATGTTTGTCTCCAGTCCTCTTGGA |
| | GGTGAAGAGACCTGAAGGGTAAGGG |
| | GGTGTGGAGGTTGTGAAGGCGGGAA |
| | GGGGGGTAGCCCCTTCACCAATGTA |
| | AACAAGGATGTGGGTTCTGCGGCCA |
| | CACTCTCCCCCGCCCTCCCCAGCGG |
| | CATTTCCAGCAAGTCACATGTCCTG |
| | CGCACAGGCTGGGGGCCCCCTGCTG |
| | CTGCCTTTCTTAGAAGCCAGGACCA |
| | CAGAGCCCGCACAGTGAGCTACTTG |
| | GGGAGCTATTTCTGTAGACTGAGCT |
| | TGGGGTACTGGGAGGCAGTGCTGTT |
| | GGCAGCTGCAGTAAACAGGAACAAA |
| | GATGAGAATGAAGGGGTTAAATAGG |
| | GGTTGGCTGGCCAGGCTCAGAGAGA |
| | TAGGCTGAGGTGCTGGAGAAAGCCC |
| | ATCTCCTATGGAAAGGTCAACGGTC |
| | ATTTCCAGGCCTGGGAGTTCTATCT |
| | TCAAGAGCTAGATGCCAGATGCAGG |
| | AAAATGGGGAAAGAGAGGAGACTGT |
| | GGAACAGGGAAGGGATCTGGGGGAA |
| | AACCCCCTGAGGGTCCCATTTCTCT |
| | GCCACTGACCCCTTTGCCTGGCAGA |
| | AAGGCTCTGCTGCCTCCTAGCTGTG |
| | TAGCAATGGATAAGGCCTTTAACCT |
| | CTCTAAGCTGAAATGTCCTCATGCA |
| | TAAGGTGGAGACAGTAACTCCTCTT |
| | CCATCTGCTGGGTGTTGTCAAAACT |
| | ACACAGGAGGTTTGCCAAGCACCTA |
| | AGGCACAGTAGGTGGTCAAGAAACA |
| | GGAACACAATTTGTCATGACGACAA |
| | TGATTCCTTCATATGCTAGTTACCC |
| | ACGAGTCAGCCAGAATGTTGCCATA |
| | ACCACTTATGAAGCCCTTCCTCATT |
| | TCTGTTGCAATTCCTCAGCCAGAGG |
| | AAAGCCCCAAATGCAGACCTAGGAT |
| | GCATGTCCTCTCCTGGCTCTCTACC |
| | TTTAGCGAAACCAAAGGTCCACAAG |
| | TCTACCTCTAGGCCGTTAGTTCTAA |
| | CAAAACTTCAGCAGTTAAATTAATA |

TABLE 1-continued

Nucleic acid sequences of various components of the lentiviral vectors for treatment of WAS as described herein.

| Element SEQ ID NO | Nucleic Acid Sequence |
|---|---|
| | TCGAATTAACAATACAGGCTTCAAA |
| | CTCTGTCTCAAAAAAAAAAAAAAAGA |
| | ATTCGTTTTTCTGACTTTCCTAGCT |
| | CCACCTCTGTCCTCCAGAAAGCCCT |
| | CCTCTTCCCAGAAGGCTGGCACACA |
| | GGGCTGGGGGCCAGGCTTGACTTCC |
| | CTGTGGAGGGGTCTGAGGTTGGGGG |
| | GATGACCTGCAGAGGTAGGGGAATT |
| | CAGAGAACTTGTTTTGATAGAAACT |
| | GAAACTCCTCCTCTTGCTGACGCTG |
| | CACTTGTGGGCAATCTGCACCTGTT |
| | CTCCCCTCCCAGAGGCCAGCTGGAA |
| | GGGGGTCCCCCACCATTCTACCTCT |
| | GTTCCCATCTCAAACAGGGCTCAGA |
| | AATCCTCAGTACAATACTACAATTG |
| | GTCCCACACCAAAGACTTTTCACAC |
| | TCCAACTCATTCTATCCTTACCAAA |
| | ACACTCTTACTTTACCCAGGAGACA |
| | CAGAAATGTGGCAAAGCTTGCCTGG |
| | GATCACAGATTTAGGGGGAGTGAAG |
| | GGGAGGCCAGGCTCTCAAAGGGTAA |
| | CTGCTGGCCCCAGCTGATACCCAGA |
| | TTTATGTTAAGAAGCAAGACATGAG |
| | AGCCTGGATTATCTTCCTATAGGGT |
| | CCTACCATTTGCTTTAGAGACATCT |
| | GAGAACTGCCTACTCCCCAGGTAGC |
| | TGCCTGCCTCCCAGAAGAGCCACAG |
| | CAAGTTCCGCTAAGGGCAAAAAAGG |
| | AAGCTAGGTGTCTACAGGGAACCTA |
| | AAAACAAACCACACTAACGTGTGTA |
| | CACACAGCTGCAGAGGGAGACAGGG |
| | ACCTGGTCTGCTCCCCACTACCCTC |
| | CTGGTCCAGTGGGAACCCTGGCCCC |
| | ACTGAGAACCAATCTCCTGAGGAGA |
| | TGAGCCAGGACAAAGGTCTCACTTG |
| | CCTGTCAAGCAGCTGTGGTGTGTCT |
| | CTTGAGGCCTCAGTTTCCCCATTTA |
| | TAAAACAATCAAAATTGATCTCAGA |
| | TCCATCCCTCCTAGTGCTGATGTTC |
| | CAAGACCAAAAGGCCCAGAAGAGTG |
| | GGCCTAGCTAATGTTTCTGGGCCTC |
| | ATCGTGGTAACATGCACAGCCCTTG |
| | CCACTCCCCCATGGCCCATGTAGAA |
| | ACAACCATGTGGCCTTCACTCTGCC |
| | CACAGAAGCTAGCACCAGGACCCTG |
| | GTCAGGGTTAGAGGTTTCTGCTGAG |
| | TCAAAGCCACATGGAGGGAGGGAGC |
| | AAGGGAGAGATGCAGAGTCATGTTT |
| | CCAGGAGGAGGTTATCTGAGCATAA |
| | CAGGGACAGGGTGGGCCACAGGATA |
| | CCTCTGAGGCTCAGGTTCCCACCTC |
| | CACTCCACCCAAGCCTTCAATGATG |
| | CTCATGAATCCCCAATAAGAGGAGG |
| | TGGGAGAGAACTGAGCGCAAGCAAT |
| | GGATATTGCTTAACTCAGGGGAACC |
| | AATGGCAGGCAGGCAGCTACCTGGG |
| | GAGTAGGCAATTCTCAGAAGTCTCT |
| | AAAGCAAATGGTAGGACCCTATAGG |
| | AAGATAATCCAGGGGAACAGAAGGC |
| | AGAAAGCCACCTGCCTCAAGACTCC |
| | CAACAACAGAGGGCCACGTGCTCCT |
| | ACTTGGAGGAGGTAAGGTCCAGAGA |
| | AGTCAAGGAACACAGCCAAGGTCAT |
| | CCAGCCAGTTGACAACCAAGCTAAG |
| | AAGCTAAGGATCCTAGGATCATAAA |
| | AAGAATGTGTCCTGGCCGGATGCGG |
| | TGGCTCATGCCTATAATCCAATCTT |
| | TTCACCTGTCTCATGGGATAATGAT |
| | CCAAGTTTTGCAGTGAGCCTGAAGC |
| | ACCCAGCTGAATGCCTAGCACACAG |
| | CAGGGGTCAAGGAAACAGTGCCCTC |
| | TATGTTTGCAGCCCCCGCCCAACTC |
| | CAACTCTCTGCTCCACGTTCCTTCC |

TABLE 1-continued

Nucleic acid sequences of various components of the lentiviral vectors for treatment of WAS as described herein.

| Element SEQ ID NO | Nucleic Acid Sequence |
|---|---|
| | ACTATTCAACACATGGCAGGAAGTC<br>AGCCTGTAGGGCTTCACACTACAGT<br>CTAAGCTGACTGCCATCTGTCCCCA<br>TCCAGGCGAGGCTGGAAACGGGGGC<br>AGCAAAAAGCCCAGGGACAAAGTCC<br>CCTTCCCAGGCACATGTATTATGCA<br>CTCTGCACCAAGGAAACCTCCAGAT<br>AAGGTCTAGAGACCAAGGGCCATGT<br>ACTTCGGGGGAGAGGCCAGAGGACT<br>TCTGAGGTTTTACAGAGAAAAGCCA<br>AAGGCAGCCCAGTCAGGGGAAATGT<br>GTAGCCATAGTGCCGATAAGGAAAG<br>GCCTTCAACCTGCCCTGGTCAGCTC<br>TTCCTGTAAGTAGAGGCCCCTTACC<br>GAAGGCCCCAGTGGGAGGAAGGGTC<br>GGGAGTATTTGGGGAGAACAGCTAG<br>ATACATATAGACACACACACACACA<br>CAAATACTGCTCTTGATACGAGTTA<br>CTACAACAAGCCAGGTCC |
| Enhancer element 2 (Slim) (SEQ ID NO: 2) | GACCTGAAGGGTAAGGGGGTGTGGA<br>GGTTGTGAAGGCGGGAAGGGGGGTA<br>GCCCCTTCACCAATGTAAACAAGGA<br>TGTGGGTTCTGCGGCCACACTCTCC<br>CCCGCCCTCCCCAGCGGCATTTCCA<br>GCAAGTCACATGTCCTGCGCACAGG<br>CTGGGGGCCCCCTGCTGCTGCCTTT<br>CTTAGAAGCCAGGACCACAGAGCCC<br>GCACAGTGAGCTACTTGGGGAGCTA<br>TTTCTGTAGACTGAGCTTGGGGTAC<br>TGGGAGGCAGTGCTGTTGGCGATCT<br>GGGGGAAAACCCCCTGAGGGTCCCA<br>TTTCTCTGCCACTGACCCCTTTGCC<br>TGGCAGAAAGGCTCTGCTGCCTCCT<br>AGCTGTGTAGCAATGGATAAGGCCT<br>TTAACCTCTCTAAGCTGAAATGTCC<br>TCATGCATAAGGTGGAGACAGTAAC<br>TCCTCTTCCATCTGCTGGGTGTTGT<br>CAAAACTACACAGGAGGTTTGCCAA<br>GCACCTAAGGCACAGTAGGTGGTCA<br>AGAAACAGGAACACAATTTGTCATG<br>ACGACAATGATTCCTTCATATGCTA<br>GTTACCCACGAGTCAGCCAGAATGT<br>TGCCATAACCACTTATGAAGCCCTT<br>CCTCATTTCTGTTGCAATTCCTCAG<br>CCAGAGGAAAGCCCCACCACCTCTG<br>TCCTCCAGAAAGCCCTCCTCTTCCC<br>AGAAGGCTGGCACACAGGGCTGGGG<br>GCCAGGCTTGACTTCCCTGTGGAGG<br>GGTCTGAGGTTGGGGGGATGACCTG<br>CAGAGGTAGGGGAATTCAGAGAACT<br>TGTTTTGATAGAAACTGAAACTCCT<br>CCTCTTGCTGACGCTGCACTTGTGG<br>GCAATCTGCACCTGTTCTCCCCTCC<br>CAGAGGCCAGCTGGAAGGGGGTCCC<br>CCACCATTCTACCTCTGTTCCCATC<br>TCAAACAGGGCTCAGAAATCCTCAG<br>AGAGCCTGGATTATCTTCCTATAGG<br>GTCCTACCATTTGCTTTAGAGACAT<br>CTGAGAACTGCCTACTCCCCAGGTA<br>GCTGCCTGCCTCCCAGAAGAGCCAC<br>AGCAAGTTCCGCTAAGGGCAAAAAA<br>GGAAGCTAGGTGTCTACAGGGAACC<br>TAAAAACAAACCACACTAACGTGTG<br>TACACACAGCTGCAGAGGGAGACAG<br>GGACCTGGTCTGCTCACAGCCCTTG<br>CCACTCCCCCATGGCCCATGTAGAA<br>ACAACCATGTGGCCTTCACTCTGCC<br>CACAGAAGCTAGCACCAGGACCCTG<br>GTCAGGGTTAGAGGTTTCTGCTGAG<br>TCAAAGCCACATGGAGGGAGGGAGC<br>AAGGGAGAGATGCAGAGTCATGTTT<br>CCAGGAGGAGGTTATCTGAGCATAA |

TABLE 1-continued

Nucleic acid sequences of various components of the lentiviral vectors for treatment of WAS as described herein.

| Element SEQ ID NO | Nucleic Acid Sequence |
|---|---|
| | CAGGGACAGGGTGGGCCACAGGATA<br>CCTCTGAGGCTCAGGTTCCCACCTC<br>CACTCCACCCTCCAACTCTCTGCTC<br>CACGTTCCTTCCACTATTCAACACA<br>TGGCAGGAAGTCAGCCTGTAGGGCT<br>TCACACTACAGTCTAAGCTGACTGC<br>CATCTGTCCCCATCCAGGCGAGGCT<br>GGAAACGGGGGCAGCAAAAAGCCCA<br>GGGACAAAGTCCCCTTCCCAGGCAC<br>ATGTATTATGCACTCTGCACCAAGG<br>AAACCTCCAGATAAGGTCTAGAGAC<br>CAAGGGCCATGTACTTCGGGGGAGA<br>GGCCAGAGGACTTCTGAGGTTTTAC<br>AGAGAAAAGCCAAAGGCAGCCCAGT<br>CAGGGGAAATGTGTAGCCATAGTGC<br>CGATAAGGAAAGGCCTTCAACCTGC<br>CCTGGTCAGCTCTTCCTGTAAGTAG<br>AGGCCCCTTACCGAAGGCCCCAGTG<br>GGAGGAAGGGTCGGGAGTA |
| 1st half of Core Sub-Element 1 of Enhancer Element 2 (SEQ ID NO: 3) | GACCTGAAGGGTAAGGGGGTGTGGA<br>GGTTGTGAAGGCGGGAAGGGGGGTA<br>GCCCCTTCACCAATGTAAACAAGGA<br>TGTGGGTTCTGCGGCCACACTCTCC<br>CCCGCCCTCCCCAGCGGCATTTCCA<br>GCAAGTCACATGTCCTGCGCACAGG<br>CTGGGGGCCCCCTGCTGCTGCCTTT<br>CTTAGAAGCCAGGACCACAGAGCCC<br>GCACAGTGAGCTACTTGGGGAGCTA<br>TTTCTGTAGACTGAGCTTGGGGTAC<br>TGGGAGGCAGTGCTGTTGGC |
| 2nd half of Core Sub-Element 1 of Enhancer Element 2 (SEQ ID NO: 4) | GATCTGGGGGAAAACCCCCTGAGGG<br>TCCCATTTCTCTGCCACTGACCCCT<br>TTGCCTGGCAGAAAGGCTCTGCTGC<br>CTCCTAGCTGTGTAGCAATGGATAA<br>GGCCTTTAACCTCTCTAAGCTGAAA<br>TGTCCTCATGCATAAGGTGGAGACA<br>GTAACTCCTCTTCCATCTGCTGGGT<br>GTTGTCAAAACTACACAGGAGGTTT<br>GCCAAGCACCTAAGGCACAGTAGGT<br>GGTCAAGAAACAGGAACACAATTTG<br>TCATGACGACAATGATTCCTTCATA<br>TGCTAGTTACCCACGAGTCAGCCAG<br>AATGTTGCCATAACCACTTATGAAG<br>CCCTTCCTCATTTCTGTTGCAATTC<br>CTCAGCCAGAGGAAAGCCCCA |
| Core Sub-Element 2 of Enhancer Element 2 (SEQ ID NO: 5) | CCACCTCTGTCCTCCAGAAAGCCCT<br>CCTCTTCCCAGAAGGCTGGCACACA<br>GGGCTGGGGGCCAGGCTTGACTTCC<br>CTGTGGAGGGGTCTGAGGTTGGGGG<br>GATGACCTGCAGAGGTAGGGGAATT<br>CAGAGAACTTGTTTTGATAGAAACT<br>GAAACTCCTCCTCTTGCTGACGCTG<br>CACTTGTGGGCAATCTGCACCTGTT<br>CTCCCCTCCCAGAGGCCAGCTGGAA<br>GGGGGTCCCCCACCATTCTACCTCT<br>GTTCCCATCTCAAACAGGGCTCAGA<br>AATCCTCA |
| Core Sub-Element 3 of Enhancer Element 2 (SEQ ID NO: 6) | GAGAGCCTGGATTATCTTCCTATAG<br>GGTCCTACCATTTGCTTTAGAGACA<br>TCTGAGAACTGCCTACTCCCCAGGT<br>AGCTGCCTGCCTCCCAGAAGAGCCA<br>CAGCAAGTTCCGCTAAGGGCAAAAA<br>AGGAAGCTAGGTGTCTACAGGGAAC<br>CTAAAAACAAACCACACTAACGTGT<br>GTACACACAGCTGCAGAGGGAGACA<br>GGGACCTGGTCTGCT |
| Core-Sub Element | CACAGCCCTTGCCACTCCCCCATGG<br>CCCATGTAGAAACAACCATGTGGCC |

TABLE 1-continued

Nucleic acid sequences of various components of the lentiviral vectors for treatment of WAS as described herein.

| Element SEQ ID NO | Nucleic Acid Sequence |
|---|---|
| 4 of Enhancer Element 2 (SEQ ID NO: 7) | TTCACTCTGCCCACAGAAGCTAGCA<br>CCAGGACCCTGGTCAGGGTTAGAGG<br>TTTCTGCTGAGTCAAAGCCACATGG<br>AGGGAGGGAGCAAGGGAGAGATGCA<br>GAGTCATGTTTCCAGGAGGAGGTTA<br>TCTGAGCATAACAGGGACAGGGTGG<br>GCCACAGGATACCTCTGAGGCTCAG<br>GTTCCCACCTCCACTCCACC |
| Core-Sub Element 5 of Enhancer Element 2 (SEQ ID NO: 8) | CTCCAACTCTCTGCTCCACGTTCCT<br>TCCACTATTCAACACATG<br>GCAGGAAGTCAGCCTGTAGGGCTTC<br>ACACTACAGTCTAAGCT<br>GACTGCCATCTGTCCCCATCCAGGC<br>GAGGCTGGAAACGGGGGCAGCAAAA<br>AGCCCAGGGACAAAGTCCCCTTCCC<br>AGGCACATGTATTATGCACTCTGCA<br>CCAAGGAAACCTCCAGATAAGGTCT<br>AGAGACCAAGGGCCATGTACTTCGG<br>GGGAGAGGCCAGAGGACTTCTGAGG<br>TTTTACAGAGAAAAGCCAAAGGCAG<br>CCCAGTCAGGGGAAATGTGTAGCCA<br>TAGTGCCGATAAGGAAAGGCCTTCA<br>ACCTGCCCTGGTCAGCTCTTCCTGT<br>AAGTAGAGGCCCCTTACCGAAGGCC<br>CCAGTGGGAGGAAGGGTCGGGAGTA |
| Enhancer element HS3 (full) (SEQ ID NO: 9) | **CTAAAAGCCACCAAAACCAAGACAG**<br>**CAATGAAAGTAACCTCTGGTCTTCC**<br>**TAACTGCTCATTATACACTAATTAT**<br>**GATGCACTAGCATGCTAAGAGACAC**<br>**TTCCACCAGCGCCATGACAGTGCCA**<br>**TGGCAACATCAAGAAGTCACCCCAC**<br>**ATGGTCTAAAAAGGGGAAGAACCTT**<br>**CAGTTCCCGGAATTGCCCACCCCTT**<br>**TCCTGGAAAACTCATGAATAATCCA**<br>**CCCCTTGTTTAGCATATAATTAAGA**<br>**AATAACTGTAAGTATCCTTAGTCCA**<br>**GCAGCCCAAGCTGCTGCTCTGCCTA**<br>**TGGAGTAGCCATTCTTTATTCCTTT**<br>**ACTTTCTTAATAAACTTGCTTTCAC**<br>**ATTAAAAACAACAACAACAACACCA**<br>**ACAACCAGCAAATATATCAGAGGCT**<br>**TAGCATCCCCTATTCAAGGGGACAG**<br>**TTCTGGAGGCCGAGAAAGAAGTAGA**<br>**AAGGTGGAGAATAAAAGACACAAAG**<br>**GAGCAGAAGAATTTTATCTTGGCCT**<br>**CCATGTGGCACCTCACAGCTTGGGA**<br>**ACAACA** |
| Enhancer element HS3 core (SEQ ID NO: 10) | CTAAAAGCCACCAAAACCAAGACAG<br>CAATGAAAGTAACCTCTGGTCTTCC<br>TAACTGCTCATTATACACTAATTAT<br>GATGCACTAGCATGCTAAGAGACAC<br>TTCCACCAGCGCCATGACAGTGCCA<br>TGGCAACATCAAGAAGTCACCCCAC<br>ATGGTCTAAAAAGGGGAAGAACCTT<br>CAGTTCCCGGAATTGCCCACCCCTT<br>TCCTGGAAAACTCATGAATAATCCA<br>CCCCTTGTTTAGCATATAAT |
| Enhancer element E9 (full) (SEQ ID NO: 11) | GGGATCTGTGTGCAGATTTACCTCT<br>ACCTACACCTGGCTGGGGATCATAA<br>AGAAAATCAAGGGATGCGCTACCTC<br>CATGAATCCAGGTTTCAGCAGAGCT<br>AAGGGAGTGAAATTTGGGGCCATTT<br>TACTTGTCTCAAACCTTGTTATCTG<br>AGAGAAAGCTAGAGCTTCCTTCTTT<br>CAGCCCCCAGAGACAATGTGGCCAG<br>GCTCCGGAGGGCTGGGAAGATGAGC<br>AATGCTTGTGAGTCACCATGATAGG<br>AAGCAGAAGGGTCAGGAAGTCCCTG<br>GGAGCAAGGCTTAGGGTTAGGGTTA |

TABLE 1-continued

Nucleic acid sequences of various components of the lentiviral vectors for treatment of WAS as described herein.

| Element SEQ ID NO | Nucleic Acid Sequence |
|---|---|
| | GGGAGAAAACACTTGGGCCTGGAGG<br>CTCGGGGCAGGCTTCCTAGAGGGGA<br>GGGGTAGGAAGAGGCAGTGACAGGG<br>CCCACAGCAATGGAGAGGAGTTGGA<br>CTGCAGGGATGGGGTAGGGGGACAG<br>ACGACAAGGGACACTCAGAAGACTA<br>ATGTCTGGGAGTGGGAAAACAGTGT<br>TTGCTCAGCCAGGAAGCTGCATCCA<br>GCTCTTTTATCATTTGTAGAAGACC<br>AAGTACCCAGGCCTGGGAGGAGCCC<br>AGAGA |
| Enhancer element E9 core (SEQ ID NO: 12) | CAAACCTTGTTATCTGAGAGAAAGC<br>TAGAGCTTCCTTCTTTCAGCCCCCA<br>GAGACAATGTGGCCAGGCTCCGGAG<br>GGCTGGGAAGATGAGCAATGCTTGT<br>GAGTCACCATGATAGGAAGCAGAAG<br>GGTCAGGAAGTCCCTGGGAGCAAGG<br>CTTAGGGTTAGGGTTAGGGAGAAAA<br>CACTTGGGCCTGGAGGCTCGGGGCA<br>GGCTTCCTAGAGGGGAGGGGTA |
| WAS cDNA (SEQ ID NO: 13) | atgagtgggggcccaatgggaggaa<br>ggcccgggggccgaggagcaccagc<br>ggttcagcagaacataccctccacc<br>ctcctccaggaccacgagaaccagc<br>gactctttgagatgcttggacgaaa<br>atgcttgacgctggccactgcagtt<br>gttcagctgtacctggcgctgcccc<br>ctggagctgagcactggaccaagga<br>gcattgtggggctgtgtgcttcgtg<br>aaggataacccccagaagtcctact<br>tcatccgcctttacggccttcaggc<br>tggtcggctgctctgggaacaggag<br>ctgtactcacagcttgtctactcca<br>cccccaccccttcttccacacctt<br>cgctggagatgactgccaagcgggg<br>ctgaactttgcagacgaggacgagg<br>cccaggccttccgggccctcgtgca<br>ggagaagatacaaaaaaggaatcag<br>aggcaaagtggagacagacgccagc<br>taccccccaccaccaacaccagccaa<br>tgaagagagaagaggagggctccca<br>cccctgcccctgcatccaggtggag<br>accaaggaggccctccagtgggtcc<br>gctctccctggggctggcgacagtg<br>gacatccagaaccctgacatcacga<br>gttcacgataccgtgggctcccagc<br>acctggacctagcccagctgataag<br>aaacgctcagggaagaagaagatca<br>gcaaagctgatattggtgcacccag<br>tggattcaagcatgtcagccacgtg<br>gggtgggacccccagaatggatttg<br>acgtgaacaacctcgacccagatct<br>gcggagtctgttctccagggcagga<br>atcagcgaggcccagctcaccgacg<br>ccgagacctctaaacttatctacga<br>cttcattgaggaccagggtgggctg<br>gaggctgtgcggcaggagatgaggc<br>gccaggagccacttccgccgccccc<br>accgccatctcgaggagggaaccag<br>ctcccccggccccctattgtggggg<br>gtaacaagggtcgttctggtccact<br>gcccccctgtacctttggggattgcc<br>ccacccccaccaacaccccggggac<br>ccccacccccaggccgagggggccc<br>tccaccaccacccccctccagctact<br>ggacgttctggaccactgccccctc<br>caccccctggagctggtgggccacc<br>catgccaccaccaccgccaccaccg<br>ccaccgccgcccagctccgggaatg<br>gaccagcccctcccccactccctcc<br>tgctctggtgcctgccgggggcctg |

TABLE 1-continued

Nucleic acid sequences of various components of the lentiviral vectors for treatment of WAS as described herein.

| Element SEQ ID NO | Nucleic Acid Sequence |
|---|---|
| | gcccctggtgggggtcggggagcgc<br>ttttggatcaaatccggcagggaat<br>tcagctgaacaagacccctggggcc<br>ccagagagctcagcgctgcagccac<br>cacctcagagctcagagggactggt<br>gggggccctgatgcacgtgatgcag<br>aagagaagcagagccatccactcct<br>ccgacgaaggggaggaccaggctgg<br>cgatgaagatgaagatgatgaatgg<br>gatgactga |
| Codon optimized WAS (SEQ ID NO: 14) | ATGAGCGGCGGCCCCATGGGCGGCC<br>GCCCCGGCGGCCGCGGCGCCCCCGC<br>CGTGCAGCAGAACATCCCCAGCACC<br>CTGCTGCAGGACCACGAGAACCAGC<br>GCCTGTTCGAGATGCTGGGCCGCAA<br>GTGCCTGACCCTGGCCACCGCCGTG<br>GTGCAGCTGTACCTGGCCCTGCCCC<br>CCGGCGCCGAGCACTGGACCAAGGA<br>GCACTGCGGCGCCGTGTGCTTCGTG<br>AAGGACAACCCCCAGAAGAGCTACT<br>TCATCCGCCTGTACGGCCTGCAGGC<br>CGGCCGCCTGCTGTGGGAGCAGGAG<br>CTGTACAGCCAGCTGGTGTACAGCA<br>CCCCCACCCCCTTCTTCCACACCTT<br>CGCCGGCGACGACTGCCAGGCCGGC<br>CTGAACTTCGCCGACGAGGACGAGG<br>CCCAGGCCTTCCGCGCCCTGGTGCA<br>GGAGAAGATCCAGAAGCGCAACCAG<br>CGCCAGAGCGGCGACCGCCGCCAGC<br>TGCCCCCCCCCCCACCCCCGCCAA<br>CGAGGAGCGCCGCGGCGGCCTGCCC<br>CCCCTGCCCCTGCACCCCGGCGGCG<br>ACCAGGGCGGCCCCCCCGTGGGCCC<br>CCTGAGCCTGGGCCTGGCCACCGTG<br>GACATCCAGAACCCCGACATCACCA<br>GCAGCCGCTACCGCGGCCTGCCCGC<br>CCCCGGCCCCAGCCCCGCCGACAAG<br>AAGCGCAGCGGCAAGAAGAAGATCA<br>GCAAGGCCGACATCGGCGCCCCCAG<br>CGGCTTCAAGCACGTGAGCCACGTG<br>GGCTGGGACCCCCAGAACGGCTTCG<br>ACGTGAACAACCTGGACCCCGACCT<br>GCGCAGCCTGTTCAGCCGCGCCGGC<br>ATCAGCGAGGCCCAGCTGACCGACG<br>CCGAGACCAGCAAGCTGATCTACGA<br>CTTCATCGAGGACCAGGGCGGCCTG<br>GAGGCCGTGCGCCAGGAGATGCGCC<br>GCCAGGAGCCCCTGCCCCCCCCCCC<br>CCCCCCCAGCCGCGGCGGCAACCAG<br>CTGCCCCGCCCCCCCATCGTGGGCG<br>GCAACAAGGGCCGCAGCGGCCCCCT<br>GCCCCCCGTGCCCCTGGGCATCGCC<br>CCCCCCCCCCCCACCCCCCGCGGCC<br>CCCCCCCCCCCGGCCGCGGCGGCCC<br>CCCCCCCCCCCCCCCCCCCGCCACC<br>GGCCGCAGCGGCCCCCTGCCCCCCC<br>CCCCCCCCGGCGCCGGCGGCCCCCC<br>CATGCCCCCCCCCCCCCCCCCCCCC<br>CCCCCCCCCCCCAGCAGCGGCAACG<br>GCCCCGCCCCCCCCCCCCTGCCCCC<br>CGCCCTGGTGCCCGCCGGCGGCCTG<br>GCCCCCGGCGGCGGCCGCGGCGCCC<br>TGCTGGACCAGATCCGCCAGGGCAT<br>CCAGCTGAACAAGACCCCCGGCGCC<br>CCCGAGAGCAGCGCCCTGCAGCCCC<br>CCCCCCAGAGCAGCGAGGGCCTGGT<br>GGGCGCCCTGATGCACGTGATGCAG<br>AAGCGCAGCCGCGCCATCCACAGCA<br>GCGACGAGGGCGAGGACCAGGCCGG<br>CGACGAGGACGAGGACGACGAGTGG<br>GACGACTAA |

TABLE 1-continued

Nucleic acid sequences of various components of the lentiviral vectors for treatment of WAS as described herein.

| Element SEQ ID NO | Nucleic Acid Sequence |
|---|---|
| Full sequence of WASVec lentiviral vector transfer plasmid with codon optimized WASp open reading frame: (sequence is beginning from the CMV) (SEQ ID NO: 29) | |

In various embodiments, the lentiviral vectors (LVs) described herein can have various "safety" features that can include, for example, the presence of an insulator (e.g., an FB insulator in the 3'LTR). Additionally, or alternatively, in certain embodiments, the HIV LTR has been substituted with an alternative promoter (e.g., a CMV) to yield a higher titer vector without the inclusion of the HIV TAT protein during packaging. Other strong promoters (e.g., RSV, and the like can also be used).

As noted above, in various embodiments the lentiviral vectors described herein contain any one or more of the elements typically found in lentiviral vectors. Such elements include, but need not be limited to a ψ region vector genome packaging signal, a Rev Responsive Element (RRE), a polypurine tract (e.g., a central polypurine tract, a 3' polypurine tract, etc.), a post-translational regulatory element (e.g., a modified Woodchuck Post-transcriptional Regulatory Element (WPRE)), an insulator, and the like, e.g., as described below.

In various embodiments the vector is a SIN vector substantially incapable of reconstituting a wild-type lentivirus through recombination.

In various embodiments the vectors described herein shows high expression in MEG-01 cells (megakaryocyte cell line), and/or in Jurkat cells (T-cell line), and/or in RAMOs cells (B-cell line). In certain embodiments the vectors described herein show high expression in CB CD34+ differentiated megakaryocytes including "pro-megakaryocytes", megakaryocytes, and platelets.

As shown above, in Example 1, the vectors described herein are believed to be effective to transduce cells at high titer and to also provide high levels of expression of a nucleic acid encoding WASp protein.

In view of these results, it is believed that LVs described herein, e.g., recombinant TAT-independent, SIN LVs that express a nucleic acid encoding a WASP can be used to effectively treat Wiskott-Aldrich Syndrome (WAS) in subjects (e.g., human and non-human mammals) It is believed these vectors can be used for the modification of stem cells (e.g., hematopoietic stem and progenitor cells) that can be introduced into a subject in need thereof for the treatment of, e.g., subjects identified as having WAS. Moreover, it is believed that the resulting cells will produce enough of the transgenic WASp protein to demonstrate significant improvement in subject health. It is also believed the vectors can be directly administered to a subject to achieve in vivo transduction of the target (e.g., hematopoietic stem or progenitor cells) and thereby also effect a treatment of subjects in need thereof.

As noted above, in various embodiments the LVs described herein can comprise various safety features. For example, the HIV LTR has been substituted with a CMV promoter to yield higher titer vector without the inclusion of the HIV TAT protein during packaging. In certain embodiments an insulator (e.g., the FB insulator) can be introduced into the 3'LTR for safety. The LVs are also constructed to provide efficient transduction and high titer.

It will be appreciated that the foregoing elements are illustrative and need not be limiting. In view of the teachings provided herein, suitable substitutions for these elements will be recognized by one of skill in the art and are contemplated within the scope of the teachings provided herein.

WAS Codon Optimization

As noted above, in various embodiments the lentiviral vector can comprise a WAS gene or cDNA. However, in certain embodiments the nucleic acid encoding WASp is codon optimized. Numerous methods of codon optimization are known to those of skill in the art. One illustrative method is JCat (Java Codon Adaptation Tool). The jCAT tool adapts gene codon usage to most sequenced prokaryotes and various eukaryotic gene expression hosts. In contrast to many tools, JCat does not require the manual definition of highly expressed genes and is, therefore, a very rapid and easy method. Further options of JCat for codon adaptation include the avoidance of unwanted cleavage sites for restriction enzymes and Rho-independent transcription terminators. The output of JCat is both graphically and as Codon Adaptation Index (CAI) values given for the input sequence and the newly adapted sequence. JCat optimization is described by Grote et al. (2005) *Nucleic Acids Res.* 33(suppl 2): W526-W531) and a JCat tool is available online at www.jcat.de.

Another codon optimization tool is provided by GeneArt (from ThermoFisher Scientific®.

Still another codon optimization tool is IDT. The IDT codon optimization tool was developed to optimize a DNA or protein sequence from one organism for expression in another by reassigning codon usage based on the frequencies of each codon's usage in the new organism. For example, valine is encoded by 4 different codons (GUG, GUU, GUC, and GUA). In human cell lines, however, the GUG codon is preferentially used (46% use vs. 18, 24, and 12%, respectively). The codon optimization tool takes this information into account and assigns valine codons with those same frequencies. In addition, the tool algorithm eliminates codons with less than 10% frequency and re-normalizes the remaining frequencies to 100%. Moreover, the optimization tool reduces complexities that can interfere with manufacturing and downstream expression, such as repeats, hairpins, and extreme GC content. The IDT optimization tool is available from IDT (Integrated DNA Technologies, Coralville, Iowa) and can be found at ww.idtdna.com/CodonOpt.

Other codon optimization tools include, but are not limited to CodonW an open source software program that can be found at codonw.sourceforge.net, and the OptimumGene™ algorithm from GenScript.

These codon optimizations are illustrative and non-limiting. Using the teaching provided here and in Example 1, the WAS codon usage can readily be optimized for particular applications.

TAT-Independent and Self Inactivating Lentiviral Vectors

To further improve safety, in various embodiments, the lentiviral vectors described herein comprise a TAT-independent, self-inactivating (SIN) configuration. Thus, in various embodiments it is desirable to employ in the LVs described herein an LTR region that has reduced promoter activity relative to wild-type LTR. Such constructs can be provided that are effectively "self-inactivating" (SIN) which provides a biosafety feature. SIN vectors are ones in which the production of full-length vector RNA in transduced cells is greatly reduced or abolished altogether. This feature minimizes the risk that replication-competent recombinants (RCRs) will emerge. Furthermore, it reduces the risk that that cellular coding sequences located adjacent to the vector integration site will be aberrantly expressed.

Furthermore, a SIN design reduces the possibility of interference between the LTR and the promoter that is driving the expression of the transgene. SIN LVs can often permit full activity of the internal promoter.

The SIN design increases the biosafety of the LVs. The majority of the HIV LTR is comprised of the U3 sequences. The U3 region contains the enhancer and promoter elements that modulate basal and induced expression of the HIV genome in infected cells and in response to cell activation. Several of these promoter elements are essential for viral replication. Some of the enhancer elements are highly conserved among viral isolates and have been implicated as critical virulence factors in viral pathogenesis. The enhancer elements may act to influence replication rates in the different cellular target of the virus As viral transcription starts at the 3' end of the U3 region of the 5' LTR, those sequences are not part of the viral mRNA and a copy thereof from the 3' LTR acts as template for the generation of both LTR's in the integrated provirus. If the 3' copy of the U3 region is altered in a retroviral vector construct, the vector RNA is still produced from the intact 5' LTR in producer cells, but cannot be regenerated in target cells. Transduction of such a vector results in the inactivation of both LTR's in the progeny virus. Thus, the retrovirus is self-inactivating (SIN) and those vectors are known as SIN transfer vectors.

In certain embodiments self-inactivation is achieved through the introduction of a deletion in the U3 region of the 3' LTR of the vector DNA, i.e., the DNA used to produce the vector RNA. During RT, this deletion is transferred to the 5' LTR of the proviral DNA. Typically, it is desirable to eliminate enough of the U3 sequence to greatly diminish or abolish altogether the transcriptional activity of the LTR, thereby greatly diminishing or abolishing the production of full-length vector RNA in transduced cells. However, it is generally desirable to retain those elements of the LTR that are involved in polyadenylation of the viral RNA, a function typically spread out over U3, R and U5. Accordingly, in certain embodiments, it is desirable to eliminate as many of the transcriptionally important motifs from the LTR as possible while sparing the polyadenylation determinants.

The SIN design is described in detail in Zufferey et al. (1998) *J Virol.* 72(12): 9873-9880, and in U.S. Pat. No. 5,994,136. As described therein, there are, however, limits to the extent of the deletion at the 3' LTR. First, the 5' end of the U3 region serves another essential function in vector transfer, being required for integration (terminal dinucleotide+att sequence). Thus, the terminal dinucleotide and the att sequence may represent the 5' boundary of the U3 sequences which can be deleted. In addition, some loosely defined regions may influence the activity of the downstream polyadenylation site in the R region. Excessive deletion of U3 sequence from the 3'LTR may decrease polyadenylation of vector transcripts with adverse consequences both on the titer of the vector in producer cells and the transgene expression in target cells.

Additional SIN designs are described in U.S. Patent Publication No: 2003/0039636. As described therein, in certain embodiments, the lentiviral sequences removed from the LTRs are replaced with comparable sequences from a non-lentiviral retrovirus, thereby forming hybrid LTRs. In particular, the lentiviral R region within the LTR can be replaced in whole or in part by the R region from a non-lentiviral retrovirus. In certain embodiments, the lentiviral TAR sequence, a sequence which interacts with TAT protein to enhance viral replication, is removed, preferably in whole, from the R region. The TAR sequence is then replaced with a comparable portion of the R region from a non-lentiviral retrovirus, thereby forming a hybrid R region. The LTRs can be further modified to remove and/or replace with non-lentiviral sequences all or a portion of the lentiviral U3 and U5 regions.

Accordingly, in certain embodiments, the SIN configuration provides a retroviral LTR comprising a hybrid lentiviral R region that lacks all or a portion of its TAR sequence, thereby eliminating any possible activation by TAT, wherein the TAR sequence or portion thereof is replaced by a comparable portion of the R region from a non-lentiviral retrovirus, thereby forming a hybrid R region. In a particular embodiment, the retroviral LTR comprises a hybrid R region, wherein the hybrid R region comprises a portion of the HIV R region (e.g., a portion comprising or consisting of the nucleotide sequence shown in SEQ ID NO: 10 in US 2003/0039636) lacking the TAR sequence, and a portion of the MoMSV R region (e.g., a portion comprising or consisting of the nucleotide sequence shown in SEQ ID NO: 9 in 2003/0039636) comparable to the TAR sequence lacking from the HIV R region. In another particular embodiment, the entire hybrid R region comprises or consists of the nucleotide sequence shown in SEQ ID NO: 11 in 2003/0039636.

Suitable lentiviruses from which the R region can be derived include, for example, HIV (HIV-1 and HIV-2), EIV, SIV and FIV. Suitable retroviruses from which non-lentiviral sequences can be derived include, for example, MoMSV, MoMLV, Friend, MSCV, RSV and Spumaviruses. In one illustrative embodiment, the lentivirus is HIV and the non-lentiviral retrovirus is MoMSV.

In another embodiment described in US 2003/0039636, the LTR comprising a hybrid R region is a left (5') LTR and further comprises a promoter sequence upstream from the hybrid R region. Preferred promoters are non-lentiviral in origin and include, for example, the U3 region from a non-lentiviral retrovirus (e.g., the MoMSV U3 region). In one particular embodiment, the U3 region comprises the nucleotide sequence shown in SEQ ID NO: 12 in US 2003/0039636. In another embodiment, the left (5') LTR further comprises a lentiviral U5 region downstream from the hybrid R region. In one embodiment, the U5 region is the HIV U5 region including the HIV att site necessary for genomic integration. In another embodiment, the U5 region comprises the nucleotide sequence shown in SEQ ID NO: 13 in US 2003/0039636. In yet another embodiment, the entire left (5') hybrid LTR comprises the nucleotide sequence shown in SEQ ID NO: 1 in US 2003/0039636.

In another illustrative embodiment, the LTR comprising a hybrid R region is a right (3') LTR and further comprises a modified (e.g., truncated) lentiviral U3 region upstream from the hybrid R region. The modified lentiviral U3 region can include the att sequence, but lack any sequences having promoter activity, thereby causing the vector to be SIN in that viral transcription cannot go beyond the first round of replication following chromosomal integration. In a particular embodiment, the modified lentiviral U3 region upstream from the hybrid R region consists of the 3' end of a lentiviral (e.g., HIV) U3 region up to and including the lentiviral U3 att site. In one embodiment, the U3 region comprises the nucleotide sequence shown in SEQ ID NO: 15 in US 2003/0039636. In another embodiment, the right (3') LTR further comprises a polyadenylation sequence downstream from the hybrid R region. In another embodiment, the polyadenylation sequence comprises the nucleotide sequence shown in SEQ ID NO: 16 in US 2003/0039636. In yet another embodiment, the entire right (5') LTR comprises the nucleotide sequence shown in SEQ ID NO: 2 or 17 of US 2003/0039636.

Thus, in the case of HIV based LV, it has been discovered that such vectors tolerate significant U3 deletions, including the removal of the LTR TATA box (e.g., deletions from −418 to −18), without significant reductions in vector titers. These deletions render the LTR region substantially transcriptionally inactive in that the transcriptional ability of the LTR in reduced to about 90% or lower.

It has also been demonstrated that the trans-acting function of Tat becomes dispensable if part of the upstream LTR in the transfer vector construct is replaced by constitutively active promoter sequences (see, e.g., Dull et al. (1998) *J Virol.* 72(11): 8463-8471. Furthermore, we show that the expression of rev in trans allows the production of high-titer HIV-derived vector stocks from a packaging construct which contains only gag and pol. This design makes the expression of the packaging functions conditional on complementation available only in producer cells. The resulting gene delivery system, conserves only three of the nine genes of HIV-1 and relies on four separate transcriptional units for the production of transducing particles.

In one embodiments illustrated in Example 1, the cassette expressing a nucleic acid encoding WASp is a SIN vector with the CMV enhancer/promoter substituted in the 5' LTR.

It will be recognized that the CMV promoter typically provides a high level of non-tissue specific expression. Other promoters with similar constitutive activity include, but are not limited to the RSV promoter, and the SV40 promoter. Mammalian promoters such as the beta-actin promoter, ubiquitin C promoter, elongation factor 1αpromoter, tubulin promoter, etc., may also be used.

The foregoing SIN configurations are illustrative and non-limiting. Numerous SIN configurations are known to those of skill in the art. As indicated above, in certain embodiments, the LTR transcription is reduced by about 95% to about 99%. In certain embodiments LTR may be rendered at least about 90%, at least about 91%, at least about 92%, at least about 93%, at least about 94%, at least about 95% at least about 96%, at least about 97%, at least about 98%, or at least about 99% transcriptionally inactive.

Insulator Element

In certain embodiments, to further enhance biosafety, insulators are inserted into the lentiviral vectors described herein. Insulators are DNA sequence elements present throughout the genome. They bind proteins that modify chromatin and alter regional gene expression. The placement of insulators in the vectors described herein offer various potential benefits including, inter alia: 1) Shielding of the vector from positional effect variegation of expression by flanking chromosomes (i.e., barrier activity); and 2) Shielding flanking chromosomes from insertional trans-activation of gene expression by the vector (enhancer blocking). Thus, insulators can help to preserve the independent function of genes or transcription units embedded in a genome or genetic context in which their expression may otherwise be influenced by regulatory signals within the genome or genetic context (see, e.g., Burgess-Beusse et al. (2002) *Proc. Natl. Acad. Sci. USA,* 99: 16433; and Zhan et al. (2001) *Hum. Genet.,* 109: 471). In the present context insulators may contribute to protecting lentivirus-expressed sequences from integration site effects, which may be mediated by cis-acting elements present in genomic DNA and lead to deregulated expression of transferred sequences. In various embodiments LVs are provided in which an insulator sequence is inserted into one or both LTRs or elsewhere in the region of the vector that integrates into the cellular genome.

The first and best characterized vertebrate chromatin insulator is located within the chicken β-globin locus control region. This element, which contains a DNase-I hypersensitive site-4 (cHS4), appears to constitute the 5' boundary of the chicken β-globin locus (Prioleau et al. (1999) *EMBO J.* 18: 4035-4048). A 1.2-kb fragment containing the cHS4 element displays classic insulator activities, including the ability to block the interaction of globin gene promoters and enhancers in cell lines (Chung et al. (1993) *Cell,* 74: 505-514), and the ability to protect expression cassettes in *Drosophila* (Id.), transformed cell lines (Pikaart et al. (1998) *Genes Dev.* 12: 2852-2862), and transgenic mammals (Wang et al. (1997) *Nat. Biotechnol.,* 15: 239-243; Taboit-Dameron et al. (1999) *Transgenic Res.,* 8: 223-235) from position effects. Much of this activity is contained in a 250-bp fragment. Within this stretch is a 49-bp cHS4 core (Chung et al. (1997) *Proc. Natl. Acad. Sci., USA,* 94: 575-580) that interacts with the zinc finger DNA binding protein CTCF implicated in enhancer-blocking assays (Bell et al. (1999) Cell, 98: 387-396).

One illustrative and suitable insulator is FB (FII/BEAD-A), a 77 bp insulator element, that contains the minimal CTCF binding site enhancer-blocking components of the chicken β-globin 5' HS4 insulators and a homologous region from the human T-cell receptor alpha/delta blocking element alpha/delta I (BEAD-I) insulator described by Ramezani et al. (2008) *Stem Cell* 26: 3257-3266. The FB "synthetic" insulator has full enhancer blocking activity. This insulator is illustrative and non-limiting. Other suitable insulators may be used including, for example, the full-length chicken beta-globin HS4 or insulator sub-fragments thereof, the ankyrin gene insulator, and other synthetic insulator elements.

Packaging Signal

In various embodiments the vectors described herein further comprise a packaging signal. A "packaging signal," "packaging sequence," or "PSI sequence" is any nucleic acid sequence sufficient to direct packaging of a nucleic acid whose sequence comprises the packaging signal into a retroviral particle. The term includes naturally occurring packaging sequences and also engineered variants thereof. Packaging signals of a number of different retroviruses, including lentiviruses, are known in the art. One illustrative, but non-limiting PSI is provided by SEQ ID NO:21.

Rev Responsive Element (RRE)

In certain embodiments the lentiviral vectors described herein comprise a Rev response element (RRE) to enhance nuclear export of unspliced RNA. RREs are well known to those of skill in the art. Illustrative RREs include, but are not limited to RREs such as that located at positions 7622-8459 in the HIV NL4-3 genome (Genbank accession number AF003887) as well as RREs from other strains of HIV or other retroviruses. Such sequences are readily available from Genbank or from the database with URL hiv-web.1an1.gov/content/index. One illustrative, but non-limiting RRE is shown in SEQ ID NO:22).

PolyPurine Tract (cPPT, 3'PPT)

In various embodiments the lentiviral vectors described herein further include a polypurine tract (e.g., central polypurine tract (cPPT), 3' poplypurine tract (3'PPT)). Insertion of a fragment containing the 3'PPT (see, e.g., SEQ ID NO:24) or the central polypurine tract (cPPT) in lentiviral (e.g., HIV-1) vector constructs is known to enhance transduction efficiency.

Expression-Stimulating Posttranscriptional Regulatory Element (PRE)

In certain embodiments the lentiviral vectors (LVs) described herein may comprise any of a variety of posttranscriptional regulatory elements (PREs) whose presence within a transcript increases expression of the heterologous nucleic acid (e.g., a nucleic acid that encodes WASp) at the protein level. PREs may be particularly useful in certain embodiments, especially those that involve lentiviral constructs with modest promoters.

One type of PRE is an intron positioned within the expression cassette, which can stimulate gene expression. However, introns can be spliced out during the life cycle events of a lentivirus. Hence, if introns are used as PRE's they are typically placed in an opposite orientation to the vector genomic transcript.

Posttranscriptional regulatory elements that do not rely on splicing events offer the advantage of not being removed during the viral life cycle. Some examples are the posttranscriptional processing element of herpes simplex virus, the posttranscriptional regulatory element of the hepatitis B virus (HPRE) and the woodchuck hepatitis virus (WPRE). Of these the WPRE is typically preferred as it contains an additional cis-acting element not found in the HPRE. This regulatory element is typically positioned within the vector so as to be included in the RNA transcript of the transgene, but outside of stop codon of the transgene translational unit.

The WPRE is characterized and described in U.S. Pat. No. 6,136,597. As described therein, the WPRE is an RNA export element that mediates efficient transport of RNA from the nucleus to the cytoplasm. It enhances the expression of transgenes by insertion of a cis-acting nucleic acid sequence, such that the element and the transgene are contained within a single transcript. Presence of the WPRE in the sense orientation was shown to increase transgene expression by up to 7- to 10-fold. Retroviral vectors transfer sequences in the form of cDNAs instead of complete intron-containing genes as introns are generally spliced out during the sequence of events leading to the formation of the retroviral particle. Introns mediate the interaction of primary transcripts with the splicing machinery. Because the processing of RNAs by the splicing machinery facilitates their cytoplasmic export, due to a coupling between the splicing and transport machineries, cDNAs are often inefficiently expressed. Thus, the inclusion of the WPRE (see, e.g., SEQ ID NO:23) in a vector results in enhanced expression of transgenes.

Transduced Host Cells and Methods of Cell Transduction.

The recombinant lentiviral vectors (LV) and resulting virus described herein are capable of transferring a heterologous nucleic acid sequence (e.g., a nucleic acid encoding WASp) into a mammalian cell. In various embodiments, for delivery to cells, vectors described herein are preferably used in conjunction with a suitable packaging cell line or co-transfected into cells in vitro along with other vector plasmids containing the necessary retroviral genes (e.g., gag and pol) to form replication incompetent virions capable of packaging the vectors of the present invention and infecting cells.

In certain embodiments the vectors are introduced via transfection into a packaging cell line. The packaging cell line produces viral particles that contain the vector genome. Methods for transfection are well known by those of skill in the art. After cotransfection of the packaging vectors and the transfer vector to the packaging cell line, the recombinant virus is recovered from the culture media and titered by standard methods used by those of skill in the art. Thus, the packaging constructs can be introduced into human cell lines by calcium phosphate transfection, lipofection or electroporation, generally together with or without a dominant selectable marker, such as neomycin, DHFR, Glutamine synthetase, followed by selection in the presence of the appropriate drug and isolation of clones. In certain embodiments the selectable marker gene can be linked physically to the packaging genes in the construct.

Stable cell lines wherein the packaging functions are configured to be expressed by a suitable packaging cell are known (see, e.g., U.S. Pat. No. 5,686,279, which describes packaging cells). In general, for the production of virus particles, one may employ any cell that is compatible with the expression of lentiviral Gag and Pol genes, or any cell that can be engineered to support such expression. For example, producer cells such as 293T cells and HT1080 cells may be used.

The packaging cells with a lentiviral vector incorporated therein form producer cells. Producer cells are thus cells or cell-lines that can produce or release packaged infectious viral particles carrying the therapeutic gene of interest (e.g., nucleic acid encoding WASp). These cells can further be anchorage dependent which means that these cells will grow, survive, or maintain function optimally when attached to a surface such as glass or plastic. Some examples of anchorage dependent cell lines used as lentiviral vector packaging cell lines when the vector is replication competent are HeLa or 293 cells and PERC.6 cells.

Accordingly, in certain embodiments, methods are provided of delivering a gene to a cell which is then integrated into the genome of the cell, comprising contacting the cell with a virion containing a lentiviral vector described herein. The cell (e.g., in the form of tissue or an organ) can be contacted (e.g., infected) with the virion ex vivo and then delivered to a subject (e.g., a mammal, animal or human) in which the gene (e.g., a nucleic acid encoding WASp) will be expressed. In various embodiments the cell can be autologous to the subject (i.e., from the subject) or it can be non-autologous (i.e., allogeneic or xenogenic) to the subject. Moreover, because the vectors described herein are capable of being delivered to both dividing and non-dividing cells, the cells can be from a wide variety including, for example, bone marrow cells, mesenchymal stem cells (e.g., obtained from adipose tissue), and other primary cells derived from human and animal sources. Alternatively, the virion can be directly administered in vivo to a subject or a localized area of a subject (e.g., bone marrow).

In certain embodiments, the lentivectors described herein will be particularly useful in the transduction of human hematopoietic progenitor cells or a hematopoietic stem cells, obtained either from the bone marrow, the peripheral blood or the umbilical cord blood, as well as in the transduction of a CD4+ T cell, a peripheral blood B or T lymphocyte cell, and the like. In certain embodiments particularly preferred targets are CD34+ hematopoetic stem and progenitor cells.

Gene Therapy

In still other embodiments, methods are provided for transducing a human hematopoietic stem cell. In certain embodiments the methods involve contacting a population of human cells that include hematopoietic stem cells with one of the foregoing lentivectors under conditions to effect the transduction of a human hematopoietic progenitor cell in said population by the vector. The stem cells may be transduced in vivo or in vitro, depending on the ultimate application. Even in the context of human gene therapy, such as gene therapy of human stem cells, one may transduce the stem cell in vivo or, alternatively, transduce in vitro followed by infusion of the transduced stem cell into a human subject. In one aspect of this embodiment, the human stem cell can be removed from a human, e.g., a WAS patient, using methods well known to those of skill in the art and transduced as noted above. The transduced stem cells are then reintroduced into the same or a different human Stem Cell/Progenitor Cell Gene Therapy In various embodiments the lentivectors described herein are particularly useful for the transduction of human hematopoietic progenitor cells or haematopoietic stem cells (HSCs), obtained either from the bone marrow, the peripheral blood or the umbilical cord blood, as well as in the transduction of a CD4+ T cell, a peripheral blood B or T lymphocyte cell, and the like. In certain embodiments particularly preferred targets are CD34+ hematopoietic stem and progenitor cells.

When cells, for instance CD34+ cells, dendritic cells, peripheral blood cells or tumor cells are transduced ex vivo, the vector particles are incubated with the cells using a dose generally in the order of between 1 to 50 multiplicities of infection (MOI) which also corresponds to $1\times10^5$ to $50\times10^5$ transducing units of the viral vector per $10^5$ cells. This can include amounts of vector corresponding to 1, 2, 3, 4, 5, 6, 7, 8, 9, 10, 15, 20, 25, 30, 35, 40, 45, and 50 MOI. Typically, the amount of vector may be expressed in terms of HT-29 transducing units (TU).

In certain embodiments cell-based therapies involve providing stem cells and/or hematopoietic precursors, transduce the cells with the lentivirus encoding, e.g., a nucleic acid that encodes WASp, and then introduce the transformed cells into a subject in need thereof (e.g., a subject with a mutation in the WAS gene).

In certain embodiments the methods involve isolating population of cells, e.g., stem cells from a subject, optionally expand the cells in tissue culture, and administer the lentiviral vector whose presence within a cell results in production of a normal WASp in the cells in vitro. The cells are then returned to the subject, where, for example, they may provide a population of red blood cells that produce the WASp.

In some illustrative, but non-limiting, embodiments, a population of cells, which may be cells from a cell line or from an individual other than the subject, can be used. Methods of isolating stem cells, immune system cells, etc., from a subject and returning them to the subject are well known in the art. Such methods are used, e.g., for bone marrow transplant, peripheral blood stem cell transplant, etc., in patients undergoing chemotherapy.

Where stem cells are to be used, it will be recognized that such cells can be derived from a number of sources including bone marrow (BM), cord blood (CB), mobilized peripheral blood stem cells (mPBSC), and the like. In certain embodiments the use of induced pluripotent stem cells (IPSCs) is contemplated. Methods of isolating hematopoietic stem cells (HSCs), transducing such cells and introducing them into a mammalian subject are well known to those of skill in the art.

In certain embodiments a lentiviral vector described herein (see, e.g., FIGS. 18-21 with a nucleic acid encoding WASp instead of mCit is used in stem cell gene therapy for WAS by introducing a nucleic acid that encodes WASp into the into the bone marrow stem cells of patients with WAS followed by autologous transplantation.

Direct Introduction of Vector

In certain embodiments direct treatment of a subject by direct introduction of the vector(s) described herein is contemplated. The lentiviral compositions may be formulated for delivery by any available route including, but not limited to parenteral (e.g., intravenous), intradermal, subcutaneous, oral (e.g., inhalation), transdermal (topical), transmucosal, rectal, and vaginal. Commonly used routes of delivery include inhalation, parenteral, and transmucosal.

In various embodiments pharmaceutical compositions can include an LV in combination with a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

In some embodiments, active agents, i.e., a lentiviral described herein and/or other agents to be administered together the vector, are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such compositions will be apparent to those skilled in the art. Suitable materials can also be obtained commercially from Alza Corporation and Nova Pharmaceuticals, Inc. Liposomes can also be used as pharmaceutically acceptable carriers. These can be prepared according to methods known to those skilled in the art, for example, as described in U.S. Pat. No. 4,522,811. In some embodiments the composition is targeted to particular cell types or to cells that are infected by a virus. For example, compositions can be targeted using monoclonal antibodies to cell surface markers, e.g., endogenous markers or viral antigens expressed on the surface of infected cells.

It is advantageous to formulate compositions in dosage unit form for ease of administration and uniformity of dosage. Dosage unit form as used herein refers to physically discrete units suited as unitary dosages for the subject to be treated; each unit comprising a predetermined quantity of a LV calculated to produce the desired therapeutic effect in association with a pharmaceutical carrier.

A unit dose need not be administered as a single injection but may comprise continuous infusion over a set period of time. Unit dose of the LV described herein may conveniently be described in terms of transducing units (T.U.) of lentivector, as defined by titering the vector on a cell line such as HeLa or 293. In certain embodiments unit doses can range from $10^3$, $10^4$, $10^5$, $10^6$, $10^7$, $10^8$, $10^9$, $10^{10}$, $10^{11}$, $10^{12}$, $10^{13}$ T.U. and higher.

Pharmaceutical compositions can be administered at various intervals and over different periods of time as required, e.g., one time per week for between about 1 to about 10 weeks; between about 2 to about 8 weeks; between about 3 to about 7 weeks; about 4 weeks; about 5 weeks; about 6 weeks, etc. It may be necessary to administer the therapeutic composition on an indefinite basis. The skilled artisan will appreciate that certain factors can influence the dosage and timing required to effectively treat a subject, including but not limited to the severity of the disease or disorder, previous treatments, the general health and/or age of the subject, and other diseases present. Treatment of a subject with a LV can include a single treatment or, in many cases, can include a series of treatments.

Illustrative, but non-limiting, doses for administration of gene therapy vectors and methods for determining suitable doses are known in the art. It is furthermore understood that appropriate doses of a LV may depend upon the particular recipient and the mode of administration. The appropriate dose level for any particular subject may depend upon a variety of factors including the age, body weight, general health, gender, and diet of the subject, the time of administration, the route of administration, the rate: of excretion, other administered therapeutic agents, and the like.

In certain embodiments lentiviral gene therapy vectors described herein can be delivered to a subject by, for example, intravenous injection, local administration, or by stereotactic injection (see, e.g., Chen et al. (1994) *Proc. Natl. Acad. Sci. USA,* 91: 3054). In certain embodiments vectors may be delivered orally or inhalationally and may be encapsulated or otherwise manipulated to protect them from degradation, enhance uptake into tissues or cells, etc. Pharmaceutical preparations can include a LV in an acceptable diluent, or can comprise a slow release matrix in which a LV is imbedded. Alternatively or additionally, where a vector can be produced intact from recombinant cells, as is the case for retroviral or lentiviral vectors as described herein, a pharmaceutical preparation can include one or more cells which produce vectors. Pharmaceutical compositions comprising a LV described herein can be included in a container, pack, or dispenser, optionally together with instructions for administration.

The foregoing compositions, methods and uses are intended to be illustrative and not limiting. Using the teachings provided herein other variations on the compositions, methods and uses will be readily available to one of skill in the art.

Example 1

Development of Lentiviral Vectors for Treatment of Wiskott-Aldrich Syndrome (WAS)

The goal of the experiments described below was to develop a novel lentiviral vector driven by endogenous regulatory elements of the native WAS gene for the treatment of Wiskott-Aldrich Syndrome. In particular, it was desired to develop a vector that has higher expression than the current WAS1.6 lentiviral vector in megakaryocytes and consequently able to restore platelet counts to normal levels in WAS patients. Additionally, it was desired to maintain at least a similar level of expression in all other hematopoietic cell lineages and to restore T, B and NK cell counts and function.

A bioinformatic analysis (using publicly available databases: Project Encode, Ensemnbl, FANTOM, VISTA Enhancer Browser, GeneHancer) was utilized to elucidate the endogenous regulatory elements of the native WAS gene.

The WAS1.6 vector is driven by a 1600 bp promoter fragment immediately upstream of the transcription start site. We identified two regulatory elements "HS1" and "HS2" within this fragment which are 417 bp and 190 bp, respectively, in size. Thus, we identified 1026 bp of inert sequence in the 1633 bp fragment which could be removed to decrease promoter size.

We note that the 1.6 kb promoter is insufficient to drive wildtype levels of expression in megakaryocytes and as a result patients remain microthrombocytopenic. In view of this we hypothesized that additional endogenous enhancer elements are necessary to drive wildtype levels of expression of WAS in megakaryocytes.

A proximal analysis of the WAS gene identified new enhancer elements "HS4" and "HS3" that contain megakaryocyte DNaseI HS sites and that may act as enhancers to boost expression in megakaryocytes. A series of lentiviral vectors (LVs) containing various combinations of these regions and a reporter gene were created to evaluate activity of these regulatory elements (see, e.g., FIG. 1, panel A). Additionally the E3 element (Thurman et al. (2012) *Nature,* 489: 75-82), proposed to be one of the strongest enhancers in the human genome has megakaryocyte hypersensitivity. Accordingly, we also constructed a vector to evaluate E3 enhancer activity in this context (see, e.g., FIG. 1, panel B).

MEG-01 cells (megakaryocyte cell lines) were transduced with the WAS vectors in order to determine if any of the newly identified enhancer elements increases expression in megakaryocyte lineage. The cells were cultured for 14 days and flow cytometry was performed for expression (mCitrine) and VCN analysis.

Figure 2:
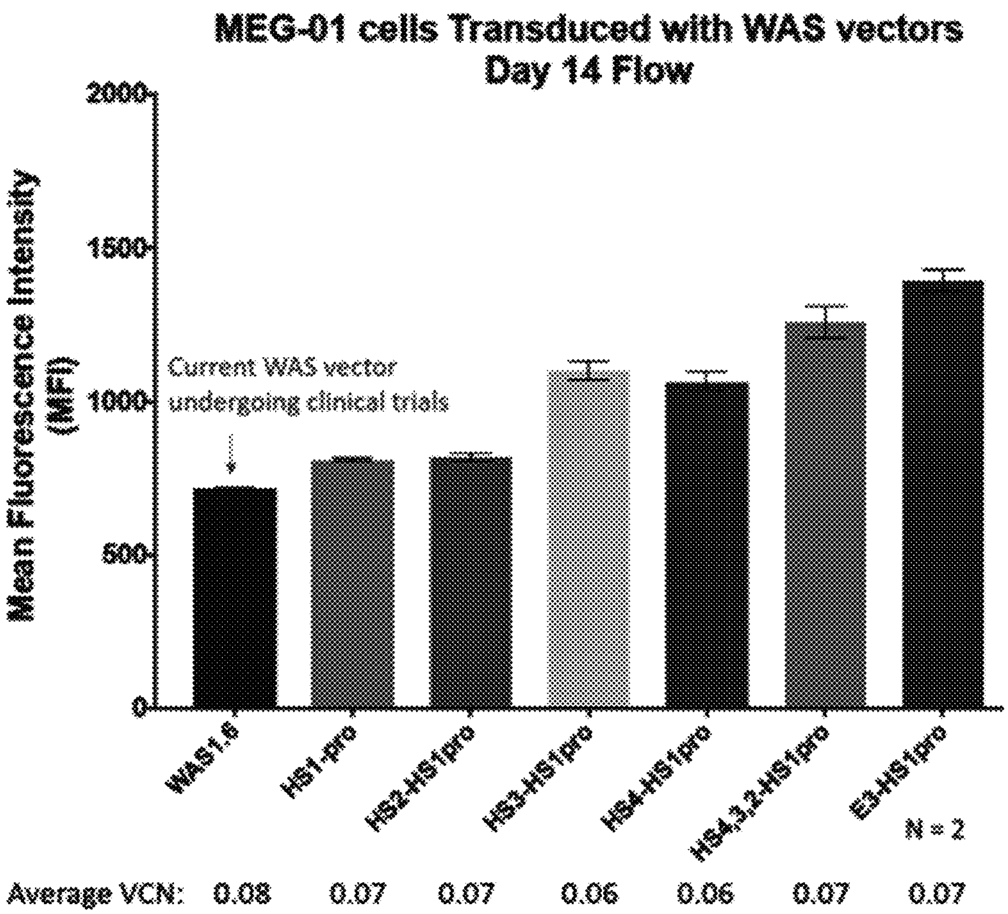
FIG. 2 shows expression levels in MEG-01 cells transduced with WAS vectors.

As shown in FIG. 2 the HS1 minimal promoter (417 bp) appears to be the main driver of expression in the 1.6 kb vector in megakaryocytes. Additionally, HS2 seems to be inert in megakaryocyte cell lines, however this element may have enhancer activity in other lineages. HS3 appears to give a major boost in expression in megakaryocyte cell lines and HS4 also appears to give a boost in expression in megakaryocyte cell lines. There is an effect of combining HS3 and HS4 and E3 is a strong non-lineage specific enhance that is also active in megakaryocytes.

The clinical 1.6 kb vector is shown to express at curative levels in all hematopoietic cell lines except for megakaryocytes (patients are no longer immune deficient but still thrombocytopenic). As we show, an illustrative slim version of WAS1.6 is HS2-HS1 since HS2-HS1 contains all the regulatory regions WAS1.6 has (while saving 1.0 kb of sequence) suggesting that this can be used as a vector backbone. Adding the novel HS3 and HS4 fragment has been shown to boost expression in megakaryocytes therefore HS4-HS3-HS2-HS1 may provide therapeutic levels of expression in all hematopoietic cell lineages. One illustrative suitable vector (HS4-HS3-HS2-HS1) is only 155 bp larger than WAS1.6, but was shown to have ~2-fold higher expression in megakaryocytes.

However, it remained to be determined if HS2-HS1pro performs the same as WAS1.6 in other cell lineages (T cells and B cells). Additionally, we wished to determine if HS3 and HS4 further boost expression in other hematopoietic cell lineages, and if the HS2 enhancer element is necessary. In this regard we recognized that HS2 enhancer may have enhancer functions in other cell types or may be completely inert. Additionally, we wanted to determine if HS1pro could perform the same as WAS1.6 and if adding HS4 and HS3 to HS2-HS1 negatively affects expression in other cell types?

To address these questions, the WAS vectors were transduced into Jurkats (T-cell line) and RAMOs (B-cell line). The cells were cultured for 14 days and expression was analyzed by flow cytometry and VCN.

Figure 3:
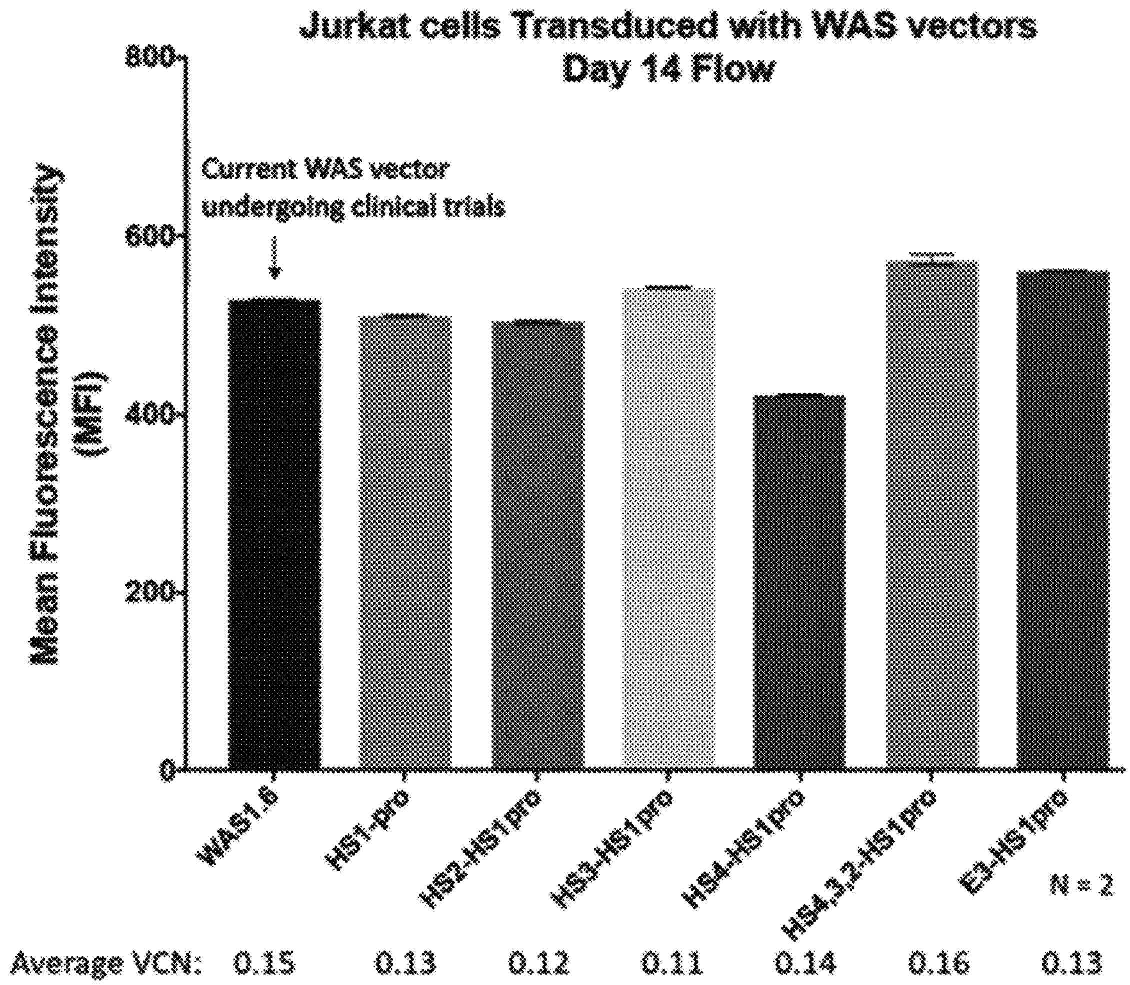
FIG. 3 shows expression levels of WAS vectors in Jurkat cells (T-cell line).
Figure 4:
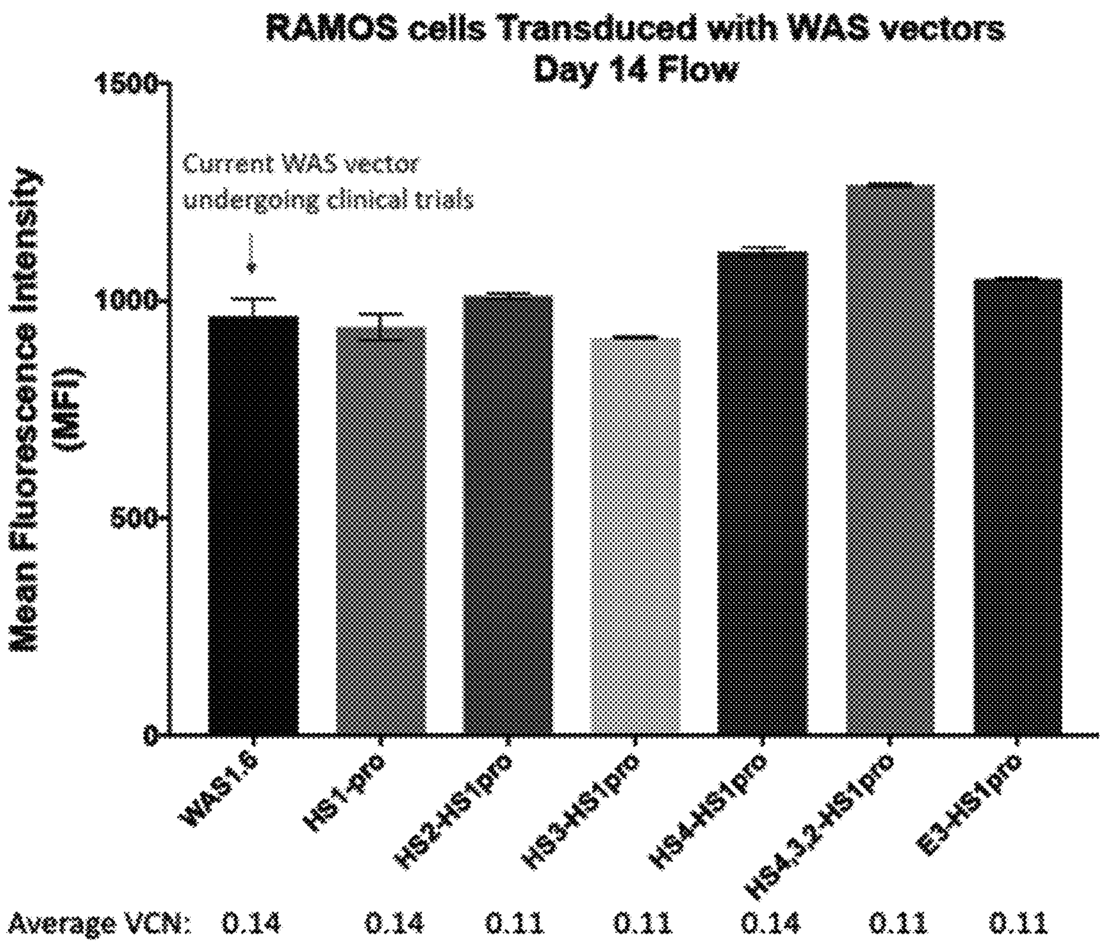
FIG. 4 shows expression levels of WAS vectors in RAMOs cells (B-cell line).

Expression levels of the WAS vectors in Jurkat cells are shown in FIG. 3 and the expression levels in RAMOs cells are show in FIG. 4. As illustrated by these figures, the bare minimal promoter HS1pro (SEQ NO:1) functions the same as WAS1.6 in all cell lines test (MEG-01, CMK, Jurkats and RAMOs). The HS2 enhancer, by itself, seems to be relatively inert (190 bp). By eliminating the inert 1 kb sequence and the 190 bp HS2 sequence we can save up to about 1.2 kb of sequence.

The HS3 enhancer appears to increase expression in megakaryocyte cell lines, but is inert in B-cells and T-cells. The HS4 enhancer appears to increase expression in megakaryocytes and B-cells but is inert in T-cells. The E3 enhancer appears to increase expression in megakaryocytes but is inert in B and T cells (non-endogenous element).

In view of these discoveries, one suitable WAS vector comprises HS4-HS3-H52-HS1pro. This vector is only 200 bp larger than WAS1.6, but provides higher expression than WAS1.6 in megakaryocytes, and B-cells and a similar level of expression compared to WAS1.6 in T-cells.

Figure 5:
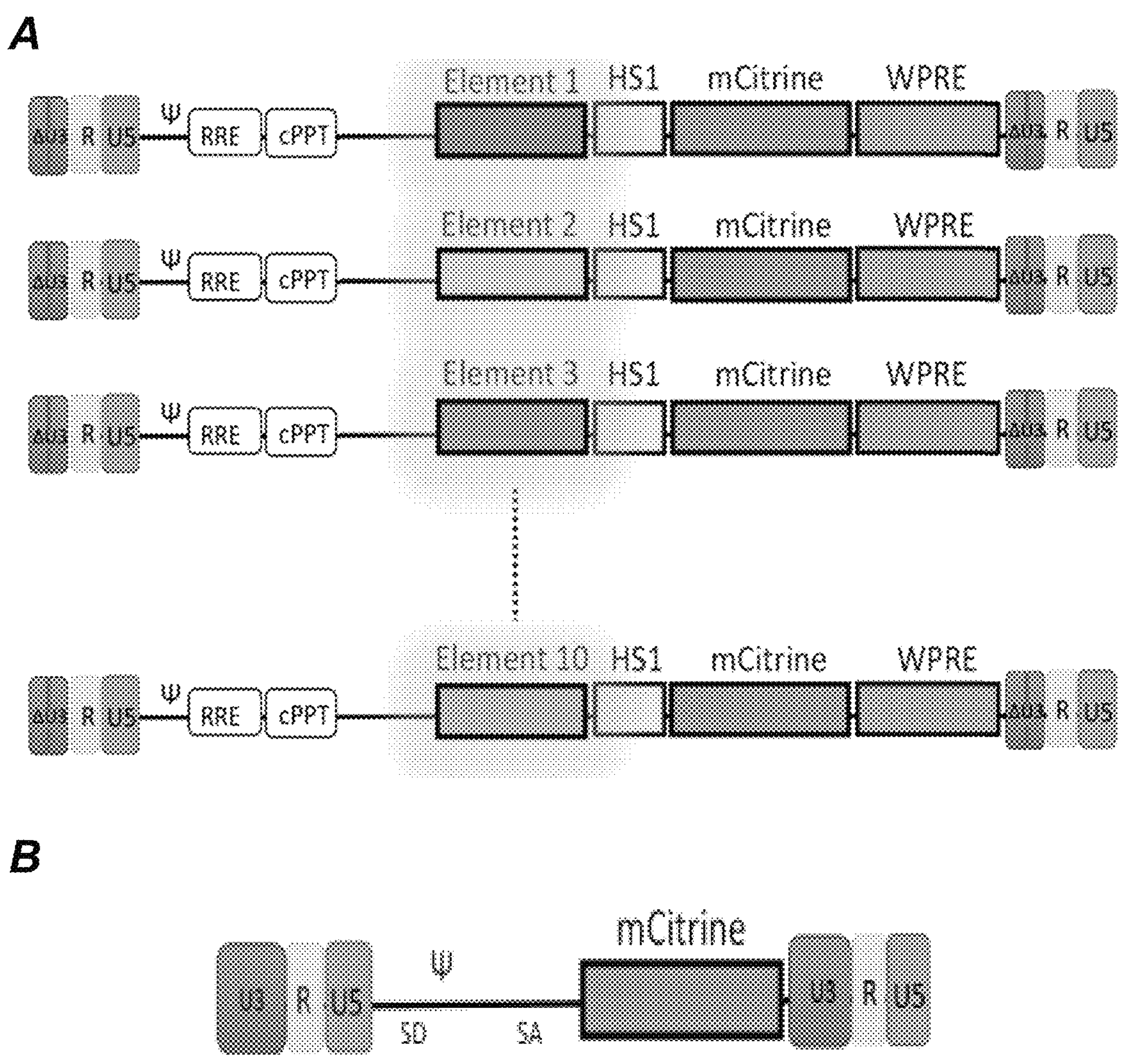
FIG. 5, panels A-B, illustrates the constructs used to identify the critical enhancer elements that regulate the WAS gene. Panel A) Ten new constructs each containing a putative enhancer element cloned upstream of the endogenous minimal WAS promoter (HS1pro). Panel B) The gamma-retroviral vector (CMMP-mCit) which was able to restore platelet counts to normal levels and used as a control.

We proceed to reanalyze the WAS locus in depth and identified 13 putative endogenous enhancer elements contained within a 1.1 million base pair window spanning 850 kb upstream and 250 kb downstream of the WAS gene. Three of the elements were previously identified in our proximal bioinformatic analysis of the WAS locus. In order to experimentally identify the critical enhancer elements that regulate the WAS gene, each putative enhancer element was cloned upstream of the endogenous minimal WAS promoter (HS1pro) to drive expression of mCitrine (see, FIG. 5, panel A). The expression of these vectors was compared to the gamma-retroviral vector (CMMP-mCit, see, FIG. 5, panel B) used in previous controls and which was able to restore platelet counts to normal levels.

Figure 6:
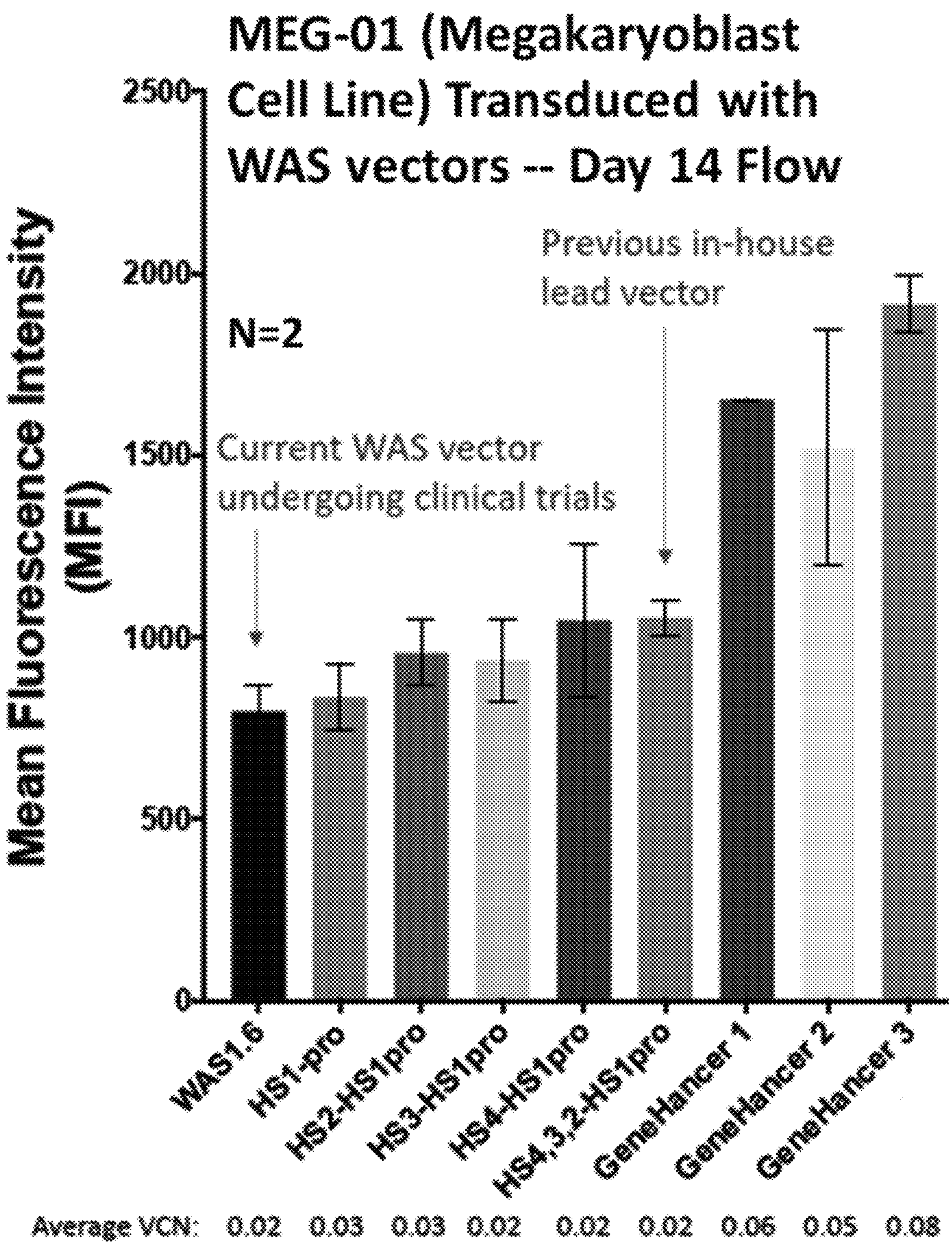
FIG. 6 shows expression levels of WAS vectors in MEG-01 (megakaryoblast cell line).
Figure 7:
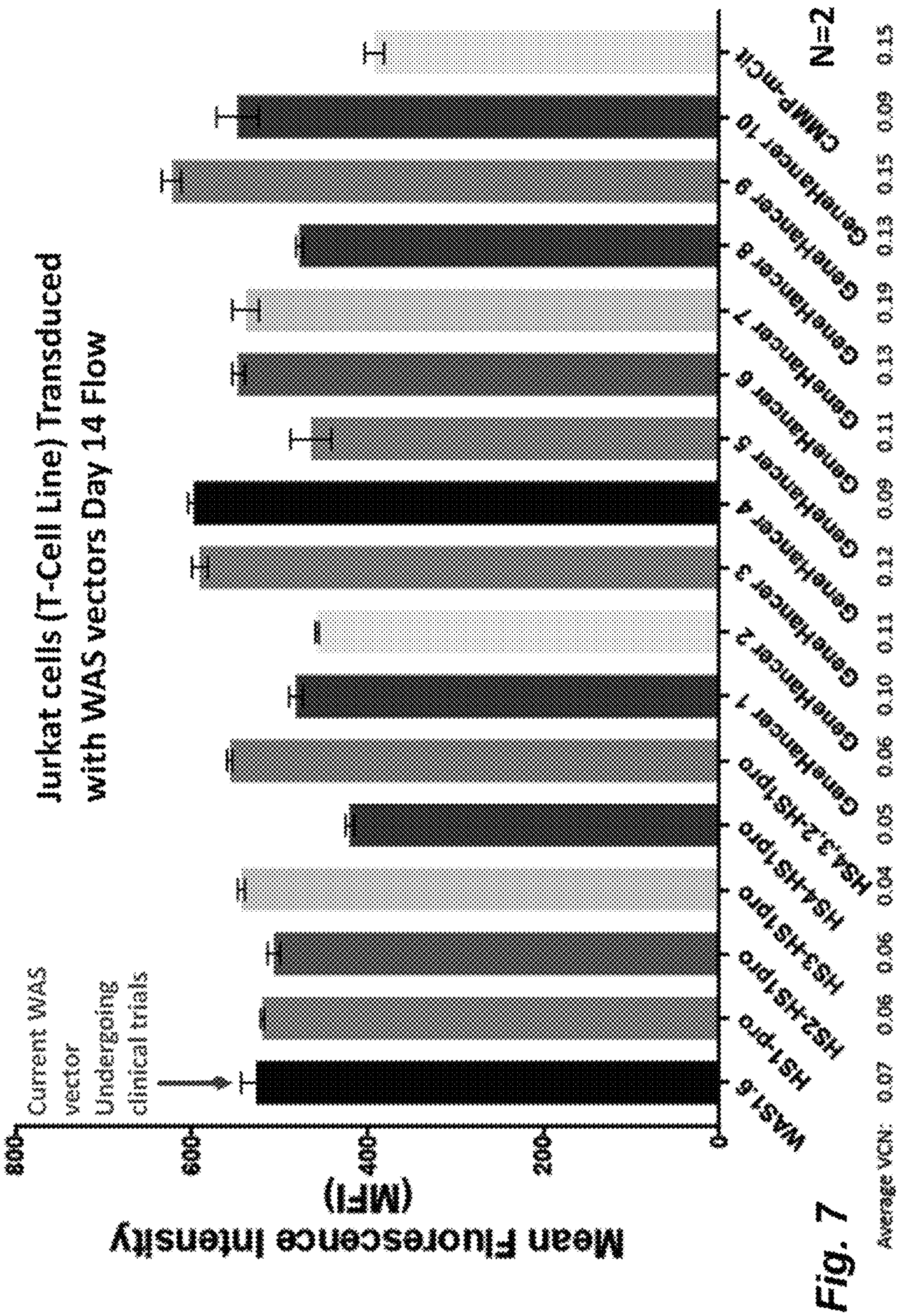
FIG. 7 shows expression levels of WAS vectors in Jurkat cells (T-cell line).
Figure 8:
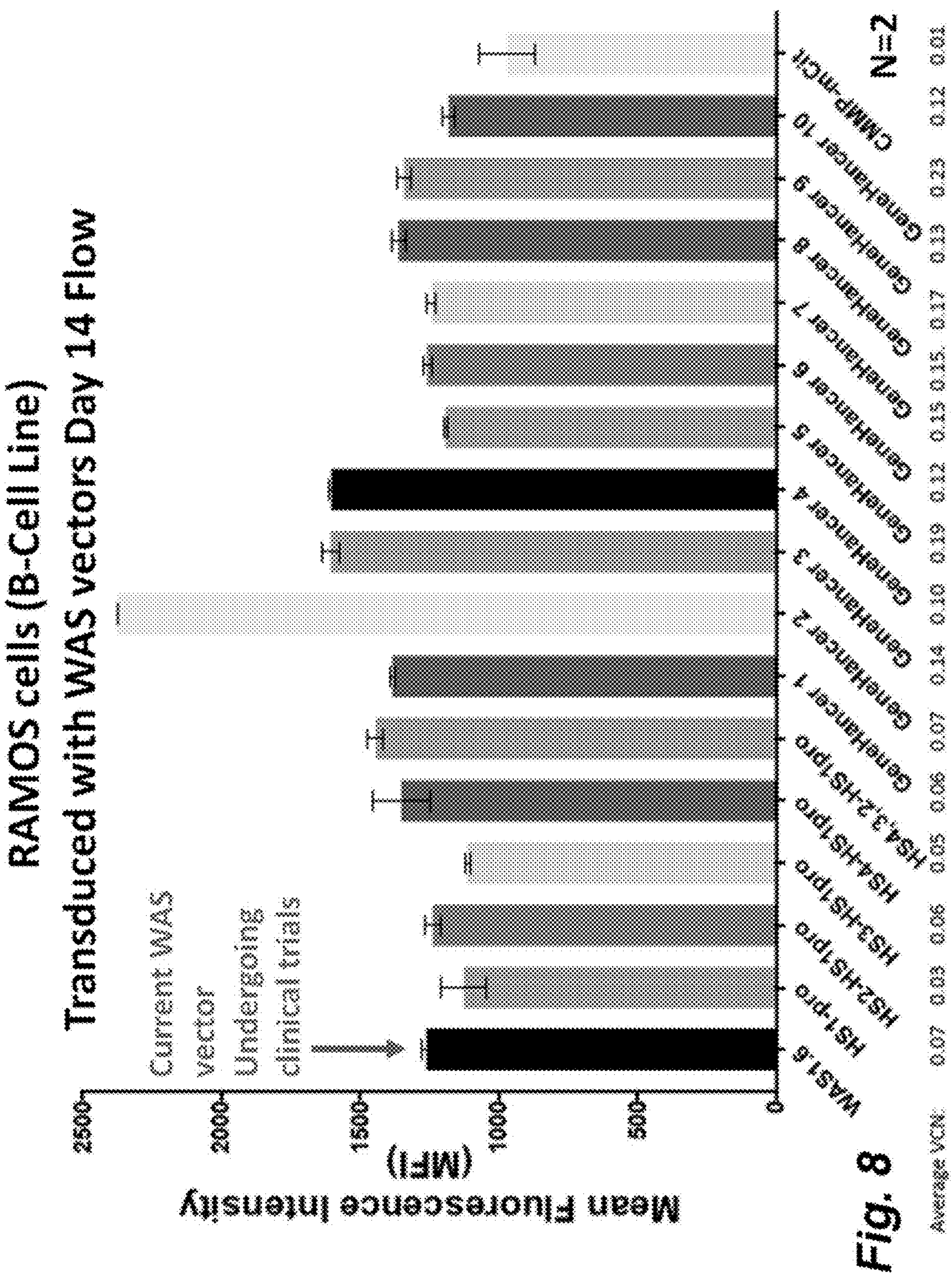
FIG. 8 shows expression levels of WAS vectors in RAMOs cells (B-cell line).

Cells were transduced with the vectors, cultured for 14 days and expression was analyzed by flow cytometry and VCN. FIG. 6 shows the data for MEG-01 (megakaryoblast cell line), FIG. 7 shows the data for Jurkat cells (T-cell line), and FIG. 8 shows the results or RAMOs cells (B-cell line). As shown in these Figures, all 10 newly identified enhancer elements increase expression in MEG-01 cells (Megakaryoblastic cell line) at levels higher than the WAS1.6 vector and our previous lentiviral vector (HS4,3,2,1). Elements 1, 3, 7, 8 and 9 each independently drive expression higher than the previous clinical γ-retroviral CMMP-mCit vector. All vectors express higher than the γ-retroviral vector and at similar levels to WAS1.6 in Jurkats (T-cell line), and all vectors express higher than the γ-retroviral vector and at similar levels to WAS1.6 in RAMOS (B-cell line). Additionally, element 2 increases expression over 2 fold higher compared to WAS1.6 and CMMP-mCit.

Figure 9:
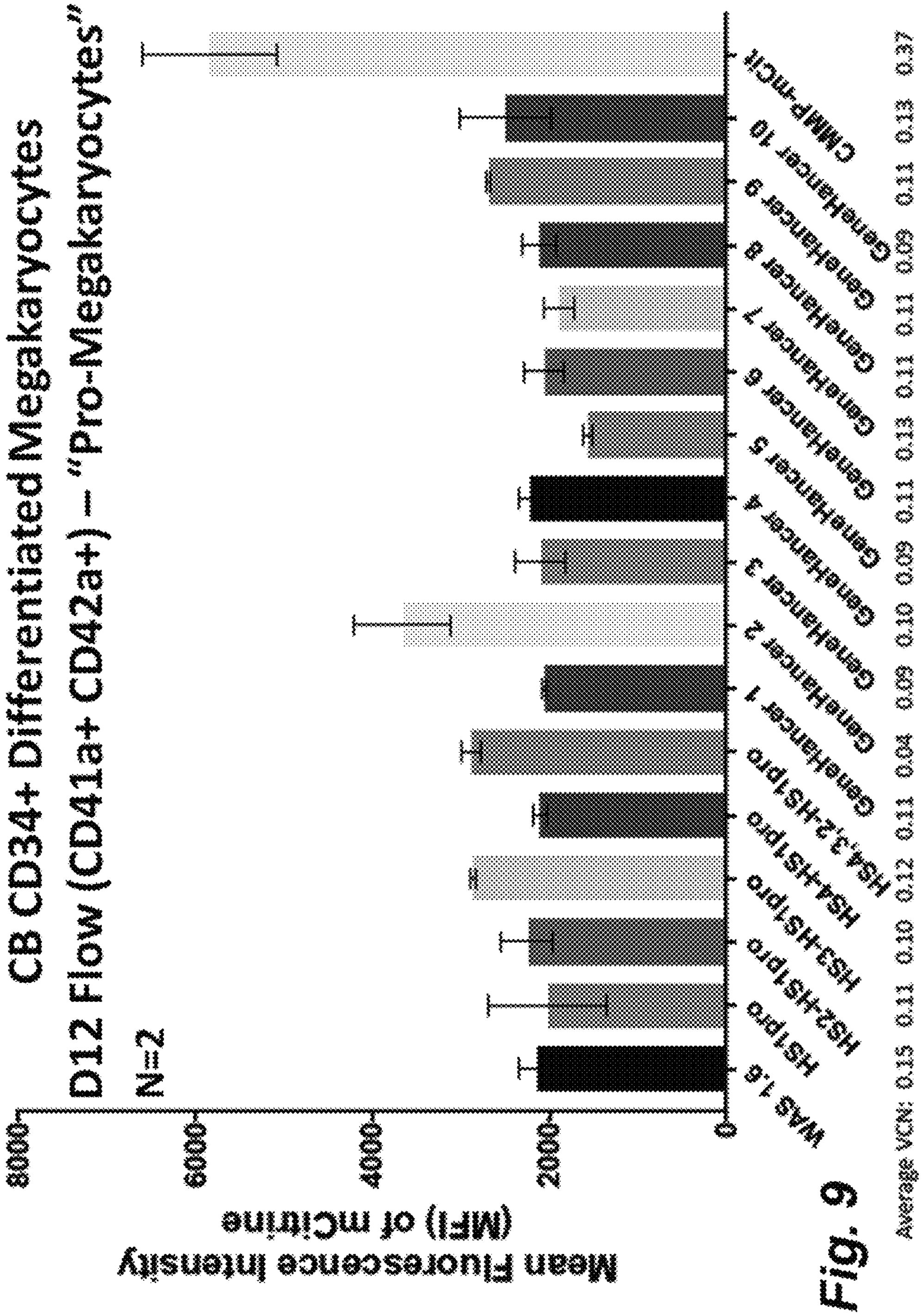
FIG. 9 shows expression levels of WAS vectors in CB CD34+ differentiated megakaryocytes "pro-megakaryocytes".
Figure 10:
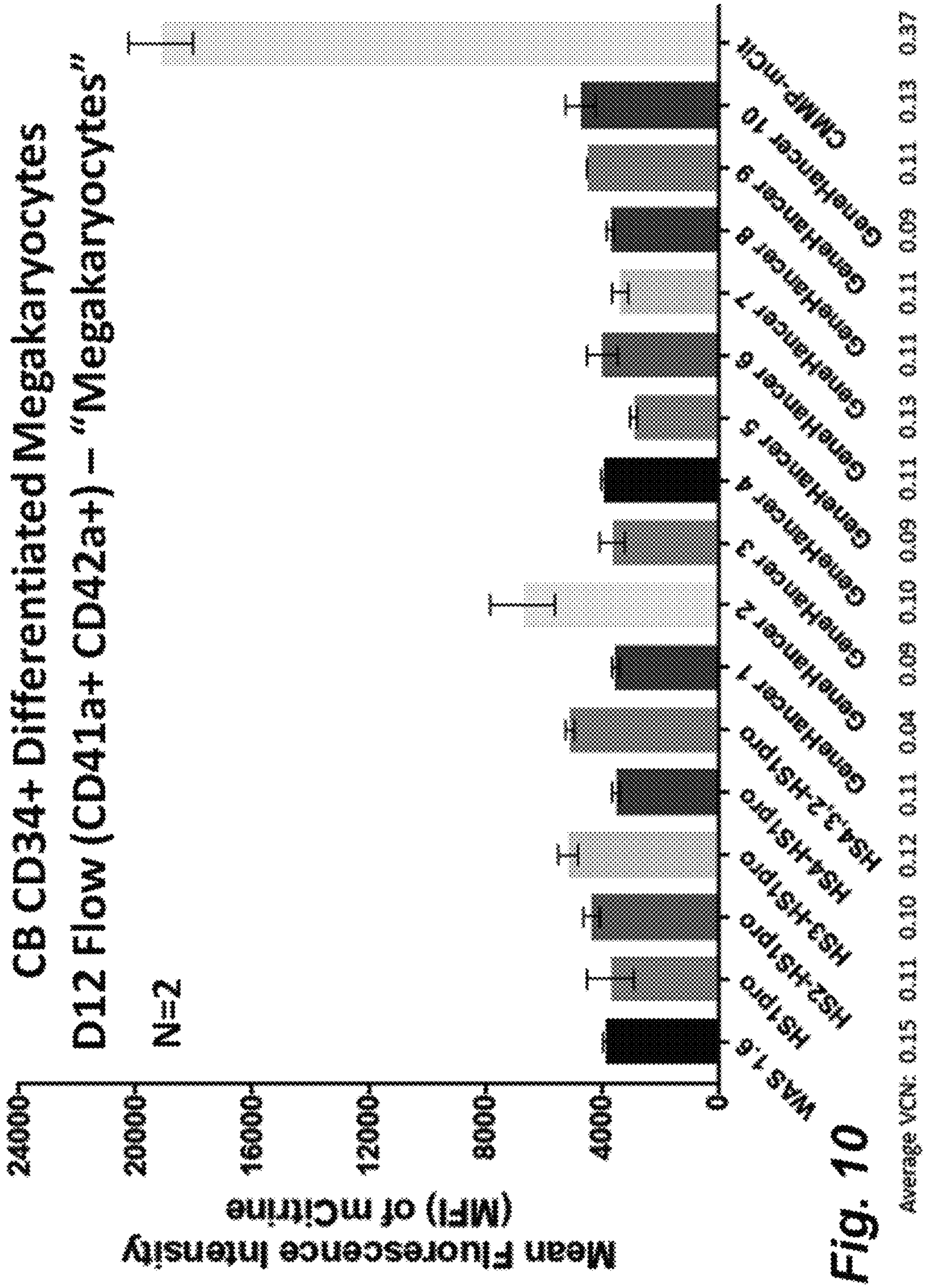
FIG. 10 shows expression levels of WAS vectors in CB CD34+ differentiated megakaryocytes "megakaryocytes".
Figure 11:
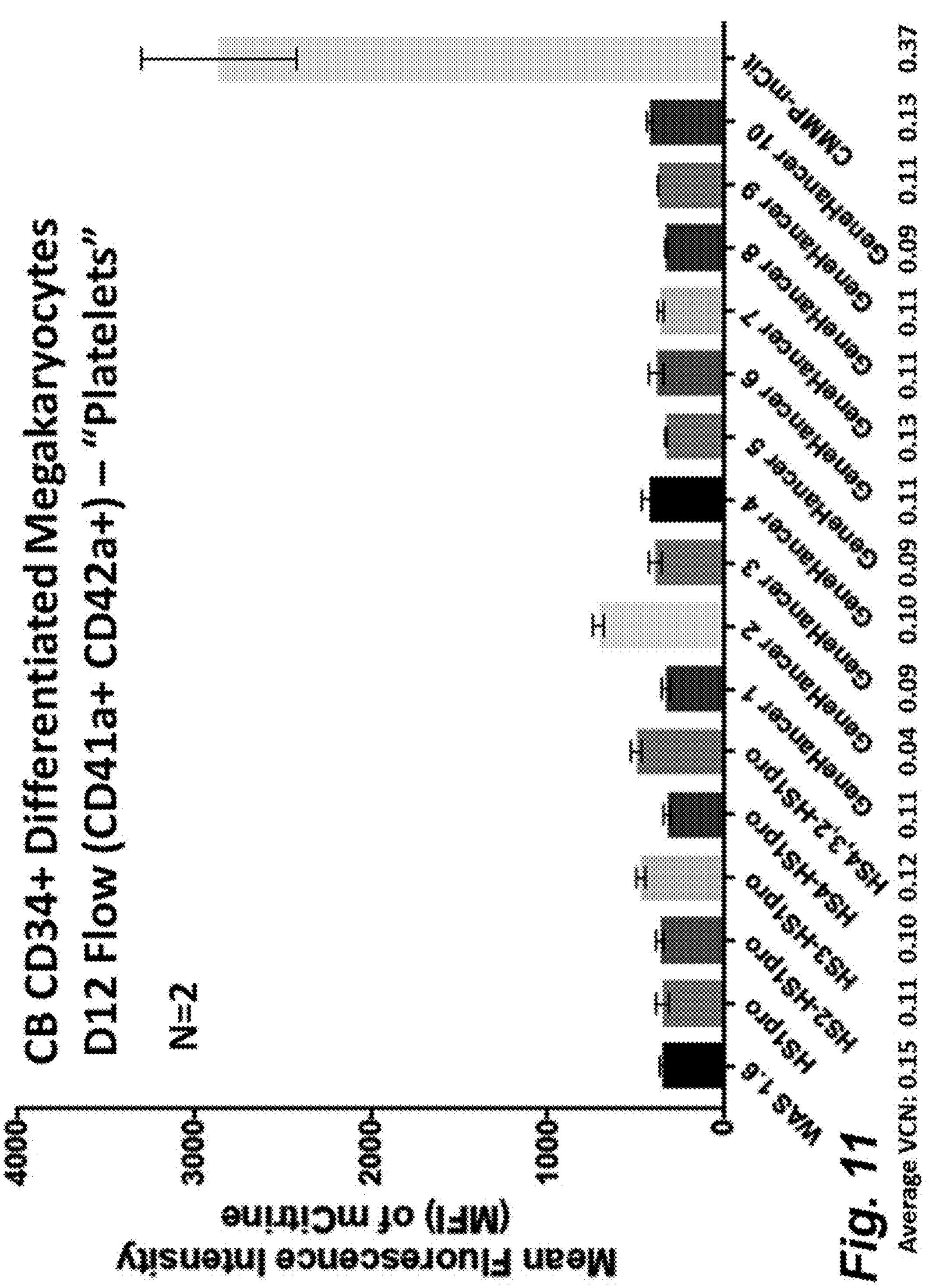
FIG. 11 shows expression levels of WAS vectors in CB CD34+ differentiated megakaryocytes "platelets".

The 10 elements were screened again in cord blood (CB) CD34+ HSPCs differentiated into megakaryocytes and platelets to confirm result from the cell lines. FIGS. 9-11 show expression levels of the WAS vectors in pro-megakaryocytes, megakaryocytes, and platelets, respectively. As shown in these figures, the data from CB CD34+ differentiated megakaryocytes differ from data from MEG-01 cells (megakaryoblast cell line). In particular, only enhancer element 2 seems to boost expression in the CB CD34+ megakaryocytes. While this construct expresses 2-fold higher than WAS 1.6, it under expresses compared to the γ-retroviral construct.

Figure 12:
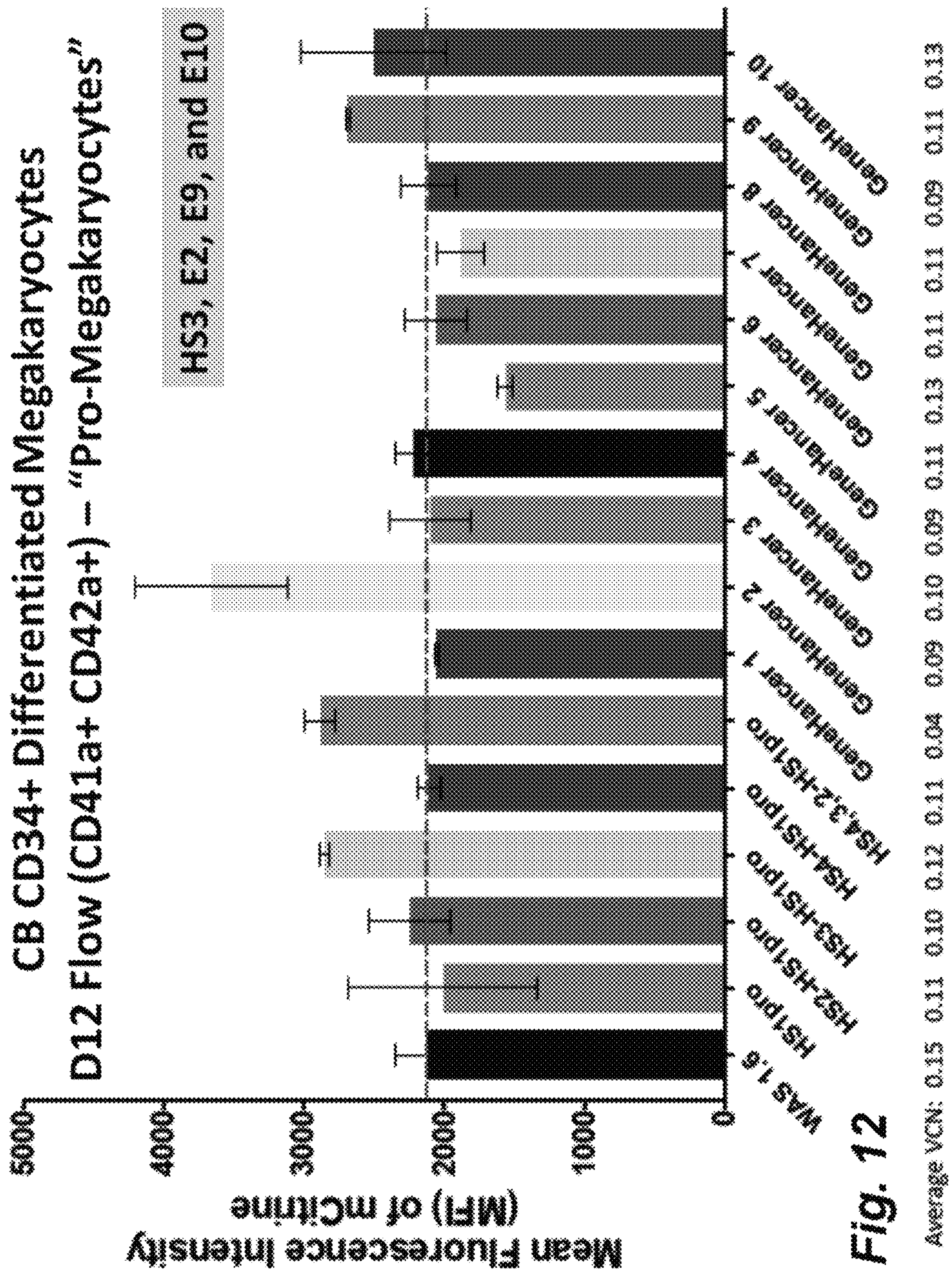
FIG. 12 WAS vectors in CB CD34+ differentiated megakaryocytes "pro-megakaryocytes".
Figure 13:
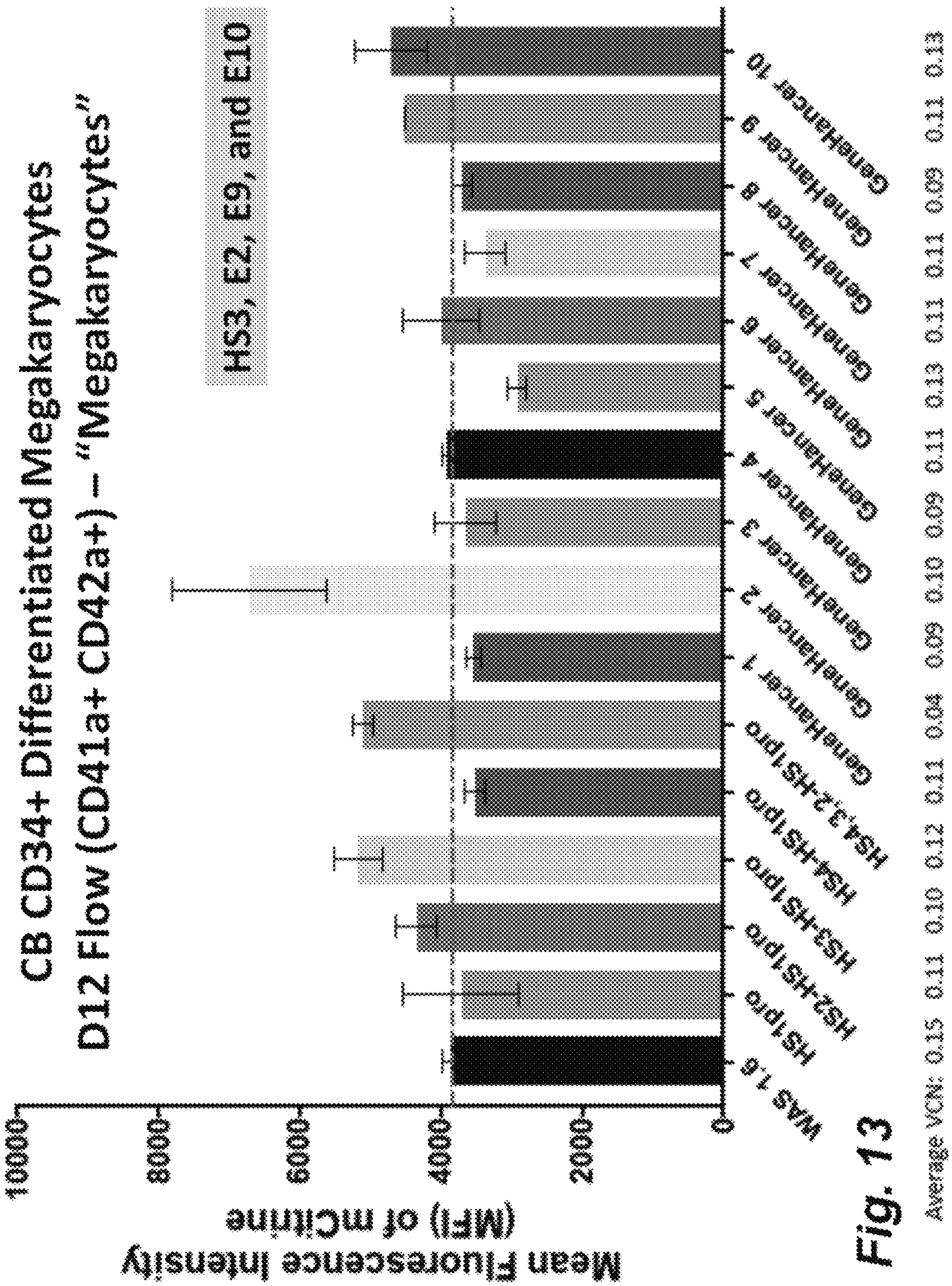
FIG. 13 shows expression levels of WAS vectors in CB CD34+ differentiated megakaryocytes "megakaryocytes".
Figure 14:
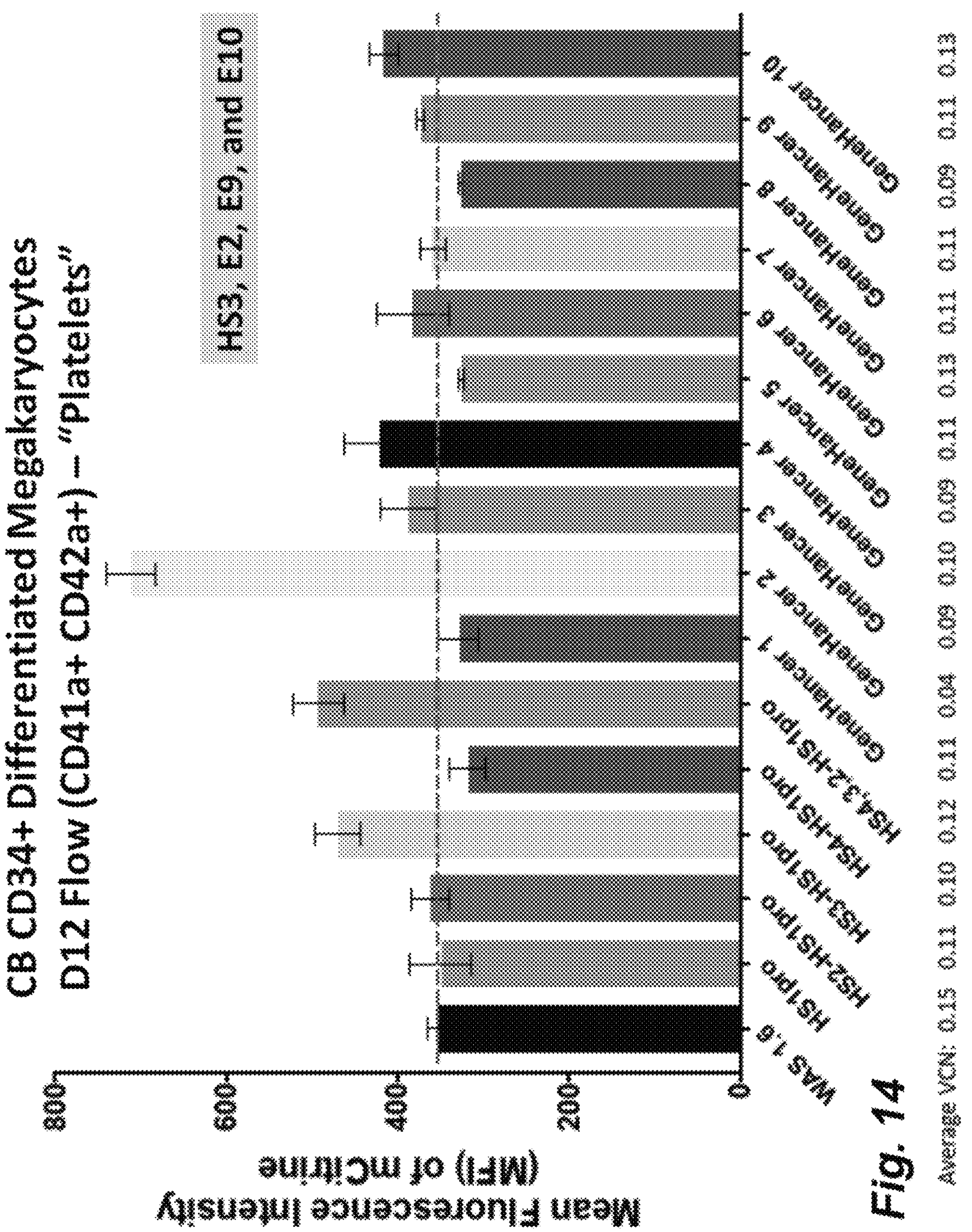
FIG. 14 shows expression levels of WAS vectors in CB CD34+ differentiated megakaryocytes "platelets".

One proposed lead vector was to comprise XXX-HS2-HS1-WASp-WPRE where XXX represents additional enhancer elements that can be added. The HS2-HS1 component comprise the two functional elements within the WAS1.6 promoter where HS1 is the main driver and HS2 provides an extra 190 bp. Various constructs comprising these elements and enhancer elements 1-10 were constructed and evaluated in pro-megakaryocytes (FIG. 12), megakaryocytes (FIG. 13), and platelets (FIG. 14).

Figure 15:
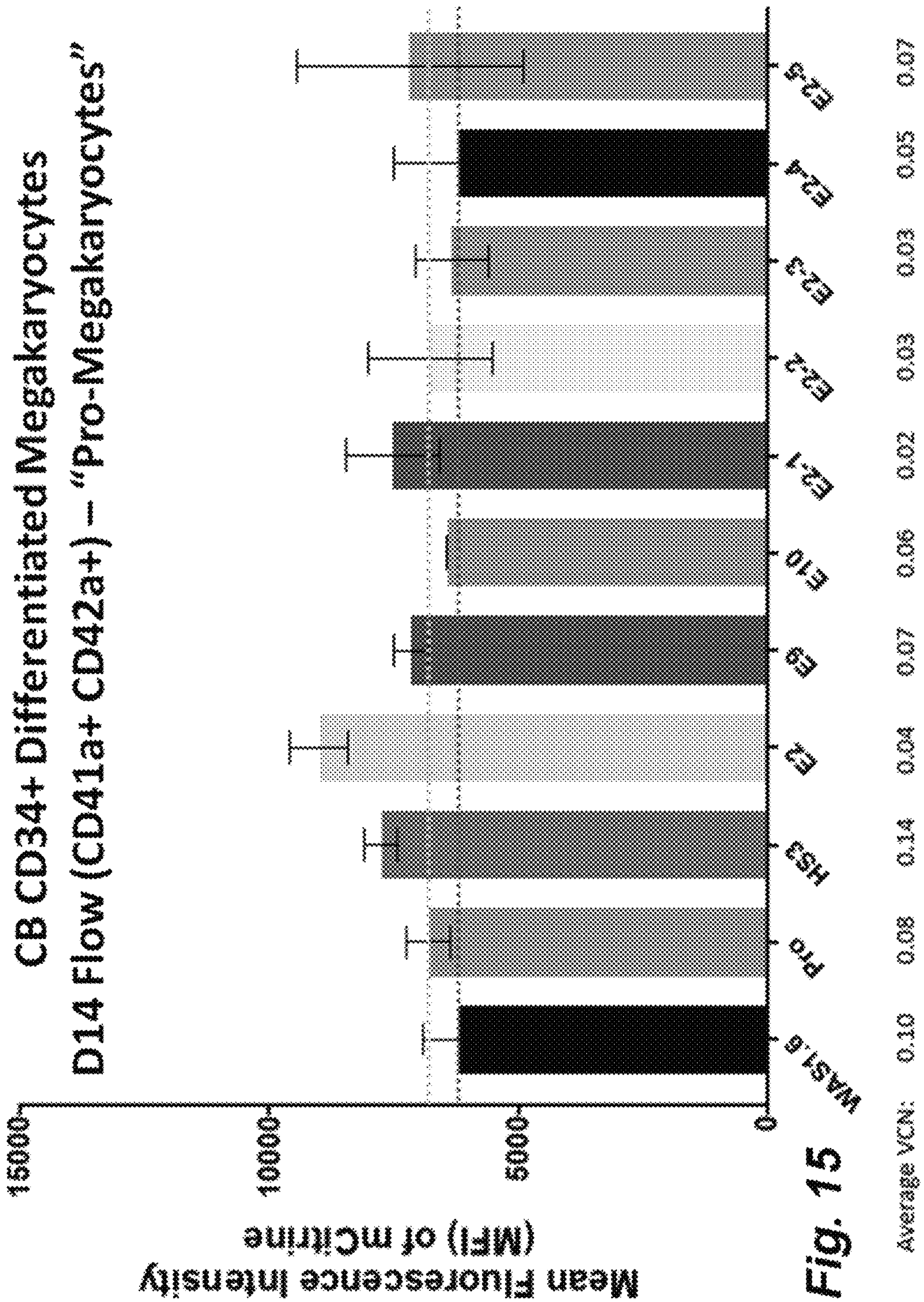
FIG. 15 shows expression levels of WAS vectors comprising each of 5 sub-elements of E2 in CB CD34+ differentiated megakaryocytes "megakaryocytes".
Figure 16:
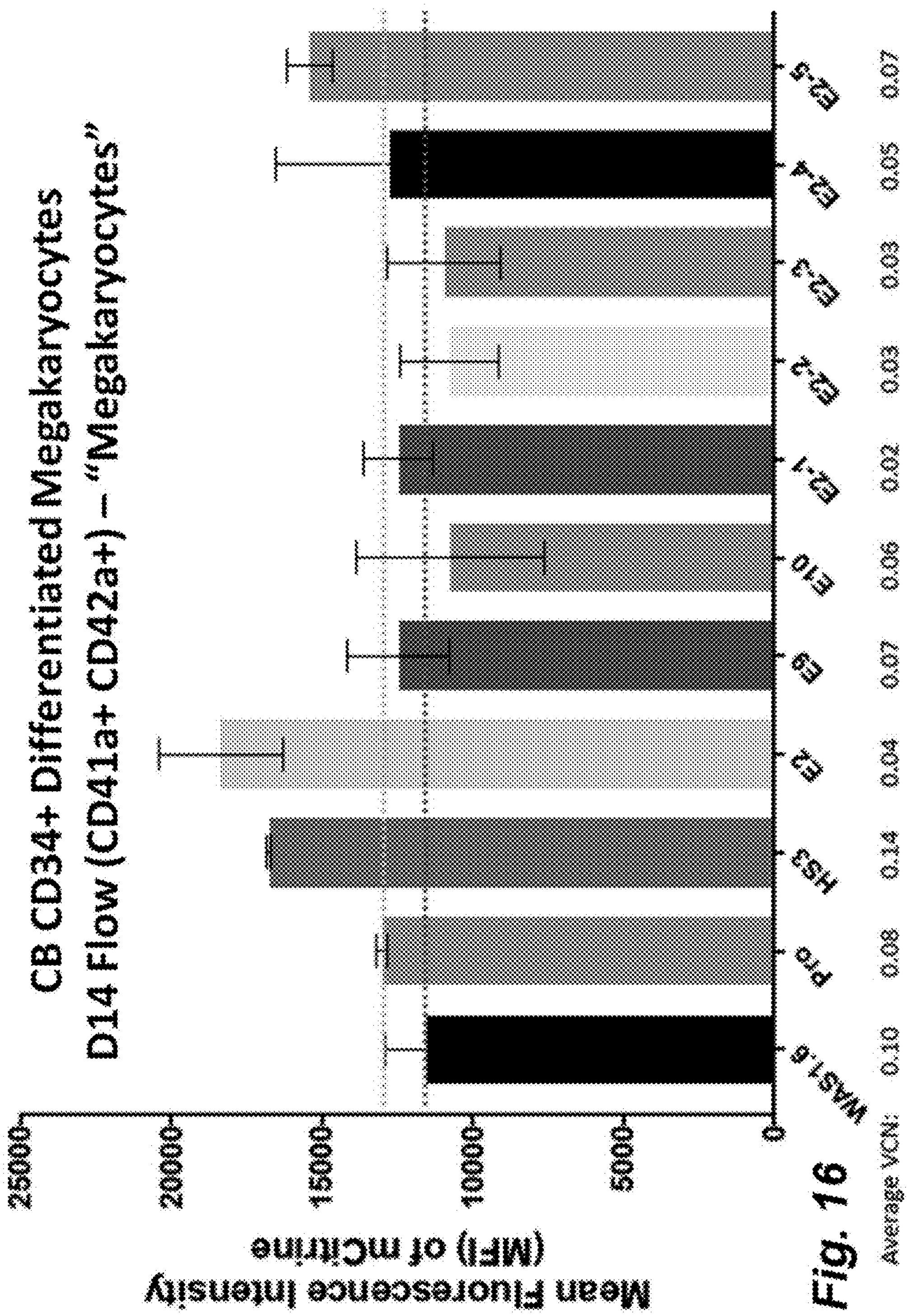
FIG. 16 shows expression levels of WAS vectors comprising each of 5 E2 fragments in CB CD34+ differentiated megakaryocytes "megakaryocytes".
Figure 17:
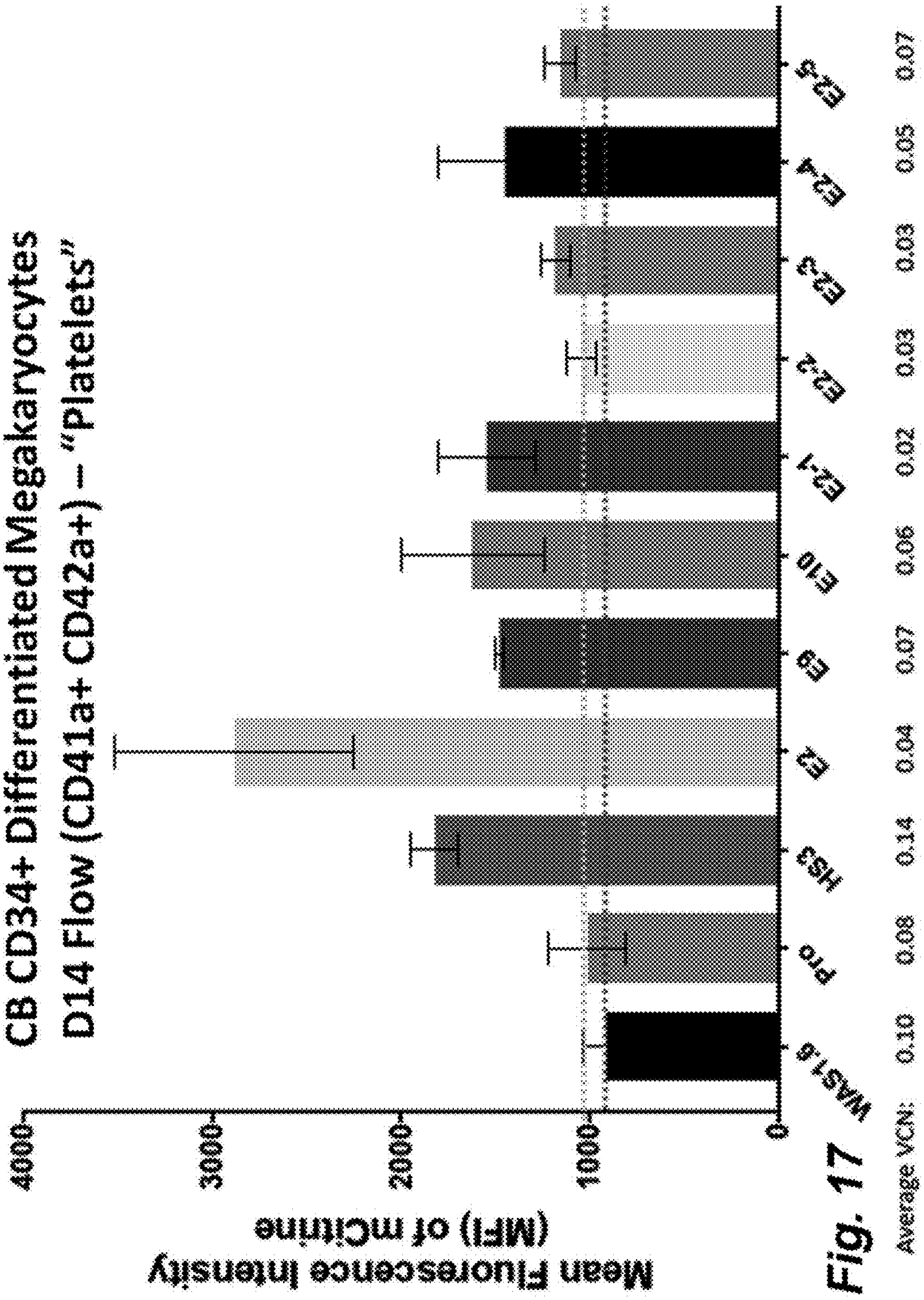
FIG. 17 shows expression levels of WAS vectors comprising each of 5 E2 fragments in in CB CD34+ differentiated megakaryocytes "platelets".

It was determined that optimal vectors could include various components of one or more of enhancer regions HS3, E2, E9, and E10. It was noted that the HS3 is 531 bp, E2 is 3678 bp, E9 is 555 bp, and E10 is 455 bp. Particularly in view of the length of enhancer region E2, it was desirable to identified smaller effective fragments of these regions. An analysis of enhancer element 2 (260 kb downstream of WAS) was found to contain 5 fragments approximating about 3.7 kb. The 5 E2 fragments: E2-1 (first half of core sub-element 1+second half of core sub-element 1, see, e.g., Table 1, SEQ ID NOs:3 and 4), respectively), E2-2 (see, e.g., Table 1, SEQ ID NO:5), E2-3 (see, e.g., Table 1, SEQ ID NO:6), E2-4 (see, e.g., Table 1, SEQ ID NO:7), and E2-5 (see, e.g., Table 1, SEQ ID NO:8) were cloned into 5 different vectors so that the most active fragments of E2 could be identified for inclusion in the vector. The expression of these vectors in in pro-megakaryocytes (FIG. 15), megakaryocytes (FIG. 16), and platelets (FIG. 17) was determined. As shown in FIGS. 15-17, no one element of E2 seems to be the main driver of expression. Sub-elements 2 and 3 of E2 seem not to have any effect on expression when tested alone. E2 is a driver of megakaryocyte expression but desirably can be slimmed down. This enhancer provides 3 fold higher expression than WAS1.6 in platelets, and 1.6 fold higher expression than WAS1.6 in megakaryocytes. However, the E2 enhancer under expresses compared to the γ-retroviral vector, but the increase compared to WAS1.6 may be sufficient to increase platelet counts to normal levels. There is a discrepancy of expression of enhancer elements between CB CD34+ differentiated megakaryocytes and megakaryocyte cell line (MEG-01 cells) as elements 1, 2, 3, 7, 8 and 9 each independently drive expression higher than the previous clinical γ-retroviral CMMP-mCit vector in MEG-01 cells, but all under express compare to CMMP-mCit in CB CD34+ megakaryocytes.

In view of these observations certain particular suitable vectors include, but are not limited to:

1) E2(all slim)-HS1pro-mCit-WPRE (5.6 kb);

2) E9(slim)-HS3(slim)-E2(all slim)-HS1pro-mCit-WPRE (6.1 kb);

3) E9(slim)-HS3(slim)-1,4,5(slim) of E2-HS1pro-mCit-WPRE (5.6 kb); and

4) E9(slim)-HS3(slim)-1st half of 1(slim) and 5(slim) of E2-HS1pro-mCit-WPRE (5.0 kb).

The sizes listed above are with the mCit reporter in the open reading frame. Sizes will differ with a nucleic acid encoding Wasp in the open reading frame.

It is noted that vector (3) above eliminates sub-elements 2 and 3 in Enhancer element 2, while vector (4) above eliminates the second half of sub-element 1, and sub-elements 2, 3, and 4 of Enhancer element 2.

It will also be recognized that for clinical use (e.g., to treat WAS) the mCitrine open reading frame will be replaced with a nucleic acid encoding the WASp protein. Illustrative nucleic acids include, but are not limited to a WAS cDNA, and a codon-optimized WAS nucleic acid.

Example 2

Identification of Lead Candidate Vector

Example 1, above, described the generation of four lead candidate vectors: 1) E2(all slim)-HS1pro-mCit-WRPE; 2) E9(slim)-HS3(slim)-E2(all slim)-HS1pro-mCit-WRPE; 3) E9(slim)-HS3(slim)-1,4,5(slim) of E2-HS1pro-mCit-WRPE; and 4) E9(slim)-HS3(slim)-$1^{st}$ half of 1 (slim) and 5 (slim) of E2-HS1pro-mCit-WRPE.

This example describes the screening of these vectors in CB CD34+ HSPC differentiation megakaryocytes and platelets to determine a lead candidate vector. Additionally, codon optimization of WASp to replace the open reading frame of mCitrine with WASp and to express the actual therapeutic protein was evaluated. Correction of WASp expression in WAS patient T and B cell lines is also demonstrated.

In order to determine a lead candidate vector, we screened the 4 candidate vectors in megakaryocytes and platelets differentiated from healthy donor (HD) cord blood (CB) CD34+ hematopoietic stem and progenitor cells (HPSCs). Single element vectors containing modified boundaries and fragments of the E2, E9 and HS3 elements are also included to determine if the modified (smaller sized elements) used to create the lead candidates still retain expression of the parental elements. WAS1.6 (the current WAS vector undergoing clinical trials) and the previously used γ-retroviral vector are also included for comparison of expression.

Figure 22:
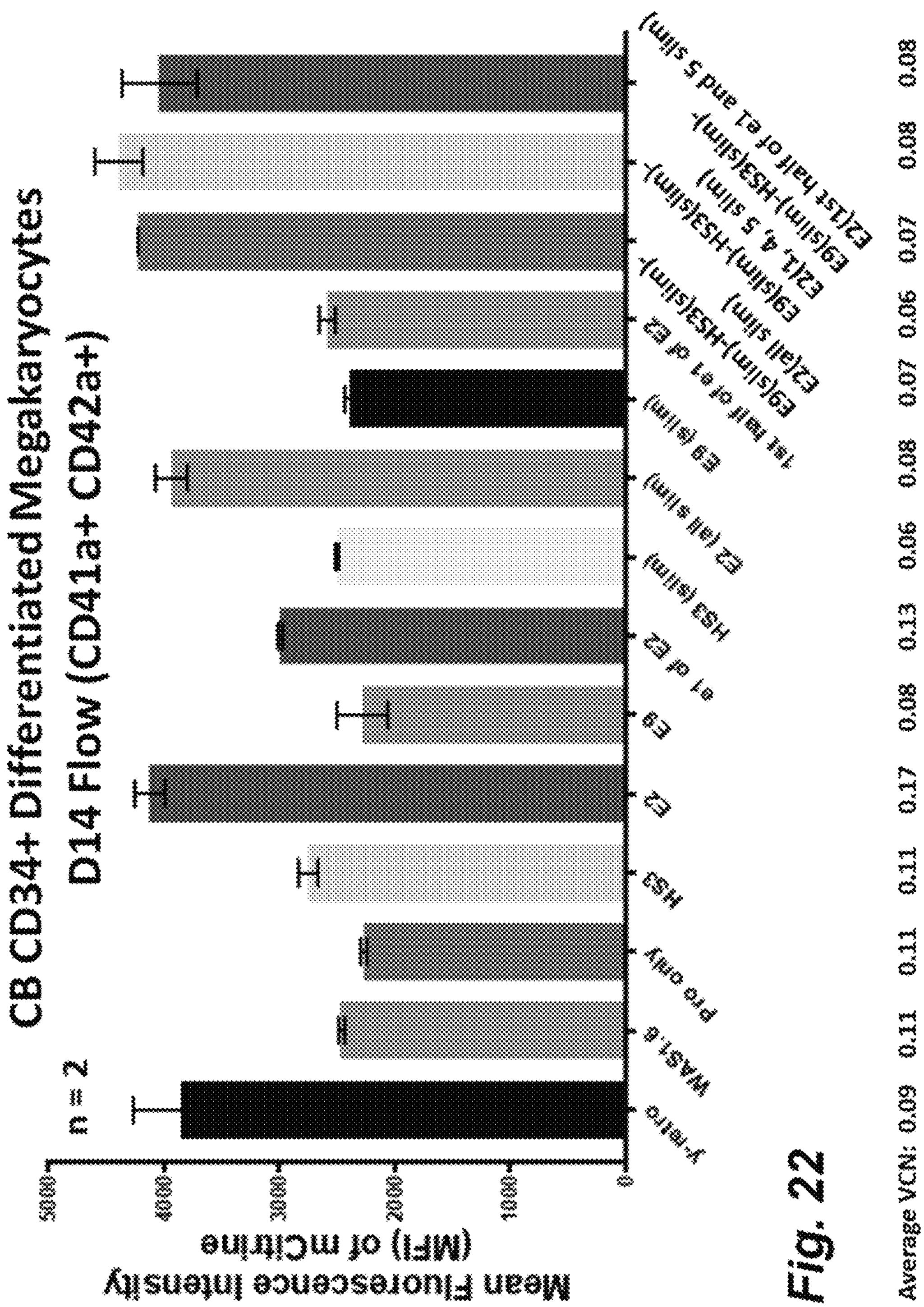
FIG. 22 shows expression of the candidate vectors in CB CD34+ differentiated megakaryocytes.

As shown in FIG. 22 the modified "slim" versions of E9, HS3 and E2 retain expression of the larger parental elements. Additionally, one lead candidate vector, E9(slim)-HS3(slim)-1,4,5(slim) of E2-HS1pro-mCit-WRPE, has similar level of expression compare to the γ-retroviral vector and a 1.8-fold higher expression than WAS1.6 in CB CD34+ HSPC differentiated megakaryocytes (FIG. 22).

Figure 23:
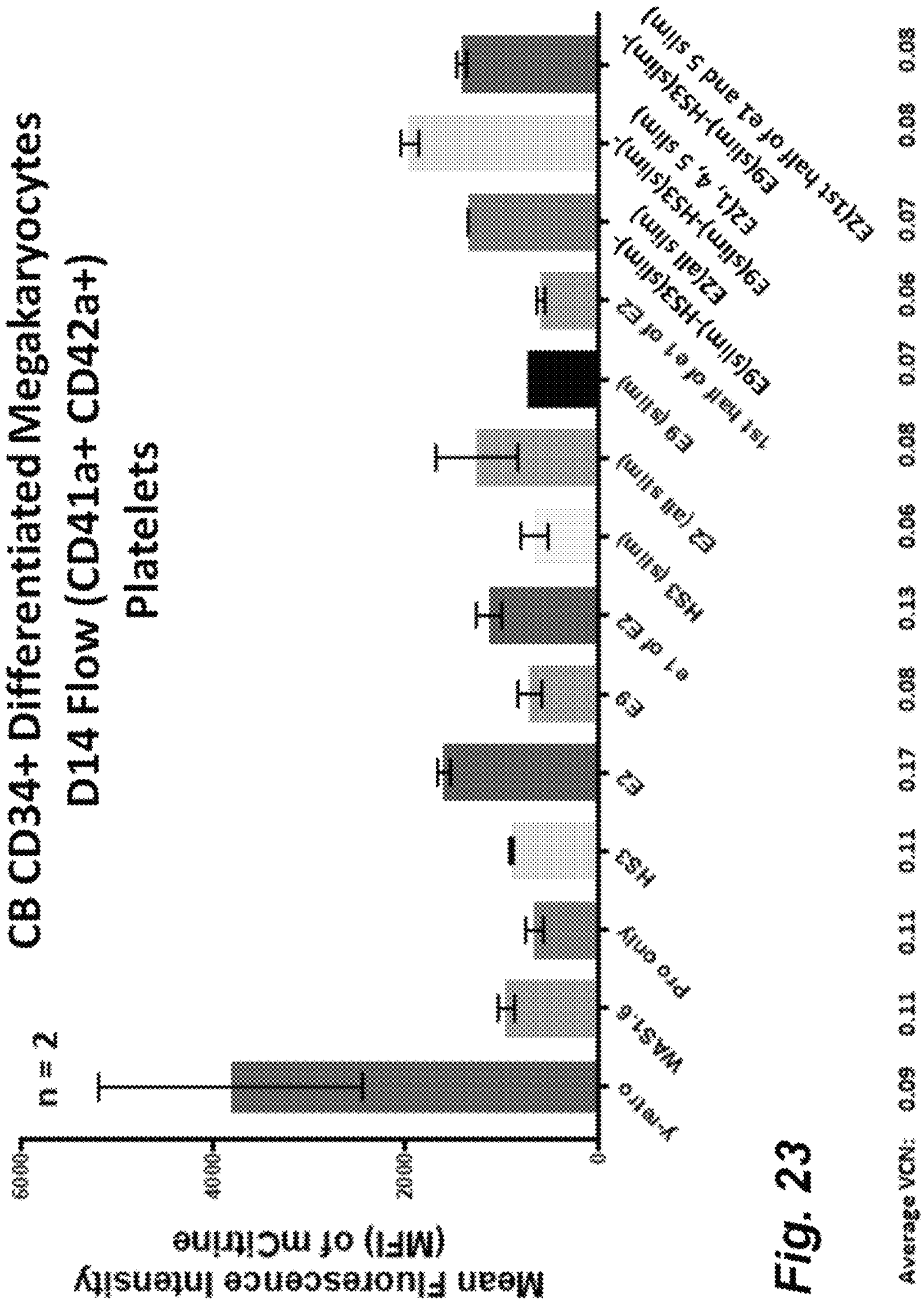
FIG. 23 shows expression of the candidate vectors in CB CD34+ differentiated platelets.

A similar result was seen in the CB CD34+ differentiated platelets as E9(slim)-HS3(slim)-1,4,5(slim) of E2-HS1pro-mCit-WRPE expresses similar to the γ-retroviral vector and 1.5 fold higher than WAS1.6 (see, e.g., FIG. 23).

In view of these data, one lead candidate vector is E9(slim)-HS3(slim)-1,4,5(slim) of E2-HS1pro-mCit-WPRE (WasVec) which:

1) Expresses equal/higher than the y-retro in CB CD34+ megakaryocytes;

2) Expresses 1.8 fold greater than WAS1.6;

5.6 kb w/mCitrine in the open reading frame;

6.4 kb w/WASp in the open reading frame; and

3) Expresses 1.5 fold greater than WAS1.6 in "platelets".

In order to screen for the ideal codon optimized sequence of WASp to further improve expression, we immortalized T and B cell lines from WAS patient and used the cell lines to screen different codon optimized versions of the WASp open reading frame in WASVec—(E9(slim)-HS3(slim)-1,4,5 (slim) of E2-HS1pro-WASp-WPRE)

The WAS B-cell and T-cell lines were transduced with different versions of WASVec, each encoding a different codon optimized version of the WASp open reading frame as follows:

cDNA (native cDNA sequence, unmodified as a control);

jCAT codon optimization;

GeneArt codon optimization;

IDT codon optimization; and

Benchling codon optimization.

Figure 24:
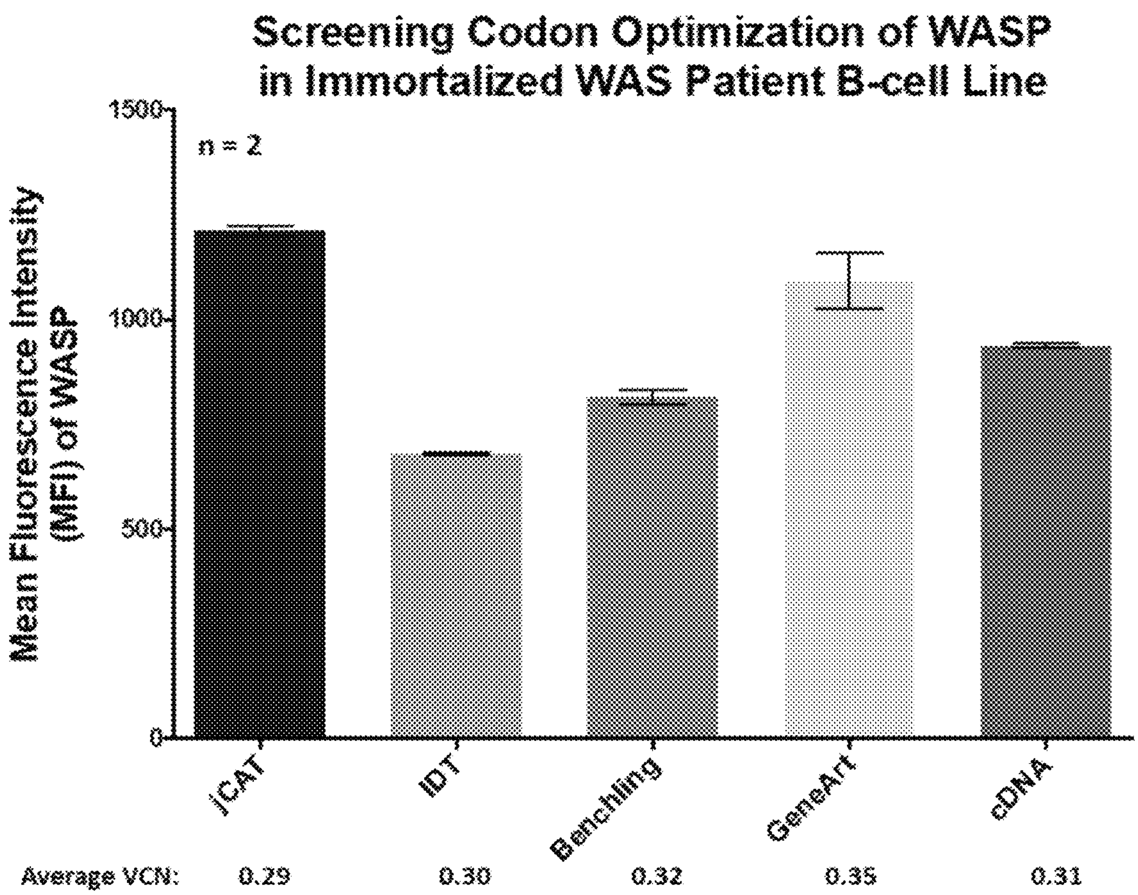
FIG. 24 shows screening of codon optimizations in an immortalized WAS patient B-cell line.
Figure 25:
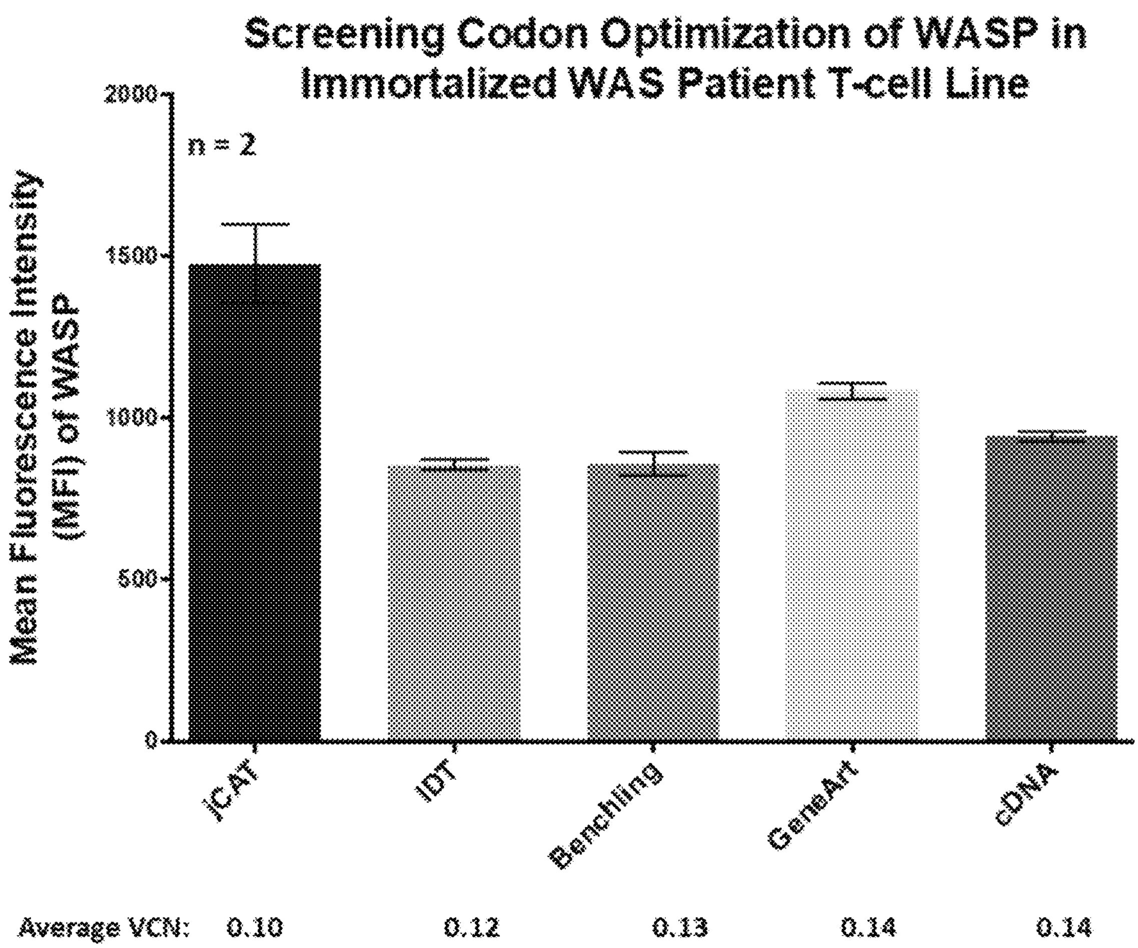
FIG. 25 shows screening of codon optimizations in an immortalized WAS patient T-cell line.

As shown in FIGS. 24, and 25, jCAT codon optimization of WASP in WASVec led to a 1.29 fold and 1.48 fold increase in expression in B cells (FIG. 24) and T cells (FIG.

Figure 26:
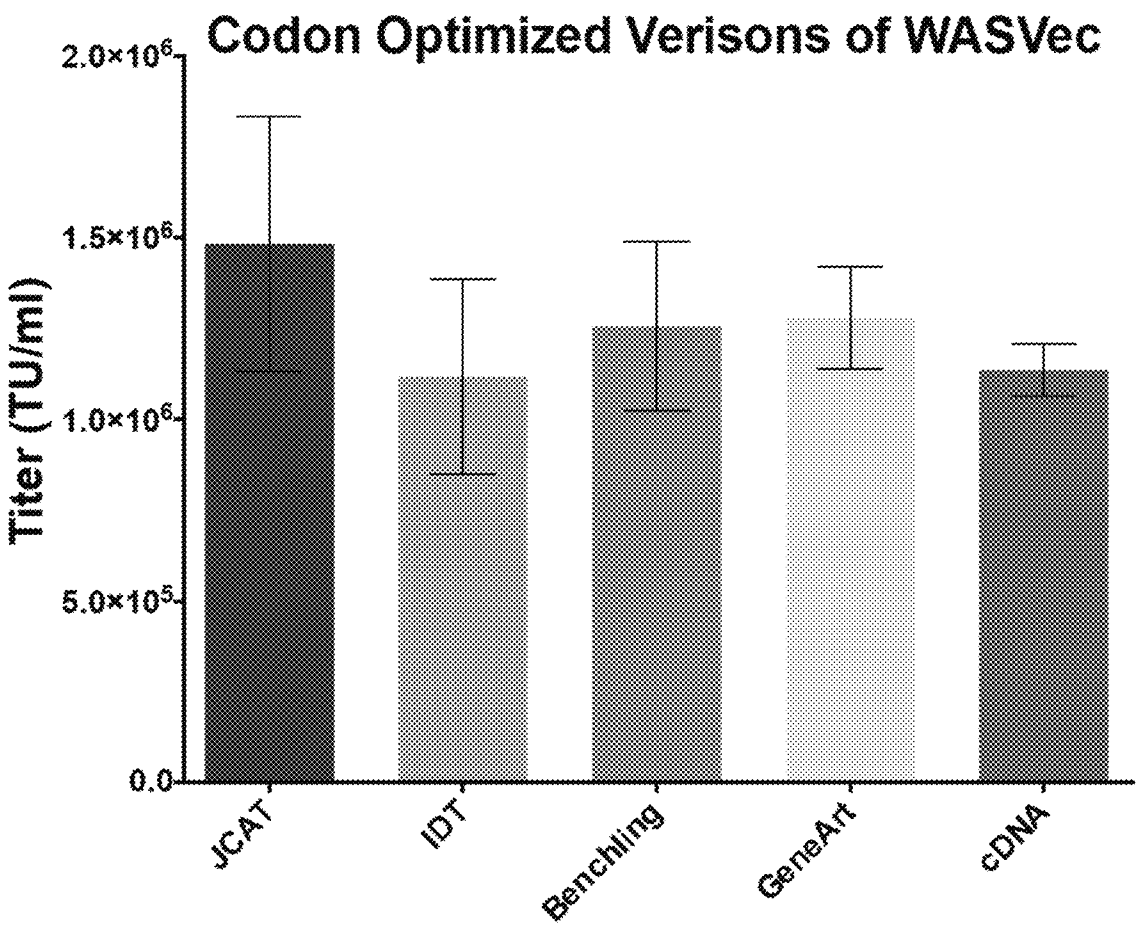
FIG. 26 shows titer produced by codon optimized versions of WASVec.

25) respectively compared to the non-codon optimized native cDNA. FIGS. 24, and 25 also show that GeneArt codon optimization led to a 1.13 fold and 1.20 fold increase in expression in B and T cells respectively compare to the native cDNA, while both IDT and Benchling codon optimizations led to a decrease in expression in B-cells and T-cells. None of the codon optimizations seem to significantly affect titer. Additionally, CAT and GeneArt may slightly increase titer (FIG. 26).

In view of these observations, one lead candidate vector is E9(slim)-HS3 (slim)-E2(1,4,5 slim)-HS1pro-WASP (jCAT codon optimized)-WPRE, aka WASVec. This vector is 6.4 kb with WASp in the open reading frame It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

SEQUENCE LISTING

SEQ ID NO: 1
HS1pro (minimal endogenous promoter of the WAS gene)
TCAGCCTCAGGCTACCTAGGTGCTTTAGAAAGGAG
GCCACCCAGGCCCATGACT
ACTCCTTGCCACAGGGAGCCCTGCACACAGATGTGCTAAG
CTCTCGCTGCCAGCCAGAGGGAGGAGGGTCTGAGCCAGTC
AGAAGGAGATGGGCCCCAGAGAGTAAGAAAGGGGGAGGAG
GACCCAAGCTGATCCAAAAGGTGGGTCTAAGCAGTCAAGT
GGAGGAGGGTTCCAATCTGATGGCGGAGGGCCCAAGCTCA
GCCTAACGAGGAGGCCAGGCCCACCAAGGGGCCCCTGGAG
GACTTGTTTCCCTTGTCCCTTGTGGTTTTTTGCATTTCCT
GTTCCCTTGCTGCTCATTGCGGAAGTTCCTCTTCTTACCC
TGCACCCAGAGCCTCGCCAGAGAAGACAAGGGCAGAAAGC
ACC SEQ ID NO: 2
Enhancer element 2 (Slim)
GACCTGAAGGGTAAGGGGGTGTGGAGGTTGTGAAGGCGGG
AAGGGGGGTAGCCCCTTCACCAATGTAAACAAGGATGTGG
GTTCTGCGGCCACACTCTCCCCCGCCCTCCCCAGCGGCAT
TTCCAGCAAGTCACATGTCCTGCGCACAGGCTGGGGGCCC
CCTGCTGCTGCCTTTCTTAGAAGCCAGGACCACAGAGCCC
GCACAGTGAGCTACTTGGGGAGCTATTTCTGTAGACTGAG
CTTGGGGTACTGGGAGGCAGTGCTGTTGGCGATCTGGGGG
AAAACCCCCTGAGGGTCCCATTTCTCTGCCACTGACCCCT
TTGCCTGGCAGAAAGGCTCTGCTGCCTCCTAGCTGTGTAG
CAATGGATAAGGCCTTTAACCTCTCTAAGCTGAAATGTCC
TCATGCATAAGGTGGAGACAGTAACTCCTCTTCCATCTGC -continued TGGGTGTTGTCAAAACTACACAGGAGGTTTGCCAAGCACC
TAAGGCACAGTAGGTGGTCAAGAAACAGGAACACAATTTG
TCATGACGACAATGATTCCTTCATATGCTAGTTACCCACG
AGTCAGCCAGAATGTTGCCATAACCACTTATGAAGCCCTT
CCTCATTTCTGTTGCAATTCCTCAGCCAGAGGAAAGCCCC
ACCACCTCTGTCCTCCAGAAAGCCCTCCTCTTCCCAGAAG
GCTGGCACACAGGGCTGGGGGCCAGGCTTGACTTCCCTGT
GGAGGGGTCTGAGGTTGGGGGGATGACCTGCAGAGGTAGG
GGAATTCAGAGAACTTGTTTTGATAGAAACTGAAACTCCT
CCTCTTGCTGACGCTGCACTTGTGGGCAATCTGCACCTGT
TCTCCCCTCCCAGAGGCCAGCTGGAAGGGGGTCCCCCACC
ATTCTACCTCTGTTCCCATCTCAAACAGGGCTCAGAAATC
CTCAGAGAGCCTGGATTATCTTCCTATAGGGTCCTACCAT
TTGCTTTAGAGACATCTGAGAACTGCCTACTCCCCAGGTA
GCTGCCTGCCTCCCAGAAGAGCCACAGCAAGTTCCGCTAA
GGGCAAAAAAGGAAGCTAGGTGTCTACAGGGAACCTAAAA
ACAAACCACACTAACGTGTGTACACACAGCTGCAGAGGGA
GACAGGGACCTGGTCTGCTCACAGCCCTTGCCACTCCCCC
ATGGCCCATGTAGAAACAACCATGTGGCCTTCACTCTGCC
CACAGAAGCTAGCACCAGGACCCTGGTCAGGGTTAGAGGT
TTCTGCTGAGTCAAAGCCACATGGAGGGAGGGAGCAAGGG
AGAGATGCAGAGTCATGTTTCCAGGAGGAGGTTATCTGAG
CATAACAGGGACAGGGTGGGCCACAGGATACCTCTGAGGC
TCAGGTTCCCACCTCCACTCCACCCTCCAACTCTCTGCTC
CACGTTCCTTCCACTATTCAACACATGGCAGGAAGTCAGC
CTGTAGGGCTTCACACTACAGTCTAAGCTGACTGCCATCT
GTCCCCATCCAGGCGAGGCTGGAAACGGGGGCAGCAAAAA
GCCCAGGGACAAAGTCCCCTTCCCAGGCACATGTATTATG
CACTCTGCACCAAGGAAACCTCCAGATAAGGTCTAGAGAC
CAAGGGCCATGTACTTCGGGGGAGAGGCCAGAGGACTTCT
GAGGTTTTACAGAGAAAAGCCAAAGGCAGCCCAGTCAGGG
GAAATGTGTAGCCATAGTGCCGATAAGGAAAGGCCTTCAA
CCTGCCCTGGTCAGCTCTTCCTGTAAGTAGAGGCCCCTTA
CCGAAGGCCCCAGTGGGAGGAAGGGTCGGGAGTA SEQ ID NO: 3
$1^{st}$ half of Core Sub-Element 1 of Enhancer Element 2
GACCTGAAGGGTAAGGGGGTGTGGAGGTTGTGAAGGCGGG
AAGGGGGGTAGCCCCTTCACCAATGTAAACAAGGATGTGG
GTTCTGCGGCCACACTCTCCCCCGCCCTCCCCAGCGGCAT
TTCCAGCAAGTCACATGTCCTGCGCACAGGCTGGGGGCCC
CCTGCTGCTGCCTTTCTTAGAAGCCAGGACCACAGAGCCC -continued

GCACAGTGAGCTACTTGGGGAGCTATTTCTGTAGACTGAG

CTTGGGGTACTGGGAGGCAGTGCTGTTGGC

SEQ ID NO: 4
$2^{nd}$ half of Core Sub-Element 1 of
Enhancer Element 2
GATCTGGGGGAAAACCCCCTGAGGGTCCCATTTCTCTGCC

ACTGACCCCTTTGCCTGGCAGAAAGGCTCTGCTGCCTCCT

AGCTGTGTAGCAATGGATAAGGCCTTTAACCTCTCTAAGC

TGAAATGTCCTCATGCATAAGGTGGAGACAGTAACTCCTC

TTCCATCTGCTGGGTGTTGTCAAAACTACACAGGAGGTTT

GCCAAGCACCTAAGGCACAGTAGGTGGTCAAGAAACAGGA

ACACAATTTGTCATGACGACAATGATTCCTTCATATGCTA

GTTACCCACGAGTCAGCCAGAATGTTGCCATAACCACTTA

TGAAGCCCTTCCTCATTTCTGTTGCAATTCCTCAGCCAGA

GGAAAGCCCCA

SEQ ID NO: 5
Core Sub-Element 2 of Enhancer Element 2
CCACCTCTGTCCTCCAGAAAGCCCTCCTCTTCCCAGAAGG

CTGGCACACAGGGCTGGGGGCCAGGCTTGACTTCCCTGTG

GAGGGGTCTGAGGTTGGGGGGATGACCTGCAGAGGTAGGG

GAATTCAGAGAACTTGTTTTGATAGAAACTGAAACTCCTC

CTCTTGCTGACGCTGCACTTGTGGGCAATCTGCACCTGTT

CTCCCCTCCCAGAGGCCAGCTGGAAGGGGGTCCCCCACCA

TTCTACCTCTGTTCCCATCTCAAACAGGGCTCAGAAATCC

TCA

SEQ ID NO: 6
Core Sub-Element 3 of Enhancer Element 2
GAGAGCCTGGATTATCTTCCTATAGGGTCCTACCATTTGC

TTTAGAGACATCTGAGAACTGCCTACTCCCCAGGTAGCTG

CCTGCCTCCCAGAAGAGCCACAGCAAGTTCCGCTAAGGGC

AAAAAAGGAAGCTAGGTGTCTACAGGGAACCTAAAAACAA

ACCACACTAACGTGTGTACACACAGCTGCAGAGGGAGACA

GGGACCTGGTCTGCT

SEQ ID NO: 7
Core-Sub Element 4 of Enhancer Element 2
CACAGCCCTTGCCACTCCCCCATGGCCCATGTAGAAACAA

CCATGTGGCCTTCACTCTGCCCACAGAAGCTAGCACCAGG

ACCCTGGTCAGGGTTAGAGGTTTCTGCTGAGTCAAAGCCA

CATGGAGGGAGGGAGCAAGGGAGAGATGCAGAGTCATGTT

TCCAGGAGGAGGTTATCTGAGCATAACAGGGACAGGGTGG

GCCACAGGATACCTCTGAGGCTCAGGTTCCCACCTCCACT

CCACC

SEQ ID NO: 8
Core-Sub Element 5 of Enhancer Element 2
CTCCAACTCTCTGCTCCACGTTCCTTCCACTATTCAACAC

ATGGCAGGAAGTCAGCCTGTAGGGCTTCACACTACAGTCT

-continued

AAGCTGACTGCCATCTGTCCCCATCCAGGCGAGGCTGGAA

ACGGGGGCAGCAAAAAGCCCAGGGACAAAGTCCCCTTCCC

AGGCACATGTATTATGCACTCTGCACCAAGGAAACCTCCA

GATAAGGTCTAGAGACCAAGGGCCATGTACTTCGGGGGAG

AGGCCAGAGGACTTCTGAGGTTTTACAGAGAAAAGCCAAA

GGCAGCCCAGTCAGGGGAAATGTGTAGCCATAGTGCCGAT

AAGGAAAGGCCTTCAACCTGCCCTGGTCAGCTCTTCCTGT

AAGTAGAGGCCCCTTACCGAAGGCCCCAGTGGGAGGAAGG

GTCGGGAGTA

SEQ ID NO: 9
Enhancer element HS3 (full)
CTAAAAGCCACCAAAACCAAGACAGCAATGAAAGTAACCT

CTGGTCTTCCTAACTGCTCATTATACACTAATTATGATGC

ACTAGCATGCTAAGAGACACTTCCACCAGCGCCATGACAG

TGCCATGGCAACATCAAGAAGTCACCCCACATGGTCTAAA

AAGGGGAAGAACCTTCAGTTCCCGGAATTGCCCACCCCTT

TCCTGGAAAACTCATGAATAATCCACCCCTTGTTTAGCAT

ATAATTAAGAAATAACTGTAAGTATCCTTAGTCCAGCAGC

CCAAGCTGCTGCTCTGCCTATGGAGTAGCCATTCTTTATT

CCTTTACTTTCTTAATAAACTTGCTTTCACATTAAAAACA

ACAACAACAACACCAACAACCAGCAAATATATCAGAGGCT

TAGCATCCCCTATTCAAGGGGACAGTTCTGGAGGCCGAGA

AAGAAGTAGAAAGGTGGAGAATAAAAGACACAAAGGAGCA

GAAGAATTTTATCTTGGCCTCCATGTGGCACCTCACAGCT

TGGGAACAACA

SEQ ID NO: 10
enhancer element HS3 core
CTAAAAGCCACCAAAACCAAGACAGCAATGAAAGTAACCT

CTGGTCTTCCTAACTGCTCATTATACACTAATTATGATGC

ACTAGCATGCTAAGAGACACTTCCACCAGCGCCATGACAG

TGCCATGGCAACATCAAGAAGTCACCCCACATGGTCTAAA

AAGGGGAAGAACCTTCAGTTCCCGGAATTGCCCACCCCTT

TCCTGGAAAACTCATGAATAATCCACCCCTTGTTTAGCAT

ATAAT

SEQ ID NO: 11
Enhancer element E9 (full)
GGGATCTGTGTGCAGATTTACCTCTACCTACACCTGGCTG

GGGATCATAAAGAAAATCAAGGGATGCGCTACCTCCATGA

ATCCAGGTTTCAGCAGAGCTAAGGGAGTGAAATTTGGGGC

CATTTTACTTGTCTCAAACCTTGTTATCTGAGAGAAAGCT

AGAGCTTCCTTCTTTCAGCCCCCAGAGACAATGTGGCCAG

GCTCCGGAGGGCTGGGAAGATGAGCAATGCTTGTGAGTCA

CCATGATAGGAAGCAGAAGGGTCAGGAAGTCCCTGGGAGC

-continued

AAGGCTTAGGGTTAGGGTTAGGGAGAAAACACTTGGGCCT GGAGGCTCGGGGCAGGCTTCCTAGAGGGGAGGGGTAGGAA GAGGCAGTGACAGGGCCCACAGCAATGGAGAGGAGTTGGA CTGCAGGGATGGGGTAGGGGGACAGACGACAAGGGACACT CAGAAGACTAATGTCTGGGAGTGGGAAAACAGTGTTTGCT CAGCCAGGAAGCTGCATCCAGCTCTTTTATCATTTGTAGA AGACCAAGTACCCAGGCCTGGGAGGAGCCCAGAGA

SEQ ID NO: 12
Enhancer element E9 core
CAAACCTTGTTATCTGAGAGAAAGCTAGAGCTTCCTTCTT TCAGCCCCCAGAGACAATGTGGCCAGGCTCCGGAGGGCTG GGAAGATGAGCAATGCTTGTGAGTCACCATGATAGGAAGC AGAAGGGTCAGGAAGTCCCTGGGAGCAAGGCTTAGGGTTA GGGTTAGGGAGAAAACACTTGGGCCTGGAGGCTCGGGGCA GGCTTCCTAGAGGGGAGGGGTA SEQ ID NO: 13
WAS cDNA
atgagtgggggcccaatgggaggaaggcccgggggccgag gagcaccagcggttcagcagaacataccctccaccctcct ccaggaccacgagaaccagcgactctttgagatgcttgga cgaaaatgcttgacgctggccactgcagttgttcagctgt acctggcgctgccccctggagctgagcactggaccaagga gcattgtggggctgtgtgcttcgtgaaggataacccccag aagtcctacttcatccgcctttacggccttcaggctggtc ggctgctctgggaacaggagctgtactcacagcttgtcta ctccacccccacccccttcttccacaccttcgctggagat gactgccaagcggggctgaactttgcagacgaggacgagg cccaggccttccgggccctcgtgcaggagaagatacaaaa aaggaatcagaggcaaagtggagacagacgccagctaccc ccaccaccaacaccagccaatgaagagagaagaggagggc tcccacccctgcccctgcatccaggtggagaccaaggagg ccctccagtgggtccgctctccctggggctggcgacagtg gacatccagaaccctgacatcacgagttcacgataccgtg ggctcccagcacctggacctagcccagctgataagaaacg ctcagggaagaagaagatcagcaaagctgatattggtgca cccagtggattcaagcatgtcagccacgtggggtgggacc cccagaatggatttgacgtgaacaacctcgacccagatct gcggagtctgttctccagggcaggaatcagcgaggcccag ctcaccgacgccgagacctctaaacttatctacgacttca ttgaggaccagggtgggctggaggctgtgcggcaggagat gaggcgccaggagccacttccgccgcccccaccgccatct cgaggagggaaccagctcccccggcccccctattgtggggg gtaacaagggtcgttctggtccactgccccctgtacctttggggattgccccacccccaccaacaccccggggacccccacccccaggccgagggggccctccaccaccacccccctccagctactggacgttctggaccactgccccctccacccccctggagctggtgggccacccatgccaccaccaccgccaccaccgccaccgccgcccagctccgggaatggaccagcccctccccccactccctcctgctctggtgcctgccgggggcctggccccctggtgggggtcggggagcgcttttggatcaaatccggcagggaattcagctgaacaagaccccctggggccccagagagctcagcgctgcagccaccacctcagagctcagagggactggtgggggccctgatgcacgtgatgcagaagagaagcagagccatccactcctccgacgaaggggaggaccaggctggcgatgaagatgaagatgatgaatgggatgactga SEQ ID NO: 14
Codon optimized WAS
ATGAGCGGCGGCCCCATGGGCGGCCGCCCCGGCGGCCGCG GCGCCCCCGCCGTGCAGCAGAACATCCCCAGCACCCTGCT GCAGGACCACGAGAACCAGCGCCTGTTCGAGATGCTGGGC CGCAAGTGCCTGACCCTGGCCACCGCCGTGGTGCAGCTGT ACCTGGCCCTGCCCCCCGGCGCCGAGCACTGGACCAAGGA GCACTGCGGCGCCGTGTGCTTCGTGAAGGACAACCCCCAG AAGAGCTACTTCATCCGCCTGTACGGCCTGCAGGCCGGCC GCCTGCTGTGGGAGCAGGAGCTGTACAGCCAGCTGGTGTA CAGCACCCCCACCCCCTTCTTCCACACCTTCGCCGGCGAC GACTGCCAGGCCGGCCTGAACTTCGCCGACGAGGACGAGG CCCAGGCCTTCCGCGCCCTGGTGCAGGAGAAGATCCAGAA GCGCAACCAGCGCCAGAGCGGCGACCGCCGCCAGCTGCCC CCCCCCCCCACCCCCGCCAACGAGGAGCGCCGCGGCGGCC TGCCCCCCCTGCCCCTGCACCCCGGCGGCGACCAGGGCGG CCCCCCCGTGGGCCCCCTGAGCCTGGGCCTGGCCACCGTG GACATCCAGAACCCCGACATCACCAGCAGCCGCTACCGCG GCCTGCCCGCCCCCGGCCCCAGCCCCGCCGACAAGAAGCG CAGCGGCAAGAAGAAGATCAGCAAGGCCGACATCGGCGCC CCCAGCGGCTTCAAGCACGTGAGCCACGTGGGCTGGGACC CCCAGAACGGCTTCGACGTGAACAACCTGGACCCCGACCT GCGCAGCCTGTTCAGCCGCGCCGGCATCAGCGAGGCCCAG CTGACCGACGCCGAGACCAGCAAGCTGATCTACGACTTCA TCGAGGACCAGGGCGGCCTGGAGGCCGTGCGCCAGGAGAT GCGCCGCCAGGAGCCCCTGCCCCCCCCCCCCCCCCCCAGC CGCGGCGGCAACCAGCTGCCCCGCCCCCCCATCGTGGGCG GCAACAAGGGCCGCAGCGGCCCCCTGCCCCCCGTGCCCCT GGGCATCGCCCCCCCCCCCCCCACCCCCCGCGGCCCCCCC -continued

```
CCCCCCGGCCGCGGCGGCCCCCCCCCCCCCCCCCCCCCG
CCACCGGCCGCAGCGGCCCCCTGCCCCCCCCCCCCCCGG
CGCCGGCGGCCCCCCCATGCCCCCCCCCCCCCCCCCCCC
CCCCCCCCCCCCAGCAGCGGCAACGGCCCCGCCCCCCCC
CCCTGCCCCCCGCCCTGGTGCCCGCCGGCGGCCTGGCCCC
CGGCGGCGGCCGCGGCGCCCTGCTGGACCAGATCCGCCAG
GGCATCCAGCTGAACAAGACCCCCGGCGCCCCCGAGAGCA
GCGCCCTGCAGCCCCCCCCCAGAGCAGCGAGGGCCTGGT
GGGCGCCCTGATGCACGTGATGCAGAAGCGCAGCCGCGCC
ATCCACAGCAGCGACGAGGGCGAGGACCAGGCCGGCGACG
AGGACGAGGACGACGAGTGGGACGACTAA
```

SEQ ID NO: 15
E2(all slim)-HS Ipro-mCit-WPRE
Sequence from CMV (red arrow in FIG. 18)
going clockwise:

```
AGTTCCGCGTTACATAACTTACGGTAAATGGCCCGCCTGG
CTGACCGCCCAACGACCCCCGCCCATTGACGTCAATAATG
ACGTATGTTCCCATAGTAACGCCAATAGGGACTTTCCATT
GACGTCAATGGGTGGAGTATTTACGGTAAACTGCCCACTT
GGCAGTACATCAAGTGTATCATATGCCAAGTACGCCCCCT
ATTGACGTCAATGACGGTAAATGGCCCGCCTGGCATTATG
CCCAGTACATGACCTTATGGGACTTTCCTACTTGGCAGTA
CATCTACGTATTAGTCATCGCTATTACCATGGTGATGCGG
TTTTGGCAGTACATCAATGGGCGTGGATAGCGGTTTGACT
CACGGGGATTTCCAAGTCTCCACCCCATTGACGTCAATGG
GAGTTTGTTTTGGCACCAAAATCAACGGGACTTTCCAAAA
TGTCGTAACAACTCCGCCCCATTGACGCAAATGGGCGGTA
GGCGTGTACGGTGGGAGGTCTATATAAGCAGAGCTCGTTT
AGTGAACCGGGGTCTCTCTGGTTAGACCAGATCTGAGCCT
GGGAGCTCTCTGGCTAACTAGGGAACCCACTGCTTAAGCC
TCAATAAAGCTTGCCTTGAGTGCTTCAAGTAGTGTGTGCC
CGTCTGTTGTGTGACTCTGGTAACTAGAGATCCCTCAGAC
CCTTTTAGTCAGTGTGGAAAATCTCTAGCagtggcgcccg
aacagggacttgaaagcgaaagggaaaccagaggagctct
ctcgacgcaggactcggcttgctgaagcgcgcacggcaag
aggcgaggggcggcgactggtgagtacgccaaaaattttg
actagcggaggctagaaggagagagatgggtgcgagagcg
tcagtattaagcgggggagaattagatcgcgatgggaaaa
aattcggttaaggccagggggaaagaaaaaatataaatta
aaacatatagtatgggcaagcagggagctagaacgattcg
cagttaatcctggcctgttagaaacatcagaaggctgtag
acaaatactgggacagctacaaccatcccttcagacagga
tcagaagaacttagatcattatataatacagtagcaaccc
```

-continued

```
tctattgtgtgcatcaaaggatagagataaaagacaccaa
ggaagctttagacaagatagaggaagagcaaaacaaaagt
aagaccaccgcacagcaagcggccgctgatcttcagacct
ggaggaggagatatgagggacaattggagaagtgaattat
ataaatataaagtagtaaaaattgaaccattaggagtagc
acccaccaaggcaaagagaagagtggtgcagagagaaaaa
agagcagtgggaataggagctttgttccttgggttcttgg
gagcagcaggaagcactatgggcgcagcgtcaatgacgct
gacggtacaggccagacaattattgtctggtatagtgcag
cagcagaacaatttgctgagggctattgaggcgcaacagc
atctgttgcaactcacagtctggggcatcaagcagctcca
ggcaagaatcctggctgtggaaagatacctaaaggatcaa
cagctcctggggatttggggttgctctggaaaactcattt
gcaccactgctgtgccttggaatgctagttggagtaataa
atctctggaacagatttggaatcacacgacctggatggag
tgggacagagaaattaacaattacacaagcttaatacact
ccttaattgaagaatcgcaaaaccagcaagaaaagaatga
acaagaattattggaattagataaatgggcaagtttgtgg
aattggtttaacataacaaattggctgtggtatataaaat
tattcataatgatagtaggaggcttggtaggtttaagaat
agtttttgctgtactttctatagtgaatagagttaggcag
ggatattcaccattatcgtttcagacccacctcccaaccc
cgaggggacccgacaggcccgaaggaatagaagaagaagg
tggagagagagacagagacagatccattcgattagtgaac
ggatctcgacggtatcggttaacttttaaaagaaaagggg
ggattggggggtacagtgcaggggaaagaatagtagacat
aatagcaacagacatacaaactaaagaattacaaaaacaa
attacaaaaattcaaaattttatcgatcacgagactagcc
tcgagGACCTGAAGGGTAAGGGGGTGTGGAGGTTGTGAAG
GCGGGAAGGGGGGTAGCCCCTTCACCAATGTAAACAAGGA
TGTGGGTTCTGCGGCCACACTCTCCCCCGCCCTCCCCAGC
GGCATTTCCAGCAAGTCACATGTCCTGCGCACAGGCTGGG
GGCCCCCTGCTGCTGCCTTTCTTAGAAGCCAGGACCACAG
AGCCCGCACAGTGAGCTACTTGGGGAGCTATTTCTGTAGA
CTGAGCTTGGGGTACTGGGAGGCAGTGCTGTTGGCGATCT
GGGGGAAAACCCCCTGAGGGTCCCATTTCTCTGCCACTGA
CCCCTTTGCCTGGCAGAAAGGCTCTGCTGCCTCCTAGCTG
TGTAGCAATGGATAAGGCCTTTAACCTCTCTAAGCTGAAA
TGTCCTCATGCATAAGGTGGAGACAGTAACTCCTCTTCCA
TCTGCTGGGTGTTGTCAAAACTACACAGGAGGTTTGCCAA
```

-continued

```
GCACCTAAGGCACAGTAGGTGGTCAAGAAACAGGAACACA
ATTTGTCATGACGACAATGATTCCTTCATATGCTAGTTAC
CCACGAGTCAGCCAGAATGTTGCCATAACCACTTATGAAG
CCCTTCCTCATTTCTGTTGCAATTCCTCAGCCAGAGGAAA
GCCCCACCACCTCTGTCCTCCAGAAAGCCCTCCTCTTCCC
AGAAGGCTGGCACACAGGGCTGGGGGCCAGGCTTGACTTC
CCTGTGGAGGGGTCTGAGGTTGGGGGGATGACCTGCAGAG
GTAGGGGAATTCAGAGAACTTGTTTTGATAGAAACTGAAA
CTCCTCCTCTTGCTGACGCTGCACTTGTGGGCAATCTGCA
CCTGTTCTCCCCTCCCAGAGGCCAGCTGGAAGGGGGTCCC
CCACCATTCTACCTCTGTTCCCATCTCAAACAGGGCTCAG
AAATCCTCAGAGAGCCTGGATTATCTTCCTATAGGGTCCT
ACCATTTGCTTTAGAGACATCTGAGAACTGCCTACTCCCC
AGGTAGCTGCCTGCCTCCCAGAAGAGCCACAGCAAGTTCC
GCTAAGGGCAAAAAAGGAAGCTAGGTGTCTACAGGGAACC
TAAAAACAAACCACACTAACGTGTGTACACACAGCTGCAG
AGGGAGACAGGGACCTGGTCTGCTCACAGCCCTTGCCACT
CCCCCATGGCCCATGTAGAAACAACCATGTGGCCTTCACT
CTGCCCACAGAAGCTAGCACCAGGACCCTGGTCAGGGTTA
GAGGTTTCTGCTGAGTCAAAGCCACATGGAGGGAGGGAGC
AAGGGAGAGATGCAGAGTCATGTTTCCAGGAGGAGGTTAT
CTGAGCATAACAGGGACAGGGTGGGCCACAGGATACCTCT
GAGGCTCAGGTTCCCACCTCCACTCCACCCTCCAACTCTC
TGCTCCACGTTCCTTCCACTATTCAACACATGGCAGGAAG
TCAGCCTGTAGGGCTTCACACTACAGTCTAAGCTGACTGC
CATCTGTCCCCATCCAGGCGAGGCTGGAAACGGGGGCAGC
AAAAAGCCCAGGGACAAAGTCCCCTTCCCAGGCACATGTA
TTATGCACTCTGCACCAAGGAAACCTCCAGATAAGGTCTA
GAGACCAAGGGCCATGTACTTCGGGGGAGAGGCCAGAGGA
CTTCTGAGGTTTTACAGAGAAAAGCCAAAGGCAGCCCAGT
CAGGGGAAATGTGTAGCCATAGTGCCGATAAGGAAAGGCC
TTCAACCTGCCCTGGTCAGCTCTTCCTGTAAGTAGAGGCC
CCTTACCGAAGGCCCCAGTGGGAGGAAGGGTCGGGAGTAc
tcgagTCAGCCTCAGGCTACCTAGGTGCTTTAGAAAGGAG
GCCACCCAGGCCCATGACTACTCCTTGCCACAGGGAGCCC
TGCACACAGATGTGCTAAGCTCTCGCTGCCAGCCAGAGGG
AGGAGGGTCTGAGCCAGTCAGAAGGAGATGGGCCCCAGAG
AGTAAGAAAGGGGGAGGAGGACCCAAGCTGATCCAAAAGG
TGGGTCTAAGCAGTCAAGTGGAGGAGGGTTCCAATCTGAT
GGCGGAGGGCCCAAGCTCAGCCTAACGAGGAGGCCAGGCC
CACCAAGGGGCCCCTGGAGGACTTGTTTCCCTTGTCCCTT
```

-continued

```
GTGGTTTTTTGCATTTCCTGTTCCCTTGCTGCTCATTGCG
GAAGTTCCTCTTCTTACCCTGCACCCAGAGCCTCGCCAGA
GAAGACAAGGGCAGAAAGCACCATGgtgagcaagggcgag
gagctgttcaccggggtggtgcccatcctggtcgagctgg
acggcgacgtaaacggccacaagttcagcgtgtccggcga
gggcgagggcgatgccacctacggcaagctgaccctgaag
ttcatctgcaccaccggcaagctgcccgtgccctggccca
ccctcgtgaccaccttcggctacggcctgatgtgcttcgc
ccgctaccccgaccacatgaagcagcacgacttcttcaag
tccgccatgcccgaaggctacgtccaggagcgcaccatct
tcttcaaggacgacggcaactacaagacccgcgccgaggt
gaagttcgagggcgacaccctggtgaaccgcatcgagctg
aagggcatcgacttcaaggaggacggcaacatcctggggc
acaagctggagtacaactacaacagccacaacgtctatat
catggccgacaagcagaagaacggcatcaaggtgaacttc
aagatccgccacaacatcgaggacggcagcgtgcagctcg
ccgaccactaccagcagaacacccccatcggcgacggccc
cgtgctgctgcccgacaaccactacctgagctaccagtcc
gccctgagcaaagaccccaacgagaagcgcgatcacatgg
tcctgctggagttcgtgaccgccgccgggatcactctcgg
catggacgagctgtacaagtgactgcaggaattcgagcat
cttaccgccatttattcccatatttgttctgtttttcttg
atttgggtatacatttaaatgttaataaaacaaaatggtg
gggcaatcatttacatttttagggatatgtaattactagt
tcaggtgtattgccacaagacaaacatgttaagaaacttt
cccgttatttacgctctgttcctgttaatcaacctctgga
ttacaaaatttgtgaaagattgactgatattcttaactat
gttgctccttttacgctgtgtggatatgctgctttaatgc
ctctgtatcatgctattgcttcccgtacggctttcgtttt
ctcctccttgtataaatcctggttgctgtctctttatgag
gagttgtggcccgttgtccgtcaacgtggcgtggtgtgct
ctgtgtttgctgacgcaacccccactggctggggcattgc
caccacctgtcaactcctttctgggactttcgctttcccc
ctcccgatcgccacggcagaactcatcgccgcctgccttg
cccgctgctggacaggggctaggttgctgggcactgataa
ttccgtggtgttgtcggggaagggcctgctgccggctctg
cggcctcttccgcgtcttcgccttcgccctcagacgagtc
ggatctccctttgggccgcctccccgcctggaattcgagc
tcggtacctttaagaccaatgacttacaaggcagctgtag
atcttagccactttttaaaagaaaaggggggactggaagg
```

Figure 19:
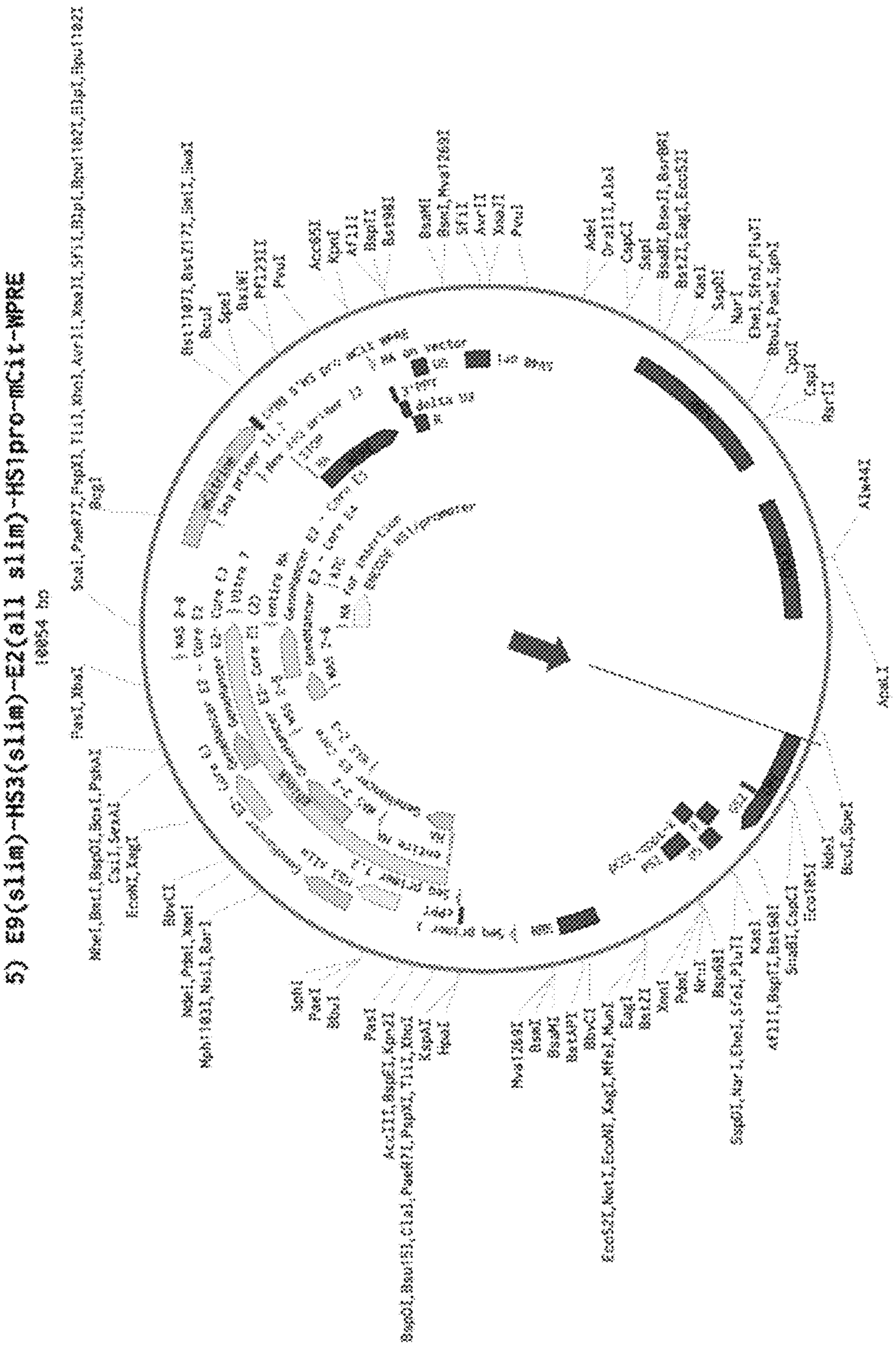
FIG. 19 shows a schematic of the E9(slim)-HS3(slim)-E2(all slim)-HS1pro-mCit-WPRE vector in which the E9(slim) and HS3(slim) elements have been added.

-continued gctaattcactcccaacgaagacaagatctgcttttttgct
tgtactgggtctctctggttagaccagatctgagcctggg
agctctctggctaactagggaacctactgcttaagcctca
ataaagcttgccttgagtgcttCAAGTAGTGTGTGCCCGT
CTGTTGTGTGACTCTGGTAACTAGAGATCCCTCAGACCCT
TTTAGTCAGTGTGGAAAATCTCTAGCagtagtagttcatg
tcatcttattattcagtatttataacttgcaaagaaatga
atatcagagagtgagaggaacttgtttattgcagcttata
atggttacaaataaagcaatagcatcacaaatttcacaaa
taaagcatttttttcactgcattctagttgtggtttgtcc
aaactcatcaatgtatcttatcatgtctggctctagctat
cccgcccctaactccgcccatcccgcccctaactccgccc
agttccgcccattctccgccccatggctgactaattttttt
ttatttatgcagaggccgaggccgcctcggcctctgagct
attccagaagtagtgaggaggcttttttggaggcctaggg
acgtacccaattcgccctatagtgagtcgtattacgcgcg
ctcactggccgtcgttttacaacgtcgtgactgggaaaac
cctggcgttacccaacttaatcgccttgcagcacatcccc
ctttcgccagctggcgtaatagcgaagaggcccgcaccga
tcgcccttcccaacagttgcgcagcctgaatggcgaatgg
gacgcgccctgtagcggcgcattaagcgcggcgggtgtgg
tggttacgcgcagcgtgaccgctacacttgccagcgccct
agcgcccgctcctttcgctttcttcccttcctttctcgcc
acgttcgccggctttccccgtcaagctctaaatcgggggc
tccctttagggttccgatttagtgctttacggcacctcga
ccccaaaaaacttgattagggtgatggttcacgtagtggg
ccatcgccctgatagacggtttttcgccctttgacgttgg
agtccacgttctttaatagtggactcttgttccaaactgg
aacaacactcaaccctatctcggtctattcttttgattta
taagggattttgccgatttcggcctattggttaaaaaatg
agctgatttaacaaaaatttaacgcgaattttaacaaaat
attaacgcttacaatttaggtggcacttttcggggaaatg
tgcgcggaacccctatttgtttatttttctaaatacattc
aaatatgtatccgctcatgagacaataaccctgataaatg
cttcaataatagcacctagatcaagagacaggatgaggat
cgtttcgcatgattgaacaagatggattgcacgcaggttc
tccggccgcttgggtggagaggctattcggctatgactgg
gcacaacagacaatcggctgctctgatgccgccgtgttcc
ggctgtcagcgcaggggcgcccggttctttttgtcaagac
cgacctgtccggtgccctgaatgaactgcaagacgaggca
gcgcggctatcgtggctggccacgacgggcgttccttgcg -continued cagctgtgctcgacgttgtcactgaagcgggaagggactg
gctgctattgggcgaagtgccggggcaggatctcctgtca
tctcaccttgctcctgccgagaaagtatccatcatggctg
atgcaatgcggcggctgcatacgcttgatccggctacctg
cccattcgaccaccaagcgaaacatcgcatcgagcgagca
cgtactcggatggaagccggtcttgtcgatcaggatgatc
tggacgaagagcatcaggggctcgcgccagccgaactgtt
cgccaggctcaaggcgagcatgcccgacggcgaggatctc
gtcgtgacccatggcgatgcctgcttgccgaatatcatgg
tggaaaatggccgcttttctggattcatcgactgtggccg
gctgggtgtggcggaccgctatcaggacatagcgttggct
acccgtgatattgctgaagagcttggcggcgaatgggctg
accgcttcctcgtgctttacggtatcgccgctcccgattc
gcagcgcatcgccttctatcgccttcttgacgagttcttc
tgaattattaacgcttacaatttcctgatgcggtattttc
tccttacgcatctgtgcggtatttcacaccgcatcaggtg
gcacttttcggggaaatgtgcgcggaacccctatttgttt
atttttctaaatacattcaaatatgtatccgctcatgacc
aaaatcccttaacgtgagttttcgttccactgagcgtcag
accccgtagaaaagatcaaaggatcttcttgagatccttt
ttttctgcgcgtaatctgctgcttgcaaacaaaaaaacca
ccgctaccagcggtggtttgtttgccggatcaagagctac
caactctttttccgaaggtaactggcttcagcagagcgca
gataccaaatactgttcttctagtgtagccgtagttaggc
caccacttcaagaactctgtagcaccgcctacatacctcg
ctctgctaatcctgttaccagtggctgctgccagtggcga
taagtcgtgtcttaccgggttggactcaagacgatagtta
ccggataaggcgcagcggtcgggctgaacggggggttcgt
gcacacagcccagcttggagcgaacgacctacaccgaact
gagatacctacagcgtgagctatgagaaagcgccacgctt
cccgaagggagaaaggcggacaggtatccggtaagcggca
gggtcggaacaggagagcgcacgagggagcttccaggggg
aaacgcctggtatctttatagtcctgtcgggtttcgccac
ctctgacttgagcgtcgatttttgtgatgctcgtcagggg
ggcggagcctatggaaaaacgccagcaacgcggcctttttt
acggttcctggccttttgctggccttttgctcacatgttc
tttcctgcgttatcccctgattctgtggataaccgtatta
ccgcctttgagtgagctgataccgctcgccgcagccgaac
gaccgagcgcagcgagtcagtgagcgaggaagcggaagag
cgcccaatacgcaaaccgcctctccccgcgcgttggccga -continued ttcattaatgcagctggcacgacaggtttcccgactggaa agcgggcagtgagcgcaacgcaattaatgtgagttagctc actcattaggcaccccaggctttacactttatgcttccgg ctcgtatgttgtgtggaattgtgagcggataacaatttca cacaggaaacagctatgaccatgattacgccaagcgcgca attaaccctcactaaagggaacaaaagctggagctgcaag cttggccattgcatacgttgtatccatatcataatatgta catttatattggctcatgtccaacattaccgccatgttga cattgattattgactagttattaatagtaatcaattacgg ggtcattagttcatagcccatatatgg SEQ ID NO: 16
E9(slim)-HS3(slim)-E2(all slim)-HS1pro-mCit-WPRE (added the E9(slim) and HS3(slim) elements)
Sequence from CMV (red arrow) going clockwise in FIG. 19:

AGTTCCGCGTTACATAACTTACGGTAAATGGCCCGCCTGG

CTGACCGCCCAACGACCCCCGCCCATTGACGTCAATAATG

ACGTATGTTCCCATAGTAACGCCAATAGGGACTTTCCATT

GACGTCAATGGGTGGAGTATTTACGGTAAACTGCCCACTT

GGCAGTACATCAAGTGTATCATATGCCAAGTACGCCCCCT

ATTGACGTCAATGACGGTAAATGGCCCGCCTGGCATTATG

CCCAGTACATGACCTTATGGGACTTTCCTACTTGGCAGTA

CATCTACGTATTAGTCATCGCTATTACCATGGTGATGCGG

TTTTGGCAGTACATCAATGGGCGTGGATAGCGGTTTGACT

CACGGGGATTTCCAAGTCTCCACCCCATTGACGTCAATGG

GAGTTTGTTTTGGCACCAAAATCAACGGGACTTTCCAAAA

TGTCGTAACAACTCCGCCCCATTGACGCAAATGGGCGGTA

GGCGTGTACGGTGGGAGGTCTATATAAGCAGAGCTCGTTT

AGTGAACCGGGGTCTCTCTGGTTAGACCAGATCTGAGCCT

GGGAGCTCTCTGGCTAACTAGGGAACCCACTGCTTAAGCC

TCAATAAAGCTTGCCTTGAGTGCTTCAAGTAGTGTGTGCC

CGTCTGTTGTGTGACTCTGGTAACTAGAGATCCCTCAGAC

CCTTTTAGTCAGTGTGGAAAATCTCTAGCagtggcgcccg aacaggacttgaaagcgaaagggaaaccagaggagctct ctcgacgcaggactcggcttgctgaagcgcgcacggcaag aggcgaggggcggcgactggtgagtacgccaaaaattttg actagcggaggctagaaggagagagatgggtgcgagagcg tcagtattaagcgggggagaattagatcgcgatgggaaaa aattcggttaaggccagggggaaagaaaaaatataaatta aaacatatagtatgggcaagcagggagctagaacgattcg cagttaatcctggcctgttagaaacatcagaaggctgtag acaaatactgggacagctacaaccatcccttcagacagga tcagaagaacttagatcattatataatacagtagcaaccc -continued tctattgtgtgcatcaaaggatagagataaaagacaccaa ggaagctttagacaagatagaggaagagcaaaacaaaagt aagaccaccgcacagcaagcggccgctgatcttcagacct ggaggaggagatatgagggacaattggagaagtgaattat ataaatataaagtagtaaaaattgaaccattaggagtagc acccaccaaggcaaagagaagagtggtgcagagagaaaaa agagcagtgggaataggagctttgttccttgggttcttgg gagcagcaggaagcactatgggcgcagcgtcaatgacgct gacggtacaggccagacaattattgtctggtatagtgcag cagcagaacaatttgctgagggctattgaggcgcaacagc atctgttgcaactcacagtctggggcatcaagcagctcca ggcaagaatcctggctgtggaaagatacctaaaggatcaa cagctcctggggatttggggttgctctggaaaactcattt gcaccactgctgtgccttggaatgctagttggagtaataa atctctggaacagatttggaatcacacgacctggatggag tgggacagagaaattaacaattacacaagcttaatacact ccttaattgaagaatcgcaaaaccagcaagaaaagaatga acaagaattattggaattagataaatgggcaagtttgtgg aattggtttaacataacaaattggctgtggtatataaaat tattcataatgatagtaggaggcttggtaggtttaagaat agtttttgctgtactttctatagtgaatagagttaggcag ggatattcaccattatcgtttcagacccacctcccaaccc cgaggggacccgacaggcccgaaggaatagaagaagaagg tggagagagagaeagagaeagateeattegattagtgaae ggatetegaeggtateggttaaettttaaaagaaaagggg ggattggggggtaeagtgeaggggaaagaatagtagaeat aatageaaaeagaeataeaaaetaaagaattaeaaaaaeaa attaeaaaaattcaaaattttatcgatcacgagactagcc tcgagCAAACCTTGTTATCTGAGAGAAAGCTAGAGCTTCC

TTCTTTCAGCCCCCAGAGACAATGTGGCCAGGCTCCGGAG

GGCTGGGAAGATGAGCAATGCTTGTGAGTCACCATGATAG

GAAGCAGAAGGGTCAGGAAGTCCCTGGGAGCAAGGCTTAG

GGTTAGGGTTAGGGAGAAAACACTTGGGCCTGGAGGCTCG

GGGCAGGCTTCCTAGAGGGGAGGGGTACTAAAAGCCACCA

AAACCAAGACAGCAATGAAAGTAACCTCTGGTCTTCCTAA

CTGCTCATTATACACTAATTATGATGCACTAGCATGCTAA

GAGACACTTCCACCAGCGCCATGACAGTGCCATGGCAACA

TCAAGAAGTCACCCCACATGGTCTAAAAAGGGGAAGAACC

TTCAGTTCCCGGAATTGCCCACCCCTTTCCTGGAAAACTC

ATGAATAATCCACCCCTTGTTTAGCATATAATGACCTGAA

-continued

GGGTAAGGGGGTGTGGAGGTTGTGAAGGCGGGAAGGGGGG
TAGCCCCTTCACCAATGTAAACAAGGATGTGGGTTCTGCG
GCCACACTCTCCCCCGCCCTCCCCAGCGGCATTTCCAGCA
AGTCACATGTCCTGCGCACAGGCTGGGGGCCCCCTGCTGC
TGCCTTTCTTAGAAGCCAGGACCACAGAGCCCGCACAGTG
AGCTACTTGGGGAGCTATTTCTGTAGACTGAGCTTGGGGT
ACTGGGAGGCAGTGCTGTTGGCGATCTGGGGGAAAACCCC
CTGAGGGTCCCATTTCTCTGCCACTGACCCCTTTGCCTGG
CAGAAAGGCTCTGCTGCCTCCTAGCTGTGTAGCAATGGAT
AAGGCCTTTAACCTCTCTAAGCTGAAATGTCCTCATGCAT
AAGGTGGAGACAGTAACTCCTCTTCCATCTGCTGGGTGTT
GTCAAAACTACACAGGAGGTTTGCCAAGCACCTAAGGCAC
AGTAGGTGGTCAAGAAACAGGAACACAATTTGTCATGACG
ACAATGATTCCTTCATATGCTAGTTACCCACGAGTCAGCC
AGAATGTTGCCATAACCACTTATGAAGCCCTTCCTCATTT
CTGTTGCAATTCCTCAGCCAGAGGAAAGCCCCACCACCTC
TGTCCTCCAGAAAGCCCTCCTCTTCCCAGAAGGCTGGCAC
ACAGGGCTGGGGGCCAGGCTTGACTTCCCTGTGGAGGGGT
CTGAGGTTGGGGGGATGACCTGCAGAGGTAGGGGAATTCA
GAGAACTTGTTTTGATAGAAACTGAAACTCCTCCTCTTGC
TGACGCTGCACTTGTGGGCAATCTGCACCTGTTCTCCCCT
CCCAGAGGCCAGCTGGAAGGGGGTCCCCCACCATTCTACC
TCTGTTCCCATCTCAAACAGGGCTCAGAAATCCTCAGAGA
GCCTGGATTATCTTCCTATAGGGTCCTACCATTTGCTTTA
GAGACATCTGAGAACTGCCTACTCCCCAGGTAGCTGCCTG
CCTCCCAGAAGAGCCACAGCAAGTTCCGCTAAGGGCAAAA
AAGGAAGCTAGGTGTCTACAGGGAACCTAAAAACAAACCA
CACTAACGTGTGTACACACAGCTGCAGAGGGAGACAGGGA
CCTGGTCTGCTCACAGCCCTTGCCACTCCCCCATGGCCCA
TGTAGAAACAACCATGTGGCCTTCACTCTGCCCACAGAAG
CTAGCACCAGGACCCTGGTCAGGGTTAGAGGTTTCTGCTG
AGTCAAAGCCACATGGAGGGAGGGAGCAAGGGAGAGATGC
AGAGTCATGTTTCCAGGAGGAGGTTATCTGAGCATAACAG
GGACAGGGTGGGCCACAGGATACCTCTGAGGCTCAGGTTC
CCACCTCCACTCCACCCTCCAACTCTCTGCTCCACGTTCC
TTCCACTATTCAACACATGGCAGGAAGTCAGCCTGTAGGG
CTTCACACTACAGTCTAAGCTGACTGCCATCTGTCCCCAT
CCAGGCGAGGCTGGAAACGGGGGCAGCAAAAAGCCCAGGG
ACAAAGTCCCCTTCCCAGGCACATGTATTATGCACTCTGC
ACCAAGGAAACCTCCAGATAAGGTCTAGAGACCAAGGGCC
ATGTACTTCGGGGGAGAGGCCAGAGGACTTCTGAGGTTTT

-continued

ACAGAGAAAAGCCAAAGGCAGCCCAGTCAGGGGAAATGTG
TAGCCATAGTGCCGATAAGGAAAGGCCTTCAACCTGCCCT
GGTCAGCTCTTCCTGTAAGTAGAGGCCCCTTACCGAAGGC
CCCAGTGGGAGGAAGGGTCGGGAGTActcgagTCAGCCTC
AGGCTACCTAGGTGCTTTAGAAAGGAGGCCACCCAGGCCC
ATGACTACTCCTTGCCACAGGGAGCCCTGCACACAGATGT
GCTAAGCTCTCGCTGCCAGCCAGAGGGAGGAGGGTCTGAG
CCAGTCAGAAGGAGATGGGCCCCAGAGAGTAAGAAAGGGG
GAGGAGGACCCAAGCTGATCCAAAAGGTGGGTCTAAGCAG
TCAAGTGGAGGAGGGTTCCAATCTGATGGCGGAGGGCCCA
AGCTCAGCCTAACGAGGAGGCCAGGCCCACCAAGGGGCCC
CTGGAGGACTTGTTTCCCTTGTCCCTTGTGGTTTTTTGCA
TTTCCTGTTCCCTTGCTGCTCATTGCGGAAGTTCCTCTTC
TTACCCTGCACCCAGAGCCTCGCCAGAGAAGACAAGGGCA
GAAAGCACCATGgtgagcaagggcgaggagctgttcaccg
gggtggtgcccatcctggtcgagctggacggcgacgtaaa
cggccacaagttcagcgtgtccggcgagggcgagggcgat
gccacctacggcaagctgaccctgaagttcatctgcacca
ccggcaagctgcccgtgccctggcccaccctcgtgaccac
cttcggctacggcctgatgtgcttcgcccgctaccccgac
cacatgaagcagcacgacttcttcaagtccgccatgcccg
aaggctacgtccaggagcgcaccatcttcttcaaggacga
cggcaactacaagacccgcgccgaggtgaagttcgagggc
gacaccctggtgaaccgcatcgagctgaagggcatcgact
tcaaggaggacggcaacatcctggggcacaagctggagta
caactacaacagccacaacgtctatatcatggccgacaag
cagaagaacggcatcaaggtgaacttcaagatccgccaca
acatcgaggacggcagcgtgcagctcgccgaccactacca
gcagaacacccccatcggcgacggccccgtgctgctgccc
gacaaccactacctgagctaccagtccgccctgagcaaag
accccaacgagaagcgcgatcacatggtcctgctggagtt
cgtgaccgccgccgggatcactctcggcatggacgagctg
tacaagtgactgcaggaattcgagcatcttaccgccattt
attcccatatttgttctgtttttcttgatttgggtataca
tttaaatgttaataaaacaaaatggtggggcaatcattta
catttttagggatatgtaattactagttcaggtgtattgc
cacaagacaaacatgttaagaaactttcccgttatttacg
ctctgttcctgttaatcaacctctggattacaaaatttgt
gaaagattgactgatattcttaactatgttgctcctttta
cgctgtgtggatatgctgctttaatgcctctgtatcatgc -continued tattgcttcccgtacggctttcgttttctcctccttgtat aaatcctggttgctgtctctttatgaggagttgtggcccg ttgtccgtcaacgtggcgtggtgtgctctgtgtttgctga cgcaacccccactggctggggcattgccaccacctgtcaa ctcctttctgggactttcgctttccccctcccgatcgcca cggcagaactcatcgccgcctgccttgcccgctgctggac aggggctaggttgctgggcactgataattccgtggtgttg tcggggaagggcctgctgccggctctgcggcctcttccgc gtcttcgccttcgccctcagacgagtcggatctccctttg ggccgcctccccgcctggaattcgagctcggtacctttaa gaccaatgacttacaaggcagctgtagatcttagccactt tttaaaagaaaaggggggactggaagggctaattcactcc caacgaagacaagatctgctttttgcttgtactgggtctc tctggttagaccagatctgagcctgggagctctctggcta actagggaacctactgcttaagcctcaataaagcttgcct tgagtgcttCAAGTAGTGTGTGCCCGTCTGTTGTGTGACT

CTGGTAACTAGAGATCCCTCAGACCCTTTTAGTCAGTGTG

Figure 20:
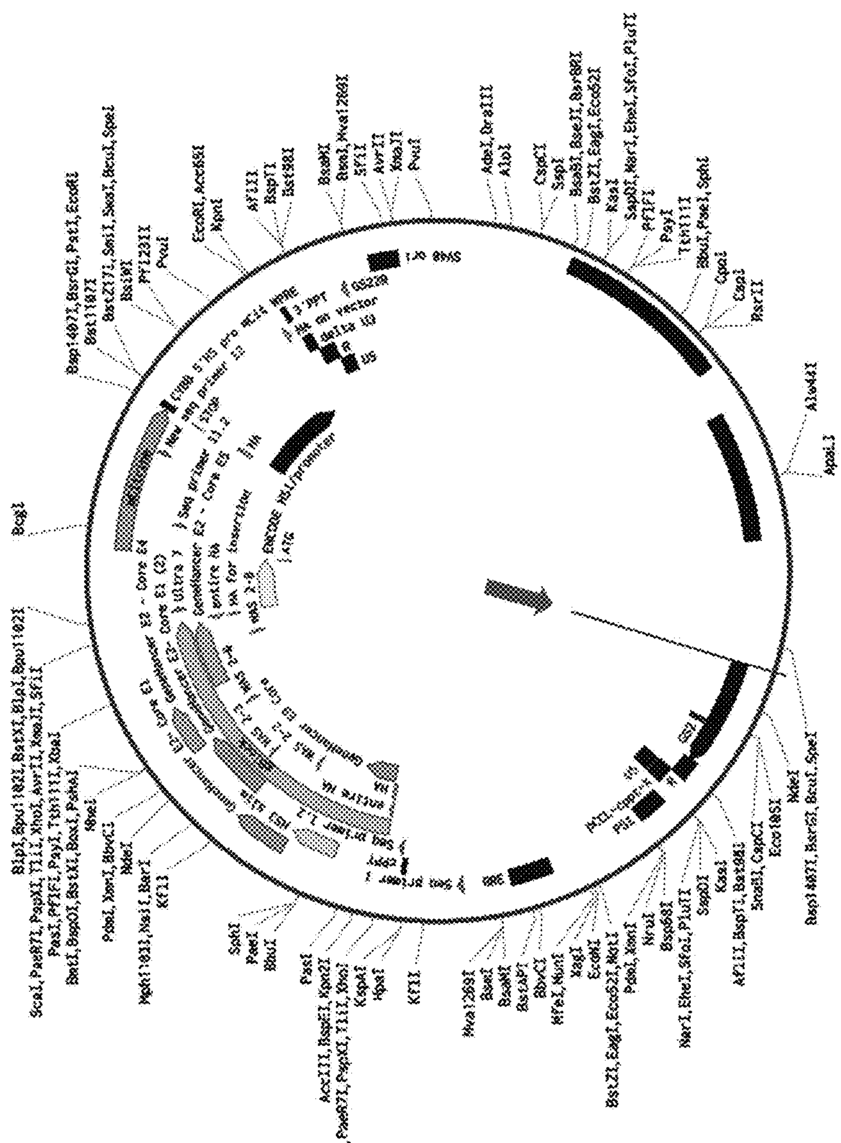
FIG. 20 shows a schematic of the E9(slim)-HS3(slim)-E2(1,4,5 slim)-HS1pro-mCit-WPRE (Deleted Core Sub-Element 2 of Element 2 and Core Sub-Element 3 of Element 2). E9slimHS3slimE2145slimHS1pro

GAAAATCTCTAGCagtagtagttcatgtcatcttattatt cagtatttataacttgcaaagaaatgaatatcagagagtg agaggaacttgtttattgcagcttataatggttacaaata aagcaatagcatcacaaatttcacaaataaagcatttttt tcactgcattctagttgtggtttgtccaaactcatcaatg tatcttatcatgtctggctctagctatcccgcccctaact ccgcccatcccgcccctaactccgcccagttccgcccatt ctccgccccatggctgactaattttttttatttatgcaga ggccgaggccgcctcggcctctgagctattccagaagtag tgaggaggcttttttggaggcctagggacgtacccaattc gccctatagtgagtcgtattacgcgcgctcactggccgtc gttttacaacgtcgtgactgggaaaaccctggcgttaccc aacttaatcgccttgcagcacatccccctttcgccagctg gcgtaatagcgaagaggcccgcaccgatcgcccttcccaa cagttgcgcagcctgaatggcgaatgggacgcgccctgta gcggcgcattaagcgcggcgggtgtggtggttacgcgcag cgtgaccgctacacttgccagcgccctagcgcccgctcct ttcgctttcttcccttcctttctcgccacgttcgccggct ttccccgtcaagctctaaatcgggggctccctttagggtt ccgatttagtgctttacggcacctcgaccccaaaaaactt gattagggtgatggttcacgtagtgggccatcgccctgat agacggtttttcgccctttgacgttggagtccacgttctt taatagtggactcttgttccaaactggaacaacactcaac cctatctcggtctattcttttgatttataagggattttgc -continued cgatttcggcctattggttaaaaaatgagctgatttaaca aaaatttaacgcgaattttaacaaaatattaacgcttaca atttaggtggcacttttcggggaaatgtgcgcggaacccc tatttgtttatttttctaaatacattcaaatatgtatccg ctcatgagacaataaccctgataaatgcttcaataatagc acctagatcaagagacaggatgaggatcgtttcgcatgat tgaacaagatggattgcacgcaggttctccggccgcttgg gtggagaggctattcggctatgactgggcacaacagacaa tcggctgctctgatgccgccgtgttccggctgtcagcgca ggggcgcccggttctttttgtcaagaccgacctgtccggt gccctgaatgaactgcaagacgaggcagcgcggctatcgt ggctggccacgacgggcgttccttgcgcagctgtgctcga cgttgtcactgaagcgggaagggactggctgctattgggc gaagtgccggggcaggatctcctgtcatctcaccttgctc ctgccgagaaagtatccatcatggctgatgcaatgcggcg gctgcatacgcttgatccggctacctgcccattcgaccac caagcgaaacatcgcatcgagcgagcacgtactcggatgg aagccggtcttgtcgatcaggatgatctggacgaagagca tcaggggctcgcgccagccgaactgttcgccaggctcaag gcgagcatgcccgacggcgaggatctcgtcgtgacccatg gcgatgcctgcttgccgaatatcatggtggaaaatggccg cttttctggattcatcgactgtggccggctgggtgtggcg gaccgctatcaggacatagcgttggctacccgtgatattg ctgaagagcttggcggcgaatgggctgaccgcttcctcgt gctttacggtatcgccgctcccgattcgcagcgcatcgcc ttctatcgccttcttgacgagttcttctgaattattaacg cttacaatttcctgatgcggtattttctccttacgcatct gtgcggtatttcacaccgcatcaggtggcacttttcgggg aaatgtgcgcggaacccctatttgtttatttttctaaata cattcaaatatgtatccgctcatgaccaaaatcccttaac gtgagttttcgttccactgagcgtcagaccccgtagaaaa gatcaaaggatcttcttgagatcctttttttctgcgcgta atctgctgcttgcaaacaaaaaaaccaccgctaccagcgg tggtttgtttgccggatcaagagctaccaactctttttcc gaaggtaactggcttcagcagagcgcagataccaaatact gttcttctagtgtagccgtagttaggccaccacttcaaga actctgtagcaccgcctacatacctcgctctgctaatcct gttaccagtggctgctgccagtggcgataagtcgtgtctt accgggttggactcaagacgatagttaccggataaggcgc agcggtcgggctgaacggggggttcgtgcacacagcccag -continued cttggagcgaacgacctacaccgaactgagatacctacag cgtgagctatgagaaagcgccacgcttcccgaagggagaa aggcggacaggtatccggtaagcggcagggtcggaacagg agagcgcacgagggagcttccagggggaaacgcctggtat ctttatagtcctgtcgggtttcgccacctctgacttgagc gtcgatttttgtgatgctcgtcaggggggcggagcctatg gaaaaacgccagcaacgcggcctttttacggttcctggcc ttttgctggccttttgctcacatgttctttcctgcgttat cccctgattctgtggataaccgtattaccgcctttgagtg agctgataccgctcgccgcagccgaacgaccgagcgcagc gagtcagtgagcgaggaagcggaagagcgcccaatacgca aaccgcctctccccgcgcgttggccgattcattaatgcag ctggcacgacaggtttcccgactggaaagcgggcagtgag cgcaacgcaattaatgtgagttagctcactcattaggcac cccaggctttacactttatgcttccggctcgtatgttgtg tggaattgtgagcggataacaatttcacacaggaaacagc tatgaccatgattacgccaagcgcgcaattaaccctcact aaagggaacaaaagctggagctgcaagcttggccattgca tacgttgtatccatatcataatatgtacatttatattggc tcatgtccaacattaccgccatgttgacattgattattga ctagttattaatagtaatcaattacggggtcattagttca tagcccatatatgg SEQ ID NO: 17
E9(slim)-HS3(slim)-E2(1, 4, 5 slim)-HS1pro-mCit-WPRE (Deleted Core Sub-Element 2 of Element 2 and Core Sub-Element 3 of Element 2) Sequence from CMV (red arrow) going clockwise in FIG. 20

AGTTCCGCGTTACATAACTTACGGTAAATGGCCCGCCTGG

CTGACCGCCCAACGACCCCCGCCCATTGACGTCAATAATG

ACGTATGTTCCCATAGTAACGCCAATAGGGACTTTCCATT

GACGTCAATGGGTGGAGTATTTACGGTAAACTGCCCACTT

GGCAGTACATCAAGTGTATCATATGCCAAGTACGCCCCCT

ATTGACGTCAATGACGGTAAATGGCCCGCCTGGCATTATG

CCCAGTACATGACCTTATGGGACTTTCCTACTTGGCAGTA

CATCTACGTATTAGTCATCGCTATTACCATGGTGATGCGG

TTTTGGCAGTACATCAATGGGCGTGGATAGCGGTTTGACT

CACGGGGATTTCCAAGTCTCCACCCCATTGACGTCAATGG

GAGTTTGTTTTGGCACCAAAATCAACGGGACTTTCCAAAA

TGTCGTAACAACTCCGCCCCATTGACGCAAATGGGCGGTA

GGCGTGTACGGTGGGAGGTCTATATAAGCAGAGCTCGTTT

AGTGAACCGGGGTCTCTCTGGTTAGACCAGATCTGAGCCT

GGGAGCTCTCTGGCTAACTAGGGAACCCACTGCTTAAGCC

TCAATAAAGCTTGCCTTGAGTGCTTCAAGTAGTGTGTGCC

-continued

CGTCTGTTGTGTGACTCTGGTAACTAGAGATCCCTCAGAC

CCTTTTAGTCAGTGTGGAAAATCTCTAGCagtggcgcccg aacagggacttgaaagcgaaagggaaaccagaggagctct ctcgacgcaggactcggcttgctgaagcgcgcacggcaag aggcgaggggcggcgactggtgagtacgccaaaaattttg actagcggaggctagaaggagagagatgggtgcgagagcg tcagtattaagcgggggagaattagatcgcgatgggaaaa aattcggttaaggccagggggaaagaaaaaatataaatta aaacatatagtatgggcaagcagggagctagaacgattcg cagttaatcctggcctgttagaaacatcagaaggctgtag acaaatactgggacagctacaaccatcccttcagacagga tcagaagaacttagatcattatataatacagtagcaaccc tctattgtgtgcatcaaaggatagagataaaagacaccaa ggaagctttagacaagatagaggaagagcaaaacaaaagt aagaccaccgcacagcaagcggccgctgatcttcagacct ggaggaggagatatgagggacaattggagaagtgaattat ataaatataaagtagtaaaaattgaaccattaggagtagc acccaccaaggcaaagagaagagtggtgcagagagaaaaa agagcagtgggaataggagctttgttccttgggttcttgg gagcagcaggaagcactatgggcgcagcgtcaatgacgct gacggtacaggccagacaattattgtctggtatagtgcag cagcagaacaatttgctgagggctattgaggcgcaacagc atctgttgcaactcacagtctggggcatcaagcagctcca ggcaagaatcctggctgtggaaagatacctaaaggatcaa cagctcctggggatttggggttgctctggaaaactcattt gcaccactgctgtgccttggaatgctagttggagtaataa atctctggaacagatttggaatcacacgacctggatggag tgggacagagaaattaacaattacacaagcttaatacact ccttaattgaagaatcgcaaaaccagcaagaaaagaatga acaagaattattggaattagataaatgggcaagtttgtgg aattggtttaacataacaaattggctgtggtatataaaat tattcataatgatagtaggaggcttggtaggtttaagaat agtttttgctgtactttctatagtgaatagagttaggcag ggatattcaccattatcgtttcagacccacctcccaaccc cgaggggacccgacaggcccgaaggaatagaagaagaagg tggagagagagacagagacagatccattcgattagtgaac ggatctcgacggtatcggttaacttttaaaagaaaagggg ggattggggggtacagtgcaggggaaagaatagtagacat aatagcaacagacatacaaactaaagaattacaaaaacaa attacaaaaattcaaaattttatcgatcacgagactagcc

```
tcgagCAAACCTTGTTATCTGAGAGAAAGCTAGAGCTTCC
TTCTTTCAGCCCCCAGAGACAATGTGGCCAGGCTCCGGAG
GGCTGGGAAGATGAGCAATGCTTGTGAGTCACCATGATAG
GAAGCAGAAGGGTCAGGAAGTCCCTGGGAGCAAGGCTTAG
GGTTAGGGTTAGGGAGAAAACACTTGGGCCTGGAGGCTCG
GGGCAGGCTTCCTAGAGGGGAGGGGTACTAAAAGCCACCA
AAACCAAGACAGCAATGAAAGTAACCTCTGGTCTTCCTAA
CTGCTCATTATACACTAATTATGATGCACTAGCATGCTAA
GAGACACTTCCACCAGCGCCATGACAGTGCCATGGCAACA
TCAAGAAGTCACCCCACATGGTCTAAAAAGGGGAAGAACC
TTCAGTTCCCGGAATTGCCCACCCCTTTCCTGGAAAACTC
ATGAATAATCCACCCCTTGTTTAGCATATAATGACCTGAA
GGGTAAGGGGGTGTGGAGGTTGTGAAGGCGGGAAGGGGGG
TAGCCCCTTCACCAATGTAAACAAGGATGTGGGTTCTGCG
GCCACACTCTCCCCCGCCCTCCCCAGCGGCATTTCCAGCA
AGTCACATGTCCTGCGCACAGGCTGGGGGCCCCCTGCTGC
TGCCTTTCTTAGAAGCCAGGACCACAGAGCCCGCACAGTG
AGCTACTTGGGGAGCTATTTCTGTAGACTGAGCTTGGGGT
ACTGGGAGGCAGTGCTGTTGGCGATCTGGGGGAAAACCCC
CTGAGGGTCCCATTTCTCTGCCACTGACCCCTTTGCCTGG
CAGAAAGGCTCTGCTGCCTCCTAGCTGTGTAGCAATGGAT
AAGGCCTTTAACCTCTCTAAGCTGAAATGTCCTCATGCAT
AAGGTGGAGACAGTAACTCCTCTTCCATCTGCTGGGTGTT
GTCAAAACTACACAGGAGGTTTGCCAAGCACCTAAGGCAC
AGTAGGTGGTCAAGAAACAGGAACACAATTTGTCATGACG
ACAATGATTCCTTCATATGCTAGTTACCCACGAGTCAGCC
AGAATGTTGCCATAACCACTTATGAAGCCCTTCCTCATTT
CTGTTGCAATTCCTCAGCCAGAGGAAAGCCCCACACAGCC
CTTGCCACTCCCCCATGGCCCATGTAGAAACAACCATGTG
GCCTTCACTCTGCCCACAGAAGCTAGCACCAGGACCCTGG
TCAGGGTTAGAGGTTTCTGCTGAGTCAAAGCCACATGGAG
GGAGGGAGCAAGGGAGAGATGCAGAGTCATGTTTCCAGGA
GGAGGTTATCTGAGCATAACAGGGACAGGGTGGGCCACAG
GATACCTCTGAGGCTCAGGTTCCCACCTCCACTCCACCCT
CCAACTCTCTGCTCCACGTTCCTTCCACTATTCAACACAT
GGCAGGAAGTCAGCCTGTAGGGCTTCACACTACAGTCTAA
GCTGACTGCCATCTGTCCCCATCCAGGCGAGGCTGGAAAC
GGGGGCAGCAAAAAGCCCAGGGACAAAGTCCCCTTCCCAG
GCACATGTATTATGCACTCTGCACCAAGGAAACCTCCAGA
TAAGGTCTAGAGACCAAGGGCCATGTACTTCGGGGGAGAG
GCCAGAGGACTTCTGAGGTTTTACAGAGAAAAGCCAAAGG
```

```
CAGCCCAGTCAGGGGAAATGTGTAGCCATAGTGCCGATAA
GGAAAGGCCTTCAACCTGCCCTGGTCAGCTCTTCCTGTAA
GTAGAGGCCCCTTACCGAAGGCCCCAGTGGGAGGAAGGGT
CGGGAGTActcgagTCAGCCTCAGGCTACCTAGGTGCTTT
AGAAAGGAGGCCACCCAGGCCCATGACTACTCCTTGCCAC
AGGGAGCCCTGCACACAGATGTGCTAAGCTCTCGCTGCCA
GCCAGAGGGAGGAGGGTCTGAGCCAGTCAGAAGGAGATGG
GCCCCAGAGAGTAAGAAAGGGGGAGGAGGACCCAAGCTGA
TCCAAAAGGTGGGTCTAAGCAGTCAAGTGGAGGAGGGTTC
CAATCTGATGGCGGAGGGCCCAAGCTCAGCCTAACGAGGA
GGCCAGGCCCACCAAGGGGCCCCTGGAGGACTTGTTTCCC
TTGTCCCTTGTGGTTTTTTGCATTTCCTGTTCCCTTGCTG
CTCATTGCGGAAGTTCCTCTTCTTACCCTGCACCCAGAGC
CTCGCCAGAGAAGACAAGGGCAGAAAGCACCATGgtgagc
aagggcgaggagctgttcaccggggtggtgcccatcctgg
tcgagctggacggcgacgtaaacggccacaagttcagcgt
gtccggcgagggcgagggcgatgccacctacggcaagctg
accctgaagttcatctgcaccaccggcaagctgcccgtgc
cctggcccaccctcgtgaccaccttcggctacggcctgat
gtgcttcgcccgctaccccgaccacatgaagcagcacgac
ttcttcaagtccgccatgcccgaaggctacgtccaggagc
gcaccatcttcttcaaggacgacggcaactacaagacccg
cgccgaggtgaagttcgagggcgacaccctggtgaaccgc
atcgagctgaagggcatcgacttcaaggaggacggcaaca
tcctggggcacaagctggagtacaactacaacagccacaa
cgtctatatcatggccgacaagcagaagaacggcatcaag
gtgaacttcaagatccgccacaacatcgaggacggcagcg
tgcagctcgccgaccactaccagcagaacacccccatcgg
cgacggccccgtgctgctgcccgacaaccactacctgagc
taccagtccgccctgagcaaagaccccaacgagaagcgcg
atcacatggtcctgctggagttcgtgaccgccgccgggat
cactctcggcatggacgagctgtacaagtgactgcaggaa
ttcgagcatcttaccgccatttattcccatatttgttctg
tttttcttgatttgggtatacatttaaatgttaataaaac
aaaatggtggggcaatcatttacatttttagggatatgta
attactagttcaggtgtattgccacaagacaaacatgtta
agaaactttcccgttatttacgctctgttcctgttaatca
acctctggattacaaaatttgtgaaagattgactgatatt
cttaactatgttgctccttttacgctgtgtggatatgctg
ctttaatgcctctgtatcatgctattgcttcccgtacggc
```

-continued tttcgttttctcctccttgtataaatcctggttgctgtct ctttatgaggagttgtggcccgttgtccgtcaacgtggcg tggtgtgctctgtgtttgctgacgcaacccccactggctg gggcattgccaccacctgtcaactcctttctgggactttc gctttccccctcccgatcgccacggcagaactcatcgccg cctgccttgcccgctgctggacaggggctaggttgctggg cactgataattccgtggtgttgtcggggaagggcctgctg ccggctctgcggcctcttccgcgtcttcgccttcgccctc agacgagtcggatctccctttgggccgcctccccgcctgg aattcgagctcggtacctttaagaccaatgacttacaagg cagctgtagatcttagccactttttaaaagaaaagggggg actggaagggctaattcactcccaacgaagacaagatctg ctttttgcttgtactgggtctctctggttagaccagatct gagcctgggagctctctggctaactagggaacctactgct taagcctcaataaagcttgccttgagtgcttCAAGTAGTG

TGTGCCCGTCTGTTGTGTGACTCTGGTAACTAGAGATCCC

Figure 21:
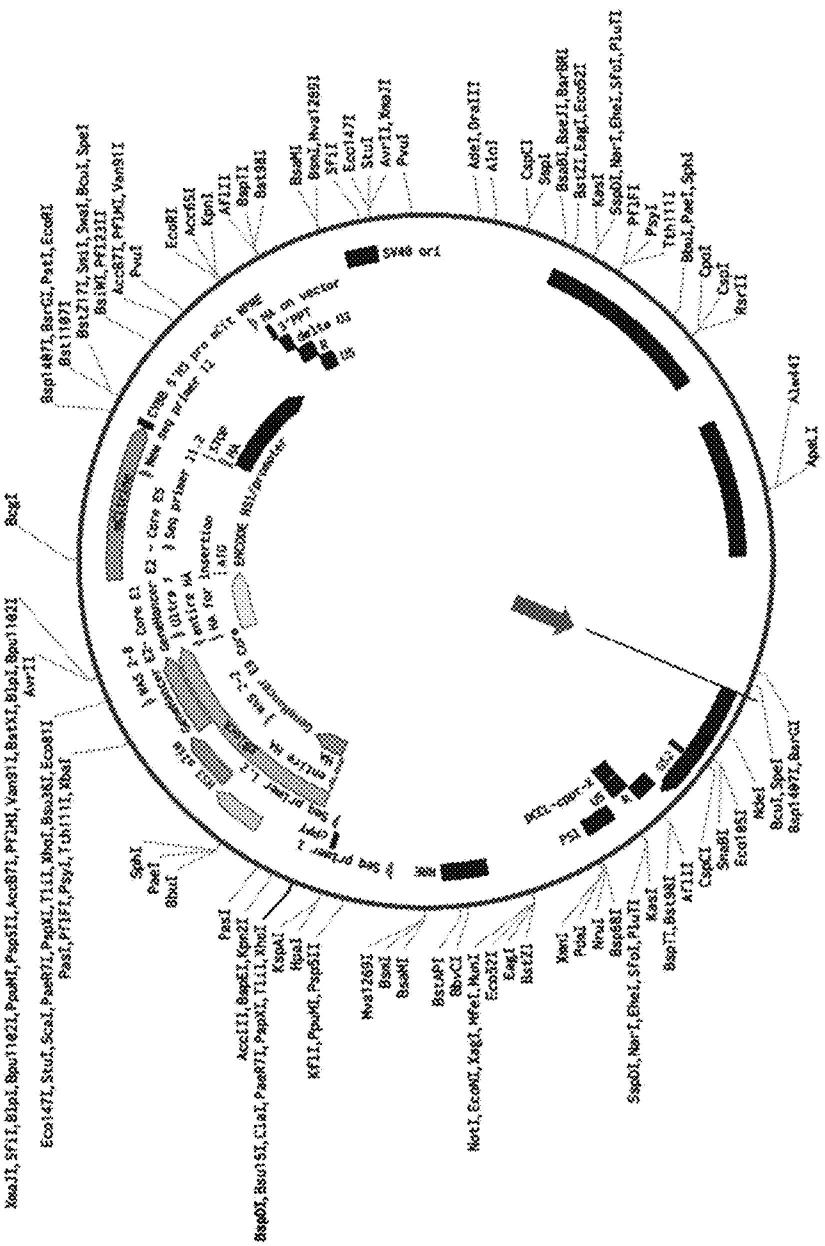
FIG. 21 shows a schematic of the E9(slim)-HS3(slim)-E2($1^{st}$ half of 1 and 5 slim)-HS1pro-mCit-WPRE (Deleted $2^{nd}$ half of Core Sub-Element 1 of Element 2, Core Sub-Element 2 of Element 2 and Core Sub-Element 3 of Element 2, and Core-Sub Element 4 of Element 2).

TCAGACCCTTTTAGTCAGTGTGGAAAATCTCTAGCagtag tagttcatgtcatcttattattcagtatttataacttgca aagaaatgaatatcagagagtgagaggaacttgtttattg cagcttataatggttacaaataaagcaatagcatcacaaa tttcacaaataaagcatttttttcactgcattctagttgt ggtttgtccaaactcatcaatgtatcttatcatgtctggc tctagctatcccgcccctaactccgcccatcccgccccta actccgcccagttccgcccattctccgccccatggctgac taatttttttatttatgcagaggccgaggccgcctcggc ctctgagctattccagaagtagtgaggaggcttttttgga ggcctagggacgtacccaattcgccctatagtgagtcgta ttacgcgcgctcactggccgtcgttttacaacgtcgtgac tgggaaaaccctggcgttacccaacttaatcgccttgcag cacatccccctttcgccagctggcgtaatagcgaagaggc ccgcaccgatcgcccttcccaacagttgcgcagcctgaat ggcgaatgggacgcgccctgtagcggcgcattaagcgcgg cgggtgtggtggttacgcgcagcgtgaccgctacacttgc cagcgccctagcgcccgctcctttcgctttcttcccttcc tttctcgccacgttcgccggctttccccgtcaagctctaa atcgggggctccctttagggttccgatttagtgctttacg gcacctcgaccccaaaaaacttgattagggtgatggttca cgtagtgggccatcgccctgatagacggtttttcgccctt tgacgttggagtccacgttctttaatagtggactcttgtt ccaaactggaacaacactcaaccctatctcggtctattct tttgatttataagggattttgccgatttcggcctattggt -continued taaaaaatgagctgatttaacaaaaatttaacgcgaattt taacaaaatattaacgcttacaatttaggtggcacttttc ggggaaatgtgcgcggaacccctatttgtttatttttcta aatacattcaaatatgtatccgctcatgagacaataaccc tgataaatgcttcaataatagcacctagatcaagagacag gatgaggatcgtttcgcatgattgaacaagatggattgca cgcaggttctccggccgcttgggtggagaggctattcggc tatgactgggcacaacagacaatcggctgctctgatgccg ccgtgttccggctgtcagcgcaggggcgcccggttctttt tgtcaagaccgacctgtccggtgccctgaatgaactgcaa gacgaggcagcgcggctatcgtggctggccacgacgggcg ttccttgcgcagctgtgctcgacgttgtcactgaagcggg aagggactggctgctattgggcgaagtgccggggcaggat ctcctgtcatctcaccttgctcctgccgagaaagtatcca tcatggctgatgcaatgcggcggctgcatacgcttgatcc ggctacctgcccattcgaccaccaagcgaaacatcgcatc gagcgagcacgtactcggatggaagccggtcttgtcgatc aggatgatctggacgaagagcatcaggggctcgcgccagc cgaactgttcgccaggctcaaggcgagcatgcccgacggc gaggatctcgtcgtgacccatggcgatgcctgcttgccga atatcatggtggaaaatggccgcttttctggattcatcga ctgtggccggctgggtgtggcggaccgctatcaggacata gcgttggctacccgtgatattgctgaagagcttggcggcg aatgggctgaccgcttcctcgtgctttacggtatcgccgc tcccgattcgcagcgcatcgccttctatcgccttcttgac gagttcttctgaattattaacgcttacaatttcctgatgc ggtattttctccttacgcatctgtgcggtatttcacaccg catcaggtggcacttttcggggaaatgtgcgcggaacccc tatttgtttatttttctaaatacattcaaatatgtatccg ctcatgaccaaaatcccttaacgtgagttttcgttccact gagcgtcagaccccgtagaaaagatcaaaggatcttcttg agatcctttttttctgcgcgtaatctgctgcttgcaaaca aaaaaaccaccgctaccagcggtggtttgtttgccggatc aagagctaccaactctttttccgaaggtaactggcttcag cagagcgcagataccaaatactgttcttctagtgtagccg tagttaggccaccacttcaagaactctgtagcaccgccta catacctcgctctgctaatcctgttaccagtggctgctgc cagtggcgataagtcgtgtcttaccgggttggactcaaga cgatagttaccggataaggcgcagcggtcgggctgaacgg ggggttcgtgcacacagcccagcttggagcgaacgaccta -continued caccgaactgagatacctacagcgtgagctatgagaaagc gccacgcttcccgaagggagaaaggcggacaggtatccgg taagcggcagggtcggaacaggagagcgcacgagggagct tccagggggaaacgcctggtatctttatagtcctgtcggg tttcgccacctctgacttgagcgtcgatttttgtgatgct cgtcaggggggcggagcctatggaaaaacgccagcaacgc ggcctttttacggttcctggccttttgctggccttttgct cacatgttctttcctgcgttatcccctgattctgtggata accgtattaccgcctttgagtgagctgataccgctcgccg cagccgaacgaccgagcgcagcgagtcagtgagcgaggaa gcggaagagcgcccaatacgcaaaccgcctctccccgcgc gttggccgattcattaatgcagctggcacgacaggtttcc cgactggaaagcgggcagtgagcgcaacgcaattaatgtg agttagctcactcattaggcaccccaggctttacacttta tgcttccggctcgtatgttgtgtggaattgtgagcggata acaatttcacacaggaaacagctatgaccatgattacgcc aagcgcgcaattaaccctcactaaagggaacaaaagctgg agctgcaagcttggccattgcatacgttgtatccatatca taatatgtacatttatattggctcatgtccaacattaccg ccatgttgacattgattattgactagttattaatagtaat caattacggggtcattagttcatagcccatatatgg SEQ ID NO: 18
E9(slim)-HS3(slim)-E2 (1st half of 1
and 5 slim)-HS1pro-mCit-WPRE (Deleted 2nd
half of Core Sub-Element 1 of Element 2
and Core-Sub Element 4 of Element 2)
Sequence from CMV (red arrow) going
clockwise in FIG. 21
AGTTCCGCGTTACATAACTTACGGTAAATGGCCCGCCTGG

CTGACCGCCCAACGACCCCCGCCCATTGACGTCAATAATG

ACGTATGTTCCCATAGTAACGCCAATAGGGACTTTCCATT

GACGTCAATGGGTGGAGTATTTACGGTAAACTGCCCACTT

GGCAGTACATCAAGTGTATCATATGCCAAGTACGCCCCCT

ATTGACGTCAATGACGGTAAATGGCCCGCCTGGCATTATG

CCCAGTACATGACCTTATGGGACTTTCCTACTTGGCAGTA

CATCTACGTATTAGTCATCGCTATTACCATGGTGATGCGG

TTTTGGCAGTACATCAATGGGCGTGGATAGCGGTTTGACT

CACGGGGATTTCCAAGTCTCCACCCCATTGACGTCAATGG

GAGTTTGTTTTGGCACCAAAATCAACGGGACTTTCCAAAA

TGTCGTAACAACTCCGCCCCATTGACGCAAATGGGCGGTA

GGCGTGTACGGTGGGAGGTCTATATAAGCAGAGCTCGTTT

AGTGAACCGGGGTCTCTCTGGTTAGACCAGATCTGAGCCT

GGGAGCTCTCTGGCTAACTAGGGAACCCACTGCTTAAGCC

TCAATAAAGCTTGCCTTGAGTGCTTCAAGTAGTGTGTGCC

-continued

CGTCTGTTGTGTGACTCTGGTAACTAGAGATCCCTCAGAC

CCTTTTAGTCAGTGTGGAAAATCTCTAGCagtggcgcccg aacagggacttgaaagcgaaagggaaaccagaggagctct ctcgacgcaggactcggcttgctgaagcgcgcacggcaag aggcgaggggcggcgactggtgagtacgccaaaaattttg actagcggaggctagaaggagagagatgggtgcgagagcg tcagtattaagcgggggagaattagatcgcgatgggaaaa aattcggttaaggccagggggaaagaaaaaatataaatta aaacatatagtatgggcaagcagggagctagaacgattcg cagttaatcctggcctgttagaaacatcagaaggctgtag acaaatactgggacagctacaaccatcccttcagacagga tcagaagaacttagatcattatataatacagtagcaaccc tctattgtgtgcatcaaaggatagagataaaagacaccaa ggaagctttagacaagatagaggaagagcaaaacaaaagt aagaccaccgcacagcaagcggccgctgatcttcagacct ggaggaggagatatgagggacaattggagaagtgaattat ataaatataaagtagtaaaaattgaaccattaggagtagc acccaccaaggcaaagagaagagtggtgcagagagaaaaa agagcagtgggaataggagctttgttccttgggttcttgg gagcagcaggaagcactatgggcgcagcgtcaatgacgct gacggtacaggccagacaattattgtctggtatagtgcag cagcagaacaatttgctgagggctattgaggcgcaacagc atctgttgcaactcacagtctggggcatcaagcagctcca ggcaagaatcctggctgtggaaagatacctaaaggatcaa cagctcctggggatttggggttgctctggaaaactcattt gcaccactgctgtgccttggaatgctagttggagtaataa atctctggaacagatttggaatcacacgacctggatggag tgggacagagaaattaacaattacacaagcttaatacact ccttaattgaagaatcgcaaaaccagcaagaaaagaatga acaagaattattggaattagataaatgggcaagtttgtgg aattggtttaacataacaaattggctgtggtatataaaat tattcataatgatagtaggaggcttggtaggtttaagaat agtttttgctgtactttctatagtgaatagagttaggcag ggatattcaccattatcgtttcagacccacctcccaaccc cgaggggacccgacaggcccgaaggaatagaagaagaagg tggagagagagaeagagaeagateeattegattagtgaae ggatetegaeggtateggttaaettttaaaagaaaagggg ggattgggggtaeagtgeaggggaaagaatagtagaeat aatageaaeagaeataeaaaetaaagaattaeaaaaaeaa attaeaaaaattcaaaattttatcgatcacgagactagcc tcgagCAAACCTTGTTATCTGAGAGAAAGCTAGAGCTTCC -continued TTCTTTCAGCCCCCAGAGACAATGTGGCCAGGCTCCGGAG
GGCTGGGAAGATGAGCAATGCTTGTGAGTCACCATGATAG
GAAGCAGAAGGGTCAGGAAGTCCCTGGGAGCAAGGCTTAG
GGTTAGGGTTAGGGAGAAAACACTTGGGCCTGGAGGCTCG
GGGCAGGCTTCCTAGAGGGGAGGGGTACTAAAAGCCACCA
AAACCAAGACAGCAATGAAAGTAACCTCTGGTCTTCCTAA
CTGCTCATTATACACTAATTATGATGCACTAGCATGCTAA
GAGACACTTCCACCAGCGCCATGACAGTGCCATGGCAACA
TCAAGAAGTCACCCCACATGGTCTAAAAAGGGGAAGAACC
TTCAGTTCCCGGAATTGCCCACCCCTTTCCTGGAAAACTC
ATGAATAATCCACCCCTTGTTTAGCATATAATGACCTGAA
GGGTAAGGGGGTGTGGAGGTTGTGAAGGCGGGAAGGGGGG
TAGCCCCTTCACCAATGTAAACAAGGATGTGGGTTCTGCG
GCCACACTCTCCCCCGCCCTCCCCAGCGGCATTTCCAGCA
AGTCACATGTCCTGCGCACAGGCTGGGGGCCCCCTGCTGC
TGCCTTTCTTAGAAGCCAGGACCACAGAGCCCGCACAGTG
AGCTACTTGGGGAGCTATTTCTGTAGACTGAGCTTGGGGT
ACTGGGAGGCAGTGCTGTTGGCCTCCAACTCTCTGCTCCA
CGTTCCTTCCACTATTCAACACATGGCAGGAAGTCAGCCT
GTAGGGCTTCACACTACAGTCTAAGCTGACTGCCATCTGT
CCCCATCCAGGCGAGGCTGGAAACGGGGGCAGCAAAAAGC
CCAGGGACAAAGTCCCCTTCCCAGGCACATGTATTATGCA
CTCTGCACCAAGGAAACCTCCAGATAAGGTCTAGAGACCA
AGGGCCATGTACTTCGGGGGAGAGGCCAGAGGACTTCTGA
GGTTTTACAGAGAAAAGCCAAAGGCAGCCCAGTCAGGGGA
AATGTGTAGCCATAGTGCCGATAAGGAAAGGCCTTCAACC
TGCCCTGGTCAGCTCTTCCTGTAAGTAGAGGCCCCTTACC
GAAGGCCCCAGTGGGAGGAAGGGTCGGGAGTActcgagTC
AGCCTCAGGCTACCTAGGTGCTTTAGAAAGGAGGCCACCC
AGGCCCATGACTACTCCTTGCCACAGGGAGCCCTGCACAC
AGATGTGCTAAGCTCTCGCTGCCAGCCAGAGGGAGGAGGG
TCTGAGCCAGTCAGAAGGAGATGGGCCCCAGAGAGTAAGA
AAGGGGGAGGAGGACCCAAGCTGATCCAAAAGGTGGGTCT
AAGCAGTCAAGTGGAGGAGGGTTCCAATCTGATGGCGGAG
GGCCCAAGCTCAGCCTAACGAGGAGGCCAGGCCCACCAAG
GGGCCCCTGGAGGACTTGTTTCCCTTGTCCCTTGTGGTTT
TTTGCATTTCCTGTTCCCTTGCTGCTCATTGCGGAAGTTC
CTCTTCTTACCCTGCACCCAGAGCCTCGCCAGAGAAGACA
AGGGCAGAAAGCACCATGgtgagcaagggcgaggagctgt
tcaccggggtggtgcccatcctggtcgagctggacggcga -continued cgtaaacggccacaagttcagcgtgtccggcgagggcgag
ggcgatgccacctacggcaagctgaccctgaagttcatct
gcaccaccggcaagctgcccgtgccctggcccaccctcgt
gaccaccttcggctacggcctgatgtgcttcgcccgctac
cccgaccacatgaagcagcacgacttcttcaagtccgcca
tgcccgaaggctacgtccaggagcgcaccatcttcttcaa
ggacgacggcaactacaagacccgcgccgaggtgaagttc
gagggcgacaccctggtgaaccgcatcgagctgaagggca
tcgacttcaaggaggacggcaacatcctggggcacaagct
ggagtacaactacaacagccacaacgtctatatcatggcc
gacaagcagaagaacggcatcaaggtgaacttcaagatcc
gccacaacatcgaggacggcagcgtgcagctcgccgacca
ctaccagcagaacacccccatcggcgacggccccgtgctg
ctgcccgacaaccactacctgagctaccagtccgccctga
gcaaagaccccaacgagaagcgcgatcacatggtcctgct
ggagttcgtgaccgccgccgggatcactctcggcatggac
gagctgtacaagtgactgcaggaattcgagcatcttaccg
ccatttattcccatatttgttctgtttttcttgatttggg
tatacatttaaatgttaataaaacaaaatggtggggcaat
catttacatttttagggatatgtaattactagttcaggtg
tattgccacaagacaaacatgttaagaaactttcccgtta
tttacgctctgttcctgttaatcaacctctggattacaaa
atttgtgaaagattgactgatattcttaactatgttgctc
cttttacgctgtgtggatatgctgctttaatgcctctgta
tcatgctattgcttcccgtacggctttcgttttctcctcc
ttgtataaatcctggttgctgtctctttatgaggagttgt
ggcccgttgtccgtcaacgtggcgtggtgtgctctgtgtt
tgctgacgcaacccccactggctggggcattgccaccacc
tgtcaactcctttctgggactttcgctttccccctcccga
tcgccacggcagaactcatcgccgcctgccttgcccgctg
ctggacaggggctaggttgctgggcactgataattccgtg
gtgttgtcggggaagggcctgctgccggctctgcggcctc
ttccgcgtcttcgccttcgccctcagacgagtcggatctc
cctttgggccgcctccccgcctggaattcgagctcggtac
ctttaagaccaatgacttacaaggcagctgtagatcttag
ccacttttaaaagaaaaggggggactggaagggctaatt
cactcccaacgaagacaagatctgctttttgcttgtactg
ggtctctctggttagaccagatctgagcctgggagctctc
tggctaactagggaacctactgcttaagcctcaataaagc
ttgccttgagtgcttCAAGTAGTGTGTGCCCGTCTGTTGT
GTGACTCTGGTAACTAGAGATCCCTCAGACCCTTTTAGTC -continued AGTGTGGAAAATCTCTAGCagtagtagttcatgtcatctt
attattcagtatttataacttgcaaagaaatgaatatcag
agagtgagaggaacttgtttattgcagcttataatggtta
caaataaagcaatagcatcacaaatttcacaaataaagca
tttttttcactgcattctagttgtggtttgtccaaactca
tcaatgtatcttatcatgtctggctctagctatcccgccc
ctaactccgcccatcccgcccctaactccgcccagttccg
cccattctccgccccatggctgactaattttttttattta
tgcagaggccgaggccgcctcggcctctgagctattccag
aagtagtgaggaggcttttttggaggcctagggacgtacc
caattcgccctatagtgagtcgtattacgcgcgctcactg
gccgtcgttttacaacgtcgtgactgggaaaaccctggcg
ttacccaacttaatcgccttgcagcacatccccctttcgc
cagctggcgtaatagcgaagaggcccgcaccgatcgccct
tcccaacagttgcgcagcctgaatggcgaatgggacgcgc
cctgtagcggcgcattaagcgcggcgggtgtggtggttac
gcgcagcgtgaccgctacacttgccagcgccctagcgccc
gctcctttcgctttcttcccttcctttctcgccacgttcg
ccggctttccccgtcaagctctaaatcgggggctcccttt
agggttccgatttagtgctttacggcacctcgaccccaaa
aaacttgattagggtgatggttcacgtagtgggccatcgc
cctgatagacggtttttcgccctttgacgttggagtccac
gttctttaatagtggactcttgttccaaactggaacaaca
ctcaaccctatctcggtctattcttttgatttataaggga
ttttgccgatttcggcctattggttaaaaaatgagctgat
ttaacaaaaatttaacgcgaattttaacaaaatattaacg
cttacaatttaggtggcacttttcggggaaatgtgcgcgg
aacccctatttgtttatttttctaaatacattcaaatatg
tatccgctcatgagacaataaccctgataaatgcttcaat
aatagcacctagatcaagagacaggatgaggatcgtttcg
catgattgaacaagatggattgcacgcaggttctccggcc
gcttgggtggagaggctattcggctatgactgggcacaac
agacaatcggctgctctgatgccgccgtgttccggctgtc
agcgcaggggcgcccggttctttttgtcaagaccgacctg
tccggtgccctgaatgaactgcaagacgaggcagcgcggc
tatcgtggctggccacgacgggcgttccttgcgcagctgt
gctcgacgttgtcactgaagcgggaagggactggctgcta
ttgggcgaagtgccggggcaggatctcctgtcatctcacc
ttgctcctgccgagaaagtatccatcatggctgatgcaat
gcggcggctgcatacgcttgatccggctacctgcccattc -continued gaccaccaagcgaaacatcgcatcgagcgagcacgtactc
ggatggaagccggtcttgtcgatcaggatgatctggacga
agagcatcaggggctcgcgccagccgaactgttcgccagg
ctcaaggcgagcatgcccgacggcgaggatctcgtcgtga
cccatggcgatgcctgcttgccgaatatcatggtggaaaa
tggccgcttttctggattcatcgactgtggccggctgggt
gtggcggaccgctatcaggacatagcgttggctacccgtg
atattgctgaagagcttggcggcgaatgggctgaccgctt
cctcgtgctttacggtatcgccgctcccgattcgcagcgc
atcgccttctatcgccttcttgacgagttcttctgaatta
ttaacgcttacaatttcctgatgcggtattttctccttac
gcatctgtgcggtatttcacaccgcatcaggtggcacttt
tcggggaaatgtgcgcggaacccctatttgtttatttttc
taaatacattcaaatatgtatccgctcatgaccaaaatcc
cttaacgtgagttttcgttccactgagcgtcagaccccgt
agaaaagatcaaaggatcttcttgagatcctttttttctg
cgcgtaatctgctgcttgcaaacaaaaaaaccaccgctac
cagcggtggtttgtttgccggatcaagagctaccaactct
ttttccgaaggtaactggcttcagcagagcgcagatacca
aatactgttcttctagtgtagccgtagttaggccaccact
tcaagaactctgtagcaccgcctacatacctcgctctgct
aatcctgttaccagtggctgctgccagtggcgataagtcg
tgtcttaccgggttggactcaagacgatagttaccggata
aggcgcagcggtcgggctgaacggggggttcgtgcacaca
gcccagcttggagcgaacgacctacaccgaactgagatac
ctacagcgtgagctatgagaaagcgccacgcttcccgaag
ggagaaaggcggacaggtatccggtaagcggcagggtcgg
aacaggagagcgcacgagggagcttccagggggaaacgcc
tggtatctttatagtcctgtcgggtttcgccacctctgac
ttgagcgtcgatttttgtgatgctcgtcaggggggcggag
cctatggaaaaacgccagcaacgcggcctttttacggttc
ctggccttttgctggccttttgctcacatgttctttcctg
cgttatcccctgattctgtggataaccgtattaccgcctt
tgagtgagctgataccgctcgccgcagccgaacgaccgag
cgcagcgagtcagtgagcgaggaagcggaagagcgcccaa
tacgcaaaccgcctctccccgcgcgttggccgattcatta
atgcagctggcacgacaggtttcccgactggaaagegggе
agtgagegeaaegeaattaatgtgagttageteaeteatt
aggeaeeeeaggetttaeaetttatgetteeggetegtat
gttgtgtggaattgtgagcggataacaatttcacacagga
aacagctatgaccatgattacgccaagcgcgcaattaacc ctcactaaagggaacaaaagctggagctgcaagcttggcc attgcatacgttgtatccatatcataatatgtacatttat attggctcatgtccaacattaccgccatgttgacattgat tattgactagttattaatagtaatcaattacggggtcatt agttcatagcccatatatgg

SEQ ID NO: 19 CMV:
AGTTCCGCGTTACATAACTTACGGTAAATGGCCCGCCTGG

CTGACCGCCCAACGACCCCCGCCCATTGACGTCAATAATG

ACGTATGTTCCCATAGTAACGCCAATAGGGACTTTCCATT

GACGTCAATGGGTGGAGTATTTACGGTAAACTGCCCACTT

GGCAGTACATCAAGTGTATCATATGCCAAGTACGCCCCCT

ATTGACGTCAATGACGGTAAATGGCCCGCCTGGCATTATG

CCCAGTACATGACCTTATGGGACTTTCCTACTTGGCAGTA

CATCTACGTATTAGTCATCGCTATTACCATGGTGATGCGG

TTTTGGCAGTACATCAATGGGCGTGGATAGCGGTTTGACT

CACGGGGATTTCCAAGTCTCCACCCCATTGACGTCAATGG

GAGTTTGTTTTGGCACCAAAATCAACGGGACTTTCCAAAA

TGTCGTAACAACTCCGCCCCATTGACGCAAATGGGCGGTA

GGCGTGTACGGTGGGAGGTCTATATAAGCAGAGCTCGTTT

AGTGAACCG

SEQ ID NO: 20 5'R/U5:
GGGTCTCTCTGGTTAGACCAGATCTGAGCCTGGGAGCTCT

CTGGCTAACTAGGGAACCCACTGCTTAAGCCTCAATAAAG

CTTGCCTTGAGTGCTTCAAGTAGTGTGTGCCCGTCTGTTG

TGTGACTCTGGTAACTAGAGATCCCTCAGACCCTTTTAGT

CAGTGTGGAAAATCTCTAGC

SEQ ID NO: 21 PSI:
Tcgacgcaggactcggcttgctgaagcgcgcacggcaaga ggcgaggggcggcgactggtgagtacgccaaaaattttga ctagcggaggctagaaggagagagatgggtgcgagagcgt cagtattaagcgggggag SEQ ID NO: 22 RRE:
Tccttgggttcttgggagcagcaggaagcactatgggcgc agcgtcaatgacgctgacggtacaggccagacaattattg tctggtatagtgcagcagcagaacaatttgctgagggcta ttgaggcgcaacagcatctgttgcaactcacagtctgggg catcaagcagctccaggcaagaatcctggctgtggaaaga tacct SEQ ID NO: 23 WPRE:
Cccatatttgttctgtttttcttgatttgggtatacattt aaatgttaataaaacaaaatggtggggcaatcatttacat ttttagggatatgtaattactagttcaggtgtattgccac aagacaaacatgttaagaaactttcccgttatttacgctc tgttcctgttaatcaacctctggattacaaaatttgtgaa agattgactgatattcttaactatgttgctccttttacgc tgtgtggatatgctgctttaatgcctctgtatcatgctat tgcttcccgtacggctttcgttttctcctccttgtataaa tcctggttgctgtctctttatgaggagttgtggcccgttg tccgtcaacgtggcgtggtgtgctctgtgtttgctgacgc aacccccactggctggggcattgccaccacctgtcaactc ctttctgggactttcgctttccccctcccgatcgccacgg cagaactcatcgccgcctgccttgcccgctgctggacagg ggctaggttgctgggcactgataattccgtggtgttgtcg gggaagggcctgctgccggctctgcggcctcttccgcgtc ttcgccttcgccctcagacgagtcggatctccctttgggc cgcctccccgcctgga SEQ ID NO: 24 3' PPT:
tttttaaaagaaaaggggggac SEQ ID NO: 25 3' delta U3/R/U5
tggaagggctaattcactcccaacgaagacaagatctgct tttgcttgtactgggtctctctggttagaccagatctga gcctgggagctctctggctaactagggaacctactgctta agcctcaataaagcttgccttgagtgcttCAAGTAGTGTG

TGCCCGTCTGTTGTGTGACTCTGGTAACTAGAGATCCCTC

AGACCCTTTTAGTCAGTGTGGAAAATCTCTAGC

SEQ ID NO: 26 SV40 ori:
Atcccgcccctaactccgcccagttccgcccattctccgc cccatggctgactaattttttttatttatgcagaggccga ggccgcctcggcctctgagctattccagaagtagtgagga ggcttttttggaggcctagg SEQ ID NO: 27 KANr:
Attgaacaagatggattgcacgcaggttctccggccgctt gggtggagaggctattcggctatgactgggcacaacagac aatcggctgctctgatgccgccgtgttccggctgtcagcg caggggcgcccggttctttttgtcaagaccgacctgtccg gtgccctgaatgaactgcaagacgaggcagcgcggctatc gtggctggccacgacgggcgttccttgcgcagctgtgctc gacgttgtcactgaagcgggaagggactggctgctattgg gcgaagtgccggggcaggatctcctgtcatctcaccttgc tcctgccgagaaagtatccatcatggctgatgcaatgcgg cggctgcatacgcttgatccggctacctgcccattcgacc accaagcgaaacatcgcatcgagcgagcacgtactcggat ggaagccggtcttgtcgatcaggatgatctggacgaagag catcaggggctcgcgccagccgaactgttcgccaggctca aggcgagcatgcccgacggcgaggatctcgtcgtgaccca -continued tggcgatgcctgcttgccgaatatcatggtggaaaatggc cgcttttctggattcatcgactgtggccggctgggtgtgg cggaccgctatcaggacatagcgttggctacccgtgatat tgctgaagagcttggcggcgaatgggctgaccgcttcctc gtgctttacggtatcgccgctcccgattcgcagcgcatcg ccttctatcgccttcttgacgagttcttctga

SEQ ID NO: 28 COLE1:

agatcaaaggatcttcttgagatcctttttttt ctgcgcgtaatctgctgcttgcaaacaaaaaaaccaccgc taccagcggtggtttgtttgccggatcaagagctaccaac tctttttccgaaggtaactggcttcagcagagcgcagata ccaaatactgttcttctagtgtagccgtagttaggccacc acttcaagaactctgtagcaccgcctacatacctcgctct gctaatcctgttaccagtggctgctgccagtggcgataag tcgtgtcttaccgggttggactcaagacgatagttaccgg ataaggcgcagcggtcgggctgaacggggggttcgtgcac acagcccagcttggagcgaacgacctacaccgaactgaga tacctacagcgtgagctatgagaaagcgccacgcttcccg aagggagaaaggcggacaggtatccggtaagcggcagggt cggaacaggagagcgcacgagggagcttccagggggaaac gcctggtatctttatagtcctgtcgggtttcgccacctct gacttgagcgtcgatttttgtgatgctcgtcaggggggcg gagcctatggaaaaacgccagcaacgcg SEQ ID NO: 29
Full sequence of WASVec lentiviral vector transfer plasmid with codon optimized WASp open reading frame: (sequence is beginning from the CMV):

AGTTCCGCGTTACATAACTTACGGTAAATGGCCCGCCTGG

CTGACCGCCCAACGACCCCCGCCCATTGACGTCAATAATG

ACGTATGTTCCCATAGTAACGCCAATAGGGACTTTCCATT

GACGTCAATGGGTGGAGTATTTACGGTAAACTGCCCACTT

GGCAGTACATCAAGTGTATCATATGCCAAGTACGCCCCCT

ATTGACGTCAATGACGGTAAATGGCCCGCCTGGCATTATG

CCCAGTACATGACCTTATGGGACTTTCCTACTTGGCAGTA

CATCTACGTATTAGTCATCGCTATTACCATGGTGATGCGG

TTTTGGCAGTACATCAATGGGCGTGGATAGCGGTTTGACT

CACGGGGATTTCCAAGTCTCCACCCCATTGACGTCAATGG

GAGTTTGTTTTGGCACCAAAATCAACGGGACTTTCCAAAA

TGTCGTAACAACTCCGCCCCATTGACGCAAATGGGCGGTA

GGCGTGTACGGTGGGAGGTCTATATAAGCAGAGCTCGTTT

AGTGAACCGGGGTCTCTCTGGTTAGACCAGATCTGAGCCT

GGGAGCTCTCTGGCTAACTAGGGAACCCACTGCTTAAGCC

-continued

TCAATAAAGCTTGCCTTGAGTGCTTCAAGTAGTGTGTGCC

CGTCTGTTGTGTGACTCTGGTAACTAGAGATCCCTCAGAC

CCTTTTAGTCAGTGTGGAAAATCTCTAGCagtggcgcccg aacagggacttgaaagcgaaagggaaaccagaggagctct ctcgacgcaggactcggcttgctgaagcgcgcacggcaag aggcgaggggcggcgactggtgagtacgccaaaaattttg actagcggaggctagaaggagagagatgggtgcgagagcg tcagtattaagcgggggagaattagatcgcgatgggaaaa aattcggttaaggccagggggaaagaaaaaatataaatta aaacatatagtatgggcaagcagggagctagaacgattcg cagttaatcctggcctgttagaaacatcagaaggctgtag acaaatactgggacagctacaaccatcccttcagacagga tcagaagaacttagatcattatataatacagtagcaaccc tctattgtgtgcatcaaaggatagagataaaagacaccaa ggaagctttagacaagatagaggaagagcaaaacaaaagt aagaccaccgcacagcaagcggccgctgatcttcagacct ggaggaggagatatgagggacaattggagaagtgaattat ataaatataaagtagtaaaaattgaaccattaggagtagc acccaccaaggcaaagagaagagtggtgcagagagaaaaa agagcagtgggaataggagctttgttccttgggttcttgg gagcagcaggaagcactatgggcgcagcgtcaatgacgct gacggtacaggccagacaattattgtctggtatagtgcag cagcagaacaatttgctgagggctattgaggcgcaacagc atctgttgcaactcacagtctggggcatcaagcagctcca ggcaagaatcctggctgtggaaagatacctaaaggatcaa cagctcctggggatttggggttgctctggaaaactcattt gcaccactgctgtgccttggaatgctagttggagtaataa atctctggaacagatttggaatcacacgacctggatggag tgggacagagaaattaacaattacacaagcttaatacact ccttaattgaagaatcgcaaaaccagcaagaaaagaatga acaagaattattggaattagataaatgggcaagtttgtgg aattggtttaacataacaaattggctgtggtatataaaat tattcataatgatagtaggaggcttggtaggtttaagaat agtttttgctgtactttctatagtgaatagagttaggcag ggatattcaccattatcgtttcagacccacctcccaaccc cgaggggacccgacaggcccgaaggaatagaagaagaagg tggagagagagacagagacagatccattcgattagtgaac ggatctcgacggtatcggttaacttttaaaagaaaagggg ggattggggggtacagtgcaggggaaagaatagtagacat aatagcaacagacatacaaactaaagaattacaaaaacaa attacaaaaattcaaaattttatcgatcacgagactagcc -continued tcgagCAAACCTTGTTATCTGAGAGAAAGCTAGAGCTTCC

TTCTTTCAGCCCCCAGAGACAATGTGGCCAGGCTCCGGAG

GGCTGGGAAGATGAGCAATGCTTGTGAGTCACCATGATAG

GAAGCAGAAGGGTCAGGAAGTCCCTGGGAGCAAGGCTTAG

GGTTAGGGTTAGGGAGAAAACACTTGGGCCTGGAGGCTCG

GGGCAGGCTTCCTAGAGGGGAGGGGTACTAAAAGCCACCA

AAACCAAGACAGCAATGAAAGTAACCTCTGGTCTTCCTAA

CTGCTCATTATACACTAATTATGATGCACTAGCATGCTAA

GAGACACTTCCACCAGCGCCATGACAGTGCCATGGCAACA

TCAAGAAGTCACCCCACATGGTCTAAAAAGGGGAAGAACC

TTCAGTTCCCGGAATTGCCCACCCCTTTCCTGGAAAACTC

ATGAATAATCCACCCCTTGTTTAGCATATAATGACCTGAA

GGGTAAGGGGGTGTGGAGGTTGTGAAGGCGGGAAGGGGGG

TAGCCCCTTCACCAATGTAAACAAGGATGTGGGTTCTGCG

GCCACACTCTCCCCCGCCCTCCCCAGCGGCATTTCCAGCA

AGTCACATGTCCTGCGCACAGGCTGGGGGCCCCCTGCTGC

TGCCTTTCTTAGAAGCCAGGACCACAGAGCCCGCACAGTG

AGCTACTTGGGGAGCTATTTCTGTAGACTGAGCTTGGGGT

ACTGGGAGGCAGTGCTGTTGGCGATCTGGGGGAAAACCCC

CTGAGGGTCCCATTTCTCTGCCACTGACCCCTTTGCCTGG

CAGAAAGGCTCTGCTGCCTCCTAGCTGTGTAGCAATGGAT

AAGGCCTTTAACCTCTCTAAGCTGAAATGTCCTCATGCAT

AAGGTGGAGACAGTAACTCCTCTTCCATCTGCTGGGTGTT

GTCAAAACTACACAGGAGGTTTGCCAAGCACCTAAGGCAC

AGTAGGTGGTCAAGAAACAGGAACACAATTTGTCATGACG

ACAATGATTCCTTCATATGCTAGTTACCCACGAGTCAGCC

AGAATGTTGCCATAACCACTTATGAAGCCCTTCCTCATTT

CTGTTGCAATTCCTCAGCCAGAGGAAAGCCCCACACAGCC

CTTGCCACTCCCCCATGGCCCATGTAGAAACAACCATGTG

GCCTTCACTCTGCCCACAGAAGCTAGCACCAGGACCCTGG

TCAGGGTTAGAGGTTTCTGCTGAGTCAAAGCCACATGGAG

GGAGGGAGCAAGGGAGAGATGCAGAGTCATGTTTCCAGGA

GGAGGTTATCTGAGCATAACAGGGACAGGGTGGGCCACAG

GATACCTCTGAGGCTCAGGTTCCCACCTCCACTCCACCCT

CCAACTCTCTGCTCCACGTTCCTTCCACTATTCAACACAT

GGCAGGAAGTCAGCCTGTAGGGCTTCACACTACAGTCTAA

GCTGACTGCCATCTGTCCCCATCCAGGCGAGGCTGGAAAC

GGGGGCAGCAAAAAGCCCAGGGACAAAGTCCCCTTCCCAG

GCACATGTATTATGCACTCTGCACCAAGGAAACCTCCAGA

TAAGGTCTAGAGACCAAGGGCCATGTACTTCGGGGGAGAG

-continued

GCCAGAGGACTTCTGAGGTTTTACAGAGAAAAGCCAAAGG

CAGCCCAGTCAGGGGAAATGTGTAGCCATAGTGCCGATAA

GGAAAGGCCTTCAACCTGCCCTGGTCAGCTCTTCCTGTAA

GTAGAGGCCCCTTACCGAAGGCCCCAGTGGGAGGAAGGGT

CGGGAGTActcgagTCAGCCTCAGGCTACCTAGGTGCTTT

AGAAAGGAGGCCACCCAGGCCCATGACTACTCCTTGCCAC

AGGGAGCCCTGCACACAGATGTGCTAAGCTCTCGCTGCCA

GCCAGAGGGAGGAGGGTCTGAGCCAGTCAGAAGGAGATGG

GCCCCAGAGAGTAAGAAAGGGGGAGGAGGACCCAAGCTGA

TCCAAAAGGTGGGTCTAAGCAGTCAAGTGGAGGAGGGTTC

CAATCTGATGGCGGAGGGCCCAAGCTCAGCCTAACGAGGA

GGCCAGGCCCACCAAGGGGCCCCTGGAGGACTTGTTTCCC

TTGTCCCTTGTGGTTTTTTGCATTTCCTGTTCCCTTGCTG

CTCATTGCGGAAGTTCCTCTTCTTACCCTGCACCCAGAGC

CTCGCCAGAGAAGACAAGGGCAGAAAGCACCATGTCTGGC

GGACCTATGGGAGGTAGACCTGGTGGAAGAGGTGCCCCCG

CCGTGCAGCAGAACATCCCCAGCACCCTGCTGCAGGACCA

CGAGAACCAGCGCCTGTTCGAGATGCTGGGCCGCAAGTGC

CTGACCCTGGCCACCGCCGTGGTGCAGCTGTACCTGGCCC

TGCCCCCCGGCGCCGAGCACTGGACCAAGGAGCACTGCGG

CGCCGTGTGCTTCGTGAAGGACAACCCCCAGAAGAGCTAC

TTCATCCGCCTGTACGGCCTGCAGGCCGGCCGCCTGCTGT

GGGAGCAGGAGCTGTACAGCCAGCTGGTGTACAGCACCCC

CACCCCCTTCTTCCACACCTTCGCCGGCGACGACTGCCAG

GCCGGCCTGAACTTCGCCGACGAGGACGAGGCCCAGGCCT

TCCGCGCCCTGGTGCAGGAGAAGATCCAGAAGCGCAACCA

GCGCCAGAGCGGCGACAGAAGGCAACTGCCTCCTCCACCT

ACACCAGCCAACGAGGAAAGAAGAGGCGGACTGCCCCCCC

TGCCTCTTCATCCTGGCGGAGATCAAGGTGGACCTCCTGT

GGGACCACTGTCTCTTGGCCTGGCCACCGTGGACATCCAG

AACCCCGACATCACCAGCAGCCGCTACCGCGGCCTGCCCG

CCCCCGGCCCCAGCCCCGCCGACAAGAAGCGCAGCGGCAA

GAAGAAGATCAGCAAGGCCGACATCGGCGCCCCCAGCGGC

TTCAAGCACGTGAGCCACGTGGGCTGGGACCCCCAGAACG

GCTTCGACGTGAACAACCTGGACCCCGACCTGCGCAGCCT

GTTCAGCCGCGCCGGCATCAGCGAGGCCCAGCTGACCGAC

GCCGAGACCAGCAAGCTGATCTACGACTTCATCGAGGACC

AGGGCGGCCTGGAGGCCGTGCGCCAGGAGATGCGCCGCCA

GGAGCCCCTGCCACCACCTCCACCTCCATCTAGAGGCGGC

AACCAGCTGCCCCGCCCTCCTATCGTTGGCGGCAACAAGG

GAAGATCTGGCCCTCTGCCTCCTGTGCCTCTGGGAATCGC

-continued

TCCACCACCACCAACACCTAGAGGCCCGCCTCCACCAGGC
AGAGGTGGTCCTCCGCCGCCACCTCCTCCAGCCACCGGCC
GCAGCGGCCCCCTTCCTCCTCCACCACCTGGTGCTGGTGG
ACCTCCAATGCCACCGCCACCGCCTCCGCCACCTCCGCCT
CCAAGTTCTGGAAATGGACCTGCTCCTCCTCCTTTGCCTC
CTGCTTTGGTTCCTGCTGGCGGATTGGCTCCAGGCGGAGG
AAGAGGCGCACTGCTGGACCAGATCCGCCAGGGCATCCAG
CTGAACAAGACCCCTGGCGCTCCTGAGAGTTCTGCTCTGC
AACCGCCACCACAGTCTAGCGAAGGACTTGTGGGAGCCCT
GATGCACGTGATGCAGAAGCGCAGCCGCGCCATCCACAGC
AGCGACGAGGGCGAGGACCAGGCCGGCGACGAGGACGAGG
ACGACGAGTGGGACGACTAActgcaggaattcgagcatct
taccgccatttattcccatatttgttctgtttttcttgat
ttgggtatacatttaaatgttaataaaacaaaatggtggg
gcaatcatttacatttttagggatatgtaattactagttc
aggtgtattgccacaagacaaacatgttaagaaactttcc
cgttatttacgctctgttcctgttaatcaacctctggatt
acaaaatttgtgaaagattgactgatattcttaactatgt
tgctccttttacgctgtgtggatatgctgctttaatgcct
ctgtatcatgctattgcttcccgtacggctttcgttttct
cctccttgtataaatcctggttgctgtctctttatgagga
gttgtggcccgttgtccgtcaacgtggcgtggtgtgctct
gtgtttgctgacgcaacccccactggctggggcattgcca
ccacctgtcaactcctttctgggactttcgctttccccct
cccgatcgccacggcagaactcatcgccgcctgccttgcc
cgctgctggacaggggctaggttgctgggcactgataatt
ccgtggtgttgtcggggaagggcctgctgccggctctgcg
gcctcttccgcgtcttcgccttcgccctcagacgagtcgg
atctccctttgggccgcctccccgcctggaattcgagctc
ggtacctttaagaccaatgacttacaaggcagctgtagat
cttagccactttttaaaagaaaaggggggactggaagggc
taattcactcccaacgaagacaagatctgctttttgcttg
tactgggtctctctggttagaccagatctgagcctgggag
ctctctggctaactagggaacctactgcttaagcctcaat
aaagcttgccttgagtgcttCAAGTAGTGTGTGCCCGTCT
GTTGTGTGACTCTGGTAACTAGAGATCCCTCAGACCCTTT
TAGTCAGTGTGGAAAATCTCTAGCagtagtagttcatgtc
atcttattattcagtatttataacttgcaaagaaatgaat
atcagagagtgagaggaacttgtttattgcagcttataat
ggttacaaataaagcaatagcatcacaaatttcacaaata -continued aagcatttttttcactgcattctagttgtggtttgtccaa
actcatcaatgtatcttatcatgtctggctctagctatcc
cgcccctaactccgcccatcccgcccctaactccgcccag
ttccgcccattctccgccccatggctgactaattttttt
atttatgcagaggccgaggccgcctcggcctctgagctat
tccagaagtagtgaggaggcttttttggaggcctagggac
gtacccaattcgccctatagtgagtcgtattacgcgcgct
cactggccgtcgttttacaacgtcgtgactgggaaaaccc
tggcgttacccaacttaatcgccttgcagcacatccccct
ttcgccagctggcgtaatagcgaagaggcccgcaccgatc
gcccttcccaacagttgcgcagcctgaatggcgaatggga
cgcgccctgtagcggcgcattaagcgcggcgggtgtggtg
gttacgcgcagcgtgaccgctacacttgccagcgccctag
cgcccgctcctttcgctttcttcccttcctttctcgccac
gttcgccggctttccccgtcaagctctaaatcgggggctc
cctttagggttccgatttagtgctttacggcacctcgacc
ccaaaaaacttgattagggtgatggttcacgtagtgggcc
atcgccctgatagacggtttttcgccctttgacgttggag
tccacgttctttaatagtggactcttgttccaaactggaa
caacactcaaccctatctcggtctattcttttgatttata
agggattttgccgatttcggcctattggttaaaaaatgag
ctgatttaacaaaaatttaacgcgaattttaacaaaatat
taacgcttacaatttaggtggcacttttcggggaaatgtg
cgcggaacccctatttgtttatttttctaaatacattcaa
atatgtatccgctcatgagacaataaccctgataaatgct
tcaataatagcacctagatcaagagacaggatgaggatcg
tttcgcatgattgaacaagatggattgcacgcaggttctc
cggccgcttgggtggagaggctattcggctatgactgggc
acaacagacaatcggctgctctgatgccgccgtgttccgg
ctgtcagcgcaggggcgcccggttctttttgtcaagaccg
acctgtccggtgccctgaatgaactgcaagacgaggcagc
gcggctatcgtggctggccacgacgggcgttccttgcgca
gctgtgctcgacgttgtcactgaagcgggaagggactggc
tgctattgggcgaagtgccggggcaggatctcctgtcatc
tcaccttgctcctgccgagaaagtatccatcatggctgat
gcaatgcggcggctgcatacgcttgatccggctacctgcc
cattcgaccaccaagcgaaacatcgcatcgagcgagcacg
tactcggatggaagccggtcttgtcgatcaggatgatctg
gacgaagagcatcaggggctcgcgccagccgaactgttcg
ccaggctcaaggcgagcatgcccgacggcgaggatctcgt
cgtgacccatggcgatgcctgcttgccgaatatcatggtg -continued gaaaatggccgcttttctggattcatcgactgtggccggc tgggtgtggcggaccgctatcaggacatagcgttggctac ccgtgatattgctgaagagcttggcggcgaatgggctgac cgcttcctcgtgctttacggtatcgccgctcccgattcgc agcgcatcgccttctatcgccttcttgacgagttcttctg aattattaacgcttacaatttcctgatgcggtattttctc cttacgcatctgtgcggtatttcacaccgcatcaggtggc acttttcggggaaatgtgcgcggaacccctatttgtttat ttttctaaatacattcaaatatgtatccgctcatgaccaa aatcccttaacgtgagttttcgttccactgagcgtcagac cccgtagaaaagatcaaaggatcttcttgagatcctttt ttctgcgcgtaatctgctgcttgcaaacaaaaaaaccacc gctaccagcggtggtttgtttgccggatcaagagctacca actctttttccgaaggtaactggcttcagcagagcgcaga taccaaatactgttcttctagtgtagccgtagttaggcca ccacttcaagaactctgtagcaccgcctacatacctcgct ctgctaatcctgttaccagtggctgctgccagtggcgata agtcgtgtcttaccgggttggactcaagacgatagttacc ggataaggcgcagcggtcgggctgaacggggggttegtge aeaeageeeagettggagegaaegaeetaeaeegaaetga -continued gataeetaeagegtgagetatgagaaagegeeacgcttcc cgaagggagaaaggcggacaggtatccggtaagcggcagg gtcggaacaggagagcgcacgagggagcttccagggggaa acgcctggtatctttatagtcctgtcgggtttcgccacct ctgacttgagcgtcgatttttgtgatgctcgtcagggggg cggagcctatggaaaaacgccagcaacgcggcctttttac ggttcctggccttttgctggccttttgctcacatgttctt tcctgcgttatcccctgattctgtggataaccgtattacc gcctttgagtgagctgataccgctcgccgcagccgaacga ccgagcgcagcgagtcagtgagcgaggaagcggaagagcg cccaatacgcaaaccgcctctccccgcgcgttggccgatt cattaatgcagctggcacgacaggtttcccgactggaaag cgggcagtgagcgcaacgcaattaatgtgagttagctcac tcattaggcaccccaggctttacactttatgcttccggct cgtatgttgtgtggaattgtgagcggataacaatttcaca caggaaacagctatgaccatgattacgccaagcgcgcaat taaccctcactaaagggaacaaaagctggagctgcaagct tggccattgcatacgttgtatccatatcataatatgtaca tttatattggctcatgtccaacattaccgccatgttgaca ttgattattgactagttattaatagtaatcaattacgggg tcattagttcatagcccatatatgg

What is claimed is:

1. A recombinant nucleic acid comprising: a nucleic acid sequence comprising or consisting of the nucleotide sequence of SEQ ID NO: 1 operably linked to a nucleic acid sequence comprising or consisting of the nucleotide sequence of SEQ ID NO:2 or a fragment thereof wherein fragment thereof comprises one of the following:

the nucleic acid sequence comprising SEQ ID NO:3;
the nucleic acid sequence comprising SEQ ID NO:4;
the nucleic acid sequence comprising SEQ ID NO:5;
the nucleic acid sequence comprising SEQ ID NO:6;
the nucleic acid sequence comprising SEQ ID NO:7; or
the nucleic acid sequence comprising SEQ ID NO:8.

2. The recombinant nucleic acid of claim 1, wherein said fragment comprises the nucleotide sequence of SEQ ID NO:3, wherein the nucleotide sequence of SEQ ID NO:3 enhances expression of the nucleotide sequence of SEQ ID NO:1.

3. The recombinant nucleic acid of claim 1, wherein said fragment comprises the nucleotide sequence of SEQ ID NO:4, wherein the nucleotide sequence of SEQ ID NO:4 enhances expression of the nucleotide sequence of SEQ ID NO:1.

4. The recombinant nucleic acid of claim 1, wherein said fragment comprises the nucleotide sequence of SEQ ID NO:5 wherein the nucleotide sequence of SEQ ID NO:5 enhances expression of the nucleotide sequence of SEQ ID NO:1.

5. The recombinant nucleic acid of claim 1, wherein said fragment comprises the nucleotide sequence of SEQ ID NO:6, wherein the nucleotide sequence of SEQ ID NO:6 enhances expression of the nucleotide sequence of SEQ ID NO:1.

6. The recombinant nucleic acid of claim 1, wherein said fragment comprises the nucleotide sequence of SEQ ID NO:7, wherein the nucleotide sequence of SEQ ID NO:7 enhances expression of the nucleotide sequence of SEQ ID NO:1.

7. The recombinant nucleic acid of claim 1, wherein said fragment comprises the nucleotide sequence of SEQ ID NO:8, wherein the nucleotide sequence of SEQ ID NO:8 enhances expression of the nucleotide sequence of SEQ ID NO:1.

8. The recombinant nucleic acid of claim 1, further comprising: a nucleic acid sequence comprising the nucleotide sequence of SEQ ID NO:9 operably linked to the nucleotide sequence of SEQ ID NO:1, wherein the nucleotide sequence of SEQ ID NO:9 enhances expression of the nucleotide sequence of SEQ ID NO:1.

9. The recombinant nucleic acid of claim 1, further comprising: a nucleic acid sequence comprising the nucleotide sequence of SEQ ID NO: 10 operably linked to the nucleotide sequence of SEQ ID NO: 1, wherein the nucleotide sequence of SEQ ID NO: 10 enhances expression of the nucleotide sequence of SEQ ID NO:1.

10. The recombinant nucleic acid of claim 1, further comprising: a nucleic acid sequence comprising the nucleotide sequence of SEQ ID NO:11 operably linked to the nucleotide sequence of SEQ ID NO: 1, wherein the nucleotide sequence of SEQ ID NO:11 enhances expression of the nucleotide sequence of SEQ ID NO:1.

11. The recombinant nucleic acid of claim 1, further comprising: a nucleic acid sequence comprising the nucleotide sequence of SEQ ID NO: 12 operably linked to the nucleotide sequence of SEQ ID NO:1, wherein the nucleotide sequence of SEQ ID NO: 12 enhances expression of the nucleotide sequence of SEQ ID NO:1.

* * * * *